United States Patent [19]

Sykes et al.

[11] Patent Number: 4,775,670

[45] Date of Patent: Oct. 4, 1988

[54] 2-OXO-1-AZETIDINESULFONIC ACID SALTS

[75] Inventors: Richard B. Sykes, Belle Mead; William L. Parker; Christopher M. Cimarusti, both of Pennington; William H. Koster, Ringoes; William A. Slusarchyk, Belle Mead, all of N.J.

[73] Assignee: E. R. Squibb & Sons, Inc., Princeton, N.J.

[21] Appl. No.: 226,562

[22] Filed: Jan. 19, 1981

Related U.S. Application Data

[63] Continuation-in-part of Ser. No. 188,893, Sep. 29, 1980, abandoned, which is a continuation-in-part of Ser. No. 119,276, Feb. 7, 1980, abandoned.

[51] Int. Cl.[4] ............... C07D 205/08; C07D 403/12; C07D 417/12; A61K 31/395
[52] U.S. Cl. ..................................... 514/210; 540/355
[58] Field of Search ................ 260/239 AL, 245.4; 542/420; 544/379, 279

[56] References Cited

U.S. PATENT DOCUMENTS

| 3,048,581 | 8/1962 | Fried | 260/239.55 |
|---|---|---|---|
| 3,971,772 | 7/1976 | Cimarusti | 260/239.55 |
| 4,225,586 | 9/1980 | Imada | 424/117 |
| 4,229,436 | 10/1980 | Imada | 424/117 |
| 4,483,797 | 11/1984 | Floyd | 540/355 |
| 4,501,697 | 2/1985 | Kronenthal | 544/355 |
| 4,529,698 | 7/1985 | Sykes | 435/121 |
| 4,533,660 | 8/1985 | Gordon | 544/355 |
| 4,610,824 | 9/1986 | Trüner | 540/355 |
| 4,632,985 | 12/1986 | Kronenthal | 540/355 |
| 4,638,062 | 1/1987 | Kronenthal | 540/355 |
| 4,647,660 | 3/1987 | Zahler | 540/355 |
| 4,734,496 | 3/1988 | Treuner | 544/355 |

FOREIGN PATENT DOCUMENTS 21678 1/1981 European Pat. Off. .
7972813 12/1980 Japan .

OTHER PUBLICATIONS

Imada, III et al. Nature 289, 590–1.

Primary Examiner—Mark L. Berch
Attorney, Agent, or Firm—Lawrence S. Levinson; Donald J. Barrack

[57] ABSTRACT

Antibacterial activity is exhibited by $\beta$-lactams having a sulfonic acid salt substituent in the 1-position and an amino or acylamino substituent in the 3-position.

48 Claims, No Drawings

2-OXO-1-AZETIDINESULFONIC ACID SALTS

This application is a continuation-in-part of copending U.S. patent application Ser. No. 188,893, filed Sept. 29, 1980, and now abandoned, which is a continuation-in-part of copending U.S. patent application Ser. No. 119,276, filed Feb. 7, 1980, and now abandoned.

BACKGROUND OF THE INVENTION

The β-lactam ring,

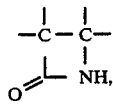

has been known since the late nineteenth century. While knowledge of β-lactam chemistry developed during the early 1900's, it was not until 1929 that Fleming reported in *Brit. J. Exper. Pathol.*, 10, 226 (1929) that a fermentation product of the organism *Penicillium notatum* had antibiotic properties. The compound which Fleming had worked with was benzylpenicillin,

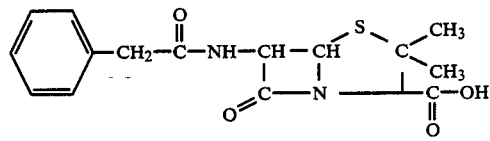

The in vivo activity of benzylpenicillin against various bacteria was reported by Chain et al. in *Lancet*, 2: 226 (1940).

During the early 1940's research in the field of penicillins was intense. This research focused first on structure elucidation and then on synthetic routes for preparing benzyl penicillin. It was not, however, until the late 1950's that a totally synthetic route was discovered for the preparation of benzyl penicillin.

U.S. Pat. No. 2,941,955, issued June 21, 1960, to Doyle et al., discloses the discovery of 6-aminopenicillanic acid,

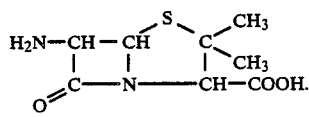

This patent was followed by U.S. Pat. No. 2,951,839, issued Sept. 6, 1960, also to Doyle et al., which discloses the use of 6-aminopenicillanic acid as a valuable intermediate which could be acylated, using art-recognized procedures, to obtain penicillin derivatives having antibiotic properties. Using 6-aminopenicillanic as a stepping stone, research chemists have prepared numerous penicillin derivatives having antibiotic activity.

The second major class of β-lactam antibiotics is the cephalosporins. In the 1940's a Cephalosporium species was found to produce an antibiotic that had activity against gram-positive and gram-negative bacteria. Work in the 1950's showed that the fermentation product of a Cephalosporium species contained not one, but several antibiotics. One of these antibiotics, cephalsporin C,

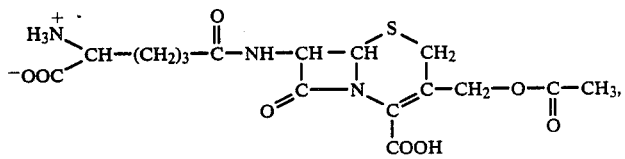

proved to be an important stepping stone in cephalosporin research. Removal of the acyl group in the 7-position of cephalosporin C yields 7-aminocephalosporanic acid,

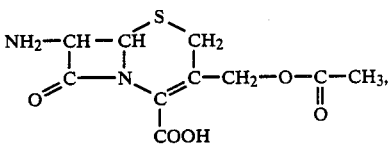

an intermediate useful for the preparation of numerous acylated compounds which are analogs of cephalosporin C.

The penicillins and cephalosporins are, of course, the most important of the β-lactam antibiotics reported to date. Others have, however, been reported. Stapley et al., *Antimicrobial Agents and Chemotherapy*, 2(3): 122 (1972) disclose that certain actinomycete cultures isolated from soil produce antibiotics characterized by a methoxy group and D-α-aminoadipic acid on the 7-carbon of the cephem nucleus. The cephamycins, as they are known, have the formula

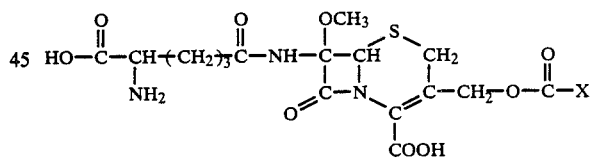

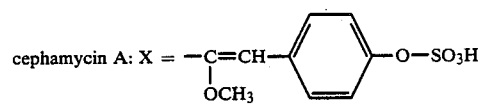

cephamycin A: X = —C=CH—⟨C₆H₄⟩—O—SO₃H
                     |
                     OCH₃

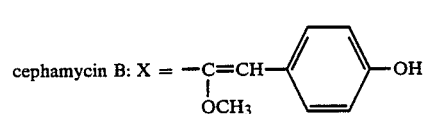

cephamycin B: X = —C=CH—⟨C₆H₄⟩—OH
                     |
                     OCH₃ cephamycin C: X = —NH₂.

Stapley et al. reported that cephamycin A and cephamycin B each exhibits a similar range of potencies against gram-negative and gram-positive bacteria, and cephamycin C had greater potency against gram-negative bacteria than against gram-positive bacteria. Cephamycin C was reported to be the most active of the three antibiotics.

Scannell et al., *The Journal of Antibiotics*, XXVIII(1): 1 (1975), disclose the isolation from a fermentation broth of Streptomyces species 372A of (S)-alanyl-3-[α-(S)-chloro-3-(S)-hydroxy-2-oxo-3-azetidinyl-methyl]-(S)-alanine, which has the formula

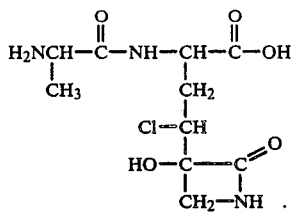

The structure of the above naturally occurring monocyclic β-lactam containing molecule is similar to the structure of the earlier discovered β-lactam containing molecules known as tabotoxins, i.e.,

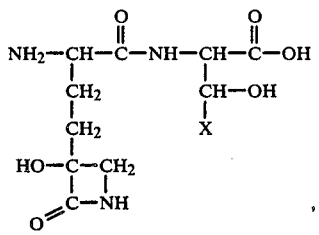

wherein X is hydrogen or methyl as reported by Stewart, *Nature*, 229: 174 (1971), and Taylor et al., *Biochem. Biophys. Acta*, 286: 107 (1972).

Recently, several novel series of naturally occurring β-lactam antibiotics have been isolated. The nocardicins, nocardicin A and B, are monocyclic β-lactams having the formula

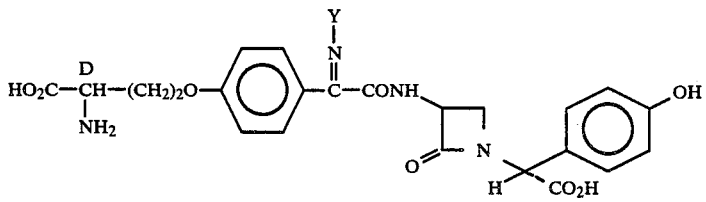

nocardicin A: Y = —syn(Z)OH
nocardicin B: Y = —anti(E)OH, as reported by Hashimoto et al., *The Journal of Antibiotics*, XXIX (9): 890 (1976).

Clavulanic acid, a bicyclic β-lactam antibiotic isolated from fermentation broths of *Streptomyces clavuligerus*, has the formula

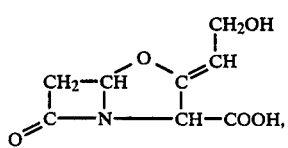

i.e., Z-(2R,5R)-3-(β-hydroxyethylidene)-7-oxo-4-oxa-1-azabicyclo[3,2,0]heptane-2-carboxylic acid, as reported by Lloyd et al., *J.C.S. Chem. Comm.*, 266 (1976).

Still another recently isolated β-lactam antibiotic is thienamycin, an antibiotic isolated from the fermentation broths of *Streptomyces cattleya*. As reported by Albers-Schonberg et al., *J.A.C.S.*, 100: 20, 6491 (1978), thienamycin has the structure

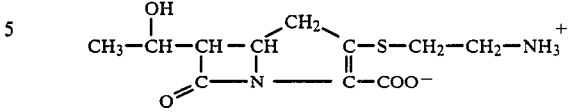

Additional fused β-lactams, olivanic acid derivatives, have recently been isolated from cultures of *Streptomyces olivaceus*. As disclosed by Brown et al., *J.C.S. Chem. Comm.*, these olivanic acid derivatives have the formulas

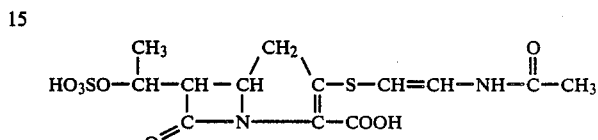

and

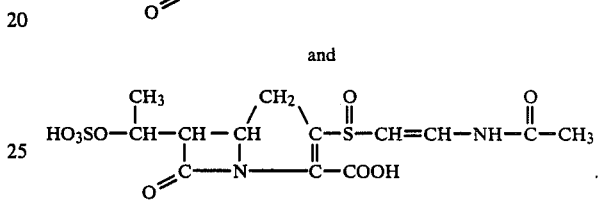

The isolation of the above antibiotics, and a discussion of their activity, is reported by Butterworth et al., *The Journal of Antibiotics*, XXXII(4): 294 (1979) and by Hood et al., *The Journal of Antibiotics*, XXXII(4): 295 (1979).

Another recently isolated β-lactam antibiotic is PS-5, reported by Okamura et al., *The Journal of Antibiotics*, XXXI: 480 (1978) and *The Journal of Antibiotics*, XXXII(4): 262 (1979). The structure of this antibiotic, which is produced by *Streptomyces cremeus* subspecies *auratilis*, is reported to be

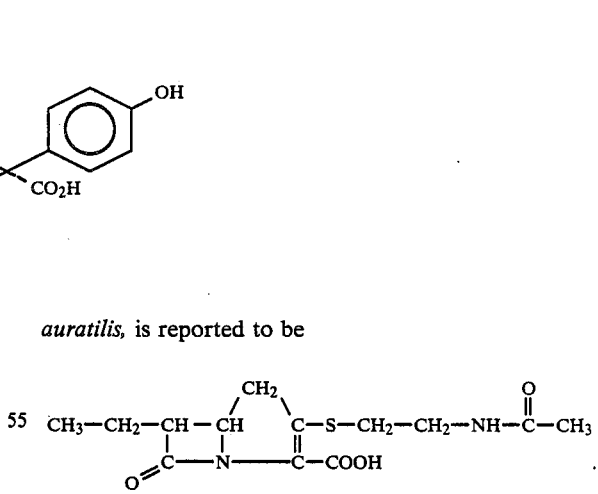

Structurally related antibiotics PS-6 and PS-7 are reported in European Patent application Ser. No. 1,567 to have the respective structures

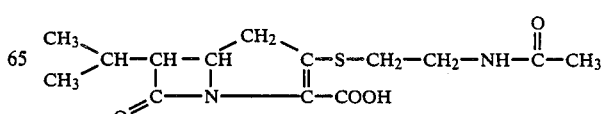

-continued
and

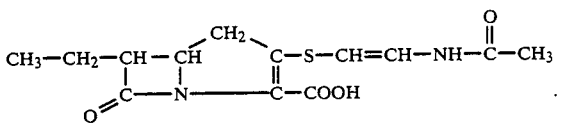

BRIEF DESCRIPTION OF THE INVENTION

This invention is directed to a novel family of β-lactam antibiotics, and to the use of such compounds as antibacterial agents. It has been discovered that the β-lactam nucleus can be biologically activated by a sulfonic acid salt substituent attached to the nitrogen atom in the nucleus.

β-Lactams having a sulfonic acid salt (including "inner salt") substituent in the 1-position and an acylamino substituent in the 3-position exhibit activity against a range of gram-negative and gram-positive bacteria.

Illustrative members of the novel family of β-lactam antibiotics of this invention are those encompassed by the formula

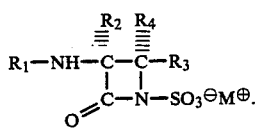   I

In addition to the above described β-lactams having a sulfonic acid salt substituent in the 1-position and an acylamino substituent in the 3-position, this invention also encompasses β-lactams having a sulfonic acid salt (including "inner salt") substituent in the 1-position and an amino substituent in the 3-position.

Illustrative compounds of this type have the formula

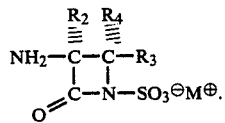   Ia

These compounds are intermediates useful for the preparation of corresponding 3-acylamino compounds.

As used in formulas I and Ia, and throughout the specification, the symbols are as defined below.

$R_1$ is acyl;

$R_2$ is hydrogen or alkoxy of 1 to 4 carbons;

$R_3$ and $R_4$ are the same or different and each is hydrogen, alkyl, cycloalkyl, phenyl or substituted phenyl, or one of $R_3$ and $R_4$ is hydrogen and the other is alkoxycarbonyl, alken-1-yl, alkyn-1-yl, 2-phenylethenyl or 2-phenylethynyl.

$M^\oplus$ is hydrogen or a cation, with the proviso that if $M^\oplus$ is hydrogen a substituent of the β-lactam contains a basic function.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3, 4, 5, 6 or 7 carbon atoms.

The terms "alkanoyl", "alkenyl", "alken-1-yl" and "alkyn-1-yl" refer to both straight and branched chain groups. Those groups having 2 to 10 carbon atoms are preferred.

The term "halogen" refers to fluorine, chlorine, bromine and iodine.

The term "protected carboxyl" refers to a carboxyl group which has been esterified with a conventional acid protecting group. These groups are well known in the art; see, for example, U.S. Pat. No. 4,144,333, issued Mar. 13, 1979. The preferred protected carboxyl groups are benzyl, benzhydryl, t-butyl, and p-nitrobenzyl esters.

The term "substituted phenyl" refers to a phenyl group substituted with 1, 2 or 3 amino($-NH_2$), halogen, hydroxy, trifluoromethyl, alkyl (of 1 to 4 carbon atoms), or alkoxy (of 1 to 4 carbon atoms) groups.

The term "acyl" includes all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_5$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

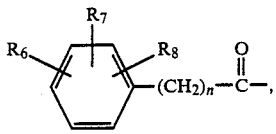

-continued

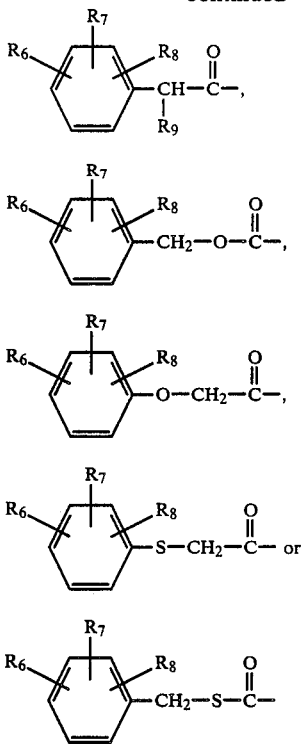

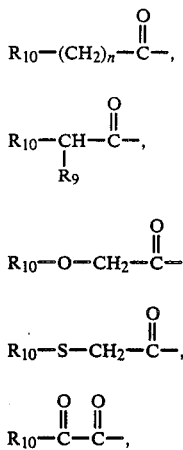

wherein n is 0, 1, 2 or 3; $R_9$ is as defined above; and $R_{10}$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl and tetrazolyl. Exemplary substituents are halogen, hydroxyl, nitro, amino, cyano, trifluoromethyl, alkyl of 1 to 4 carbon atoms, alkoxy of 1 to 4 carbon atoms, or

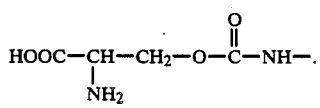

Preferred heteroaromatic acyl groups include those groups of the above formulas wherein $R_{10}$ is 2-amino-4-thiazolyl, 2-amino-5-halo-4-thiazolyl, 4-aminopyrimidin-2-yl, 5-amino-1,2,4-thiadiazol-5-yl, 2-thienyl, 2-furanyl, or 6-aminopyridin-2-yl.

wherein n is 0, 1, 2 or 3; $R_6$, $R_7$, and $R_8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_9$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

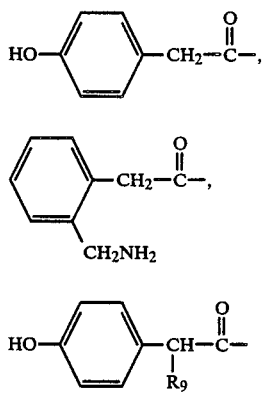

($R_9$ is preferably a carboxyl salt or sulfo salt) and

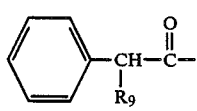

($R_9$ is preferably a carboxyl salt or sulfo salt).

(c) Heteroaromatic groups having the formula (d) [[(4-Substituted-2,3-dioxo-1-piperazinyl)carbonyl[amino]arylacetyl groups having the formula

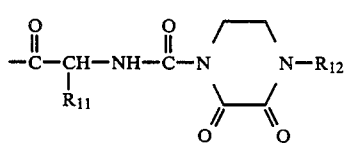

wherein $R_{11}$ is an aromatic group (including carbocyclic aromatics such as those of the formula

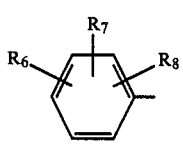

and heteroaromatics as included within the definition of $R_{10}$); and $R_{12}$ is alkyl, substituted alkyl (wherein the alkyl group is substituted with one or more halogen, cyano, nitro, amino or mercapto groups), arylmethyleneamino (i.e., —N=CH—$R_{11}$ wherein $R_{11}$ is as defined above), arylcarbonylamino (i.e.,

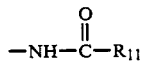

wherein $R_{11}$ is as defined above) or alkylcarbonylamino.

Preferred [[(4-substituted-2,3-dioxo-1-piperazinyl)-carbonyl]amino]arylacetyl groups include those wherein $R_{12}$ is ethyl, phenylmethyleneamino or 2-furylmethyleneamino.

(e) (Substituted oxyimino)arylacetyl groups having the formula

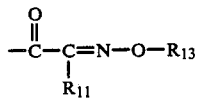

wherein $R_{11}$ is as defined above and $R_{13}$ is hydrogen, alkyl, cycloalkyl, alkylaminocarbonyl, arylaminocarbonyl (i.e.,

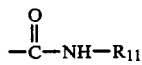

wherein $R_{11}$ is as defined above) or substituted alkyl (wherein the alkyl group is substituted with 1 or more halogen, cyano, nitro, amino, mercapto, alkylthio, aromatic group (as defined by $R_{11}$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy (phenylmethoxy)phosphinyl, or dialkoxyphosphinyl substituents).

Preferred (substituted oxyimino)arylacetyl groups include those wherein $R_{11}$ is 2-amino-4-thiazolyl. Also preferred are those groups wherein $R_{13}$ is methyl, ethyl, carboxymethyl, 2-carboxyisopropyl or 2,2,2-trifluoroethyl.

(f) (Acylamino)arylacetyl groups having the formula

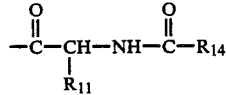

wherein $R_{11}$ is as defined above and $R_{14}$ is

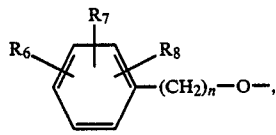

amino, alkylamino, (cyanoalkyl)amino, amido, alkylamido, (cyanoalkyl)amido,

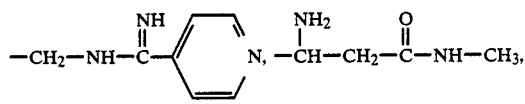

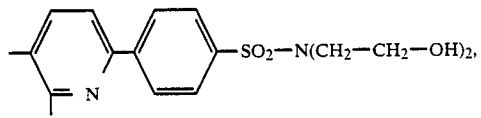

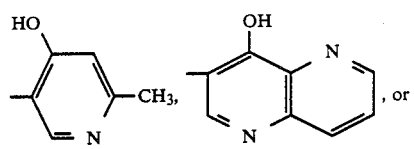

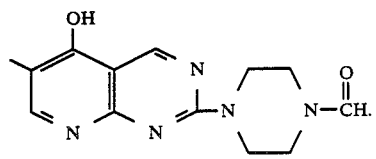

Preferred (acylamino)arylacetyl groups of the above formula include those groups wherein $R_{14}$ is amino, or amido. Also preferred are those groups wherein $R_{11}$ is phenyl or 2-thienyl.

(g) [[[3-Substituted-2-oxo-1-imidazolidinyl]carbonyl]amino]arylacetyl groups having the formula

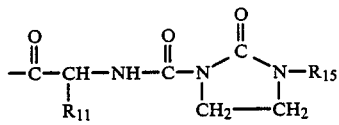

wherein $R_{11}$ is as defined above and $R_{15}$ is hydrogen, alkylsulfonyl, arylmethyleneamino (i.e., —N=CH—$R_{11}$ wherein $R_{11}$ is as defined above),

(wherein $R_{16}$ is hydrogen, alkyl or halogen substituted alkyl), aromatic group (as defined by $R_{11}$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_{11}$ is phenyl or 2-thienyl. Also preferred are those groups wherein $R_{15}$ is hydrogen, methylsulfonyl, phenylmethyleneamino or 2-furylmethyleneamino.

The term "cation", as used throughout the specification, refers to any positively charged atom or group of atoms. The "—SO$_3{}^{\ominus}$M$^{\oplus}$" substituent on the nitrogen atom of the β-lactams of this invention encompasses all sulfonic acid salts. Pharmaceutically acceptable salts are, of course, preferred, although other salts are also useful in purifying the products of this invention or as intermediates for the preparation of pharmaceutically acceptable salts. The cationic portion of the sulfonic acid salts of this invention can be obtained from either organic or inorganic bases. Such cationic portion includes, but is not limited to, the following ions: ammonium; substituted ammonium, such as alkylammonium (e.g., tetra-n-butylammonium, referred to hereinafter as tetrabutylammonium); alkali metal, such as lithium, sodium and potassium; alkaline earth metal, such as calcium and magnesium; pyridinium; dicyclohexylammonium; hydrabaminium; benzathinium; N-methyl-D-glucaminium.

As set forth in formula I, and in the definitions following formula I, $M^\oplus$ can be hydrogen provided the $R_1$ group contains a basic function. Such compounds are often referred to in the art as "inner salts" by virtue of a positive and negative charge in the molecule.

As is described hereinafter, the β-lactams of this invention can be prepared by synthetic means. The non-alkoxylated 4-unsubstituted β-lactams of formula I, i.e., those compounds of formula I wherein $R_2$, $R_3$ and $R_4$ are hydrogen can be prepared using 6-aminopenicillanic acid or a 6-acylaminopenicillanic acid as a starting material. The β-lactams of formula I wherein $R_2$ is alkoxy can be prepared from the corresponding non-alkoxylated β-lactam. Some of the compounds of this invention may be crystallized or recrystallized from solvents containing water. In these cases water of hydration may be formed. This invention contemplates stoichiometric hydrates as well as compounds containing variable amounts of water that may be produced by processes such as lyophilization.

Some of the β-lactams of formula I have also been prepared by biological means. Cultivation of a strain of the microorganism *Chromobacterium violaceum* SC 11,378, yields a salt of (R)-3-(acetylamino)-3-methoxy-2-oxo-1-azetidinesulfonic acid. Cultivation of various acetic acid bacteria, e.g., Gluconobacter species SC 11,435, yields a salt of (R)-3-[[N-(D-γ-glutamyl)D-alanyl]amino]-3-methoxy-2-oxo-1-azetidinesulfonic acid.

β-Lactams having a sulfonic acid salt substituent in the 1-position and an amino or acylamino substituent in the 3-position contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C).

With respect to the preferred β-lactams of formulas I and Ia, the structural formulas have been drawn to show the stereochemistry at the chiral center in the 3-position. Because of the nomenclature convention, those compounds of formulas I and Ia wherein $R_2$ is hydrogen have the S configuration and those compounds of formulas I and Ia wherein $R_2$ is alkoxy have the R configuration.

Also included within the scope of this invention are racemic mixtures which contain the above-described β-lactams.

DETAILED DESCRIPTION OF THE INVENTION

β-Lactams having a sulfonic acid salt substituent in the 1-position of the β-lactam nucleus and an acylamino substituent in the 3-position of the β-lactam nucleus have activity against a range of gram-negative and gram-positive organisms. The sulfonic acid salt substituent is essential to the activity of the compounds of this invention.

The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

SYNTHETIC PRODUCTION OF COMPOUNDS OF THIS INVENTION

The β-lactams of this invention can be prepared by synthetic means. An $-SO_3^\ominus M^\oplus$ substituent can be introduced onto the nitrogen atom of a β-lactam nucleus having a 3-acylamino substituent by reacting the precursor compound with a complex of pyridine and sulfur trioxide, dimethylformamide and sulfur trioxide or 2,6-lutidine and sulfur trioxide (preformed or formed in situ). This method yields 2-oxo-1-azetidinesulfonic acid salts, which, using conventional techniques can be converted to other salts.

An alternative procedure for introducing an $-SO_3^\ominus M^\oplus$ substituent onto the nitrogen atom of a β-lactam nucleus comprises first silylating the precursor compound and then subjecting the silated compound to a silyl interchange reaction with trimethylsilyl chlorosulfonate or similar reagent.

These general procedures and alternative procedures, are described in greater detail in the following two sections of the "Detailed Description of the Invention" and in the specific embodiments of the examples.

SYNTHETIC PRODUCTION OF PRODUCTS OF FORMULA I WHEREIN $R_2$ IS HYDROGEN

The β-lactams of formula I wherein $R_2$ is hydrogen can be prepared from a 3-benzyloxycarbonylamino-2-azetidinone having the formula

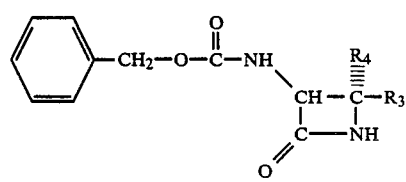

or from corresponding 2-azetidinones having other (e.g., triphenylmethyl) nitrogen protecting groups.

The addition of a sulfo ($SO_3^-$) group to the 1-position of the compound of formula II yields a compound having the formula

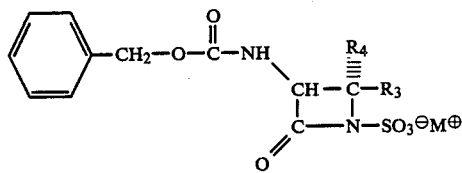

III

The compound of formula III is not only an antibiotic product of formula I, but also is a valuable intermediate for the preparation of other products of formula I.

One method for introducing the sulfo group to the 1-position of a 3-benzyloxycarbonylamino-2-azetidinone (formula II) comprises reacting the compound with a complex of pyridine and sulfur trioxide. The reaction can be run in an organic solvent or in a mixture of organic solvents, preferably a mixture of a polar solvent such as dimethylformamide and a halogenated hydrocarbon such as dichloromethane. This reaction yields a compound of formula III wherein $M^{\oplus}$ is pyridinium ion. Instead of using a pre-formed complex of pyridine and sulfur trioxide, the complex can be formed in situ, e.g., using chlorosulfonyltrimethylsilyl ester and pyridine as reagents. Alternatively, a complex of dimethylformamidesulfur trioxide or 2,6-lutidine-sulfur trioxide can be used.

Using conventional techniques (e.g., ion-exchange resins, crystallization, or ion-pair extraction) the pyridinium salt formed by the above procedure can be converted to other salts. These techniques are also useful for converting the products of formula I or any of the intermediates described herein to other salts.

A second method for introducing the sulfo group to the 1-position of a 3-benzyloxycarbonylamino-2-azetidinone (formula II) comprises first silylating the compound and then subjecting the silated compound to a silyl interchange reaction. Exemplary silylating agents are monosilyltrifluoroacetamide, trimethylsilylchloride/triethylamine, and bis-trimethylsilyltrifluoroacetamide, and an exemplary reagent useful for the silyl interchange reaction is trimethylsilyl chlorosulfonate.

A salt of a 3-(benzyloxycarbonylamino)-1-sulfo-2-azetidinone (formula III) can be converted to the key intermediate

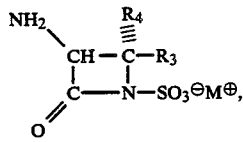

IV i.e., a salt of a 3-amino-1-sulfo-2-azetidinone. From this key intermediate, using conventional acylation techniques, it is possible to prepare all of the products of formula I wherein $R_2$ is hydrogen.

In converting a salt of a 3-(benzyloxycarbonylamino)-1-sulfo-2-azetidinone (formula III) to a salt of formula IV it is desirable to utilize a soluble salt, such as the tetrabutylammonium salt. Reduction of a salt of formula III to the intermediates of formula IV can be accomplished by catalytic (e.g., palladium on charcoal) hydrogenation.

Exemplary acylation techniques for converting a compound of formula IV to a product of formula I wherein $R_2$ is hydrogen include reaction with a carboxylic acid ($R_1$—OH), or corresponding carboxylic acid halide or carboxylic acid anhydride. The reaction with a carboxylic acid proceeds most readily in the presence of a carbodiimide such as dicyclohexylcarbodiimide and a substance capable of forming an active ester in situ such as N-hydroxybenzotriazole. In those instances when the acyl group ($R_1$) contains reactive functionality (such as amino or carboxyl groups) it may be necessary to first protect those functional groups, then carry out the acylation reaction, and finally deprotect the resulting product.

An alternative synthesis for preparing the compounds of formula I wherein $R_2$ is hydrogen comprises a reduction of a 3-benzyloxycarbonylamino-2-azetidinone (formula II) to yield

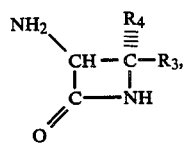

V i.e., a 3-amino-2-azetidinone. The reduction can be accomplished by catalytic (e.g., palladium on charcoal) hydrogenation. A 3-amino-2-azetidinone (formula V) can be acylated using conventional acylation techniques (these have been exemplified above under the process description for converting a compound of formula IV to a product of formula I) to yield an intermediate having the formula

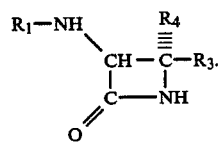

VI

A sulfo group can be introduced in the 1-position of a compound of formula VI using either of the techniques described above for introducing a sulfo group in the 1-position of a 3-benzyloxycarbonylamino-2-azetidinone of formula II (i.e., reaction with a complex of either pyridine, dimethylformamide, or 2,6-lutidine and sulfur trioxide, or silylation followed by a silyl interchange reaction).

Still another synthesis for preparing the compounds of formula I wherein $R_2$ is hydrogen comprises the use of a 3-azido-2-azetidinone having the formula

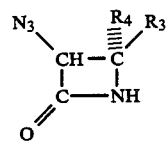

VII

A sulfo group can be introduced in the 1-position of a compound of formula VII using either of the techniques described above for introducing a sulfo group in the 1-position of a 3-benzyloxycarbonylamino-2-azetidinone of formula II (i.e., reaction with a complex of either pyridine, dimethylformamide, or 2,6-lutidine and sulfur trioxide, or silylation followed by a silyl interchange reaction) yielding an intermediate having the formula

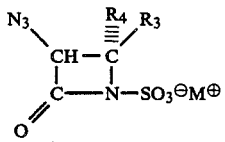

i.e., a salt of a 3-azido-1-sulfo-2-azetidinone. Reduction of an intermediate of formula VIII yields the corresponding intermediate having the formula

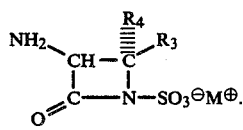

The reduction can be accomplished by catalytic (e.g., palladium on charcoal or platinum oxide) hydrogenation or with reducing agents such as zinc or triphenylphosphine. As described above, from these key intermediates (compounds of formula IV), using conventional acylation techniques, it is possible to prepare all of the products of formula I wherein $R_2$ is hydrogen.

Alternatively, a 3-azido-2-azetidinone of formula VII can be reduced to the corresponding 3-amino-2-azetidinone having the formula

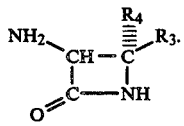

The reduction can be accomplished by catalytic (e.g., palladium on charcoal or platinum oxide) hydrogenation or with reducing agents such as zinc or triphenylphosphine. A 3-amino-2-azetidinone of formula V can be reacted as described above (i.e., first acylated and then treated as described above to introduce a sulfo group in the 1-position) to yield the products of formula I wherein $R_2$ is hydrogen.

Still another synthesis for preparing the compounds of formula I wherein $R_2$, $R_3$ and $R_4$ are each hydrogen utilizes a 6-acylaminopenicillanic acid having the formula

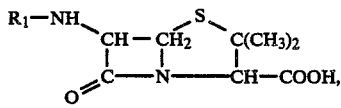

or a salt thereof as the starting material. By adapting procedures described in the literature, 3-acylamino-2-azetidinone can be obtained from the corresponding 6-acylaminopenicillanic acid of formula IX: see, for example, *Chem. Soc. Special Publication* No. 28, pg. 288 (1977), *The Chemistry of Penicillins*, Princeton University Press, pg. 257, and *Synthesis*, 494 (1977).

As described in the literature 6-acylaminopenicillanic acid, or a salt thereof, can be desulfurized to yield a compound having the formula

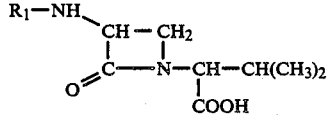

by reduction using Raney nickel. The reaction can be run in water under reflux conditions.

Replacement of the carboxyl group of a compound of formula X with an acetate group followed by hydrolysis yields the corresponding 3-acylamino-2-azetidinone having the formula

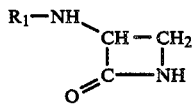

Treatment of a compound of formula X with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

A sulfo group can be introduced in the 1-position of a compound of formula XI (yielding products of formula I wherein $R_2$, $R_3$ and $R_4$ are each hydrogen) using either of the techniques described above for introducing a sulfo group in the 1-position of a 3-benzyloxycarbonylamino-2-azetidinone of formula II (i.e., reaction with a complex of either pyridine, dimethylformamide, or 2,6-lutidine and sulfur trioxide, or silylation followed by a silyl interchange reaction).

Still another variation of the above-described synthetic routes for preparing a compound of this invention (formula I) wherein $R_2$, $R_3$, and $R_4$ are each hydrogen comprises first desulfurizing 6-aminopenicillanic acid, acylating the resulting compound to yield a compound of formula X and then proceeding as described above to obtain first a 3-acylamino-2-azetidinone of formula XI and then a product of formula I.

The azetidinones of formula I wherein $R_2$ is hydrogen and at least one of $R_3$ and $R_4$ is hydrogen can also be prepared from amino acids having the formula

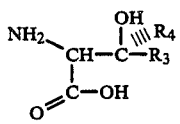

(at least one of $R_3$ and $R_4$ is hydrogen). The amino group is first protected with a classical protecting group, e.g., t-butoxycarbonyl (referred to hereinafter as "Boc"). The carboxyl group of the protected amino acid is then reacted with an amine having the formula

Y—O—NH$_2$,     XIII wherein Y is alkyl or benzyl, in the presence of a carbodiimide to yield a compound having the formula

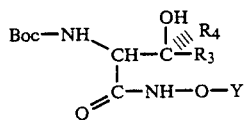

XIV (at least one of $R_3$ and $R_4$ is hydrogen). The hydroxyl group of a compound of formula XIV is converted to a leaving group with a classical reagent, e.g., methanesulfonyl chloride (methanesulfonyl is referred to hereinafter as "Ms").

The fully protected compound having the formula

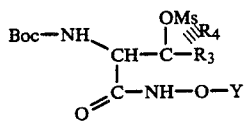

XV (as least one of $R_3$ and $R_4$ is hydrogen) is cyclized by treatment with base, e.g., potassium carbonate. The reaction is preferably carried out in an organic solvent such as acetone, under reflux conditions, and yields a compound having the formula

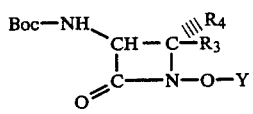

XVI (at least one of $R_3$ and $R_4$ is hydrogen).

Alternatively, cyclization of a compound of formula XIV can be accomplished without first converting the hydroxyl group to a leaving group. Treatment of a compound of formula XIV with triphenylphosphine and diethylazodicarboxylate, yields a compound of formula XVI wherein at least one of $R_3$ and $R_4$ is hydrogen.

Both of the methods disclosed above for ring closure of a compound of formula XIV result in the inversion of the stereochemistry at the carbon atom bearing the $R_3$ and $R_4$ substituents.

Removal of the protecting group from the 1-position of an azetidinone of formula XVI can be accomplished via sodium reduction when Y is alkyl, and yields an intermediate having the formula

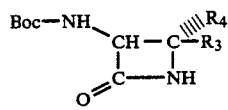

XVII (at least one of $R_3$ and $R_4$ is hydrogen). If Y is benzyl, catalytic (e.g., palladium on charcoal) hydrogenation will initially yield the corresponding N-hydroxy compound, which upon treatment with titanium trichloride yields an intermediate of formula XVII wherein at least one of $R_3$ and $R_4$ is hydrogen.

A sulfo group can be introduced in the 1-position of a compound of formula XVII using either of the techniques described above for introducing a sulfo group in the 1-position of a 3-benzyloxycarbonylamino-2-azetidinone of formula II (i.e., reaction with a complex of either pyridine, dimethylformamide, or 2,6-lutidine and sulfur trioxide, or silylation followed by a silyl interchange reaction) yielding a compound having the formula

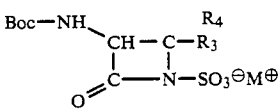

XVIII (at least one of $R_3$ and $R_4$ is hydrogen).

Deprotection of a sulfonated azetidinone of formula XVIII by standard procedures (for a Boc protecting group treatment with formic acid is effective) yields a zwitterion having the formula

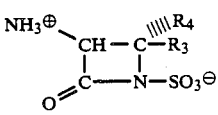

XIX (at least one of $R_3$ and $R_4$ is hydrogen). Conventional acylation techniques can be employed to convert a zwitterion of formula XIX to the corresponding product of formula I.

An alternative procedure for preparing a compound of formula I wherein $R_2$ is hydrogen and at least one of $R_3$ and $R_4$ is hydrogen, utilizes as a starting material an amino acid amide having the formula

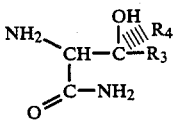

XX (at least one of $R_3$ and $R_4$ is hydrogen). Protection of the amino group with a classical protecting group, e.g., benzyloxycarbonyl (referred to hereinafter as Z) or Boc, and conversion of the hydroxyl group to a leaving group Ms yields a compound having the formula

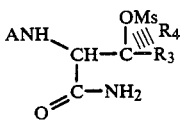

XXI (at least one of $R_3$ and $R_4$ is hydrogen), wherein A is a protecting group.

Sulfation of a compound of formula XXI with a complex of 2-picoline and sulfur trioxide yields a compound having the formula

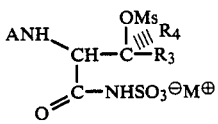

XXII (at least one of $R_3$ and $R_4$ is hydrogen). The complex of 2-picoline and sulfur trioxide can be prepared by reacting chlorosulfonic acid and 2-picoline in an organic solvent, e.g., a halogenated hydrocarbon such as methylene chloride, at a reduced temperature.

Cyclization of a compound of formula XXII is accomplished with base, e.g., potassium carbonate. The reaction is preferably carried out in a mixture of water and an organic solvent (e.g., a halogenated hydrocarbon such as 1,2-dichloroethane) under reflux conditions and yields a compound having the formula

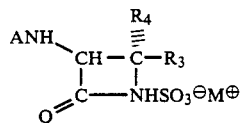   XXIII (at least one of $R_3$ and $R_4$ is hydrogen).

Deprotection of a sulfonated azetidinone of formula XXIII, wherein A is a Z protecting group, by catalytic hydrogenation yields a compound having the formula

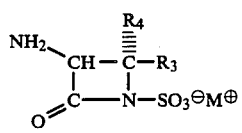   XXIV (at least one of $R_3$ and $R_4$ is hydrogen), which can be converted to the corresponding zwitterion having the formula

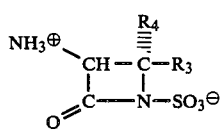   XIX (at least one of $R_3$ and $R_4$ is hydrogen) by treatment with formic acid.

Deprotection of a sulfonated azetidinone of formula XXIII wherein A is a Boc protecting group using acidic conditions (e.g., using formic acid) yields the corresponding zwitterion of formula XIX.

The starting azetidinones of formulas II and VII are obtainable using any one of numerous procedures.

3-Benzyloxycarbonylamino-2-azetidinone (formula II, $R_3$ and $R_4$ are each hydrogen) can be obtained from 6-aminopenicillanic acid or a salt thereof, utilizing the adapted literature procedures described above (for the conversion of 6-acylaminopenicillanic acid to 3-acylamino-2-azetidinone to obtain the compound having the formula

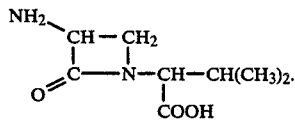   XXV

Acylation of the compound of formula XXV to obtain the corresponding 3-benzyloxycarbonylamino derivative having the formula

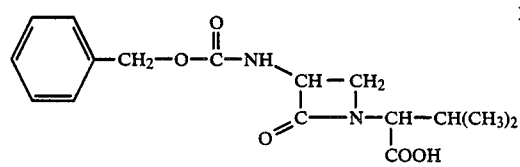   XXVI can be accomplished using art-recognized acylation techniques and reagents, e.g., benzyl chloroformate, phenylbenzylcarbonate or p-nitrophenylbenzylcarbonate.

Replacement of the carboxyl group of the compound of formula XXVI with an acetate group followed by hydrolysis yields 3-benzyloxycarbonylamino-2-azetidinone (formula II, $R_3$ and $R_4$ are each hydrogen). Treatment of a compound of formula XXVI with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

A 3-azido-2-azetidinone of formula VII can be prepared by first reacting on olefin having the formula

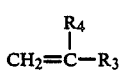   XXVII with a halosulfonylisocyanate (preferably chlorosulfonylisocyanate) having the formula

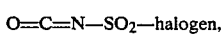   XXVIII to yield an azetidinone having the formula

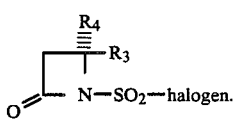   XXIX

Reductive hydrolysis of an azetidinone of formula XXIX yields an N-unsubstituted β-lactam having the formula

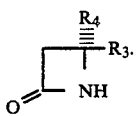   XXX

For a more detailed description of the above described reaction sequence reference can be made to the literature; see, for example, Chem. Soc. Rev., 5, 181 (1976) and J. Org. Chem., 35, 2043 (1970).

An azido group can be introduced in the 3-position of an azetidinone of formula XXX by reaction of the compound with an arylsulfonyl azide (such as toluenesulfonyl azide) to obtain a starting azetidinone having the formula

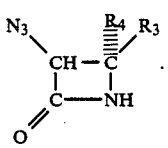   VII

The reaction proceeds best by first protecting the azetidinone nitrogen with a silyl residue (e.g., t-butyldimethylsilyl, or t-butyldiphenylsilyl), then generating the anion at the 3-position of the nucleus with a strong organic base (e.g., lithium diisopropylamine) at a low temperature, and then treating the anion with toluenesulfonyl azide. The resulting intermediate is quenched with trimethylsilyl chloride, and subsequent acid hydrolysis or fluoride solvolysis of the N-protecting group yields the compound of formula VII.

A 3-azido-2-azetidinone of formula VII wherein $R_4$ is hydrogen can be prepared by first reacting a primary amine having the formula

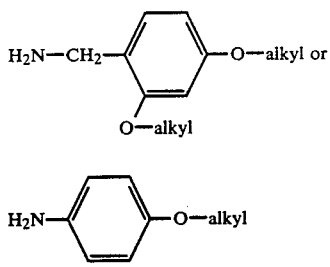
XXXI

XXXIa with an aldehyde having the formula

XXXII (or a hemiacetal) to yield the corresponding Schiff base. A [2+2] cycloaddition reaction of the Schiff base with an activated form of α-azidoacetic acid yields a 3-azido-2-azetidinone having the formula

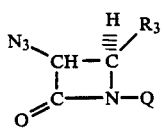
XXXIII wherein Q is

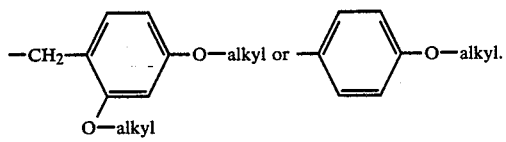

Oxidative removal of the 1-substituent yields the corresponding compound having the formula

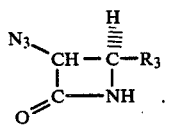
XXXIV

A compound of formula II wherein $R_4$ is hydrogen can be obtained using a procedure analogous to that described above for the preparation of a 3-azido-2-azetidinone of formula VII wherein $R_4$ is hydrogen. In place of an activated form of α-azidoacetic acid, an activated form of α-phthalimidoacetic acid is used, yielding a compound having the formula

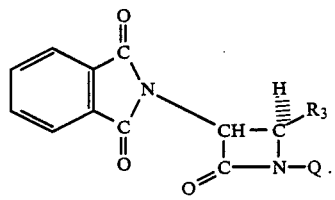
XXXV

Reaction of a compound of formula XXXV with a reagent such as methyl hydrazine (to cleave the phthaloyl group), followed by the introduction of a benzyloxycarbonyl protecting group on the 3-nitrogen substituent, and oxidative removal of the 1-protecting group will yield a compound of formula III wherein $R_4$ is hydrogen.

An alternative procedure for preparing a compound of formula II (or corresponding 2-azetidinone with a different protecting group for the 3-nitrogen containing substituent), wherein one of $R_3$ and $R_4$ is hydrogen, and the other is alken-1-yl, alkyn-1-yl, 2-phenylethenyl or 2-phenylethynyl, utilizes a starting material having the formula

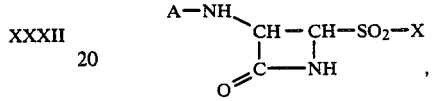
XXXVI wherein A is a nitrogen protecting group (triphenylmethyl is preferred) and X is alkyl or phenyl. Reaction of a compound of formula XXXVI with 1 equivalent of a methyl Grignard reagent followed by slightly more than 1 equivalent of the appropriate Grignard reagent having the formula

halo—Mg—R,  XXXVII wherein R is alkyl, alken-1-yl, alkyn-1-yl, 2-phenylethenyl or 2-phenylethynyl, yields a compound having the formula

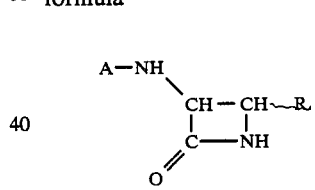
XXXVIII

The 3-benzyloxycarbonylamino-2-azetidinones of formula II can be obtained by first reducing a 3-azido-2-azetidinone of formula VII to obtain the corresponding 3-amino-2-azetidinone and then acylating the 3-amino-2-azetidinone to obtain the corresponding compound having the formula

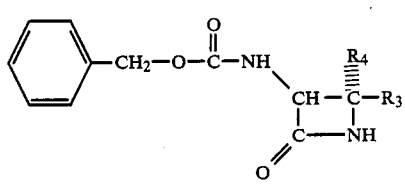
II

SYNTHETIC PRODUCTION OF PRODUCTS OF FORMULA I WHEREIN $R_2$ IS ALKOXY

The β-lactams of formula I wherein $R_2$ is alkoxy can be prepared from the corresponding compound of formula I wherein $R_2$ is hydrogen. Halogenation of the amide nitrogen of a non-alkoxylated compound of formula I yields an intermediate having the formula

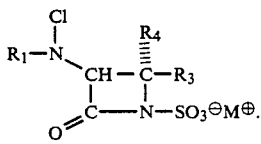

IXL

Reagents and procedures for N-chlorinating amides are known in the art. Exemplary reagents are tert.-butyl hypochlorite, sodium hypochlorite, and chlorine. The reaction can be run in an organic solvent (e.g., a lower alkanol such as methanol) or in a two phase solvent system (e.g., water/methylene chloride) in the presence of a base such as sodium borate decahydrate. The reaction is preferably run at a reduced temperature.

Reaction of an intermediate of formula IXL with an alkoxylating agent, e.g., an alkali metal alkoxide yields a product of formula I wherein $R_2$ is alkoxy, in combination with its enantiomer. The reaction can be run in an organic solvent, e.g., a polar organic solvent such as dimethylformamide, at a reduced temperature.

An alternative synthesis for preparing the compounds of formula (wherein $R_2$ is alkoxy comprises first alkoxylating an intermediate of formula VI wherein $R_1NH$ is a carbamate (e.g., $R_1$ is benzyloxycarbonyl) and then introducing a sulfo group in the 1-position of the resulting compound. Chlorination of a compound of formula VI using the procedure described above (for chlorination of a non-alkoxylated compound of formula I to yield a compound of formula IXL) yields an intermediate having the formula

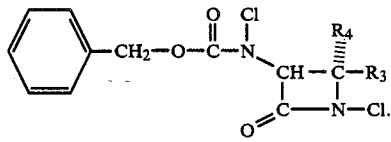

XL

Using the alkoxylation procedure described above (for converting a compound of formula IXL product of formula I), and subsequently adding a reducing agent such as trimethylphosphite, the compound of formula XL can be converted to an intermediate having the formula

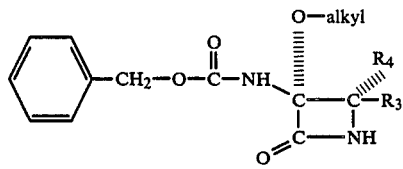

XLI in combination with its enantiomer. A sulfo group can be introduced in the 1-position of a compound of formula XLI using either of the techniques described above for introducing a sulfo group in the 1-position of 3-benzyloxycarbonylamino-2-azetidinone (i.e., reaction with a complex of either pyridine, dimethylformamide or 2,6-lutidine and sulfur trioxide, or silylation followed by a silyl interchange reaction).

Still another synthesis for preparing the products of formula I wherein $R_2$ is alkoxy comprises the initial preparation of a key intermediate having the formula

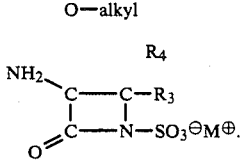

XLII or an intermediate of formula XLII in combination with its enantiomer. Such an intermediate can be obtained by reduction of a salt of 3-alkoxy-3-benzyloxycarbonylamino-2-oxo-1-azetidinesulfonic acid using catalytic (e.g., palladium on charcoal) hydrogenation. Acylation with the appropriate acid chloride yields the various products of formula I (wherein $R_2$ is alkoxy) from an intermediate of formula XLII.

The above procedures yield those products of formula I wherein $R_2$ is alkoxy as a racemic mixture. If desired the enantiomer having the R configuration can be isolated from the racemic mixture using conventional techniques such as fractional crystallization of a suitable salt with an optically active organic amine or by ion-paired chromatography utilizing an optically active cation.

Still another synthesis for preparing the products of formula I wherein $R_2$ is alkoxy and $R_3$ and $R_4$ are hydrogen comprises the preparation of a β-lactam intermediate having the formula

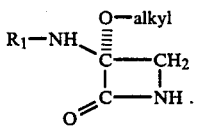

XLIII

An intermediate of formula XLIII can be obtained by first desulfurizing the corresponding 6-acylamino-6-alkoxypenicillanic acid or 7-acylamino-7-alkoxycephalosporanic acid by reduction using Raney nickel. The reaction can be run in water under reflux conditions; the resulting compound has the structural formula

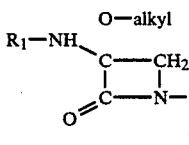

XLIV

Replacement of the carboxyl group of the compound of formula XLIV with an acetate group followed by hydrolysis yields a 3-acylamino-3-alkoxy-2-azetidinone of formula XLIV. Treatment of a compound of formula XLIV with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

Introduction of a sulfo group in the 1-position of a compound of formula XLIII can be accomplished by reacting the intermediate with a complex of dimethylformamide and sulfur trioxide.

The above-described synthetic procedures for the production of the compounds of this invention have been illustrated with specific reference to the preparation of the products of formula I. As will be recognized by the practitioner of this invention, the processes have broader applicability and can be used to prepare other compounds falling within the scope of this invention; i.e., β-lactams having a sulfonic acid salt substituent (—SO₃⊖M⊕) in the 1-position of the β-lactam nucleus, an amino (—NH₂) or acylamino substituent in the 3-position of the β-lactam nucleus, and various substituents in the 4-position of the β-lactam nucleus. Utilizing the above described procedures, and starting materials prepared according to literature procedures, β-lactam antibiotics can be prepared having the formula

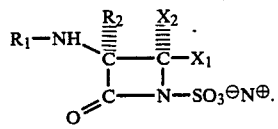    XLV

In formula XLV, one of $X_1$ and $X_2$ is hydrogen and the other is: halogen; carboxyl; —CH₂X₃ wherein $X_3$ is azido, amino(—NH₂), hydroxy, alkylsulfonyloxy, (phenyl or substituted phenyl)sulfonyloxy, phenyl, substituted phenyl, halogen, benzylthio, (substituted phenyl)methylthio, triphenylthio, cyano or mercapto; —O—X₅ wherein $X_5$ is alkyl, phenyl, substituted phenyl, alkanoyl, or

The preferred products of this invention are those having the formula

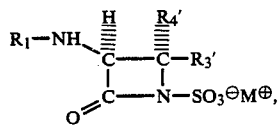    XLVI wherein $R_3'$ and $R_4'$ are each hydrogen or one of $R_3'$ and $R_4'$ is hydrogen and the other is alkyl. Particularly preferred products of this invention are those products of formula XLVI wherein one of $R_3'$ and $R_4'$ is hydrogen and the other is methyl or ethyl.

BIOLOGICAL PRODUCTION OF THE ANTIBIOTIC EM5117

Salts of (R)-3-(acetylamino)-3-methoxy-2-oxo-1-azetidinesulfonic acid (formula I, $R_1$ is acetyl and $R_2$ is methoxy; referred to hereinafter as EM5117) can also be prepared by cultivation of a strain of the microorganism *Chromobacterium violaceum* SC 11,378, which has been deposited in the American Type Culture Collection as A.T.C.C. No. 31532.

THE MICROORGANISM

The microorganism used for the production of EM5117 is a strain of *Chromobacterium violaceum* SC 11,378. A subculture of the microorganism can be obtained from the permanent collection of the American Type Culture Collection, Rockville, Md. Its accession number in the repository is A.T.C.C. No. 31532. In addition to the specific microorganism described and characterized herein, it should be understood that mutants of the microorganism (e.g., mutants produced through the use of x-rays, ultraviolet radiation or nitrogen mustards) can also be cultured to produce EM5117.

*Chromobacterium violaceum* SC 11,378, A.T.C.C. No. 31532 can be isolated from a moist soil sample containing the microorganism by first stamping the soil sample on a medium containing:

| Soil Extract | 400 ml |
|---|---|
| Distilled Water | 600 ml |
| Yeast Extract | 5.0 g |
| Glucose | 10.0 g |
| Agar | 17.5 g |

The medium is adjusted to pH 6.0 and sterilized in an autoclave at 121° C. for 20 minutes. After 24 to 72 hours incubation at 25° C. colonies of the *Chromobacterium violaceum* SC 11,378 are isolated from the plated soil. These isolated colonies are then grown on a medium containing:

| Yeast Extract | 1 g |
|---|---|
| Beef Extract | 1 g |
| NZ amine A | 2 g |
| Glucose | 10 g |
| Agar | 15 g |
| Distilled water to | 1 liter |

The medium is adjusted to pH 7.3 and autoclaved at 121° C. for 30 minutes.

*Chromobacterium violaceum* SC 11,378 is a gram negative rod often showing barring, bipolar staining and lipid inclusions. It is motile by a single polar flagellum with occassional lateral flagella which are smaller in size.

On nutrient agar *Chromobacterium violaceum* SC 11,378 produces violet colonies. The pigment is enhanced on media rich in tryptophane and yeast extract. In nutrient broth it produces a violet ring on the wall of the tube but no confluent pellicle. The violet pigment is soluble in ethanol but insoluble in water and chloroform.

*Chromobacterium violaceum* SC 11,378 is mesophilic, growing over a range of 15°–37° C.; no growth occurs at 4° C. or above 37° C. Casein is hydrolyzed strongly by the microorganism, which is oxidase positive. In the presence of *Chromobacterium violaceum* SC 11,378 glucose, fructose and trehalose are fermented (method of Hugh & Leifson, 1953). L-Arabinose is not utilized by the microorganism either fermentatively or oxidatively. Hydrogen cyanide is produced by the microorganism and aesculin hydrolysis is negative.

The above described key characteristics provide the basis for the identification of the microorganism as *Chromobacterium violaceum* as distinguished from *Chromobacterium lividum*, the only other species of the genus Chromobacterium recognized in the 8th edition of Bergey's Manual of Determinative Bacteriology.

Additional strains of *Chromobacterium violaceum* can also be cultured to produce EM5117.

THE ANTIBIOTIC

To obtain the antibiotic EM5117, *Chromobacterium violaceum* SC 11,378 A.T.C.C. No. 31532 is grown at, or about, 25° C. under submerged aerobic conditions on an aqueous nutrient medium containing an assimilable carbohydrate and nitrogen source. The fermentation is carried out until substantial antibiotic activity is imparted to the medium, usually about 18 to 24 hours, preferably about 20 hours.

Using the following procedure, EM5117 can be separated from the fermentation medium and purified. After the fermentation has been completed the broth can be centrifuged to remove the mycelium or, alternatively, filtration can be used to remove the mycelium from the broth. After removing the mycelium from the broth EM5117 can be extracted from the broth. Preferably the broth is extracted at pH 5 ion-pair extraction with cetyldimethylbenzylammonium chloride in methylene chloride and back-extracted into aqueous sodium iodide (adjusted to pH 5 with acetic acid). After concentration of the sodium iodide extract in vacuo, an aqueous solution of the residue can be washed with butanol. Concentration of the resulting aqueous solution to dryness yields a residue which is dissolved, to the extent possible, in methanol. Centrifugation can be used to separate insolubles which are washed with methanol and then discarded.

Purification of the antibiotic can be accomplished by dissolving the methanol concentrate in methanol/water (1:1) and applying it to a chromatography column, e.g., one comprising Sephadex G-10 in the same solvent mixture. After elution with the same mixture active fractions are combined and concentrated to dryness. The residue is mixed with methanol and insoluble material is filtered out and discarded.

Further purification is achieved by applying the methanol soluble material to a column of DEAE cellulose. The column can be eluted with a linear gradient prepared from pH 5 sodium 0.0.M phosphate buffer and pH 5 sodium 0.1M phosphate buffer. Active fractions are combined, concentrated and methanol insoluble materials are removed and discarded.

Still further purification of EM5117 is accomplished by dissolving this material in water and placing the solution on a column of Sephadex LH-20, and eluting the column with water. Active fractions are combined and concentrated. Further purification of EM5117 is then accomplished by dissolving the material in water, placing the solution on a column of Diaion HP-20AG and eluting with water. Active fractions are combined and concentrated. The concentrate is dissolved in water and passed through a column of Dowex 50W-X2, potassium form, washing with water. The effluent can be concentrated to yield a crystalline material which is relatively pure potassium salt of EM5117.

The above described isolation and purification process yields the potassium salt of EM5117. Other salts can be prepared corresponding to the form of the ion exchange resin utilized in the final purification step.

BIOLOGICAL PRODUCTION OF THE ANTIBIOTIC EM5210

Salts of (R)-3-[[N-(D-$\gamma$-glutamyl)-D-alanyl]amino]-3-methoxy-2-oxo-1-azetidinesulfonic acid (formula I, $R_1$ is D-$\gamma$-glutamyl-D-alanyl and $R_2$ is methoxy; referred to hereinafter as EM5210) can also be prepared by cultivation of various acetic acid bacteria.

THE MICROORGANISM

The microorganism Gluconobacter species SC11,435 can be used for the production of EM5210. A subculture of the microorganism can be obtained from the permanent collection of the American Type Culture Collection, Rockville, Md. Its accession number in the repository is A.T.C.C. No. 31581. In addition to the specific microorganism described and characterized herein, it should be understood that mutants of the microorganism (e.g., mutants produced through the use of x-rays, ultraviolet radiation or nitrogen mustards) can also be cultured to produce EM5210.

Gluconobacter species SC11,435, A.T.C.C. No. 31581 can be isolated from ground moss containing the microorganism by first incubating the ground moss in a 10% aqueous pectin solution (pH 2.5) for 7 days at 25° C. The organism can then be isolated by plating on a medium containing:

| *Extract of *Spartina patens* Grass | 400 ml |
|---|---|
| Distilled Water | 600 ml |
| Yeast Extract | 5 g |
| Glucose | 10 g |
| Crude Flake Agar | 17.5 g |

*Extract of *Spartina patens* grass is prepared by adding 500 g of chopped, dried grass to 3 liters of tap water, brought to a boil and simmered for 30 minutes.

The medium is adjusted to pH 6.0 and sterilized in an autoclave at 121° C. for 20 minutes. After about 18 hours incubation at 25° C., colonies of the Gluconobacter species SC11,435 are isolated from the plated pectin enrichment solution. These isolated colonies are then grown on a medium containing:

| Yeast Extract | 1 g |
|---|---|
| Beef Extract | 1 g |
| NZ amine A | 2 g |
| Glucose | 10 g |
| Agar | 15 g |
| Distilled Water to | 1 liter |

The medium is adjusted to pH 7.3 and autoclaved at 121° C. for 30 minutes.

Gluconobacter species SC11,435 is a pleiomorphic gram negative rod motile by means of one to three polar Flagella. It is obligately aerobic, catalase positive and oxidative. It is differentiated from Pseudomonas in that it is cytochrome oxidase negative and tolerant of extremely acid conditions. These characteristics indicate that the microorganism is more closely related to the acetic acid bacteria than to true Pseudomonads.

On BBL Trypticase soy agar Gluconobacter species SC11,435 grows as a mixture of rough and smooth colony types. The rough type is associated with a faint yellow soluble pigment whereas the smooth type is mucoid and pigmentless. Dissociation between the two types is influenced by media, temperature and storage conditions. EM5210 activity tends to decrease in cultures where the rough component is dominant.

On BBL Wart agar (pH 4.8) Gluconobacter species SC11,435 grows luxuriantly as heaped up mucoid slimy colonies. Similar growth is obtained on malt-yeast extract agar (1% each) adjusted to pH 4.5.

On medium containing 1% yeast extract, 10% glucose, 3% calcium cabonate and 2.5% agar, sufficient acid is produced from the glucose to produce a zone of clearing of the calcium carbonate around the growth. This is a characteristic feature of Acetobacter and Gluconobacter.

In the presence of Gluconobacter species SC11,435:(i) a brown soluble pigment is produced on yeast extract-glycerol and yeast extract-calcium lactate agar plates, (ii) acid is produced on glucose, fructose, galactose, mannose, xylose, mannitol and arabinose, but no growth or acid production occurs on rhamnose, lactose, sucrose or maltose, when these sugars are incorporated into Hugh and Leifson's medium.

The biological production of EM5210 is not limited to Gluconobacter species SC11,435, but is broadly distributed throughout the acetic bacteria. The following cultures can each be used for the production of EM5210:

Acetobacter pasteurianus subsp. pasteurianum A.T.C.C. 6033

Acetobacter aceti subsp. aceti A.T.C.C. 15973

Gluconobacter oxydans subsp. oxydans A.T.C.C. 19357

Gluconobacter oxydans subsp. suboxydans A.T.C.C. 23773

Gluconobacter oxydans subsp. oxydans A.T.C.C. 15178

Acetobacter aceti subsp. liquefaciens A.T.C.C. 23751

Acetobacter peroxydans A.T.C.C. 12874

Gluconobacter oxydans subsp. suboxydans A.T.C.C. 19441

Acetobacter sp. A.T.C.C. 21780

Gluconobacter oxydans subsp. industralis A.T.C.C. 11894.

THE ANTIBIOTIC

To obtain the antibiotic EM5210, Gluconobacter species SC11,435 A.T.C.C. No. 31581 or one of the microorganisms listed above, can be grown at, or about, 25° C. under submerged aerobic conditions on an aqueous nutrient medium containing an assimilable carbon and nitrogen source. The fermentation is carried out until substantial antibiotic activity is imparted to the medium, usually about 16 to 24 hours, preferably about 20 hours.

Using the following procedure EM5210 can be separated from the fermentation medium and purified. After the fermentation has been completed the broth is centrifuged to remove the bacteria and the antibiotic is removed from the broth supernate at pH 3.7 by absorption onto an anion exchange resin e.g., Dowex 1-X2. Antibiotic is eluted from the resin with sodium chloride at about pH 4, and the eluate is concentrated and passed through a charcoal column. EM5210 is then eluted from the charcoal with methanol:water, 1:1. The active fractions are collected and dried, and then placed on an anion exchange column, e.g., Dowex 1-X2, and eluted with a gradient of sodium chloride buffered at pH 4. Active fractions are concentrated and desalted on a macroreticular styrene-divinylbenzene copolymer resin (Dianion HP 20AG) column. Active fractions eluted with water are concentrated and freeze dried and this material represents the sodium salt of EM5210.

The above described purification procedure will yield the sodium salt of EM5210. Other salts can be obtained by changing the salt used to elute EM5210 in the ion-exchange chromatography described above, e.g., using potassium chloride to give the potassium salt.

The following examples are specific embodiments of this invention.

EXAMPLE 1

(S)-N-(2-Oxo-1-sulfo-3-azetidinyl)-2-phenylacetamide, potassium salt

Method I (A)

1-[(1R)-carboxy-2-methyl(propyl)]-2-oxo-(3S)[phenyl[acetyl(amino)]]acetidine

Raney nickel is washed with water by decantation for several hours until the pH of the water (5-6 times volume of that of the Raney nickel) is 7.6.

To a solution of 9.0 g of penicillin G (Na+) in 500 ml of water is added 54 g (90 ml) of Raney nickel. The flask, fitted with a reflux condenser, is immersed in a bath at 155° C. When refluxing begins, it is continued for 15 minutes. The flask is immediately cooled in an ice-water bath, and the Raney nickel is removed by filtration through Celite. The pH is adjusted to 3 using dilute HCl, and the aqueous solution is concentrated to ca. 150 ml and cooled. The oily layer crystallizes upon scratching. After washing with water and drying in vacuo for 3 hours at 50° C. there is 3.83 g of the title compound.

(B)

1-[Acetyloxy-2-methyl(propyl)]-2-oxo-(3S)-[phenyl[acetyl(amino)]]azetidine

Nitrogen is bubbled for 15 minutes through a stirred suspension of 608 mg (2 mmol) of the above compound in 20 ml of dry acetonitrile. A water bath at 40°-45° C. is used for several minutes to dissolve all of the acid. The water bath is removed, and powdered cupric acetate monohydrate (182 mg, 1 mmol) is added, followed after 1 minute of stirring, by 886 mg (2 mmol) of lead tetracetate. The mixture is stirred at room temperature for 20 minutes. The acetonitrile solution is decanted from the precipitate, and the solids are washed with ethyl acetate. The combined acetonitrile-ethyl acetate solution is evaporated to a residue, which is taken up in ethyl acetate-water. The ethyl acetate layer is washed sequentially with water (3 times), aqueous sodium bicarbonate (pH 7), and water. The ethyl acetate layer is dried over sodium sulfate and evaporated to a residue (515 mg), which is used without further purification in the next reaction.

(C)

2-Oxo-(3S)-[phenyl[acetyl(amino)]]azetidine

To a solution of 911 mg (2.86 mmol) of the above compound in 21 ml of methanol is added 3.5 ml of water followed by 383 mg (2.86 mmol) of potassium carbonate. The mixture is stirred under nitrogen for 1 minute, and then 160 mg (4.30 mmol) of sodium borohydride is added. The reaction is stirred at room temperature for 20 minutes. The methanol is removed in vacuo, and the residue is taken up in ethyl acetate and a small amount of water. This is adjusted to pH 2.5. The ethyl acetate layer is washed at pH 7.0 with aqueous sodium bicarbonate and then a small volume of water and finally dried over sodium sulfate and evaporated to give the crude product (493 mg). Addition of a small amount of ethyl acetate gives 250 mg (43% yield) of the desired crystalline product. Further quantities of product can be obtained by crystallization or chromatography.

(D)

(S)-N-(2-Oxo-1-sulfo-3-azetidinyl)-2-phenylacetamide, potassium salt

Pyridine.SO$_3$ complex (215 mg, 1.35 mmol) is added to a stirred solution of 251 mg (1.23 mmol) of the above product in 2 ml of dry dimethylformamide and 2 ml of dry methylene chloride under nitrogen at room temperature. The mixture is stirred for 3 hours. The solvents are removed in vacuo, and the residue is taken up in methylene chloride-water. The pH is adjusted to 6.5 using 2N potassium hydroxide. The aqueous layer is washed with methylene chloride (3 times) filtered and evaporated to a residue. The residue is stirred with 20 ml of methanol, and the potassium sulfate is removed by filtration. The filtrate is evaporated to a residue, which is stirred with 10–15 ml of methanol. The solids are collected to give 49 mg of the title compound, melting point 189° C., dec.

Anal. Calc'd for C$_{11}$H$_{11}$N$_2$O$_5$SK: C, 40.99; H, 3.44; N, 8.69; S, 9.93. Found: C, 45.96; H, 3.83; N, 9.86; S, 8.99.

METHOD II

A solution of 660 mg of (S)-2-oxo-3-[[(phenylmethoxy)carbonyl]amino]-1-azetidinesulfonic acid, potassium salt (see Example 3) in 13 ml of water is stirred in an atmosphere of hydrogen for 2 hours with 200 mg of 10% palladium on charcoal. The catalyst is filtered and the filtrate diluted with an equal volume of acetone and cooled in an ice bath. Over 30 minutes, phenylacetyl chloride (eight 40 μl portions) and 10% potassium bicarbonate solution are added (pH kept between 5.2–5.8). After 40 minutes, the solution is concentrated in vacuo to remove acetone and applied to a 200 ml HP-20 column. Elution with water and then water-acetone (9:1) gives 160 mg of crude product after TLC examination of Rydon positive fractions, followed by pooling and evaporation. Crystallization from methanol-ether gives 101 mg of the title compound, melting point 210° C., dec. Anal. Cald'd for C$_{11}$H$_{11}$N$_2$O$_5$SK.½H$_2$O: C, 39.86; H, 3.65; N, 8.45; S, 9.68; K, 11.80. Found: C, 40.01; H, 3.37; N, 8.59; S, 9.59; K, 11.98.

Method III

To a solution of (S)-3-amino-2-oxo-1-azetidinesulfonic acid, tetrabutylammonium salt (121 mg; see Example 6A) in dry methylene chloride (3 ml) is added 40 mg of phenylacetic acid and 61 mg of dicyclohexylcarbodiimide. The mixture is stirred for 48 hours at room temperature, and filtered to remove dicyclohexylurea. The solvent is removed in vacuo and the compound residue is taken up in acetone, filtered and the title compound precipitated by the addition of 5 ml of acetone saturated with potassium iodide. The supernatant is decanted, the residue washed with acetone (3 times) and, after drying, 48 mg of product is obtained.

Method IV

A solution of 2.83 g of (S)-2-oxo-3[[(phenylmethoxy)carbonyl]amino]-1-azetidinesulfonic acid, pyridine salt (see Example 2) in 36 ml of water is stirred in an atmosphere of hydrogen with 707.5 mg of 10% palladium on charcoal (175 ml of hydrogen taken up). After 2 hours the slurry is filtered, and the filtrate cooled to 0° C. and diluted with 46 ml of acetone (initial pH=4.25 adjusted to pH 6.7 with cold 10% potassium bicarbonate solution). A solution of 2.4 ml of phenylacetyl chloride in 10 ml of acetone is added dropwise over 15 minutes. The pH is maintained between 5.2 to 5.8 by the simultaneous addition of cold 10% potassium bicarbonate solution. After 45 minutes the slurry is diluted with 93 ml of 0.5M potassium phosphate (pH=4.2) and concentrated to remove acetone. The slurry is filtered and washed with water. The filtrate and washings are combined and applied to a 450 ml HP-20 column. Elution with 1 liter of 0.5M potassium phosphate (pH=4.2), 1 liter of water, and then 2.5 liters of 9:1 water-acetone gives 1.285 g of the title compound in fractions 14–19 (fraction 1–15 were 200 ml, fractions 16–21 were 100 ml).

EXAMPLE 2

(S)-2-Oxo-3-[[(phenylmethoxy)carbonyl]amino]-1-azetidinesulfonic acid, pyridine (1:1) salt

Method I

(A)

1-[(1R)-Carboxy-2-methyl(propyl)]-2-oxo-(3S)[[(phenylmethoxy)carbonyl]amino]azetidine A slurry of 6-aminopenicillanic acid (12.98 g, 0.06 mole) in 140 ml of water containing 5.18 g of sodium bicarbonate (stirred for ca. 10 minutes without complete solution) is added in one portion to a well-stirred (mechanical stirrer) suspension of Raney nickel (washed with water to pH 8.0, 260 ml of slurry=130 g) in a 70° C. oil bath. After 15 minutes the slurry is cooled, filtered, and the filtrate treated with 5.18 g of sodium bicarbonate and a solution of 11.94 g (0.07 mole) of benzyl chloroformate in 12 ml of acetone. After 30 minutes, the solution is acidified to pH 2.5 and extracted with methylene chloride. The organic layer is dried, evaporated, and triturated with etherhexane to give a total of 6.83 g of the title compound.

(B)

1-[(Acetyloxy)-2-methyl(propyl)]-2-oxo-(3S)[[(phenylmethoxy)carbonyl]amino]azetidine A solution of 6.83 g (0.0213 mole) of the above acid in 213 ml of acetonitrile is treated with 1.95 g (0.0107 mole) of cupric acetate monohydrate and 9.5 g (0.0213 mole) of lead tetraacetate. The slurry is immersed in a 65° C. oil bath and stirred with a stream of nitrogen bubbling through the slurry until the starting material is consumed. The slurry is filtered and the solids washed with ethyl acetate. The combined filtrate and washings are evaporated in vacuo and the residue taken up in 100 ml each of ethyl acetate and water and adjusted to pH 7. The ethyl acetate layer is separated, dried, and evaporated to give 6.235 g of the title compound.

(C)

(S)-(2-Oxo-3-azetidinyl)carbamic acid, phenylmethyl ester

A solution of 3.12 g (0.0093 mole) of the above acetate in 70 ml of methanol and 7 ml of water is cooled to −15° C. and 1.33 g of potassium carbonate and 349 mg of sodium borohydride are added. The reaction mixture is stirred at −15° C.-0° C. After the reaction is complete (ca. 2 hours), the mixture is neutralized to pH 7 with 2N HCl and concentrated in vacuo. The concentrate is adjusted to pH 5.8, saturated with salt and extracted with ethyl acetate (3 times). The organic layer is dried and evaporated in vacuo. The residue is combined with material from a similar experiment and triturated with ether to give 3.30 g of the title compound.

(D)

(S)-2-Oxo-3-[[(phenylmethoxy)carbonyl]amino]-1-azetidinesulfonic acid, pyridine salt Method I A solution of 440 mg (0.002 mole) of the above azetidinone in 2 ml each of dry methylene chloride and dry dimethylformamide is stirred for 2 hours under nitrogen with 350 mg (0.0022 mole) of pyridine-sulfur trioxide complex. The bulk of the solvent is then removed in vacuo and the residue triturated with ethyl acetate to give 758 mg of solid, which is primarily the title compound.

Method II

Chlorosulfonyltrimethylsilyl ester (18.87 g) is added dropwise at −20° C. to 7.0 g of anhydrous pyridine with stirring under a nitrogen atmosphere. When the addition is complete, stirring is continued for 30 minutes at room temperature, and trimethylchlorosilane is then removed in vacuo. A solution of 20 g of the above azetidinone (Method I, part C) in 120 ml of dimethylformamide and 120 ml of methylene chloride is added and stirred at ambient temperature is continued for 3.5 hours. The solvent is distilled off in vacuo and the oily residue crystallized by addition of ethyl acetate, yielding 31 g of the title compound.

EXAMPLE 3

(S)-2-Oxo-3-[[(phenylmethoxy)carbonyl]amino]-1-azetidinesulfonic acid, potassium salt Method I (S)-2-Oxo-3-[[(phenylmethoxy)carbonyl]amino]-1-azetidinesulfonic acid, pyridine salt (135 mg; see Example 2) is dissolved in 2 ml of 0.5M monobasic potassium phosphate (adjusted to pH 5.5 with 2N potassium hydroxide) and applied to a 25 ml HP-20AG column. The column is eluted with 100 ml of buffer, 200 ml of water and 100 ml of 1:1 acetone-water. Fractions (25 ml) 14–15 are highly Rydon positive. Evaporation yields 80 mg of material which is primarily the title compound.

Method II (S)-2-Oxo-3-[[(phenylmethoxy)carbonyl]amino]-1-azetidinesulfonic acid, pyridine salt (600 mg; see Example 2) is dissolved in 2 ml of water and mixed with 15 ml of pH 5.5 monobasic potassium phosphate buffer. A solid forms and the slurry is cooled to 0° C., filtered, washed with cold buffer, cold 50% ethanol, ethanol and ether to give 370 mg of the title compound (containing excess potassium ion by analysis). A solution of 280 mg of the salt in 10 ml of water is applied to a 100 ml HP-20 column. The column is eluted with 200 ml of water and then water-acetone (9:1). Fractions (50 ml) are collected; evaporation of fraction 7 gives a solid. Trituration with acetone, filtration, and drying in vacuo gives 164 mg of the title compound, melting point 193°–196° C.

Anal. Calc'd for $C_{11}H_{11}N_2O_6SK \cdot \frac{1}{2}H_2O$: C, 38.02; H, 3.48; N, 8.06; S, 9.23; K, 11.25. Found: C, 38.19; H, 3.24; N, 8.15; S, 9.12; K, 11.53.

Method III (S)-(2-Oxo-3-azetidinyl)carbamic acid, phenylmethyl ester (20.0 g, see Example 2C) is suspended in 200 ml of acetonitrile, 21.6 ml of monotrimethylsilyltrifluoroacetamide (25.3 g) is added and the mixture is heated to 50° C. with stirring for 1 hour. After cooling in an ice bath to 0° C., 17.2 g of trimethylsilyl chlorosulfonate is dropped in and the solution is stirred at ambient temperature for 6 hours. To the solution is added 24.2 g of potassium ethyl hexanoate in 100 ml of butanol and stirring is continued for an additional 1 hour. The slurry is poured into 1 liter of dry diethyl ether and the precipitate is filtered off and dried in vacuo. The compound is dissolved in 500 ml of water, the pH is adjusted to 5.0 with potassium carbonate, insoluble material is filtered off and the mother liquor is freeze dried. The yield of crude compound is 19.4 g. The compound contains small amounts of potassium chloride which is removed by chromatography.

EXAMPLE 4

(S)-2-Oxo-3-[[(phenylmethoxy)carbonyl]amino]-1-azetidinesulfonic acid, tetrabutylammonium salt (1:1)

Method I (S)-2-Oxo-3-[[(phenylmethoxy)carbonyl]amino]-1-azetidinesulfonic acid, pyriding salt (1:1) (34.3 g; see Example 2) is dissolved in 800 ml of water. The solution is cleared with charcoal, 30.7 g of tetrabutylammonium hydrogen sulfate in 80 ml water is added and the pH is adjusted to 5.5 with 1N-potassium hydroxide. The solvent is removed in vacuo until a volume of about 200 ml is reached. The precipitated tetrabutylammonium salt is filtered off and dried in vacuo. The compound can be recrystallized from water or dissolved in methylene chloride, filtered and precipitated by addition of ether. Yield 34.3 g melting point 108°–110° C.

Method II (S)-2-Oxo-3-[[(phenylmethoxy)carbonyl]amino]-1-azetidinesulfonic acid, potassium salt (1:1) (20.2 g; see Example 3) is dissolved in 500 ml of water, filtered and 20.3 g of tetrabutylammonium hydrogen sulfate in 100 ml of water is added. The pH is brought to 5.5 with 1N potassium hydroxide. The volume is reduced in vacuo to about 100 ml and the precipitated tetrabutylammonium salt is filtered off. The compound is dissolved in 30 ml of methylene chloride, filtered and precipitated by addition of ether, yielding 21 g of the title compound, melting point 109°–111° C.

EXAMPLE 5

(3S)-α-[[(2-Oxo-1-sulfo-3-azetidinyl)amino]carbonyl]-benzeneacetic acid, phenylmethyl ester, potassium salt (1:1)

(A)

(S)-3-Amino-2-Azetidinone (S)-(2Oxo-3-azetidinyl)carbamic acid, phenylmethyl ester (3 g; see Example 2C) is hydrogenated in 100 ml of methanol in the presence of 1 g of palladium on charcoal catalyst. When the theoretical amount of hydrogen is absorbed, the catalyst is filtered off and the filtrate evaporated to dryness. On standing, 1.1 g of the title compound crystallizes.

(B)

(3S)-α-[[(2-Oxo-3-azetidinyl)amino]carbonyl]benzeneacetic acid, phenylmethyl ester The above azetidinone (3.0 g) is dissolved in 100 ml of dimethylformamide. The solution is cooled to 0° C. and 4.5 g of N-methylmorpholine is added followed (dropwise) by 10.8 g of α-(chlorocarbonyl)benzeneacetic acid, phenylmethyl ester in 50 ml of acetonitrile with stirring. The mixture is stirred for about 16 hours at 5° C. The solvent is distilled off in vacuo and 100 ml of water is added to the residue. The aqueous suspension is extracted twice with 100 ml portions of methylene chloride. The organic layers are combined, washed with sodium bicarbonate, 2N phosphoric acid and water, dried with sodium sulfate, filtered and evaporated to dryness. The residue is crystallized with ethyl acetate and petroleum ether, yielding 8.7 g, melting point 164°–166° C.

(C)

(3S)-α-[[(2-Oxo-1-sulfo-3-azetidinyl)amino]carbonyl]-benzeneacetic acid, phenylmethyl ester, potassium salt (1:1)

The above compound (6.9 g) is suspended in 150 ml of acetonitrile. Monotrimethylsilyltrifluoroacetamide (5.7 g) is added and the solution is heated for 30 minutes at 50° C. with stirring. The solution is cooled to 0° C. and 3.9 g trimethylsilyl chlorosulfonate is added dropwise. When the addition is complete the mixture is heated to 50° C. for 5 hours. After cooling to 20° C., 7.6 g of potassium ethyl hexanoate in 10 ml of butanol is added and stirring is continued for 30 minutes. On addition of 300 ml of ether the title compound precipitates and is filtered off. The crude product is stirred with 100 ml of dry acetonitrile for 30 minutes and filtered off, yielding 4.5 g of the title compound, melting point 118°–120° C. Further purification of the crude product followed by freeze-drying yields pure material having a melting point of 188°–190° C.

EXAMPLE 6

(S)-3-[[(2-Amino-4-thiazolyl)acetyl]amino]-2-oxo-1-azetidinesulfonic acid, potassium salt (A)

(S)-3-Amino-2-oxo-1-azetidinesulfonic acid, tetrabutylammonium salt (S)-2-Oxo-3-[[(phenylmethoxy)carbonyl]amino]-1-azetidinesulfonic acid, tetrabutylammonium salt (2 g; see Example 4) is dissolved in 100 ml of dimethylformamide and hydrogenated for about 30 minutes with 1 g of palladium on charcoal (10%) as catalyst. The catalyst is filtered off and the dimethylformamide is removed leaving the title compound as an oil.

(B)

(S)-3-[[(2-Amino-4-thiazolyl)acetyl]amino]-2-oxo-1-azetidinesulfonic acid, potassium salt The above compound (2 g), 0.5 g of aminothiazole acetic acid and 0.4 g of hydroxybenzotriazole are stirred at 0° C. in 100 ml of dry dimethylformamide, while a solution of 0.7 g of dicyclohexylcarbodiimide in 10 ml of dimethylformamide is added dropwise. After the addition is complete, stirring is continued for 12 hours. at 20° C. Insoluble urea is filtered off and the solvent is evaporated in vacuo. The oily residue is treated with a solution of potassium perfluorobutane sulfonate in 20 ml of acetone at room temperature for 15 minutes. After the addition of 200 ml of dimethyl ether the title compound precipitates, and is filtered off, dried and purified via a 300 ml HP-20 chromatography column using water as eluent. The yield is 850 mg of the title compound, melting point >300° C.

EXAMPLE 7

[3S(±)]-3-[[(Formyloxy)phenylacetyl]amino]-2-oxo-1-azetidinesulfonic acid, potassium salt (S)-3-Amino-2-oxo-1-azetidinesulfonic acid, tetrabutylammonium salt (1.5 g; see Example 6A) in 100 ml of dimethylformamide and 2 ml of propylene oxide are cooled to 0° C. A solution of O-formylmandelic acid chloride in 10 ml of acetonitrile is added dropwise with stirring. The temperature is maintained for 1 hour and the solvent is then distilled off in vacuo. The oily residue is treated with a solution of 2 g of potassium perfluorobutane sulfonate in 15 ml of acetone. After adding 200 ml of ether, the title compound crystallizes and is filtered off yielding 1.5 g of product. The product is purified by HP-20 chromatography.

EXAMPLE 8

[3S(±)]-3-[[(Formyloxy)phenylacetyl]amino]-2-oxo-1-azetidinesulfonic acid, potassium salt Following the procedure of Example 7, but substituting D-O-formylmandelic acid chloride for O-formylmandelic acid chloride, yields the title compound, melting point 120°–125° C., after freeze drying.

EXAMPLE 9

[3S(−)]-3-[[(Formyloxy)phenylacetyl]amino-2-oxo-1-azetidinesulfonic acid, potassium salt Following the procedure of Example 7, but substituting L-O-formylmandelic acid chloride for O-formylmandelic acid chloride, yields the title compound, containing 1 mole of water, melting point, 203°–205° C. After careful drying the product melts at 228°–230° C.

EXAMPLE 10

(S)-2-Oxo-3-[(1-oxooctyl)amino]-1-azetidinesulfonic acid, potassium salt (S)-3-Amino-2-oxo-1-azetidinesulfonic acid, tetrabutylammonium salt (1.5 g; see Example 6A) in 100 ml of dimethylformamide and 2 ml of propylene oxide are cooled to 0° C. At this temperature a solution of 0.8 g of caprylic acid chloride in 20 ml of dry acetone is added dropwise and stirring is continued for 30 minutes. The solvent is evaporated in vacuo, and the oily residue is treated with 2 g of potassium perfluorobutane sulfonate in 15 ml of acetone. The acetone is distilled off in vacuo. The residue is dissolved in 5 ml of water and chromatographed using 300 ml of HP-20 resin and water/acetone (9:1) as eluent, yielding 0.9 g of the title compound, melting point 173°–180° C., after freeze-drying.

EXAMPLE 11

[3S(Z)]-3-[[(2-Amino-4-thiazolyl)[[[hydroxy(phenylmethoxy)phosphinyl]methoxy]imino]acetyl]amino]-2-oxo-1-azetidinesulfonic acid, potassium salt (S)-3-Amino-2-oxo-1-azetidinesulfonic acid, tetrabutylammonium salt (0.8 g; see Example 6A) in 30 ml of dimethylformamide, 0.9 g of (Z)-2-amino-α-[[[hydroxy(phenylmethoxy)phosphinyl]methoxy]imino]-4-thiazoleacetic acid, 0.3 g of hydroxybenzotriazole and 0.7 g of dicyclohexylcarbodiimide are stirred for 24 hours at room temperature. The precipitated urea is filtered off and the solvent is removed in vacuo. The reamining oil is treated with an equivalent amount of potassium perfluorobutane sulfonate in 10 ml of acetone. The title compound is filtered off and purified using HP-20 resin and water as eluent, yielding 500 mg, melting point 210°–215° C., dec.

EXAMPLE 12

[3S(Z)]-3-[[(2-Amino-4-thiazolyl)(ethoxyimino)acetyl]amino]-2-oxo-1-azetidinesulfonic acid, potassium salt (S)-3-Amino-2-oxo-1-azetidinesulfonic acid, tetrabutylammonium salt (1.5 g; see Example 6A) in 100 ml of dimethylformamide, 0.6 g of hydoxybenzotriazole, 1 g of dicyclohexylcarbodiimide and 0.8 g of (Z)-2-amino-α-(ethoxyimino)-4-thiazoleacetic acid are stirring at room temperature for 24 hours. The solvent is distilled off and the residue is dissolved in 30 ml of acetone. Urea is filtered off and the mother liquor is treated with a solution of 2 g of potassium perfluorobutane sulfonate in 20 ml of acetone. After the addition of 200 ml of ether the title compound precipitates, is filtered off and dried. Purification is accomplished by chromatography using an HP-20 column and water as eluent, yielding 1.1 g of the title compound, melting point 180°–185° C., dec.

EXAMPLE 13

[3S(E)]-3-[[(2-Amino-4-thiazolyl)(ethoxyimino)acetyl]amino]-2-oxo-1-azetidinesulfonic acid, potassium salt Following the procedure of Example 12, but substituting (E)-2-amino-α-(ethoxyimino)-4-thiazoleacetic acid for (Z)-2-amino-α-(ethoxyimino)-4-thiazoleacetic acid, yields the title compound, melting point 160°–170° C. after freeze drying.

EXAMPLE 14

[3S(Z)-3-[[(2-Amino-4-thiazolyl)](2,2,2-trifluoroethoxy)imino]acetyl]amino]-2-oxo-1-azetidinesulfonic acid, potassium salt Following the procedure of Example 12, but substituting (Z)-2-amino-α-[(2,2,2-trifluoroethoxy)imino]-4-thiazoleacetic acid for (Z)-2-amino-α-(ethoxyimino)-4-thiazoleacetic acid, yields the title compound melting point 160°–170° C. after freeze-drying.

EXAMPLE 15

(S)-2-Oxo-3-[(1-oxopropyl)amino]-1-azetidinesulfonic acid, potassium salt

Method I (S)-3-Amino-2-oxo-1-azetidinesulfonic acid, tetrabutylammonium salt (1.5 g; see Example 6A) in 100 ml of dry dimethylformamide and 4 ml of propylene oxide are cooled to 0° C. with stirring. At this temperature 0.5 g of propionic acid chloride in 10 ml of acetonitrile is added dropwise and the mixture is stirred for 2 hours. The solvent is distilled off in vacuo and the oily residue is treated with an equivalent amount of potassium perfluorobutane sulfonate in 5 ml of acetone. On addition of ether the title compound crystallizes and is filtered off, yielding 0.8 g of product, melting point 135°–140° C. after freeze-drying.

Method II (S)-2-Oxo-3-[[(phenylmethoxy)carbonyl]amino]-1-azetidinesulfonic acid, tetrabutylammonium salt (4 g; see Example 4) is hydrogenated in 100 ml of diglyme with 1 g of palladium on charcoal. The hydrogenation is complete after 2.5 hours. The catalyst is filtered off and 2 ml of propylene oxide is added. After cooling to 0° C., 0.5 g propionic acid chloride in 10 ml dry diglyme is added with stirring. After 30 minutes the solvent is removed in vacuo and the oily residue is treated with an equivalent amount of potassium perfluorobutane sulfonate in 20 ml of acetone. After the addition of ether, the title compound crystallizes, is filtered off and recrystallized from water/acetone, yielding 0.9 g of product, melting point 156°–160° C. (dec.).

EXAMPLE 16

[3S(±)]-3-[(Hydroxyphenylacetyl)amino]-2-oxo-1-azetidinesulfonic acid, potassium salt (S)-3-Amino-2-oxo-1-azetidinesulfonic acid, tetrabutylammonium salt (1.5 g; see Example 6A) in 100 ml of dry dimethylformamide is stirred for about 16 hours with 1.5 g of dicyclohexylcarbodiimide, 0.5 g of hydroxybenzotriazole and 0.6 g of mandelic acid. The solvent is removed in vacuo and the residue is dissolved in 20 ml of acetone. The precipitated urea is filtered off and the mother liquor is treated with an equivalent amount of potassium perfluorobutane sulfonate. After the addition of ether the title compound precipitates and is filtered off, yielding 1.4 g of crude product. After recrystallization from water, the product has a melting point of 138°–140° C.

EXAMPLE 17

(S)-3-[[[(Cyanomethyl)thio]acetyl]amino]-2-oxo-1-azetidinesulfonic acid, potassium salt (S)-3-Amino-2-oxo-1-azetidinesulfonic acid, tetrabutylammonium salt (1.5 g; see Example 6A) and 0.72 g of [(cyanomethyl)thio]acetic acid are dissolved in 70 ml of acetonitrile and a solution of 1.04 grams of dicyclohexylcarbodiimide in acetonitrile is added dropwise. The mixture is stirred for about 16 hours at 0° C. and the precipitated dicyclohexylurea is filtered off, the filtrate evaporated and the oily residue dissolved in acetone. On the addition of a saturated solution of potassium iodide in acetone, the title compound precipitates, yielding 1.1 g of product, melting point 150°–155° C.

EXAMPLE 18

(S)-2-Oxo-3-[(1H-tetrazol-1-ylacetyl)amino]-1-azetidinesulfonic acid, potassium salt To a solution of 0.005 mole of (S)-3-amino-2-oxo-1-azetidinesulfonic acid, tetrabutylammonium salt (see Example 6A) in 70 ml of dimethylformamide is added 0.77 g of 1H-tetrazole-1-acetic acid and a solution of 1.13 g of dicyclohexylcarbodiimide in 5 ml of dimethylformamide. The mixture is stirred for about 16 hours at room temperature and the solvent is removed in vacuo. The remaining oil is dissolved in 20 ml of acetone and treated with 0.006 mole of a solution of potassium perfluorobutane sulfonate in acetone, yielding 1.5 g of the title compound, melting point 170°–175° C., dec.

EXAMPLE 19

(S)-2-Oxo-3-[(2H-tetrazol-2-ylacetyl)amino]-1-azetidinesulfonic acid, potassium salt Following the procedure of Example 18, but substituting 2H-tetrazole-2-acetic acid for 1H-tetrazole-1-acetic acid, yields the title compound, melting point 175°–177° C., dec.

EXAMPLE 20

(S)-2-Oxo-3-[(2-thienylacetyl)amino]-1-azetidinesulfonic acid, potassium salt Following the procedure of Example 18, but substituting 2-thiopheneacetic acid for 1H-tetrazole-1-acetic acid, yields the title compound, melting point 180°–190° C., dec.

EXAMPLE 21

[3S(Z)]-3-[[(2-Amino-4-thiazolyl)(methoxyimino)acetyl]amino]-2-oxo-1-azetidinesulfonic acid, potassium salt (S)-3-Amino-2-oxo-1-azetidinesulfonic acid, tetrabutylammonium salt (prepared as described in Example 6A from 7.9 g of (S)-2-oxo-3-[[(phenylmethoxy)carbonyl]amino]-1-azetidinesulfonic acid, tetrabutylammonium salt) is cooled to 0° C. and 3.53 g of (Z)-2-amino-α-(methoxyimino)-4-thiazoleacetic acid is added, followed by a solution of 3.27 g of dicyclohexylcarbodiimide in 10 ml of dimethylformamide. The mixture is stirred for 16 hours at 5° C., filtered and the solvent removed in vacuo. The residue is dissolved in acetone and filtered. On addition of 60 ml of a 10% solution of potassium perfluorobutane sulfonate in acetone, 4.7 g of crude product crystallizes. The crude product is purified by chromatography on HP-20, 100–200 mesh to yield 3.0 g of the title compound, melting point 235° C.

EXAMPLE 22

(3S)-α-[[(2-Oxo-1-sulfo-3-azetidinyl)amino]carbonyl]-benzeneacetic acid, dipotassium salt (3S)-α-[[(2-Oxo-1-sulfo-3-azetidinyl)amino]carbonyl]benzeneacetic acid, phenylmethyl ester, potassium salt (100 mg; see Example 5) is dissolved in 20 ml of anhydrous methanol. Palladium on charcoal (10 mg, 10%) is added and the mixture is treated with hydrogen for 15 minutes. The catalyst is filtered off, and the methanol evaporated in vacuo. The residue is dissolved in 5 ml of water and the pH adjusted to 6 with 1N potassium hydroxide. After freeze drying crude product is obtained. The crude material is chromatographed over HP 20 resin (water as eluent), yielding 60 mg of the title compound melting point 80°–85° C.

EXAMPLE 23

(S)-3-(Acetylamino)-2-oxo-1-azetidinesulfonic acid, potassium salt

Method I (A)

(S)-3-Amino-2-oxo-1-azetidinesulfonic acid, potassium salt (S)-3-(Benzyloxycarbonylamino)-2-oxo-1-azetidinesulfonic acid, potassium salt (169 mg; see Example 3) is dissolved in 4.0 ml water and hydrogenated over 37 mg of 10% palladium on charcoal for 1 hour 40 minutes. The catalyst is removed by filtration and washed with 1 ml of 50% aqueous acetone.

(B)

(S)-3-(Acetylamino)-2-oxo-1-azetidinesulfonic acid, potassium salt

The above solution of the free amine is diluted with 3.5 ml of acetone and stirred in an ice bath. Acetyl chloride (320 μl) is added over ca. 15 minutes in small portions and alternated with solid potassium bicarbonate to maintain pH 6.5–7.2. After 30 minutes a silica gel TLC in acetone:acetic acid (19:1) and the Rydon test indicated the reaction to be essentially finished. Six ml of 0.5M pH 5.5 monobasic potassium phosphate buffer are added and the solution is acidified to pH 4.8 with 2N hydrochloric acid. The acetone is removed in vacuo and the aqueous solution thus obtained is passed through a 50 ml HP-20 AG column to give 2.197 g of solid. This is digested with methanol to yield 282 mg of extractable material which still contains some salt. The product is further purified by passage through an IRC-50 column, followed by acidification to pH 3.8 with subsequent stripping to dryness in vacuo. Trituration with acetone gives 64 mg of desired product containing ca. 0.5 equivalent of inorganic potassium salts. Final passage through a 200 ml HP-20 AG column, followed by lyophilization from 0.5 ml of water gives 22 mg of product as amorphous powder which is dried in vacuo for 2 hours at 50° C., melting point 170°–180° C. after softening at 100° C.

Anal. for $C_5H_7O_5N_2SK$, Calc'd: C, 24.38; H, 2.87; N, 11.37; K, 15.9. Found: C, 26.06; H, 3.14; N, 9.96; K, 18.04.

Method II

A solution of 2.0 g of (S)-2-oxo-3-[[(phenylmethoxy)-carbonyl]amino]-1-azetidinesulfonic acid, pyridine salt (see Example 2) in 25 ml of water is hydrogenated over 500 mg of 10% palladium on charcoal. After 2 hours the solution is filtered, cooled to 0° C. and 40 ml of acetone is added. The pH of the solution is kept between 5.2–5.8 by simultaneous addition of acetyl chloride and cold 10% potassium bicarbonate solution. The pH of the solution is adjusted to 4.2 with acetyl chloride and the solution is concentrated on the rotary evaporator to remove acetone. Chromatography on a 300 ml HP-20 AG column (water eluant—25 ml fractions) gives 900 mg of the title compound in fractions 13 and 14 contaminated with some potassium acetate. Rechromatography on HP-20 AG gives an analytical sample, melting point 205°–210° C.

Anal. calc'd for $C_5H_7N_2O_5SK$: C, 24.38; H, 2.86; N, 11.38; S, 13.02; K, 15.88. Found: C, 24.23; H, 2.81; N, 11.25; S, 12.86; K, 15.74.

EXAMPLE 24

(S)-2-Oxo-3-[(phenoxyacetyl)amino]-1-azetidinesulfonic acid, potassium salt (S)-3-Amino-2-oxo-1-azetidinesulfonic acid, tetrabutylammonium salt (1.5 g; see Example 6A) in 100 ml of dry dimethylformamide is cooled to 0° C. Propylene oxide (2 ml) is added and 1 g of phenoxyacetyl chloride is added dropwise with stirring. The reaction is completed within 1 hour. The solvent is removed in vacuo and the residue is treated with an equivalent amount of potassium perfluorobutane sulfonate in 20 ml of acetone. On addition of ether the title compound (1

EXAMPLE 25

[3S(R*)]-3-[[[[[3-[(2-Furanylmethylene)amino]-2-oxo-1-imidazolidinyl]carbonyl]amino]phenylacetyl]amino]-2-oxo-1-azetidinesulfonic acid, potassium salt (S)-2-Oxo-3-[[(phenylmethoxy)carbonyl]amino]-1-azetidinesulfonic acid, tetrabutylammonium salt (3 g; see Example 4) is hydrogenated in 100 ml of dimethylformamide with 1.5 g of palladium on charcoal. After 0.5 hours, the catalyst is filtered off and 1.8 g of dicyclohexylcarbodiimide, 2 g of (R)-α-[[[3-[(2-furanylmethylene)amino]-2-oxo-1-imidazolidinyl]carbonyl]amino]benzeneacetic acid and 0.9 g of hydroxybenzotriazole are added. After 3 hours the reaction mixture is evaporated to dryness, dissolved in 50 ml of dry acetone and the precipitated urea removed by filtration. An equivalent amount of potassium perfluorobutane sulfonate in 20 ml of acetone is added and the title compound precipitates. Crystallization is completed by addition of 200 ml ether. After filtration the title compound is recrystallized from water, yielding 2 g, melting point 220°–225° C., dec.

EXAMPLE 26

[3S(R*)]-2-Oxo-3-[[[[(2-oxo-1-imidazolidinyl)carbonyl]amino]phenylacetyl]amino]-1-azetidinesulfonic acid, potassium salt (S)-2-Oxo-3-[[(phenylmethoxy)carbonyl]amino]-1-azetidinesulfonic acid, tetrabutylammonium salt (3 g; see Example 4) is hydrogenated in 100 ml of dry dimethylformamide with 1.5 g of palladium on charcoal; the catalyst is filtered off after 30 minutes. (R)-α-[[(2-Oxo-1-imidazolidinyl)carbonyl]amino]benzeneacetic acid (1.8 g), 1.3 g of dicyclohexylcarbodiimide and 0.9 g hydroxybenzotriazole are added and the solution is stirred for 2.5 hours. The solvent is removed in vacuo and the residue is dissolved in 50 ml of acetone. The precipitated urea is filtered off and the mother liquor is treated with an equivalent amount of potassium perfluorobutane sulfonate in 20 ml of acetone. The title compound crystallizes and is filtered off after the addition of 200 ml of ether, yielding 1.8 g of product, melting point 210°–215° C. after recrystallization from water/acetone.

EXAMPLE 27

[3S(Z)]-3-[[(Methoxyimino)phenylacetyl]amino]-2-oxo-1-azetidineslfonic acid, potassium salt (A)

[3S(Z)]-3-[[(Methoxyimino)phenylacetyl]amino]-2-azetidinone (Z)-α-(Methoxyimino)benzeneacetic acid (3.58 g) is dissolved in methylene chloride, cooled to 5° C., and treated with a solution of 4.53 g of dicyclohexylcarbodiimide in 50 ml of methylene chloride. The mixture is stirred for 30 minutes at 5° C. and a solution of 1.72 g of 3-amino-2-azetidinone (see Example 5A) in 100 ml of methylene chloride is added. The reaction mixture is kept at 5° C. for 1 hour and for 2 hours at room temperature. After removal of the dicyclohexylurea by filtration, the filtrate is evaporated, yielding 6.6 grams of crude product. This material is purified by chromatography on 750 grams of silica gel, using a mixture of methylene chloride/ethyl acetate (7:3) as eluent, yielding 2.9 g of product.

(B)

[3S(Z))]-3-[[(Methoxyimino)phenylacetyl]amino]-2-oxo-1-azetidinesulfonic acid, potassium salt Pyridine (0.5 ml) is dissolved in 5 ml of absolute methylene chloride, cooled to −30° C. and a solution of 0.93 ml of trimethylsilyl chlorosulfonate in 5 ml of methylene chloride is added. The mixture is stirred at room temperature for 30 minutes and evaporated in vacuo to dryness. The residue is dissolved in 10 ml of dimethylformamide and treated at room temperature with a solution of 1.23 g of the above azetidinone in 10 ml of dimethylformamide. After stirring for two hours at room temperature, the solution is evaporated to dryness to yield 2.1 g of crude [3S(Z)]-3-[[(methoxyimino)-phenylacetyl]amino]-2-oxo-1-azetidinesulfonic acid, pyridine salt.

Treatment of the pyridine salt with tetrabutylammonium hydrogen sulfate yields the corresponding tetrabutylammonium salt which is extracted with methylene chloride and remains as an oil after evaporation.

Treatment of the tetrabutylammonium salt with an equimolar amount of potassium perfluorobutane sulfonate in acetone, evaporation, and treatment of the residue with ether, yields 1.6 grams of the title potassium salt which is purified by chromatography on HP-20. Elution is carried out with water/acetone 90:10 and yields a product having a melting point of 220° C., dec.

EXAMPLE 28

[3S(Z)]-3-[[(2-Amino-4-thiazolyl)[[2-(diphenylmethoxy)-1,1-dimethyl-2-oxoethoxy]imino]acetyl]amino]-2-oxo-1-azetidinesulfonic acid, potassium salt (1:1)

A solution of 0.005 mole of (S)-3-amino-2-oxo-1-azetidinesulfonic acid, tetrabutylammonium salt (see Example 6A) and 0.006 mole of (Z)-2-amino-α-[[2-(diphenylmethoxy)-1,1-dimethyl-2-oxoethoxy]imino]-4-thiazoleacetic acid in 60 ml of dimethylformamide is treated with 0.7 g of hydroxybenzotriazole and 1.13 g of dicyclohexylcarbodiimide. The mixture is stirred for about 16 hours at room temperature, filtered and the filtrate evaporated. The residue is dissolved in 30 ml of acetone, filtered and treated with 20 ml of a solution of 10% potassium perfluorobutane sulfonate in acetone. After the addition of petroleum ether the title compound precipitates and is treated with ether and filtered to yield 3.8 g of product, melting point 190° C., dec.

EXAMPLE 29

[3S(Z)]-3-[[(2-Amino-4-thiazolyl)[(1-carboxy-1-methylethoxy)imino]acetyl]amino]-2-oxo-1-azetidinesulfonic acid, dipotassium salt

[3S(Z)]-3-[[(2-Amino-4-thiazolyl)[[2-(diphenylmethoxy)-1,1-dimethyl-2-oxoethoxy]imino]acetyl]amino]-2-oxo-1-azetidinesulfonic acid, potassium salt (2 g; see Example 28) is suspended in 5 ml of anisole and 25 ml of trifluoroacetic acid is added at −10° C. The mixture is stirred for 10 minutes at −10° C. Ether (100 ml) is added slowly at −10° C. and subsequently 50 ml of petroleum ether is added. The precipitate is filtered to yield 1.6 g of the trifluoroacetic acid salt. This is suspended in 20 ml of water at 0° C., adjusted to pH 5.5 with diluted potassium hydroxide and purified on an

EXAMPLE 30

[3S(Z)]-3-[[(2-Amino-4-thiazolyl)[[2-(diphenylmethoxy)-2-oxoethoxy]imino]acetyl]amino]-2-oxo-1-azetidinesulfonic acid, potassium salt Following the procedure described in Example 28, but substituting (Z)-2-amino-α-[[2-(diphenylmethoxy)-2-oxoethoxy]imino]-4-thiazoleacetic acid for (Z)-2-amino-α-[[2-(diphenylmethoxy)-1,1-dimethyl-2-oxoethoxy]imino]-4-thiazoleacetic acid, yields the title compound, melting point 180° C., dec.

EXAMPLE 31

[3S(±)-3-[(Azidophenylacetyl)amino]-2-oxo-1-azetidinesulfonic acid, potassium salt

Method I (A)

(±,S)-α-Azido-N-(2-oxo-3-azetidinyl)benzeneacetamide (S)-3-Amino-2-azetidinone (2.15 g; see Example 5A) and 2.1 g of sodium bicarbonate are dissolved in 50 ml of acetone/water (2:1). (±)-α-Azidobenzeneacetyl chloride (5 g) dissolved in 10 ml of acetone is added dropwise while maintaining the temperature at 0°-5° C. and the pH at 6.8 with sodium bicarbonate. After stirring for 1 hour, the acetone is distilled off and the remaining aqueous solution is adjusted to pH 8 with sodium carbonate and extracted with three 50 ml portions of methylene chloride. Evaporation of the sodium sulfate dried organic layers yields 3.6 g of the title compound as an oil which crystallizes after triturating with ether. Recrystallization from methylene chloride/ether, yields the title compound, melting point 97°-100° C.

(B)

[3S(±)]-3-[(Azidiophenylacetyl)amino]-2-oxo-1-azetidinesulfonic acid, potassium salt A solution of 2.45 g of the above azetidinone and 3 g of monosilyltrifluoroacetamide in 20 ml of acetonitrile are kept for 1 hour at 40° C. After cooling to 0° C. the solution is treated with 1.88 g of trimethylsilyl chlorosulfonate and stirred for 5 hours under argon. Finally 6.12 ml of a 2N solution of potassium-2-ethyl hexanoate in n-butanol are added and stirring is continued for 45 minutes. The solution is poured into 300 ml of ether and the precipitate is filtered off. A filtered solution of 1.2 g of precipitate in phosphate buffer (pH 5.5) is chromatographed on 100 ml of HP-20. Elution is performed with: (1) 20 ml buffer; (2) 200 ml H₂O; (3) 200 ml water:acetone (9:1); (4) 200 ml water:acetone (3:1). The elution is monitored with TLC (Rydon test on SiO₂). 25 ml fractions are taken and from fractions 15 and 16 280 mg of the title compound are obtained. A second column chromatography of this material yields 120 mg of the title compound, melting point 148° C., dec.

Method II (S)-3-Amino-2-oxo-1-azetidinesulfonic acid, tetrabutylammonium salt (2.03 g; see Example 6A) and 0.9 g of (±)-α-azido-benzeneacetic acid are dissolved in 30 ml of acetonitrile and a solution of 1.03 g of dicyclohexylcarbodiimide in 10 ml of acetonitrile is added. The temperature is maintained for one hour at 0° C. and for 10 hours at room temperature. After filtering off the resultant precipitate, the solvent is distilled off in vacuo and the oily residue is dissolved in 20 ml of acetone and treated with 1.70 g potassium perfluorobutane sulfonate in acetone. The addition of 10 ml of ether crystallizes the title compound, melting point 149° C., dec.

Method III

α-Azidiophenylacetyl chloride (2.5 g) is added to a solution of 4.06 g of 3-amino-2-oxo-1-azetidinesulfonic acid, tetrabutylammonium salt (see Example 6A) and 5 g of propylene oxide in 30 ml of acetonitrile. After stirring for two hours the solvent is distilled off in vacuo and the oily residue is treated with one equivalent amount of potassium perfluorobutane sulfonate in acetone. After the addition of ether the title compound crystallizes and is filtered off, melting point 148°-149° C. dec.

EXAMPLE 32

[3S(D)]-3-[[[[[(4-Methoxyphenyl)methoxy]carbonyl]amino]phenylacetyl]amino]-2-oxo-1-azetidinesulfonic acid, potassium salt To a solution of 2.03 g of 3-amino-2-oxo-1-azetidinesulfonic acid, tetrabutylammonium salt (2.03 g; see Example 6A) and 1.58 g of D-α-[[[(4-methoxyphenyl)methoxy]carbonyl]amino]benzeneacetic acid in 50 ml of acetonitrile, a solution of 1.03 g of dicyclohexylcarbodiimide in 10 ml of acetonitrile is added dropwise. The temperature is maintained at 5° C. for one hour and for 6 hours at room temperature. Separation of the formed dicyclohexyl urea and distilling off the solvent yields the title compound as an oily residue. Treating this oil in acetone with potassium perfluorobutane sulfonate and ether yields 2.4 g of product, melting point 108°-111° C. dec.

EXAMPLES 33-37

Following the procedure of Example 32, but substituting the compound listed in column I for (D)-α-[[[(4-methoxyphenyl)methoxy]carbonyl]amino]benzeneacetic acid, yields the compound listed in column II.

| Example | | |
|---|---|---|
| 33 | (D)-α-[[[(4-methoxyphenyl)methoxy]-carbonyl]amino]-2-thiopheneacetic acid | [3 S (D)]-3-[[[[[(4-methoxyphenyl)methoxy]carbonyl]amino]-2-thienylacetyl]amino]-2-oxo-1-azetidinesulfonic acid, potassium salt, melting point 144–146° C., dec. |
| 34 | (±)-2-amino-α-[[[(4-methoxyphenyl)-methoxy]carbonyl]amino]-4-thiazoleacetic acid | [3S(±)]-3-[[(2-amino-4-thiazolyl)-[[[(4-methoxyphenyl)methoxy]-carbonyl]amino]acetyl]amino]-2-oxo-1-azetidinesulfonic acid, potassium salt, melting point 232–234° C. |
| 35 | (±)-α-[[[(4-methoxyphenyl)methoxy]- | [3S(±)]-3-[[2-furanyl[[[(4- |

| Example | | |
|---|---|---|
| | carbonyl]amino]-2-furanacetic acid | methoxyphenyl)methoxy]carbonyl]-amino]acetyl]amino-2-oxo-1-azetidinesulfonic acid, potassium salt, melting point 124–126° C., dec. |
| 36 | (L)-α-[[[(4-methoxyphenyl)methoxy]-carbonyl]amino]benzeneacetic acid | [3 S (L)]-3-[[[[[(4-methoxyphenyl)-methoxy]carbonyl]amino]phenylacetyl]amino]-2-oxo-1-azetidine-sulfonic acid, potassium salt, melting point 172–175° C., dec. |
| 37 | (L)-α-[[[(4-methoxyphenyl)methoxy]-carbonyl]amino]-2-thiopheneacetic acid | [3 S (L)]-3-[[[[[(4-methoxyphenyl)-methoxy]carbonyl]amino]-2-thienylacetyl]amino]-2-oxo-1-azetidine-sulfonic acid, potassium salt, melting point 146–148° C. |

EXAMPLE 38

(3S)-3-[[[[(Methylthio)thioxomethyl]thio]phenylacetyl-]amino]-2-oxo-1-azetidinesulfonic acid, tetrabutylammonium salt A solution of 1.03 g of (±)-α-[[(methylthio)thioxomethyl]thio]benzeneacetic acid and 1.63 g of 3-amino-2-oxo-1-azetidinesulfonic acid, tetrabutylammonium salt (see Example 6A) in 30 ml of acetonitrile is treated with 0.8 g of dicyclohexylcarbodiimide dissolved in 10 ml of acetonitrile at −5° C. After stirring for about 16 hours the formed dicyclohexyl urea is filtered off and the mother liquor is evaporated. The remaining oily residue is chromatographed on a column of 400 g of silica (ethyl/acetate/methanol/water (8.5:1:0.5) is the eluent), yielding 1.3 g of the title compound.

EXAMPLE 39

3(S)-3-[[[[(Methylthio)thioxomethyl]thio]phenylacetyl-]amino]-2-oxo-1-azetidinesulfonic acid, potassium salt (3S)-3-[[[[(Methylthio)thioxomethyl]thio]-phenylacetyl]amino-2-oxo-1-azetidinesulfonic acid, tetrabutylammonium salt (1.3 g; see Example 38) is dissolved in acetone and treated with an equivalent amount of potassium perfluorobutane sulfonate. The addition of ether crystallizes the title compound, which is filtered off, yield 0.18 g of product, melting point 157° C., dec.

EXAMPLE 40

[3S(D)]-3-[[[[(4-Ethyl-2,3-dioxo-1-piperazinyl)carbonyl]amino]-2-thienylacetyl]amino]-2-oxo-1-azetidinesulfonic acid, potassium salt (D)-α-[[(4-Ethyl-2,3-dioxo-1-piperazinyl)carbonyl-]amino]-2-thiopheneacetic acid (3.25 g), 4.20 g of 3-amino-2-oxo-1-azetidinesulfonic acid, tetrabutylammonium salt (see Example 6A) and 1.3 g of N-hydroxybenzotriazole are dissolved in 25 ml of acetonitrile. Dropwise addition of 2.06 g of dicyclohexylcarbodiimide dissolved in 10 ml of acetonitrile at −10° C. takes 20 minutes and stirring is continued for about 16 hours. Formed urea is filtered off, and the solvent is evaporated in vacuo. The remaining oil is dissolved in 50 ml of acetone and after treatment with an equivalent amount of potassium perfluorobutane sulfonate, the title compound crystallizes, melting point 185°–187° C., dec.

EXAMPLE 41

[3-S(±)]-3-[(Bromophenylacetyl)amino]-2-oxo-1-azetidinesulfonic acid, potassium salt α-Bromophenylacetyl chloride (1.4 g) in 10 ml of acetonitrile is added dropwise to a solution of 5 mM 3-amino-2-oxo-1-azetidinesulfonic acid, tetrabutylammonium salt, and 3 g of propylene oxide in acetonitrile at 0° C. After three hours stirring, the solvent is distilled off and the remaining oily residue is dissolved in 30 ml of acetone. The equivalent amount of potassium perfluorobutane sulfonate in acetone is added. The addition of ether crystallizes the title compound, melting point 135°–137° C. dec.

EXAMPLE 42

[3S(±)-3-[[[(Aminocarbonyl)amino]-2-thienylacetyl-]amino]-2-oxo-1-azetidinesulfonc acid, potassium salt

Method I

To a solution of 2 g of (S)-3-amino-2-oxo-1-azetidinesulfonic acid, tetrabutylammonium salt and 1.5 g of propylene oxide in acetonitrile is added 1.1 g of (±)-2-amino-4-(2-thienyl)-5(4H)-oxazolone, hydrochloride. After three hous stirring at 0° C. and one half at room temperature, the solvent is distilled off and the oily residue is dissolved in 30 ml of acetone. By adding the equivalent amount of potassium perfluorobutane sulfonate in acetone, the title compound crystallizes out. Purification by column chromatography on HP-20 using water as eluent yields the title compound, melting point 218°–222° C., dec.

Method II

To a suspension of 2 g of (±)-α-[(aminocarbonyl-)amino]-2-thiopheneacetic acid, 10 mM of (S)-3-amino-2-oxo-1-azetidinesulfonic acid, tetrabutylammonium salt and 10 mM of N-hydroxybenzotriazole in 50 ml of acetonitrile at 0° C. is added (with stirring) 10 mM of dicyclohexylcarbodiimide dissolved in 15 ml of acetonitrile. Stirring is continued for one hour at −15° C. and for about 16 hours at room temperature. After filtering off the dicyclohexyl urea, the solvent is evaporated and the oily residue is dissolved in 50 ml of acetone. Adding the equivalent amount of potassium perfluorobutane sulfonate in acetone yields crystalline product. Purification by column chromatography on HP-20, using water as an eluent, yields the title compound, melting point 220°–223° C.

EXAMPLE 43

[3S(±)]-3-[[[[(Methylamino)carbonyl]amino]-2-thienylacetyl]amino]-2-oxo-1-azetidinesulfonic acid, potassium salt (±)-α-[[(Methylamino)carbonyl]amino]-2-thiopheneacetic acid (0.54 g) and 1.00 g of (S)-3-amino-2-oxo-1-azetidinesulfonic acid, tetrabutylammonium salt (see Example 6A) are dissolved in 20 ml of acetonitrile and 0.5 g of dicyclohexylcarbodiimide is added at a temperature of 0° C. After stirring for 8 hours the dicyclohexylurea is filtered off and after distilling off the solvent the oily residue is dissolved in 50 ml acetone and the equivalent amount of potassium perfluorobutane sulfonate is added. Crystalline product is filtered off and purification is performed on HP-20 using water as an eluent, melting point 205° C., dec.

EXAMPLE 44

[3S(±)]-3-[[[(Aminooxoacetyl)amino]-2-thienylacetyl]amino]-2-oxo-1-azetidinesulfonic acid, potassium salt Following the procedure of Example 42, method II, but substituting (±)-α-[(aminooxoacetyl)amino]-2-thiopheneacetic acid for (±)-α-[(aminocarbonyl)amino]-2-thiopheneacetic acid, yields the title compound, melting point 218°-222° C.

EXAMPLE 45

[3S(R*)]-3-[[[[(4-Ethyl-2,3-dioxo-1-piperazinyl)carbonyl]amino]phenylacetyl]amino]-2-oxo-1-azetidinesulfonic acid, potassium salt Following the procedure of Example 40, but substituting (R)-α-[[(4-ethyl-2,3-dioxo-1-piperazinyl)carbonyl]amino]benzeneacetic acid for (D)-α-[[(4-ethyl-2,3-dioxo-1-piperazinyl)carbonyl]amino]-2-thiopheneacetic acid, yields the title compound, melting point 155°-157° C., dec.

EXAMPLE 46

3-(Acetylamino)-3-methoxy-2-oxo-1-azetidinesulfonic acid, potassium salt

Method I (A)

3-[(N-Acetyl-N-chloro)amino]-2-oxo-1-azetidinesulfonic acid, mixed sodium and potassium salt To a solution of 3-(acetylamino)-2-oxo-1-azetidinesulfonic acid, potassium salt (172 mg, see Example 23) in methanol (17 ml) containing 4% sodium borate decahydrate cooled to −15° to −10° C. is added tert-butyl hypochlorite (110 μl). The mixture is stirred in the cold for 1 hour, 45 minutes, poured into 0.5M monobasic potassium phosphate solution (50 ml), and the pH is lowered to 5.5. Solvent is removed in vacuo, and the residue is dissolved in a minimum amount of water and chromatographed on HP-20AG, 100-200 mesh (140 ml). Elution with water yields an oil (63 mg) which crystallizes on standing. Trituration with methanol/ether and then ether gives a solid (53 mg) melting point 124° C., slow dec.

(B)

3-(Acetylamino)-3-methoxy-2-oxo-1-azetidinesulfonic acid, potassium salt

3-[(N-Acetyl-N-chloro)amino]-2-oxo-1-azetidinesulfonic acid mixed salt (37 mg) is dissolved in 1.5 ml of dry dimethylformamide and added to a solution of lithium methoxide (50 mg) in methanol (1 ml) at −78° C. After stirring for 15 minutes at −78° C., a 0.5M solution of monobasic potassium phosphate (10 ml) is added, and the solution is then acidified to pH 4 with 1N hydrochloric acid. To the solution is added tetrabutylammonium hydrogen sulfate (70 mg) and the solution is extracted four times with methylene chloride. The combined extracts are dried (sodium sulfate) and solvent is removed by vacuo to give 55 mg of an oil. Chromatography on 5.5 g of silica gel yields the oily product (41 mg) as the tetrabutylammonium salt (eluted with 8% methanol:92% methylene chloride). The oil (31 mg) is dissolved in water and passed through an ion-exchange column (5 ml of AG 50W-X2, K⊕ form, 200–400 mesh, 0.6 meq/ml). Removal of water in vacuo gives an oil which crystallizes from methanol-ether. Trituration twice with ether gives the product as a colorless powder (11 mg); melting point 182°-183° C., dec.

Method II (A)

3-Amino-3-methoxy-2-oxo-1-azetidinesulfonic acid, tetrabutylammonium salt

A 4% sodium borate decahydrate in methanol solution (100 μl) is added to a suspension of 10% palladium on charcoal (30 mg) in methanol (2 ml), and the mixture is stirred under an atmosphere of hydrogen for 15 minutes. 3-Methoxy-2-oxo-3-[[(phenylmethoxy)carbonyl]amino]-1-azetidinesulfonic acid, tetrabutylammonium salt (60 mg; see Example 49) in methanol (2 ml) is added and the mixture is vigorously stirred for 15 minutes under a hydrogen atmosphere. Catalyst is removed by filtration through Celite on a millipore filter (0.5 mμ), and solvent is removed from the filtrate in vacuo, and the residue is extracted with methylene chloride. Removal of solvent under reduced pressure yields 35 mg of the title compound, as an oil.

(B)

3-(Acetylamino)-3-methoxy-2-oxo-1-azetidinesulfonic acid, potassium salt

To a solution of 3-amino-3-methoxy-2-oxo-1-azetidinesulfonic acid, tetrabutylammonium salt (35 mg) in methylene chloride (10 ml) at 0° C. is added propylene oxide (2 ml) and acetyl chloride (74 μl). After 2 hours the solvent is removed under reduced pressure and the residual oil is chromatographed on silica gel (4 g). Elution with (6–8% methanol in methylene chloride gives an oil (18 mg) which is dissolved in water and passed through an ion-exchange resin (3 ml of AG 50W-X2, K⊕ form, 0.6 meq/ml). Removal of water from the eluate in vacuo yields the desired product (10 mg).

EXAMPLE 47

N-(3-Methoxy-2-oxo-1-sulfo-3-azetidinyl)-2-phenylacetamide, tetrabutylammonium salt (A)

N-Chloro-N-(2-oxo-1-sulfo-3-azetidinyl)-2-phenylacetamide, potassium salt

To a solution of (S)-N-(2-oxo-1-sulfo-3-azetidinyl)-2-phenylacetamide, potassium salt (50 mg; see Example 1) in methanol containing 4% sodium borate decahydrate (5 ml) cooled in a −5° C. bath is added tert-butyl hypochlorite (20 μl). After stirring for 32 minutes, the mixture is poured into 0.5M pH 5.5 potassium phosphate buffer at 0° C. The resultant solution (pH 5.9) is adjusted to pH 4.5, concentrated in vacuo to remove methanol, and chromatographed on HP-20AG, 100-200 mesh (100 ml). After washing the column with 0.5M pH 5.5 buffer (100 ml) and water the desired product is eluted with 9:1 water:acetone. Concentration in vacuo gives 50 mg of the title compound.

(B)

N-(3-Methoxy-2-oxo-1-sulfo-3-azetidinyl)-2-phenylacetamide, tetrabutylammonium salt To a stirring solution of lithium methoxide (160 mg) in 5 ml of methanol cooled to −78° C. is added a solution of N-chloro-N-(2-oxo-1-sulfo-3-azetidinyl)-2-phenylacetamide, potassium salt (149 mg) in 10 ml of dry dimethylformamide. After addition is complete, the mixture is stirred for 15 minutes at −78° C., poured into 0.5N monobasic potassium phosphate solution (100 ml), and washed three times with methylene chloride. Tetrabutylammonium bisulfate (213 mg) is added to the aqueous layer, which is then extracted three times with methylene chloride. The combined extracts are dried (sodium sulfate), and solvent is removed in vacuo giving an oil (271 mg). Chromatography of the oil on silica gel (25 g) and elution with 4% methanol:96% methylene chloride yields 149 mg of the product as an oil.

EXAMPLE 48

N-(3-Methoxy-2-oxo-1-sulfo-3-azetidinyl)-2-phenylacetamide, potassium salt

N-(3-Methoxy-2-oxo-1-sulfo-3-azetidinyl)-2-phenylacetamide, tetrabutylammonium salt (91 mg; see Example 47) is dissolved in water and passed through an ion-exchange column (10 ml of AG 50W-X2, K$^\oplus$ form). The eluate is concentrated in vacuo and the residual oil solidifies on scratching with a methanol-acetone-ether mixture. After triturating twice with ether, the product is obtained as a solid (53 mg): $\nu_{max}$1762, 1665 cm$^{-1}$; NMR (CD$_3$OD) δ 3.41 (S, 3H, OCH$_3$), 3.59 (S, 2H, CH$_2$), 3.84 (ABq, J=6.3 Hz, 2H, H$_4$), 7.30 (m, 5H, aromatic).

EXAMPLE 49

3-Methoxy-2-oxo-3-[[(phenylmethoxy)carbonyl]amino]-1-azetidinesulfonic acid, tetrabutylammonium salt

Method I

(A)

2-Oxo-3-[N-chloro-N-[(phenylmethoxy)carbonyl]amino]-1-azetidinesulfonic acid, tetrabutylammonium salt (S)-2-Oxo-3-[[(phenylmethoxy)carbonyl]amino]-1-azetidinesulfonic acid, tetrabutylammonium salt (0.9 g; see Example 4) dissolved in 80 ml of methylene chloride is added to a mixture (cooled to 0°-5° C.) of 3.17 g of sodium borate decahydrate and 11.8 ml of a 5.25% sodium hypochlorite solution in 70 ml of water. The reaction mixture is vigorously stirred for 55 minutes while cooling in an ice bath. After diluting the mixture with 0.5M monobasic potassium phosphate solution, the product is extracted with methylene chloride (three 150 ml portions). Combination of the extracts, drying (sodium sulfate), and removal of solvent in vacuo yields the title compound as an oil (0.94 g).

(B)

3-Methoxy-2-oxo-3-[[(phenylmethoxy)carbonyl]amino]-1-azetidinesulfonic acid, tetrabutylammonium salt To a stirring solution of lithium methoxide (667 mg) in anhydrous methanol (10 ml) at −78° C. is added a solution of 2-oxo-3-[N-chloro-N-[(phenylmethoxy)carbonyl]amino]-1-azetidinesulfonic acid, tetrabutylammonium salt (0.94 g) in dry dimethylformamide (10 ml). After stirring the mixture at −78° C. for 1 hour, it is poured into 0.5M monobasic potassium phosphate solution and extracted with methylene chloride (three 150 ml portions). The combined extracts are dried (sodium sulfate) and solvent is removed in vacuo to given an oil (0.83 g). The desired product is obtained by chromatographing the oil on silica gel (100 g) and eluting with 4-5% methanol in methylene chloride to give an oil (513 mg): $\lambda_{max}$(neat) 1767, 1720 cm$^{-1}$; NMR (CDCl$_3$) δ 3.40 (S, OCH$_3$), 3.03 (ABq, J=6.5 Hz, H$_4$), 5.08 (S, CH$_2$), 6.00 (S, NH), 7.27 (S, aromatic).

Method II

To a solution of 3-benzyloxycarbonylamino-3-methoxy-2-oxo-1-azetidinesulfonic acid, potassium salt (400 mg) in water is added a 0.1M tetrabutylammonium bisulfate solution (10.9 ml, adjusted to pH 4.3 with potassium hydroxide). The mixture is extracted three times with methylene chloride, the extracts are combined, dried (Na$_2$SO$_4$) and solvent is removed in vacuo to give a foam (625 mg).

EXAMPLE 50

3-Methoxy-2-oxo-3-[[(phenylmethoxy)carbonyl]amino]-1-azetidinesulfonic acid, potassium salt

Method I

(A)

2-Oxo-3-[N-chloro-N-[(phenylmethoxy)carbonyl]amino]-1-azetidinesulfonic acid, potassium salt To a solution of (S)-2-oxo-3-[[(phenylmethoxy)carbonyl]amino]-1-azetidinesulfonic acid, potassium salt (1.00 g; see Example 3) in methanol (90 ml) containing 4% sodium borate decahydrate at −10° C. is added tert-butyl hypochlorite (420 μl). After stirring for 2 hours at −10° C. 0.5M monobasic potassium phosphate solution (100 ml) is added and the pH is adjusted to 6 with 1N hydrochloric acid. After concentration of the solvent in vacuo to 30 ml, the aqueous solution is chromatographed on HP-20AG, 100-200 mesh (200 ml). After passage of a solution of monobasic potassium phosphate (50 g) in water (1000 ml), followed by water (2000 ml), the product is eluted with 10% acetone-90% water. Solvent is removed in vacuo and the title compound is crystallized from water to give a solid (530 mg), melting point 173°-175° C.

(B)

3-Methoxy-2-oxo-3-[[(phenylmethoxy)carbonyl]amino]-1-azetidinesulfonic acid, potassium salt To a solution of lithium methoxide (874 mg) in dry methanol (10 ml) at −78° C. is added 2-oxo-3-[N-chloro-N-[(phenylmethoxy)carbonyl]amino]-1-azetidinesulfonic acid, potassium salt (857 mg) in dry dimethylformamide (13 ml). After 15 minutes at −78° C. the mixture is poured into 0.5M monobasic potassium phosphate solution (200 ml) and the pH is adjusted to 5.5 with 1N hydrochloric acid. The aqueous mixture is washed with methylene chloride (three 100 ml portions), and tetrabutylammonium bisulfate (1.169 g) is added. The product is extracted with methylene chloride (three 200 ml portions), dried (sodium sulfate), filtered, and concentrated in vacuo. The residual oil is chromatographed on silica gel (150 g) and the product is eluted with 2–4% methanol in methylene chloride yielding the tetrabutylammonium salt of the product as an oil (701 mg). A portion of the oil (51 mg) is dissolved in water and passed through an ion-exchange column (3 ml of AG 50W-X2, 200–400 mesh, K⊕ form, 0.6 meq/ml). Concentration of the eluate in vacuo yields an oil (30 mg), which is crystallized by scratching with acetone: $\nu_{max}$(KBr) 1760, 1725 cm$^{-1}$; NMR (D$_2$O) δ 3.48 (S, 3H, OCH$_3$), 3.92 (S, 2H, H$_4$); 5.20 (S, 2H, CH$_2$), 7.42 (S, 5H, aromatic).

Method II (A)

1-Chloro-3-(N-chloro-N-[(phenylmethoxy)carbonyl]-2-azetidinone

A solution of 3-[[(phenylmethoxy)carbonyl]amino]-2-azetidinone (440 mg.; see Example 2C) in 40 ml of 4% methanolic borax is cooled to 0° C. and 0.5 ml of t-butyl hypochlorite is added. After 30 minutes at 0° C., the solution is poured into 200 ml of cold water and extracted with two 100 ml portions of ethyl acetate. The combined ethyl acetate layer is washed with water, dried, and evaporated in vacuo to give 546 mg of the title compound as an oil.

(B)

3-Methoxy-3-[[(phenylmethoxy)carbonyl]amino]-2-azetidinone

A solution of 730 mg (0.0025 mole) of 1-chloro-3-[N-chloro-N-[(phenylmethoxy)carbonyl]amino]-2-azetidinone in 5 ml of tetrahydrofuran is cooled to =78° C. and 4 ml of methanol containing 285 mg of lithium methoxide is added. After 20 minutes at −78° C., 0.6 ml of acetic acid and 0.6 ml of trimethylphosphite are added. The solution is stirred for 5 minutes at −78° C., allowed to warm to ambient temperature and stirred for 30 minutes. The resulting solution is diluted with ethyl acetate, washed with 5% sodium bicarbonate, water, 5% potassium bisulfate, water, saturated salt solution, and dried. Solvent removal gives an oil that is applied to four 20×20 cm×1 mm silica gel plates. Development with benzene:ethyl acetate (1:1) and isolation of the major UV-active band of Rf=0.25 gives 91 mg of oil that crystallizes from ether to give a solid. Recrystallization from ether gives the title compound, melting point 112°–114° C.

(C)

3-Methoxy-2-oxo-3-oxo-3-[[(phenylmethoxy)carbonyl]amino]-1-azetidinesulfonic acid, potassiun salt A solution of 25 mg of 3-methoxy-3-[[(phenylmethoxy)carbonyl]amino]-2-azetidinone in 0.175 ml each of dichloromethane and dimethylformamide is stirred for 24 hours with 55.4 mg of a complex of pyridine-sulfur trioxide. The resulting slurry is diluted with 5 ml of cold 0.5M monobasic potassium phosphate (adjustd to pH 4.5) and extracted with ethyl acetate. The aqueous layer is applied to a 40 ml HP-20 AG column. Elution with additional buffer, water, and water-acetone (9:1) gives 32 mg of the title compound as an oil that slowly solidifies. Crystallization from acetone gives the title compound, melting point 196°–198° C., dec.

EXAMPLE 51

3-[[1,3-Dioxo-2-phenyl-3-(phenylmethoxy)propyl]amino]-3-methoxy-2-oxo-1-azetidinesulfonic acid, potassium salt (A)

3-[[1,3-Dioxo-2-phenyl-3-(phenylmethoxy)propyl]amino]-3-methoxy-2-oxo-1-azetidinesulfonic acid, tetrabutylammonium salt Crude 3-amino-3-methoxy-2-oxo-1-azetidinesulfonic acid, tetrabutylammonium salt (431 mg, see Example 74), containing borax, is dissolved in 30 ml of dry acetonitrile. Dry pyridine (317 μl) is added and the solution stirred well at −10° C. under dry nitrogen. α-(Benzyloxycarbonyl)phenylacetyl chloride (568 mg) in 3 ml of dry acetonitrile is added dropwise. Thin layer chromatography indicates the reaction to be complete after 15 minutes. Potassium phosphate buffer (0.5M, pH 5.5, 17 ml) is added and most of the acetonitrile is removed in vacuo. The residue is diluted with water and extracted three times with equal volumes of methylene chloride. The extract is dried over anhydrous sodium sulfate and evaporated in vacuo to give 1.032 g of crude product, which is dissolved in 3 ml of methylene chloride and chromatographed on a silica column using methylene chloride-methanol to give 470 mg of the title compound.

(B)

3-[[1,3-Dioxo-2-phenyl-3-(phenylmethoxy)propyl]amino]-3-methoxy-2-oxo-1-azetidinsulfonic acid, potassium salt 3-[[1,3-Dioxo-2-phenyl-3-(phenylmethoxy)propyl]amino]-3-methoxy-2-oxo-1-azetidinesulfonic acid, tetrabutylammonium salt (470 mg) is dissolved in 15 ml of 30% acetone:water and put through a Dowex 50WX2(K+form) column using the same solvent as eluent. The total eluate is evaporated in vacuo to yield 345 mg of an amorphous solid which is lyophilized to an amorphous powder, melting point 100°–120° C.

Anal. for C$_{20}$H$_{19}$O$_8$N$_2$SK Calc'd: C, 49.37; H, 3.94 N, 5.76; S, 6.59. Found: C, 49.08; H, 4.00; N, 5.58; S, 6.29.

EXAMPLE 52

(±)-3-[[[(Cyanomethyl)thio]acetyl]amino]-3-methoxy-2-oxo-1-azetidinesulfonic acid, potassium salt.3

To a solution of 3-amino-3-methoxy-2-oxo-1-azetidinesulfonic acid, tetrabutylammonium salt (414 mg, see Example 74) in dry acetonitrile (50 ml) at −20° C. is added diethylaniline (210 μl) and cyanomethylthioacetyl chloride (169 mg). After 10 minutes the solvent is removed under reduced pressure and a 0.1M solution of tetrabutylammonium sulfate (22.8 ml) adjusted to pH 4.3 with potassium hydroxide is added and the product extracted with three 50 ml portions of methylene chloride, dried, filtered and concentrated under reduced pressure. The oily residue is purified on silica gel (60 g) and the product (294 mg) is eluted with 4% methanol-methylene chloride. The purified product is passed through an ion exchange resin (16 ml AG 50W-X2(K+form), 0.6 mequiv./ml 200–400 mesh). Removal of water gives 164 mg of partially purified product. The product is further purified on Diaion AG HP 20 (100 ml) using water as eluent. The solvent is removed under reduced pressure to give 126 mg of product which is triturated with ether to give 76 mg of the title compound, melting point 110°–125° C.

Anal. Calc'd for $C_8H_{10}N_3S_2O_6K$: C, 27.66; H, 2.88; N, 12.10; S, 18.44. Found: C, 27.25; H, 3.00; N, 10.84; S, 17.53.

EXAMPLES 53–56

Following the procedure of Example 42, Method II, but substituting the compound listed in Column I for (±)-α-[(aminocarbonyl)amino]-2-thiopheneacetic acid, yields the compound listed in Column II.

| Column I | Column II |
| --- | --- |
| 53. (±)-α-[(aminooxoacetyl)amino]-2-furanacetic acid | [3S(±)-3-[[[(aminooxoacetyl)-amino]-2-furanylacetyl]amino]-2-oxo-1-azetidinesulfonic acid, potassium salt, melting point 212–215° C., dec. |
| 54. (±)-α[[[(cyanomethyl)amino]oxo-acetyl]amino]-2-thiopheneacetic acid | [3S(±)]-3-[[[[(cyanomethyl)amino]-oxoacetyl]amino]-2-thienylacetyl]amino]-2-oxo-1-azetidinesulfonic acid, potassium salt, melting point 195–197° C., dec. |
| 55. (R)—α-[(aminooxoacetyl)amino]-benzeneacetic acid | [3S(R*)]—3-[[[(aminooxoacetyl)amino]-phenylacetyl]amino]-2-oxo-1-azetidine-sulfonic acid, potassium salt, melting point 207–209° C. |
| 56. (R)—α-[(aminocarbonyl)amino]benzene-acetic acid | [3S(R*)]—3-[[[(aminocarbonyl)amino]-phenylacetyl]amino]-2-oxo-1-azetidine-sulfonic acid, potassium salt, melting point 225° C., dec. |

EXAMPLE 57

[3S(±)]-3-[[2-(Methylthio)-1-oxopropyl]amino]-2-oxo-1-azetidinesulfonic acid, potassium salt Following the procedure of Example 31, Method II, but substituting (±)-2-(methylthio)propanoic acid for (±)-α-azido-benzeneacetic acid, yields the title compound, melting point 173° C., dec.

EXAMPLE 58

[3S(R*)]-3-[[[[2,3-Dioxo-4-[(phenylmethylene)amino]-1-piperazinyl]carbonyl]amino]phenylacetyl]amino]-2-oxo-1-azetidinesulfonic acid, potassium salt (R)-α-[[[2,3-Dioxo-4-[(phenylmethylene)amino]-1-piperazinyl]carbonyl]amino]benzeneacetic acid (0.7 g) and (S)-3-amino-2-oxo-1-azetidinesulfonic acid, tetrabutylammonium salt (0.8 g; see Example 6A) are dissolved in 20 ml of acetonitrile. While stirring, 0.4 g of dicyclohexylcarbodiimide is added dropwise at 0° C. Stirring is continued for 18 hours and, after filtration, the solvent is distilled off leaving an oily residue. The residue is dissolved in acetone and treated with potassium perfluorobutane sulfonate to precipitate the title compound. Purification by column chromatography on HP-20 using water as eluent yields the title compound, melting point 193°–194° C.

EXAMPLE 59

[3S(Z)]-3-[[(2-Amino-4-thiazolyl)[(2-methoxy-2-oxoethoxy)imino]acetyl]amino]-2-oxo-1-azetidinesulfonic acid, potassium salt (Z)-2-Amino-α-[(2-methoxy-2-oxoethoxy)imino]-4-thiazoleacetic acid (1.3 g) and (S)-3-amino-2-oxo-1-azetidinesulfonic acid, tetrabutylammonium salt (2.03 g; see Example 6A) is dissolved in 50 ml of acetonitrile and 1.03 g of dicyclohexylcarbodiimide dissolved in 5 ml of acetonitrile is added dropwise at 0° C. After stirring for 15 hours and filtering off dicyclohexyl urea the solvent is distilled off. The remaining oily residue is dissolved in acetone and treated with the equivalent amount of potassium perfluorobutane sulfonate. The title compound is isolated and purified by column chromatography on HP-20 using water as eluent, yielding the title compound melting point 195°–198° C.

EXAMPLE 60

[3S(R*)]-3-[[[[3-[[(4-Chlorophenyl)methylene]amino]-2-oxo-1-imidazolidinyl]carbonyl]amino]phenylacetyl]amino]-1-azetidinesulfonic acid, potassium salt (S)-3-Amino-2-oxo-1-azetidinesulfonic acid, tetrabutylammonium salt (1.5 g; see Example 6A) in 100 ml of absolute diglyme (diethyleneglycoldimethyl ether), 1.5 g of (R)-α-[[[3-[[(4-chlorophenyl)methylene]amino]-2-oxo-1-imidazolidinyl]carbonyl]amino]benzeneacetic acid, an equivalent amount of dicyclohexylcarbodiimide, and 0.5 g of hydroxybenzotriazole are stirred together for 12 hours. The solvent is removed in vacuo and the residue is dissolved in 50 ml of acetone and filtered. Acetone is distilled off and the residue is dissolved in 200 ml of methylene chloride. The solution is washed with aqueous sodium bicarbonate and then with aqueous sodium chloride solution. The methylene chloride layer is dried over sodium sulfate, evaporated to dryness and crystallized by the addition of ether. The compound is recrystallized from acetone-ether. The resulting white crystalline powder is dissolved in acetone and treated with an equivalent amount of potassium perfluorobutane sulfonate in acetone. The title compound precipitates and is filtered off, yielding 1.4 g of product melting point 217°–222° C.

EXAMPLE 61

[3S(R*)]-3-[[[[2-Oxo-3-[(phenylmethylene)amino]-1-imidazolidinyl]carbonyl]amino]phenylacetyl]amino]-1-azetidinesulfonic acid, potassium salt (S)-3-Amino-2-oxo-1-azetidinesulfonic acid, tetrabutylammonium salt (2.25 g; see Example 6A) in 100 ml of dry dimethylformamide (DMF), an equivalent of dicyclohexylcarbodiimide, 2.5 g of (R)-α-[[[2-oxo-3-[(phenylmethylene)amino]-1-imidazolidinyl]carbonyl]amino]benzeneacetic acid and 0.85 q of hydroxybenzotriazole are stirred together at ambient temperature for

EXAMPLE 62

[3S(R*)]-3-[[[[[3-(Methylsulfonyl)-2-oxo-1-imidazolidinyl]carbonyl]amino]phenylacetyl]amino]-2-oxo-1-azetidinesulfonic acid, potassium salt (S)-3-Amino-2-oxo-1-azetidinesulfonic acid, tetrabutylammonium salt (2.25 g; see Example 6A) in 60 ml of dimethylformamide is stirred for 12 hours with 1.9 g of (R)-α-[[[3-(methylsulfonyl)-2-oxo-1-imidazolidinyl]carbonyl]amino]benzeneacetic acid, 0.75 g of hydroxybenzotriazole and 2.3 g of dicyclohexylcarbodiimide. The solvent is removed in vacuo and the residue is dissolved in 20 ml of acetone and filtered. The mother liquor is treated with 1.87 g of potassium perfluorobutane sulfonate in 20 ml of acetone. After the addition of ether, the title compound precipitates, yielding 2.0 g of material. The compound is purified by recrystallization from water and has a melting point of 240°–245° C., dec.

EXAMPLE 63

[3S(R*)]-3-[(Hydroxyphenylacetyl)amino]-2-oxo-1-azetidinesulfonic acid, potassium salt (S)-3-Amino-2-oxo-1-azetidinesulfonic acid, tetrabutylammonium salt (1.5 g; see Example 6A) in 100 ml of dry dimethylformamide is stirred for about 16 hours with 1.5 g of dicyclohexylcarbodiimide, 0.5 g of hydroxybenzotriazole and 0.6 g of R-α-hydroxybenzeneacetic acid. The solvent is removed in vacuo and the residue is dissolved in 20 ml of acetone. The precipitated urea is filtered off and the mother liquor is treated with an equivalent amount of potassium perfluorobutane sulfonate. After addition of ether, the title compound precipitates and is filtered off, yielding 1.3 g of crude product. The product is purified by chromatography using HP-20 and water/acetone (9:1) as eluent, and has a melting point of 145°–150° C., dec.

EXAMPLE 64

[3S(S*)]-3-[(Hydroxyphenylacetyl)amino]-2-oxo-1-azetidinesulfonic acid, potassium salt Following the procedure of Example 63, but substituting (S)-α-hydroxybenzeneacetic acid for (R)-α-hydroxybenzeneacetic acid, yields the title compound, melting point 195°–197° C.

EXAMPLE 65

[3S(±)]-2-Oxo-3-[(phenylsulfoacetyl)amino]-1-azetidinesulfonic acid, potassium salt (1:2)

(S)-3-Amino-2-oxo-1-azetidinesulfonic acid, tetrabutylammonium salt (2.25 g; see Example 6A) in 100 ml of dry diglyme, 2.4 g of triethylamine and 0.3 g of dimethylaminopyridine are cooled to 0° C. (R)-α-(Chlorocarbonyl)benzenemethanesulfonic acid (1.8 g) in 20 ml of diglyme is added dropwise. The temperature is maintained for 2 hours, the solvent is distilled off in vacuo and the residue is dissolved in acetone. The insoluble precipitate is filtered off and the mother liquor is treated with an equivalent amount of potassium perfluorobutane sulfonate. After the addition of ether, the title compound precipitates and is filtered off, yielding 1.4 of crude product; melting point 240°–245° C. dec., after recrystallization from water/acetone.

EXAMPLE 66

[3S(Z)]-3-[[(2-Amino-4-thiazolyl)[[(diethoxyphosphinyl)methoxy]imino]acetyl]amino]-2-oxo-1-azetidinesulfonic acid, potassium salt (S)-3-Amino-2-oxo-1-azetidinesulfonic acid, tetrabutylammonium salt (2.25 g; see Example 6A) in 100 ml of dry dimethylformamide is treated with 1.87 g of (Z)-2-amino-α-[[(diethoxyphosphinyl)methoxy]imino]-4-thiazoleacetic acid, 0.75 g of hydroxybenzotriazole and 2.29 g of dicyclohexylcarbodiimide for 12 hours with stirring. The precipitated urea is filtered off and the solvent removed in vacuo. The remaining oil is treated with an equivalent amount of potassium perfluorobutane sulfonate in 20 ml of acetone. After the addition of ether, the title compound precipitates and is filtered off, yielding 2.77 g of crude product. Purification of this crude product by column chromatography using HP-20 and water/acetone (9:1) as eluent yields the title compound, melting point 155°–160° C., dec.

EXAMPLE 67

[3S(Z)]-3-[[(2-Amino-4-thiazolyl)[[2-(1,1-dimethylethoxy)-2-oxo-1-phenylethoxy]imino]acetyl]amino]-2-oxo-1-azetidinesulfonic acid, potassium salt (S)-3-Amino-2-oxo-1-azetidinesulfonic acid, tetrabutylammonium salt (2.25 g; see Example 6A) in 60 ml of dimethylformamide is stirred at room temperature with 2.4 g of (Z)-2-amino-α-[[2-(1,1-dimethylethoxy)-2-oxo-1-phenylethoxy]imino]-4-thiazolacetic acid, 1 g of hydroxybenzotriazole and 1.5 g of dicyclohexylcarbodiimide for 12 hours. The solvent is removed in vacuo and the residue is dissolved in 50 ml of acetone. The precipitated urea is filtered off and the mother liquor is treated with an equivalent amount of potassium perfluorobutane sulfonate. After the addition of ether, the title compound crystallizes and is filtered off. Purification of the compound is achieved by HP-20 column chromatography using water/acetone (7:3) as eluent, yielding 1 g of product, melting point >250° C., dec.

EXAMPLE 68

[3S(Z)]-3-[[(2-Amino-4-thiazolyl)[(1H-tetrazol-5-ylmethoxy)imino]acetyl]amino]-2-oxo-1-azetidinesulfonic acid, potassium salt (S)-3-Amino-2-oxo-1-azetidinesulfonic acid, tetrabutylammonium salt (1.9 g; see Example 6A) in 60 ml of dimethylformamide is treated with 1.4 g of (Z)-2-amino-α-[(1H-tetrazol-5-ylmethoxy)imino]-4-thiazoleacetic acid, 0.7 g of hydroxybenzotriazole and 1.4 g of dicyclohexylcarbodiimide with stirring for 24 hours. After the solvent is removed in vacuo, the residue is dissolved in acetone and the precipitated urea filtered off. The mother liquor is treated with an equivalent amount of potassium perfluorobutane sulfonate in 10 ml of acetone. The title compound is precipitated by the addition of 200 ml of ether. Purification is achieved by HP-20 column chromatography using HP-20 resin and water as eluent and yields 1.05 g of product, melting point 250° C., dec.

EXAMPLE 69

[3S(Z)]-3-[[(2-Amino-4-thiazolyl)[(phenylmethoxy)imino]acetyl]amino]-2-oxo-1-azetidinesulfonic acid, potassium salt (S)-3-Amino-2-oxo-1-azetidinesulfonic acid, tetrabutylammonium salt (1.5 g; see Example 6A), 1.23 g of (Z)-2-amino-α-[(phenylmethoxy)imino]-4-thiazoleacetic acid, 0.57 g of hydroxybenzotriazole and 1.14 g of dicyclohexylcarbodiimide are stirred in 60 ml of dimethylformamide at room temperature for 24 hours. The precipitated urea is filtered off, the solvent removed and the residue treated with an equivalent amount of potassium perfluorobutane sulfonate in 10 ml of acetone. After the addition of 200 ml of ether, the title compound precipitates, is filtered off and is purified by HP-20 column chromatography using water/acetone (9:1) as eluent, yielding 1 g of material, melting point 200° C., dec.

EXAMPLE 70

[3S(Z)]-3-[[(2-Amino-4-thiazolyl)[(carboxymethoxy)imino]acetyl]amino]-2-oxo-1-azetidinesulfonic acid, potassium salt (1:1)

[3S(Z)]-3-[[(2-Amino-4-thiazolyl)[[2-(diphenylmethoxy)-2-oxoethoxy]imino]acetyl]amino]-2-oxo-1-azetidinesulfonic acid, potassium salt (1:1) (1.3 g; see Example 30) is mixed with 5 ml of anisole. At −15° C. 25 ml of trifluoroacetic acid is added and the mixture is stirred for 10 minutes. Ether (100 ml) is added slowly at −10° C. and subsequently 50 ml of petroleum ether. The precipitate is suspended with cooling in 20 ml of water and adjusted to pH 5.0 with diluted potassium hydroxide. The product is purified by chromatography on an HP-20 column, yielding 3.0 g of the title compound, melting point 230°–235° C., dec.

EXAMPLE 71

[3S(Z)]-3-[[(2-Amino-4-thiazolyl)[[2-oxo-2-(phenylmethoxy)ethoxy]imino]acetyl]amino]-2-oxo-1-azetidinesulfonic acid, potassium salt Following the procedure of Example 28, but substituting (Z)-2-amino-α-[[2-oxo-2-(phenylmethoxy)ethoxy]imino]-4-thiazoleacetic acid for (Z)-2-amino-α-[[2-(diphenylmethoxy)-1,1-dimethyl-2-oxoethoxy]imino]-4-thiazoleacetic acid, yields the title compound, melting point ca. 170° C., dec.

EXAMPLE 72

[3S(Z)]-3-[[[(2-Amino-2-oxoethoxy)imino](2-amino-4-thiazolyl)acetyl]amino]-2-oxo-1-azetidinesulfonic acid, potassium salt Following the procedure described in Example 28, but substituting (Z)-2-amino-α-[(2-amino-2-oxoethoxy)imino]-4-thiazoleacetic acid for (Z)-2-amino-α-[[2-(diphenylmethoxy)-1,1-dimethyl-2-oxoethoxy]imino]-4-thiazoleacetic acid, yields the title compound melting point 205°–210° C., dec.

EXAMPLE 73

[3S(Z)]-3-[[(2-Amino-4-thiazolyl)(hydroxyimino)acetyl]amino]-2-oxo-1-azetidinesulfonic acid, potassium salt A solution of 0.6 grams of 90% hydroxybenzotriazole in 100 ml of dimethylformamide is stirred for one hour with 10 grams of 4A molecular sieves, filtered, and the filtrate added to a solution of 0.004 mole of (S)-3-amino-2-oxo-1-azetidinesulfonic acid, tetrabutylammonium salt (see Example 6A) in dimethylformamide. (Z)-2-Amino-α-(hydroxyimino)-4-thiazoleacetic acid (0.89 g) is added, followed by the addition of 0.91 g of dicyclohexylcarbodiimide. The mixture is stirred for about 16 hours, evaporated in vacuo and the residue dissolved in 20 ml of acetone and filtered. The addition of a solution of potassium perfluorobutane sulfonate causes the title compound to precipitate. Chromatography on HP-20 resin yields 0.44 g of product, melting point >240° C.

EXAMPLE 74

3-Methoxy-2-oxo-3-[(2-thienylacetyl)amino]-1-azetidinesulfonic acid, potassium salt (A)

3-Amino-3-methoxy-2-oxo-1-azetidinesulfonic acid, tetrabutylammonium salt (±)-3-Methoxy-3-[[(phenylmethoxy)carbonyl]amino]-2-oxo-1-azetidinesulfonic acid, tetrabutylammonium salt (143 mg, see Example 49) is dissolved in 15 ml of dry methanol. $Na_2B_4O_7 \cdot 10H_2O$ (12 mg, 0.1 equiv.) is added, followed by 10% palladium on carbon (72 mg). The mixture is hydrogenated at one atmosphere pressure for 15 minutes. The catalyst is removed by filtration and the filtrate evaporated in vacuo, yielding 114 mg of the title compound.

(B)

3-Methoxy-2-oxo-3-[(2-thienylacetyl)amino]-1-azetidinesulfonic acid, tetrabutylammonium salt 3-Methoxy-3-amino-2-oxo-1-azetidinesulfonic acid, tetrabutylammonium salt (102 mg) is dissolved in 10 ml of dry acetonitrile. Dry pyridine (56.5 μl) is added and the solution is stirred well at −10° C. under dry nitrogen. Thienylacetyl chloride (44 μl) in 1 ml of dry acetonitrile is added dropwise. In 15 minutes the reaction is complete as shown by thin layer chromatography. Potassium phosphate buffer (0.5M, pH 5.5, 4.2 ml) and tetrabutylammonium sulfate (8.5 mg, 0.1 equiv.) are added and most of the acetonitrile is removed in vacuo. The residue is diluted with water and extracted with three 20 ml portions of methylene chloride. The extract is dried over anhydrous sodium sulfate and evaporated in vacuo to yield 107 mg of a gum. The crude product is purified by chromatography on silica gel using methylene chloride-methanol, yielding 66 mg of the title compound.

(C)

3-Methoxy-2-oxo-3-[(2-thienylacetyl)amino]-1-azetidinesulfonic acid, potassium salt 3-Methoxy-2-oxo-3-[(2-thienylacetyl)amino]-1-azetidinesulfonic acid tetrabutylammonium salt (154 mg) is dissolved in 3 ml of 30% acetone-water, passed through a column of Dowex 50W-X2 (K+form) and eluted with the same solvent. The total eluate is evaporated in vacuo to yield 95 mg of product which is lyophilized to give an amorphous powder, melting point 120°–135° C.

Anal. Calc'd for $C_{10}H_{11}N_2O_6S_2K$: C, 33.51; H, 3.09; N, 7.82; S, 17.89. Found: C, 33.46; H, 3.08; N, 7.92; S, 17.64.

EXAMPLE 75

[3S(Z)]-3-[[(2-Amino-4-thiazolyl)[(carboxymethoxy)imino]acetyl]amino]-2-oxo-1-azetidinesulfonic acid, potassium salt

[3S(Z)]-3-[[(2-Amino-4-thiazolyl)[[2-oxo-2-(phenylmethoxy)ethoxy]imino]acetyl]amino]-2-oxo-1-azetidinesulfonic acid, potassium salt (0.1 g; see Example 71) is dissolved in a mixture of 5 ml of ethanol and 5 ml of water and hydrogenated at room temperature in the presence of 0.2 g of 10% palladium on charcoal. After 2 hours the catalyst is filtered off and the remaining solution is freeze-dried yielding the title compound.

EXAMPLE 76

3-[[(S)-[(Aminocarbonyl)amino]-2-thienylacetyl]amino]-3-methoxy-2-oxo-1-azetidinesulfonic acid, potassium salt, isomer A To a solution of 3-amino-3-methoxy-2-oxo-1-azetidinesulfonic acid, tetrabutylammonium salt (277 mg; see Example 46, method II, part A) in 15 ml of dry acetonitrile at $-20°$ C. is added pyridine (71 μl) 0.888 mmole) and (D)-2-amino-4-(2-thienyl)-5-(4H)-oxazoline hydrochloride (166 mg). The mixture is stirred for 10 minutes and a second aliquot of pyridine (71 μl) and oxazoline (166 mg) is added. After another 10 minutes the solvent is removed under reduced pressure and the residue is dissolved in a water-acetone mixture and passed through an ion-exchange resin (20 ml AG 50W-X2, K+ form, 200–400 mesh). Removal of the water from fractions 2–3 gives a mixture of diastereomers (248 mg).

The product is purified and the diastereomers separated on Diaion AG HP 20 (130 ml) and eluted with water. Isomer A is eluted in fractions 23–28 (30 mg), and isomer B in fractions 35–45 (30 mg) (8 ml fractions). The middle fractions (10 mg) are combined with fractions from other runs and a total of 35 mg of isomer A and 59 mg of isomer B is isolated.

Anal. Calc'd: $C_{11}H_{13}N_4O_7S_2 \cdot K \cdot \frac{1}{2}H_2O$ C, 31.05; H, 3.29; N, 13.18. Found: C, 30.95; H, 2.97; N, 12.98.

EXAMPLE 77

3-Methoxy-2-oxo-3-[(phenylsulfoacetyl)amino]-1-azetidinesulfonic acid, dipotassium salt To a stirred solution of crude 3-amino-3-methoxy-2-oxo-1-azetidinesulfonic acid, tetrabutylammonium salt (366 mg; see Example 74A) and 38 mg of borax in 35 ml of dry acetonitrile at $-10°$ C. under nitrogen is added 0.53 ml of dry pyridine followed by a two minute addition of a solution of α-sulfophenylacetyl chloride monoetherate (348 mg) in 8 ml of acetonitrile. After 20 minutes the solvent is removed in vacuo and the residue is treated with 35 ml of 0.5M pH 5.5 potassium phosphate buffer. Tetrabutylammonium hydrogen sulfate (383 mg) is added and the mixture is extracted three times with methylene chloride. The methylene chloride is dried (sodium sulfate) and evaporated to give 685 mg of crude product.

The crude product is combined with 115 mg of crude from a second run and the combined material is purified on a column of SiliCAR CC-4 using methylene chloride and then 2, 4, 6, 8 and 10% methanol in methylene chloride as eluent. The product, a mixture (about 6:1) of racemic diastereomers in the tetrabutylammonium salt form, is converted to the potassium salt by passage through Dowex 50W-X2 (K+ form) resin using 20% acetone in water as solvent. The product is lyophilized yielding 171 mg of the title compound, melting point 205°–210° C., dec.

Anal. Calc'd for $C_{12}H_{12}N_2O_9S_2K_2 \cdot H_2O$: C, 29.51; H, 2.89; N, 5.74; S, 13.10. Found: C, 29.45; H, 2.74; N, 5.51; S, 12.82.

EXAMPLE 78

3-[(Carboxyphenylacetyl)amino]-3-methoxy-2-oxo-1-azetidinesulfonic acid, dipotassium salt 3-[[1,3-Dioxo-2-phenyl-3-(phenylmethoxy)propyl]amino]-3-methoxy-2-oxo-1-azetidinesulfonic acid, potassium salt (39 mg; see Example 51) is dissolved in methanol (5 ml). Anhydrous potassium carbonate (3.9 mg) and 10% palladium on carbon (19 mg) are added and the mixture is hydrogenated at atmospheric pressure for 20 minutes. The catalyst is removed by filtration and the filtrate is evaporated in vacuo to yield a glassy residue (34 mg) which is lyophilized to an amorphous powder, melting point 178°–190° C., dec.

Anal. for $C_{13}H_{12}O_8N_2S$ $K_2 \cdot 0.5H_2O$: C, 35.20; H, 3.18; N, 6.32; S, 7.23. Found: C, 35.51; H, 2.96; N, 6.29; S, 6.92.

EXAMPLE 79

[3S(Z)]-3-[[(2-Amino-4-thiazolyl)[[2-(1,1-dimethylethoxy)-1-(methylthio)-2-oxoethoxy]imino]acetyl]amino]-2-oxo-1-azetidinesulfonic acid, potassium salt Following the procedure of Example 73, but substituting (Z)-2-amino-α-[[2-(1,1-dimethylethoxy)-1-(methylthio)-2-oxoethoxy]imino]-4-thiazoleacetic acid for (Z)-2-amino-α-(hydroxyimino)-4-thiazoleacetic acid, yields the title compound, melting point 130° C., dec.

EXAMPLE 80

(±)-3-Butoxy-3-[[(phenylmethoxy)carbonyl]amino]-2-oxo-1-azetidinesulfonic acid, potassium salt A solution of 185 mg of 2-oxo-3-[N-chloro-N-[(phenylmethoxy)carbonyl]amino]-1-azetidinesulfonic acid, tetrabutylammonium salt (see Example 49A) in 1 ml of dimethylformamide is cooled to $-78°$ C. and 0.73N lithium n-butoxide (3.8 ml) in n-butanol is added at $-78°$ C. After 15 minutes, 0.5M monobasic potassium phosphate buffer is added and the product extracted into dichloromethane (three 40 ml portions), dried over sodium sulfate, filtered and concentrated in vacuo to give 179 mg of the corresponding tetrabutylammonium salt of the title compound.

To a solution of 109 mg of the tetrabutylammonium salt in acetone is added perfluorobutylsulfonic acid, potassium salt (60 mg) in acetone. The solvent is removed in vacuo and ethyl acetate is added. The product crystallizes and is collected and dried to yield 66 mg of the title compound, melting point 186.5°–187.5° C., dec.

EXAMPLE 81

[3±(E)]-3-Methoxy-3-[[(methoxyimino)[2-[[(phenylmethoxy)carbonyl]amino]-4-thiazolyl]acetyl]amino-2-oxo-1-azetidinesulfonic acid, potassum salt A suspension of 3-amino-3-methoxy-2-oxo-1-azetidinesulfonic acid, tetrabutylammonium salt (Example 46, Method II, part A) (0.175 mmole) and sodium borate (0.0175 mmole) in 2 ml of dichloromethane at 0° C. is treated with 28 μl of pyridine and 0.175 mmole of (E)-α-(methoxyimino)-2-[[(phenylmethoxy)carbonyl]amino]-4-thiazolylacetyl chloride. After 1 hour, the mixture is diluted with dichloromethane and quenched with water. The organic layer is washed with water, saturated salt, dried, and evaporated in vacuo. The residue is purified on Mallinckrodt SilicAR CC-4 silica gel (20 g) to give 43 mg of the corresponding tetrabutylammonium salt of the title compound.

The tetrabutylammonium salt (43 mg) is dissolved in 0.5 ml of acetone and 20 mg of potassium perfluorobutane sulfonate in 0.5 ml of acetone is added. After addition of 3 ml of ether the solid is collected and dried in vacuo to give 28 mg of the title compound melting point 144°–146° C., dec.

EXAMPLE 82

[3±(Z)]-3-Methoxy-3-[[(methoxyimino)[2-[[(phenylmethoxy)carbonyl]amino]-4-thiazolyl]acetyl]amino]-2-oxo-1-azetidinesulfonic acid, potassium salt Following the procedure of Example 81, but substituting (Z)-α-(methoxyimino)-2-[[(phenylmethoxy)carbonyl]amino]-4-thiazolylacetyl chloride for (E)-α-(methoxyimino)-2-[[(phenylmethoxy)carbonyl]amino]-4-thiazolylacetyl chloride, yields the title compound, melting point 168°–172° C., dec.

EXAMPLE 83

3-[[(R)-α-[[(4-Ethyl-2,3-dioxo-1-piperazinyl)carbonyl]amino]phenylacetyl]amino]-3-methoxy-2-oxo-1-azetidinesulfonic acid, potassum salt To a stirred solution of 0.69 mmole of 3-amino-3-methoxy-2-oxo-1-azetidinesulfonic acid, tetrabutylammonium salt (Example 46, Method II, part A) in 30 ml of dry acetonitrile at −20° C. under nitrogen is added 242 μl of dry pyridine followed by a solution of 352 mg of (R)-α-[[(4-ethyl-2,3-dioxo-1-piperazinyl)carbonyl]amino]phenylacetyl chloride in 4 ml of acetonitrile. After 1 hour 84 μl of pyridine is added followed by an additional 117 mg of the above named acid chloride in 1 ml of acetonitrile. The reaction is stirred for 20 minutes, diluted with 24 ml of 0.5M pH 5.5 monobasic potassium phosphate buffer and concentrated in vacuo to remove acetonitrile. The aqueous remainder is extracted three times with methylene chloride and the combined extracts are dried (Na$_2$SO$_4$) and evaporated leaving 546 mg of residue. Passage of the residue through a silica gel column using methylene chloride and then 2%, 4% and 6% methanol in methylene chloride, provides two fractions (285 mg and 173 mg) of the corresponding tetrabutylammonium salt of the title compound.

Passage of the 173 mg fraction through 4.5 g of Dowex 50-X2 (K+) resin using acetone-water as eluent yields 119 mg of the title compound. A 104 mg portion of this material is applied to a column of HP 20-AG resin in water. Sequential elution with water, 5% acetone in water and 10% acetone in water yields 60 mg of product as a mixture (ca. 1:1) of diastereomers. Lyophilization of the 60 mg fraction yields a solid, metling point 171°–172° C., dec.

EXAMPLE 84

N-(3-Butoxy-2-oxo-1-sulfo-3-azetidinyl)-2-phenylacetamide, tetrabutylammonium salt Following the procedure of Example 80, but substituting N-chloro-N-(2-oxo-1-sulfo-3-azetidinyl)-2-phenylacetamide, tetrabutylammonium salt (see Example 47A for preparation of the corresponding potassium salt) for 2-oxo-3-[N-chloro-N-[(phenylmethoxy)carbonyl]amino]-1-azetidinesulfonic acid, tetrabutylammonium salt, yields the title compound as an oil: nmr (CDCl$_3$) 3.62 (s, 2H, C$_6$H$_5$CH$_2$), 4.03 (ABq, 2H, ν=7 cps, C-4 CH$_2$), 6.98 (s, 1H, NH) and 7.30 ppm (S, 5H, C$_6$H$_5$).

EXAMPLE 85

(R)-3-Methoxy-2-oxo-3-[(phenylacetyl)amino]-1-azetidinesulfonic acid, potassium salt A 1M solution of dimethylformamide-sulfur trioxide complex is prepared by the slow addition of trimethylsilyl chlorosulfonate to dimethylformamide at 0° C. followed by evacuation at 0.1 mm for 30 minutes at 0°–25° C. Under an argon atmosphere, 50 mg of (R)-N-(3-methoxy-2-oxo-1-azetidinyl)phenylacetamide is dissolved in 0.2 ml of anhydrous dimethylformamide and cooled to 0° C. Cold 1M dimethylformamide-sulfur trioxide solution (0.428 ml) is added, the mixture is stirred for 2 hours and poured into 15 ml of 0.5N monobasic potassium phosphate. The solution is extracted twice with dichloromethane (discard) and 73 mg of tetrabutylammonium bisulfate is added. Extraction with dichloromethane (three 10 ml portions) gives a viscous oil after drying and evaporation in vacuo. Chromatography on Mallincrodt CC-4 silica gel (50:1) using 2% methanol in dichloromethane as eluant gives 34 mg of (R)-3-methoxy-2-oxo-3-[(phenylacetyl)amino[-1-azetidinesulfonic acid, tetrabutylammonium salt. Ion exchange on Dowex 50W-X2 (K+, 10 equivalents) give the title potassium salt after lyophilization of the aqueous eluate: melting point 130° C., dec., [α]$_D$= +52°, water).

EXAMPLE 86

(S)-3-[[[[(1-Ethyl-4-hydroxy-3-methyl-1H-pyrazolo[3,4-b]pyridin-5-yl)carbonyl]amino]phenylacetyl]amino]-2-oxo-1-azetidinesulfonic acid, potassium salt Following the procedure of Example 73, but substituting α-[[(1-ethyl-4-hydroxy-3-methyl-1H-pyrazolo[3,4-b]pyridin-5-yl)carbonyl]amino]benzeneacetic acid for (Z)-2-amino-α-(hydroxyimino)-4-thiazoleacetic acid, yields the title compound, melting point 233°–236° C., dec.

EXAMPLE 87

(R)-3-Acetylamino-3-methoxy-2-oxo-1-azetidinesulfonic acid, potassium salt (A)

3-Acetylamino-1-[1-carboxy-2-methyl(propyl)](3R)-3-methoxy-2-oxoazetidine

To a solution of (6R-cis)-7-acetylamino-7-methoxy-3-methyl-8-oxo-5-thia-1-azabicyclo[4.2.0]oct-2-ene-2-carboxylic acid (650 mg) and sodium bicarbonate (191 mg) in water is added a slurry (11 ml) of commercial grade Raney nickel (0.6 g/ml), which has been washed to neutrality with water. The mixture is lowered into an oil bath preheated to 170° C. and proceeds to reflux in 2–3 minutes, while maintaining the bath temperature at 150°–170° C. After refluxing for 15 minutes, the reaction is quenched by cooling in an ice bath. Catalyst is removed by filtration through Celite and the filtrate (pH 11) is adjusted to pH 2 with 1N hydrochloric acid. After extracting the aqueous solution five times with ethyl acetate, the combined extracts are dried (Na$_2$SO$_4$) and solvent is removed in vacuo to give an oil (487 mg).

63

Chromatography on silica gel yields the product (eluted in chloroform) as an oil (381 mg).

(B)

3-Acetylamino-1-[-1-(acetyloxy)-2-methyl(-propyl)](3R)-3-methoxy-2-oxoazetidine

The above azetidinone (464 mg) is dissolved in dry acetonitrile (15 ml) and the solution is purged with argon for 15 minutes. Copper acetate (359 mg) is added, stirred for one minute to dissolve the salt, and the lead tetraacetate (797 mg) is added. While argon continues to bubble through the mixture, the temperature of the reaction is raised by lowering the flask into an oil bath, preheated and maintained at 55°–65° C. for 15 minutes. The mixture is allowed to cool to room temperature, filtered through Celite and the filter pad is washed well with acetonitrile. Solvent is removed in vacuo from the combined filtrate and washings. The residue is taken up in water, and extracted four times with ethyl acetate. The combined extracts are dried (Na$_2$SO$_4$) and solvent is removed in vacuo to yield the desired product as an oil (382 mg).

(C)

(R)-N-(3-Methoxy-2-oxo-1-azetidinyl)acetamide

The above oil is dissolved in a methanol (10 ml):water (1 ml) mixture, cooled in an ice-methanol bath at −10° to −15° C. and potassium carbonate (194 mg) is added followed by sodium borohydride (53 mg). After stirring at −15° to −8° C. for 110 minutes, solvent is removed in vacuo, the residue is taken up in water and the solution is adjusted to pH 6 with 1N hydrochloric acid. Exhaustive extraction with ethyl acetate, drying (Na$_2$SO$_4$), and removal of solvent in vacuo yields an oil (224 mg). Chromatography of the oil on silica gel, eluting with 5% methanol:95% methylene chloride giving an oil (169 mg). The title compound crystallizes from ether-pentane to give 131 mg of material, melting point 106°–112° C. (sintering 103.5° C.).

(D)

(R)-3-Acetylamino-3-methoxy-2-oxo-1-azetidinesulfonic acid, potassium salt

Under an argon atmosphere, 50 mg of (R)-3-acetylamino-3-methoxy-2-oxo-1-azetidine is placed in a flask and cooled to 0° C. A 1M solution of dimethylformamide-sulfur trioxide complex in dimethylformamide (0.95 ml) is then added and the solution is stirred for 15 minutes. The contents of the flask are then poured into 40 ml of 0.5N K$_2$HPO$_4$ soultion and extracted twice with 10 ml of methylene chloride. Tetrabutylammonium sulfate (1.2 equivalents) is added to the aqueous solution and the resulting mixture is extracted with four 10 ml portions of methylene chloride. The extracts are then dried over Na$_2$SO$_4$ and concentrated to afford 39 mg of product. The tetrabutylammonium salt is converted to the title potassium salt by passing it through a column of Dowex 50-X2 (K+). Concentration of the aqueous fraction gives 19 mg of the potassium salt.

64

EXAMPLE 88

(±)-3-[(Azidophenylacetyl)amino]-3-methoxy-2-oxo-1-azetidinesulfonic acid, potassium salt

(A)

(±)-3-[(Azidophenylacetyl)amino]-3-methoxy-2-oxo-1-azetidinesulfonic acid, tetrabutylammonium salt 3-Amino-3-methoxy-2-oxo-1-azetidinesulfonic acid tetrabutylammonium salt (202 mgs; see Example 74A) is dissolved in 20 ml of dry acetonitrile. To the well stirred solution at −20° C. under dry nitrogen are added dry pyridine (167 μl) and α-azidophenylacetyl chloride (96 μl). After 20 minutes, 0.5M pH 5.5 monobasic potassium phosphate buffer (12 ml) is added and the acetonitrile removed in vacuo. The aqueous residue is extracted three times with methylene chloride. The extract is dried over anhydrous sodium sulfate and evaporated in vacuo to give 281 mg of crude product as a gum. This is purified by chromatography through a column of silica gel (30 g) using methylene chloride and mixtures of methylene chloride-methanol up to 6% methanol, and yielding 231 mg of the title compound.

(B)

(±)-3-[(Azidophenylacetyl)amino]-3-methoxy-2-oxo-1-azetidinesulfonic acid, potassium salt (±)-3-[(Azidophenylacetyl)amino]-3-methoxy-2-oxo-1-azetidinesulfonic acid, tetrabutylammonium salt (231 mg) in 30% acetone:water (15 ml) is passed through a column of Dowex 50W-X2 (K+ form; 3 ml) and eluted with water. The total eluate is evaporated in vacuo to give a colorless glass (168 mg) as a 1:1 mixture of diastereomers. Passage of this through a 60 ml column of HP20-AG using water and water:10% acetone gives 71 mg of a 1:1 mixture of racemic diastereomers and 70 mg of a 1:3 mixture of racemic diastereomers. The 1:1 mixture is lyophilized and dried in vacuo at 40° C. to give the dried product as a hemihydrate, melting point dec. 130° C.

Analysis for C$_{12}$H$_{12}$N$_5$O$_6$.K.0.5H$_2$O: Calc'd: C, 35.90; H, 3.26; N, 17.45; S, 7.98. Found: C, 35.94; H, 3.07; N, 17.24; S, 8.02.

EXAMPLE 89

3-[(Azidophenylacetyl)amino]-3-methoxy-2-oxo-1-azetidinesulfonic, potassium salt, isomer A The 1:3 mixture of racemic diastereomers obtained in Example 88B is allowed to stand in deuterated water at room temperature, and isomer A crystallizes. After refrigeration, the mother liquor is removed, and the crystals (28 mg) are dried in vacuo at 40° C., melting point 130° C., dec.

EXAMPLE 90

[3±(R*)]-3-[[[[(4-Ethyl-2,3-dioxo-1-piperazinyl)carbonyl]amino]phenylacetyl]amino]-3-methoxy-2-oxo-1-azetidinesulfonic acid, potassium salt To a stirred solution of 3-amino-3-methoxy-2-oxo-1-azetidinesulfonic acid, tetrabutylammonium salt (0.69 mmol; see Example 74A) in 30 ml of dry acetonitrile at −20° C. under nitrogen is added 242 μl of dry pyridine followed by a solution of 352 mg of (R)-α-[[(4-ethyl-2,3-dioxo-1-piperazinyl)carbonyl]amino]phenylacetyl chloride in 4 ml of acetonitrile. After 1 hour, 84 μl of pyridine is added followed by 117 mg more of the acid chloride in 1 ml of acetonitrile. The reaction is stirred for 20 minutes, diluted with 24 ml of 0.5M pH 5.5 monobasic potassium phosphate buffer, and concentrated in vacuo to remove acetonitrile. The aqueous remainder is extracted three times with methylene chloride and the combined methylene chloride extract is dried ($Na_2SO_4$) and evaporated to a residue (546 mg). Passage of this material through a column of SilicAR CC-4, using methylene chloride and then 2%, 4%, and finally 6% methanol in methylene chloride provides two fractions (285 mg and 173 mg) of purified product in the tetrabutylammonium salt form.

Passage of the 173 mg portion through 4.5 g of Dowex 50-X2(K+) resin using acetone-water yields 119 mg of potassium salt. A 104 mg portion of this material is applied to a column of HP20-AG resin in water. Sequential elution with water, 5% acetone in water, and finally 10% acetone in water provides 60 mg of product as a mixture (ca. 1:1) of diastereomers and 21 mg of product as a mixture (ca. 9:1) of diastereomers. Lyophilization of the 60 mg fraction yields the title compound, melting point 171°–172° C., dec.

Analysis for $C_{19}H_{22}N_5O_9SK \cdot H_2O$: Calc'd: C, 41.23; H, 4.37; N, 12.65; S, 5.78. Found: C, 41.39; H, 4.12; N, 12.58; S, 5.63.

Lyophilization of the 21 mg fraction yields the title compound, melting point 171°–172° C., dec.

Analysis for $C_{19}H_{22}N_5O_9SK \cdot H_2O$: Calc'd: C, 41.23 H, 4.37; N, 12.65. Found: C, 41.43; H, 4.11; N, 12.28.

Treatment of the 285 mg fraction of tetrabutylammonium salt with Dowex 50-X2(K+) provides 145 mg of potassium salt, which is combined with the remaining 15 mg of the aforementioned 119 mg portion of Dowex resin derived potassium salt. Passage of this material through HP20-AG, as already described, provides an additional 31 mg of product as a mixture (ca. 1:1) of diastereomers and an additional 42 mg of product as a mixture (ca. 9:1) of diastereomers. The total amount of (1:1) mixture of diastereomers is 91 mg, and the total amount of (9:1) mixture of diastereomers is 63 mg.

EXAMPLE 91

[3S(Z)]-3-[[(Methoxyimino)[2-[[(phenylmethoxy)carbonyl]amino]-4-thiazolyl]acetyl]amino]-2-oxo-1-azetidinesulfonic acid, potassium salt To a solution of (S)-3-amino-2-oxo-1-azetidinesulfonic acid, tetrabutylammonium salt (0.170 mmol; see Example 6A) and sodium borate (0.170 mmol) in 2 ml of methylene chloride at 0° C. is added pyridine (62 μl) and (Z)-α-(methoxyimino)-2-[[(phenylmethoxy)carbonyl]amino]-4-thiazoleacetyl chloride (0.51 mmol). The reaction mixture, after 40 minutes, is diluted with methylene chloride and water, followed by 0.1M tetrabutylammonium sulfate buffered to pH 4 (5.1 ml). The organic layer is separated and washed with water, adjusted to pH 2, water adjusted to pH 7, water saturated with sodium chloride, dried over sodium sulfate, filtered, and concentrated in vacuo. The residue is purified on SilicAR CC-4 silica gel (10 g) and eluted with 10% methanol/methylene chloride.

The tetrabutylammonium salt, after dissolution in acetone/water, is passed through an ion-exchange resin (8 ml, AG 50W-X2, K+ form 100–200 mesh). Removal of the water in vacuo from fractions 1–2 give 40 mg of the title compound, melting point 172°–174° C., dec.

Analysis for $C_{17}H_{16}N_5O_8S_2K \cdot H_2O$: Calc'd: C, 37.84; Found: C, 37.95; H, 3.30; N, 12.73; S, 11.53.

EXAMPLE 92

(±)-3-Butoxy-2-oxo-3-[(phenylacetyl)amino]-1-azetidinesulfonic acid, potassium salt (A)

3-[Chloro(phenylacetyl)amino]-2-oxo-1-azetidinesulfonic acid tetrabutylammonium salt A solution of (S)-2-oxo-3-[[(phenylmethoxy)carbonyl]amino]-1-azetidinesulfonic acid, tetrabutylammonium salt (350 mg; see Example 4) in methylene chloride (3 ml) is added to a suspension of sodium borate (1.27 g) in a 5.25% solution of sodium hypochlorite (4.72 ml) and water (20 ml) at 0° C. After 1 hour 0.5M monobasic potassium phosphate (25 ml) is added and the mixture is extracted three times with methylene chloride (50 ml portions). The organic extracts are dried over sodium sulfate, filtered and concentrated in vacuo to give 344 mg of the title compound.

(B)

(±)-3-Butoxy-2-oxo-3-[(phenylacetyl)amino]-1-azetidinesulfonic acid, tetrabutylammonium salt A solution of 3-[[chloro(phenylmethoxy)carbonyl]amino]-1-azetidinesulfonic acid, tetrabutylammonium salt (344 mg) in dimethylformamide (5 ml) is added to 0.73N n-lithium butoxide in n-butanol (6 ml) in dimethylformamide (1 ml) at −78° C. under an inert atmosphere. After 10 minutes the mixture is diluted with 0.5M monobasic potassium phosphate solution (175 ml). After extracting three times with methylene chloride, the organic extract is dried over sodium sulfate, filtered, and the solvent removed in vacuo. The residue is purified on SilicAR CC-4 silica gel (80 g) and the title compound (130 mg) is eluted with 4–8% methanol in methylene chloride.

(C)

(±)-3-Butoxy-2-oxo-3-[(phenylacetyl)amino]-1-azetidinesulfonic acid, potassium salt (±)-3-Butoxy-2-oxo-3-[(phenylacetyl)amino]-1-azetidinesulfonic acid, tetrabutylammonium salt (43 mg) is dissolved in a water-acetone mixture (9:1) and placed on a cation exchange column (Dowex AGMP 50W-X2, 100–200 mesh, 5 g, K+ form). The product is eluted with water and the eluate concentrated in vacuo to give 20 mg of the title compound, melting point 122°–125° C.

Analysis calc'd for $C_{15}H_{19}N_2O_6SK \cdot \frac{1}{2}H_2O$: C, 44.66; H, 4.96; N, 6.95; S, 7.94. Found: C, 44.77; H, 4.76; N, 6.76; S, 7.75.

EXAMPLE 93

(±)-3-Ethoxy-2-oxo-3-[(phenylacetyl)amino]-1-azetidinesulfonic acid, potassium salt 3-[Chloro(phenylacetyl)amino]-2-oxo-1-azetidinesulfonic acid, tetrabutylammonium salt (200 mg; see example 92A) in dimethylformamide (4 ml) is added to 0.5N lithium ethoxide in ethanol (12.20 ml) at −78° C. under an inert atmosphere. After 10 minutes the mixture is diluted with 0.5M monobasic potassium phosphate solution (15 ml). After extracting three times with methylene chloride, the organic layer is dried over sodium sulfate, filtered and the solvent removed in vacuo. The residue is purified on SilicAR CC-4 silica gel (20 g) and the tetrabutylammonium salt of the product (40 mg) is eluted with 2% methanol in methylene chloride.

The tetrabutylammonium salt is dissolved in a water-acetone mixture (9:1) and placed on a cation exchange column (Dowex AGMP 50W-X2, 100–200 mesh (5 g, K+ form)). The product is eluted with water and the eluate concentrated in vacuo to give 25 mg of the title compound, melting point 94°–96° C.

Analysis calc'd for $C_{13}H_{15}N_2O_6SK$: C, 42.62; H, 4.10; N, 7.65; S, 8.74. Found: C, 40.36; H, 3.66; N, 6.77; S, 8.44.

EXAMPLE 94

[3±(Z)]-3-[[(2-Amino-4-thiazolyl)methoxyimino)acetyl]amino]-3-methoxy-2-oxo-1-azetidinesulfonic acid, potassium salt 3-Amino-3-methoxy-2-oxo-1-azetidinesulfonic acid, tetrabutylammonium salt (see Example 46, method II, part A) is dissolved in acetonitrile (20 ml) and pyridine (1 ml) and added to a vigorously stirring suspension of (Z)-α-(methoxyimino)-2-amino-4-thiazoleacetyl chloride in acetonitrile (20 ml) cooled to 0°–5° C. After stirring cold for 1 hour the mixture is diluted with 0.5M monobasic potassium phosphate solution (100 ml) (pH of the mixture is 4.8) and solvent is removed in vacuo. The residue is taken up in a minimal amount of water containing a small amount of acetone. Chromatography on ion exchange resin (AG 50W-X2, 100–200 mesh, K+ form 200 ml) gives the crude product as the potassium salt upon elution with water. Further purification on HP-20 resin (200 ml) using water as the eluant gives 59 mg of the product as a powder after trituration with acetonitrile-ether and then twice with ether. The product is an amorphous powder that melts slowly and decomposes above 150° C.

Analysis calc'd for $C_{10}H_{12}N_5O_7SK$: C, 28.77; H, 2.90; N, 16.78; S, 15.36; K, 9.37. Found: C, 27.77; H, 2.82; N, 15.87; S, 13.63; K, 10.11.

EXAMPLE 95

[3R(R*) and 3S(S*)]-3-[[[(Aminocarbonyl)amino]phenylacetyl]amino]-3-methoxy-2-oxo-1-azetidinesulfonic acid, potassium salt (A)

(±)-3-[(Aminophenylacetyl)amino]-3-methoxy-2-oxo-1-azetidinesulfonic acid, inner salt (±)-3-[(Azidophenylacetyl)amino]-3-methoxy-2-oxo-1-azetidinesulfonic acid, potassium salt (209 mg; see Example 88) is dissolved in 60 ml of dry methanol. Anhydrous trifluoroacetic acid (0.6 ml) and 10% palladium on carbon (105 mg) are added and the mixture is hydrogenated for 1 hour. The catalyst is removed by filtration and the filtrate is evaporated in vacuo to yield 271 mg of crude product.

(B)

[3R(R*) and 3S(S*)]-3-[[[(Aminocarbonyl)amino]phenylacetyl]amino]-3-methoxy-2-oxo-1-azetidinesulfonic acid, potassium salt (±)-3-[(Aminophenylacetyl)amino]-3-methoxy-2-oxo-1-azetidinesulfonic acid, potassium salt (271 mg) is dissolved in 6.5 ml of water. Potassium cyanate (87 mg) is added and the mixture is stirred at room temperature for 3 hours. The solution is concentrated in vacuo to approximately 2 ml and chromatographed on a 100 ml column of HP20-AG using water as eluant. Isomer A (29 mg) is isolated after lyophilization, melting point 160° C., dec.

Analysis for $C_{13}H_{15}N_4O_7SK$ monohydrate: Calc'd: C, 36.44; H, 3.99; N, 13.07; S, 7.48. Found: C, 36.35; H, 3.79; N, 12.81; S, 7.32.

EXAMPLE 96

[3R(S*) and 3S(R*)]-3-[[[(Aminocarbonyl)amino]phenylacetyl]amino]-3-methoxy-2-oxo-1-azetidinesulfonic acid, potassium salt Along with [3R(R*) and 3S(S*)]-3-[[[(aminocarbonyl)amino]phenylacetyl]amino-3-methoxy-2-oxo-1-azetidinesulfonic acid, potassium salt produced in Example 95, there are produced 21 mg of [3R(S*) and 3S(R*)]-3-[[[(aminocarbonyl)amino]phenylacetyl]amino]-3-methoxy-2-oxo-1-azetidinesulfonic acid, potassium salt as a lyophilate, melting point 160° C. dec.

Analysis for $C_{13}H_{15}N_4O_7SK$ sesquihydrate: Calc'd: C, 35.69; H, 4.14; N, 12.81; S, 7.33. Found: C, 35.98; H, 3.87; N, 12.50; S, 7.32.

EXAMPLE 97

[3±(S*)]-3-Methoxy-3-[[[[[2-oxo-3-[(phenylmethylene)amino]-1-imidazolidinyl]carbonyl]amino]-2-thienylacetyl]amino]-2-oxo-1-azetidinesulfonic acid, potassium salt To a stirred solution of 3-amino-3-methoxy-2-oxo-azetidinesulfonic acid, tetrabutylammonium salt (306 mg of crude material assumed to contain 274 mg of organic material, prepared as described in Example 74) in 20 ml of dry acetonitrile at −20° C. under nitrogen is added 0.30 ml of dry pyridine (3.72 mmol) followed by 484 mg of (S)-[[[2-oxo-3-phenylmethylene)amino]-1-imidazolidinyl]carbonyl]amino]-2-thienylacetyl chloride partially dissolved and suspended in 10 ml of dry acetonitrile. The reaction is stirred and allowed to rise to 0° C. over the course of 1 hour.

The reaction was diluted with a large volume of methylene chloride and then treated with 22 ml of 0.5M pH 5.5 monobasic potassium phosphate buffer. The aqueous layer is washed with methylene chloride and the combined methylene chloride extract is washed with water, dried ($Na_2SO_4$), and evaporated to a residue (508 mg). This residue is chromatographed on 50 g of silicAR CC-4, using methylene chloride and then 2% and 4% methanol in methylene chloride to give 251 mg of the tetrabutylammonium salt of the title compound.

To this salt (251 mg) in acetone is added a solution of 107 mg of perfluorobutanesulfonic acid potassium salt in several milliliters of acetone. Ethyl acetate is added, and the precipitate is washed three times with ethyl acetate by centrifugation, and dried in vacuo at 40° C./1 mm for 2 hours to give 95 mg of desired potassium salt as a mixture (ca. 1:2) of diastereomers having a melting point 200° C., dec.

Calc'd for $C_{21}H_{21}N_6O_8S_2K$: C, 42.85; H, 3.60; N, 14.28; S, 10.87. Found: C, 43.02; H, 3.74; N, 13.94; S, 10.71.

EXAMPLE 98

(±-cis)-4-Methyl-2-oxo-3-[[(phenylmethoxy)carbonyl]amino]-1-azetidinesulfonic acid, potassium salt (A)

N-Benzyloxy-t-boc*-allothreonine amide

A solution of 6.9 g of d,l-t-boc-allothreonine and the free amine from 5.3 g of o-benzylhydroxylamine.HCl (~0.033 mole, ethyl acetate-sodium bicarbonate liberation) in 80 ml of tetrahydrofuran is treated with 4.82 g of N-hydroxybenzotriazole and 6.5 g of dicyclohexylcarbodiimide in 20 ml of tetrahydrofuran. After stirring for about 16 hours at room temperature the slurry is filtered, concentrated in vacuo and chromatographed on a 400 ml of silica gel column. Elution with 5–10% ethyl acetate in chloroform gives 6.8 g of the title compound in fractions (200 ml each) 7–22.

*"boc" is used to describe butoxycarbonyl (B)

(±-cis)-N-Benzyloxy-3-t-butoxycarbonylamino-4-methylazetidinone

A solution of 6.8 g of N-benzyloxy-t-boc-allothreonine amide in 200 ml of tetrahydrofuran is stirred for about 16 hours with 5.24 g of triphenylphosphine and 3.2 ml of diethylazodicarboxylate. The solvents are evaporated in vacuo and the residue is chromatographed on a 500 ml silica gel column. Elution with methylene chloride followed by crystallization from ether gives a total of 2.65 g of azetidinone. Rechromatography of the mother liquors and mixed fractions give an additional 0.6 g. Crystallization of a portion twice from ether (−20° C.) gives the analytical sample of the title compound melting point 140°–142° C.

(C)

(±-cis)-3-t-Butoxycarbonylamino-1-hydroxy-4-methylazetidinone

A solution of 3.2 g of cis-N-benzyloxy 3-t-butoxycarbonylamino-4-methylazetidinone in 200 ml of 95% ethanol is stirred in an atmosphere of hydrogen with 0.7 g of 10% palladium on charcoal. After 40 minutes the slurry is filtered (uptake 249 ml) and the filtrate is evaporated and triturated with ether to give, in two crops, 2.05 g of solid, melting point 134°–136° C.

(D)

(±-cis)-3-t-Butoxycarbonylamino-4-methylazetidinone

A solution of 2.05 g of cis-3-t-butyloxycarbonylamino-1-hydroxy-4-methylazetidinone in 60 ml of methanol is treated with a total of 90 ml of 4.5M ammonium acetate (40, 20 and 30 ml portions) and 45 ml of 1.5M titanium trichloride (20, 10 and 15 ml portions) the second and third additions are made after 15 and 120 minutes, respectively. After 135 minutes the solution is diluted with an equal volume of 8% sodium chloride and extracted with three 300 ml portions of ethyl acetate. The combined organic layer is washed with a mixture of 100 ml each of 5% sodium bicarbonate and saturated salt, dried, and evaporated. Trituration with ether gives, in two crops, 1.65 g of solid. A portion of the first crop is recrystallized from ether to give the analytical sample, melting point 176°–178.5° C.

(E)

(±-cis)-3-Benzyloxycarbonylamino-4-methylazetidinone

A solution of 1.55 g of cis-3-t-butoxycarbonylamino-4-methylazetidinone in 4 ml each of methylene chloride and anisole is cooled to 0° C. and 50 ml of cold trifluoroacetic acid is added. After 90 minutes the solvents are evaporated in vacuo (benzene added and evaporated three times). The residue is dissolved in 25 ml of acetone, the initial pH (2.5) is raised to 7 with 5% sodium bicarbonate, and 2 ml of benzylchloroformate is added. The solution is kept at 0° C. and pH 7 for 4 hours and the acetone is removed in vacuo to give a slurry that is filtered. The filtrate is saturated with salt and extracted with methylene chloride. The solid is dissolved in methylene chloride and dried. The organic layers are combined, concentrated, and the residue chromatographed on a 200 ml silica gel column. Elution with 3:1 chloroform, ethyl acetate gives 850 mg of the title compound in fractions (100 ml each) 4–11. Crystallization of a small sample from ether gives the analytical sample, melting point 165°–166° C.

(F)

(±-cis)-4-Methyl-2-oxo-3-[[(phenylmethoxy)carbonyl]amino]-1-azetidinesulfonic acid, potassium salt To a suspension of cis-3-benzyloxycarbonylamino-4-methylazetidinone (0.75 g) in 7 ml each of dimethylformamide (dried with 4A sieves activated at 320° C. for 15 hours under argon flow) and methylene chloride (dried through basic $Al_2O_3$) is added 1.66 g of pyridine-sulfur trioxide complex. After 3 hours stirring at room temperature under nitrogen, an additional amount of pyridine-sulfur trioxide complex (1.66 g) is added. The reaction mixture is then stirred at room temperature under nitrogen for about 16 hours. The dimethylformamide is removed in vacuo to give 4.6 g of residue which is dissolved in 300 ml of 0.5M monobasic potassium phosphate solution (40° C. for 10–15 minutes). The solution is cooled, passed through a column of HP-20 resin (3 cm×60 cm) with 400 ml of 0.5M monobasic potassium phosphate 1 L of distilled water and (14:1) water:acetone to give 280 mg of product in fractions 13 to 26 (100 ml each). Crystallization from MeOH: petroleum ether gives 757.5 mg of an analytical sample, melting point 214°–215.5° C., dec.

Analysis calc'd for $C_{12}H_{13}N_2SO_6K$: C, 40.90; H, 3.72 N, 7.95; S, 9.10; K, 11.10. Found: C, 40.43; H, 3.60; N, 7.89; S, 8.69; K, 10.82.

EXAMPLE 99

(3S-trans)-4-Methyl-2-oxo-3-[[(phenylmethoxy)carbonyl]amino]-1-azetidinesulfonic acid, potassium salt Following the procedure of Example 98, but substituting 1-t-boc-threonine for d,l-t-boc-allothreonine, yields the title compound, melting point 133°–135° C.

Analysis calc'd for $C_{12}H_{13}N_2O_6SK$: C, 40.90; H, 3.72; N, 7.95; S, 9.10; K, 11.10. Found: C, 40.72; H, 3.60; N, 7.99; S, 8.80; K, 10.82.

EXAMPLE 100

(3S-trans)-4-Methyl-2-oxo-3-[(phenylacetyl)amino]-1-azetidinesulfonic acid, potassium salt (A)

(3S)-3-Amino-4-methyl-2-oxo-1-azetidinesulfonic acid, tetrabutylammonium salt (3S-trans)-4-Methyl-2-oxo-3-[[(phenylmethoxy)carbonyl]amino]-1-azetidinesulfonic acid, potassium salt (352.4 mg; see Example 99) is dissolved in 20 ml of distilled water and treated with 373.5 mg (1 mmole) of tetrabutyl ammonium hydrogen sulfate. After 10 minutes stirring at room temperature, the solution is extracted three times with 10 ml portions of methylene chloride after saturation with sodium chloride. The methylene chloride is dried over sodium sulfate and evaporated in vacuo to give 536 mg of the tetrabutylammonium salt which is hydrogenated with 270 mg of 10% palladium on charcoal in 25 ml of dimethylformamide. The mixture is filtered through Celite and washed twice with 2.5 ml portions of dimethylformamide to yield the title compound in solution.

(B)

(3S-trans)-4-Methyl-2-oxo-3-[(phenylacetyl)amino]-1-azetidinesulfonic acid, potassium salt The crude (3S)-3-amino-4-methyl-2-oxo-1-azetidinesulfonic acid, tetrabutylammonium salt from part A (the combined filtrate and washings) are treated at 0° C. with 206 mg of dicyclohexylcarbodiimide, 153 mg of N-hydroxybenzotriazole, and 138 mg of phenylacetic acid. The reaction mixture is stirred at 0° C. for 1 hour and then at room temperatrure for 2 hours. The resulting precipitate is filtered, the filtrate is evaporated in vacuo, the residue is dissolved in 10 ml of acetone and filtered. The filtrate is treated with 25 ml of acetone saturated with potassium iodide and then 200 ml of ether. The resulting solid (752.7 mg) is a mixture of the potassium and tetrabutylammonium salts of the title compound. The solid is dissolved in 50 ml of 0.5 monobasic potassium phosphate and applied to an HP-20 column. Elution with water and then water-acetone gives several fractions that are combined and evaporated to give the purified tetrabutylammonium salt. An aqueous solution of this material is passed through Dowex 50W-X2 ($K^+$ form) to give the title potassium salt (121.4 mg). Trituration with acetone-hexane yields 104.6 mg of the title compound, melting point 211°–213° C.

Analysis calc'd from $C_{12}H_{13}N_2O_5SK.\frac{1}{2}H_2O$: C, 41.72; H, 4.09; N, 8.11; S, 9.28; K, 11.32. Found: C, 41.70; H, 4.01; N, 8.07; S, 9.01; K, 11.02.

EXAMPLE 101

(cis)-4-Methyl-2-oxo-3-[(phenylacetyl)amino]-1-azetidinesulfonic acid, potassium salt A solution of 320 mg of (±-cis)-4-methyl-2-oxo-3-[[(phenylmethoxy)carbonyl]amino]-1-azetidinesulfonic acid, potassium salt (see example 98) is prepared in 20 ml of water containing 483 mg of tetrabutylammonium hydrogen sulfate and adjusted to pH 5.5. Extraction with six 25 ml portions of methylene chloride gives 517.3 mg of oil. A solution of this material in 15 ml of dimethylformamide is stirred with 400 mg of 10% palladium on charcoal in an atmosphere of hydrogen for 90 minutes. The catalyst is filtered and the filtrate stirred with 150 mg of phenylacetic acid, 169 mg of N-hydroxybenzotriazole and 247 mg of dicyclohexylcarbodiimide for 7.5 hours. The solvent is removed in vacuo and the residue is dissolved in 20 ml of acetone and filtered. The filtrate is treated with 25 ml of 0.044M potassium iodide in acetone. Dilution with an equal volume of ether gives a solid (330 mg) which is applied to a 50 ml HP-20 column in 20 ml of 0.05M monobasic potassium phosphate. Elution with 200 ml of water followed by 1:9 acetone-water gives Rydon positive material in fractions (50 ml) 6–10. Evaporation of fractions 7–9 gives 81 mg of solid. Recrystallization from acetonitrile-water gives 46 mg of the title compound, which decomposes at >205° C. A second crop (6 mg) is obtained from the filtrate. A further 5 mg is obtained from fractions 6 and 10 by evaporation and recrystallization.

Analysis calc'd for $C_{12}H_{13}N_2O_5SK$: C, 42.84; H, 3.89 N, 8.33; S, 9.53; K, 11.62. Found: C, 42.75; H, 3.82; N, 8.32; S, 9.26 K, 11.63.

EXAMPLE 102

[3S-[3α(Z),4β]]-3-[[(2-Amino-4-thiazolyl)(methoxyimino)acetyl]amino]-4-methyl-2-oxo-1-azetidinesulfonic acid, potassium salt (A)

(3S-trans)-4-Methyl-2-oxo-3-[[(phenylmethoxy)carbonyl]amino]-1-azetidinesulfonic acid, tetrabutylammonium salt (3S-trans)-4-Methyl-2-oxo-3-[[(phenylmethoxy)carbonyl]amino]-1-azetidinesulfonic acid, potassium salt (352.4 mg; see Example 99) is dissolved in 20 ml of water and tetrabutylammonium hydrogen sulfate (373.5 mg) is added. The aqueous solution is extracted three times with methylene chloride and the combined extracts are dried over sodium sulfate. After removal of the solvent, 534.6 mg of the title compound is obtained.

(B)

[3S-[3α(Z),4β]]-3-[[(2-Amino-4-thiazolyl)(methoxyimino)acetyl]amino]-4-methyl-2-oxo-1-azetidinesulfonic acid, potassium salt A solution of 534.6 mg of (3S-trans)-4-methyl-2-oxo-3-[[(phenylmethoxy)carbonyl]amino]-1-azetidinesulfonic acid, tetrabutylammonium salt in 20 ml of dimethylformamide is hydrogenated with 220 mg of 10% palladium on charcoal at atmospheric pressure for 2.75 hours; the uptake of hydrogen is 26.3 ml. The mixture is filtered and washed twice with 2.5 ml of dimethylformamide. The filtrate and washings (total ca. 25 ml) are stirred under nitrogen with 161 mg of (Z)-α-(methoxyimino)-2-amino-4-thiazoleacetic acid, 136 mg of N-hydroxybenzotriazole and 164.8 mg of dicyclohexylcarbodiimide. The mixture is stirred under nitrogen for about 16 hours. The dimethylformamide is removed in vacuo and the gummy residue is dissolved in acetone and filtered to remove urea. To the filtrate is added a solution containing 272 mg (0.8 mmole) of perfluorobutanesulfonic acid, potassium salt in 0.8 ml of acetone. The slurry is diluted with an equal volume of ether and filtered to give 325.5 mg of crude product which is purified through chromatography on 75 ml of HP-20AG. Elution with 400 ml of water and 400 ml of (9:1) water:acetone mixture (50 ml fractions) gives 335 mg in fractions 3 to 10. After trituration with acetone-hexane, 97.3 mg of an analytical sample is obtained from frac-

EXAMPLE 103

[3S-[3α(Z),4β]]-3-[[(2-Amino-4-thiazolyl)[(1-carboxy-1-methylethoxy)imino]acetyl]amino]-4-methyl-2-oxo-1-azetidinesulfonic acid, dipotassium salt

(A)

N-Benzyloxy-t-boc-threonine amide

A solution of 8.76 g of t-boc-threonine and the free amine from 6.4 g of O-benzylhydroxylamine HCl (ethyl acetate-sodium bicarbonate liberation) in 100 ml of tetrahydrofuran is treated with 6.12 g of N-hydroxybenzotriazole and 8.24 g of dicyclohexylcarbodiimide in 20 ml of tetrahydrofuran. The mixture is stirred under nitrogen for 26 hours, filtered, and evaporated in vacuo. The residue is chromatographed on a 300 g silica gel column (elution with chloroform and chloroform-ethyl acetate (3:1)) yielding 7.2 g of compound. Crystallization from ether-hexane gives 4.18 g of the title compound.

(B)

(3S-trans)-N-Benzyloxy-3-t-butoxycarbonylamino-4-methylazetidinone

A solution of 12.67 g of N-benzyloxy-t-boc-threonine amide, 11.5 g of triphenylphosphine, and 6.23 ml of diethylazodicarboxylate in 380 ml of tetrahydrofuran is stirred under nitrogen for about 16 hours. The solution is evaporated and chromatographed on a 900 gram silica gel column. Elution with chloroform-ethyl acetate (3:1) gives 13.69 g of compound that crystallizes from ether-hexane to yield 9.18 g of the title compound.

(C)

(3S-trans)-3-t-Butoxycarbonylamino-1-hydroxy-4-methylazetidinone

A solution of 9.18 g of (3S-trans)-N-benzyloxy-3-t-butoxycarbonylamino-4-methylazetidinone in 300 ml of 95% ethanol is stirred in an atmosphere of hydrogen with 1.85 g of 10% palladium on charcoal. After 141 minutes the slurry is filtered and evaporated in vacuo. The residue is recrystallized from ether-hexane to yield 5.12 g of the title compound.

(D)

(3S-trans)-3-t-Butoxycarbonylamino-4-methylazetidinone

A solution of 4.98 of (3S-trans)-3-t-butoxycarbonylamino-1-hydroxy-4-methylazetidinone in 200 ml of methanol is treated with 132 ml of 4.5M ammonium acetate and then 66 ml of 1.5M titanium trichloride and stirred for 4.5 hours. The aqueous solution is diluted with an equal volume of 8% sodium chloride and extracted with ethyl acetate to give 3.48 g of crude product. Recrystallization from ether-hexane yields 3.3 g of the title compound.

(E)

(3S-trans)-3-Benzyloxycarbonylamino-4-methylazetidinone

A solution of 3.3 g of (3S-trans)-3-t-butoxycarbonylamino-4-methylazetidinone in 10 ml each of dichloromethane and anisole is cooled to 0° C. and 112 ml of trifluoroacetic acid is added. The solution is stirred for 90 minutes and evaporated in vacuo (benzene added and evaporated three times). The residue is dissolved in 70 ml of acetone and the solution is adjusted to pH 7 with 5% sodium bicarbonate solution. A total of 5.33 g of benzyl chloroformate is added over 1 hour at pH 6.5-7.5. The mixture is stirred for 30 minutes at pH 7, diluted with 100 ml of saturated salt, and extracted with ethyl acetate (three 400 ml portions). The residue obtained by evaporation is chromatographed on a 1 liter silica gel column. Elution with chloroform-ethyl acetate (4:1) gives 2.19 g of compound. Crystallization from ether-hexane yields 1.125 g of the title compound.

(F)

(3S-trans)-4-Methyl-2-oxo-3-[[(phenylmethoxy)carbonyl]amino]-1-azetidinesulfonic acid, tetrabutylammonium salt A solution of 600 mg of (3S-trans)-3-benzyloxycarbonylamino-4-methylazetidinone in 2 ml of dimethylformamide is cooled to 0° C. and 4 ml of 0.8M sulfur trioxide in dimethylformamide is added. The solution is stirred at room temperature under nitrogen for 1 hour and poured into 80 ml of cold 0.5M monobasic potassium phosphate (adjusted to pH 5.5). The solution is extracted with three 50 ml portions of methylene chloride (discarded) and 868 mg of tetrabutylammonium bisulfate is added. The resulting solution is extracted with four 75 ml portions of methylene chloride. The combined organic layer is washed with 8% aqueous sodium chloride, dried, and evaporated in vacuo yielding 1.54 g of the title compound.

(G)

[3S-[3α(Z),4β]]-3-[[(2-Amino-4-thiazolyl)[(1-diphenylmethoxycarbonyl-1-methylethoxy)imino]acetyl]amino]-4-methyl-2-oxo-1-azetidinesulfonic acid, potassium salt A solution of 1.54 g of (3S-trans)-4-methyl-2-oxo-3-[[(phenylmethoxy)carbonyl]amino]-1-azetidinesulfonic acid, tetrabutylammonium salt in 45 ml of dimethylformamide is stirred in an atmosphere of hydrogen with 800 mg of 10% palladium on charcoal for 2 hours. The catalyst is filtered and the filtrate stirred for about 16 hours with 1.24 g of (Z)-2-amino-α-[(1-diphenylmethoxycarbonyl-1-methylethoxy)imino]-4-thiazoleacetic acid, 0.4 g of N-hydroxybenzotriazole, and 580 mg of dicyclohexylcarbodiimide. The slurry is evaporated in vacuo and the residue is triturated with 20 ml of acetone and filtered. The filtrate (plus 2 ml of washings) is treated with 868 mg of potassium perfluorobutanesulfonate in 3 ml of acetone. Dilution with 75 ml of ether gives a solid that is isolated by decantation of the mother liquor, trituration with ether, and filtration to give 0.91 g of the title compound. The mother liquor is diluted with a further 100 ml of ether to give a second crop, 0.45 g, of the title compound.

(H)

[3S-[3α(Z),4β]]-3-[[(2-Amino-4-thiazolyl)[(1-carboxy-1-methylethoxy)imino]acetyl]amino]-4-methyl-2-oxo-1-azetidinesulfonic acid, dipotassium salt A slurry of 140 mg of [3S-[3α(Z),4β]]-3-[[(2-amino-4-thiazolyl)[(1-diphenylmethoxycarbonyl)-1-methylethoxy)imino]acetyl]amino]-4-methyl-2-oxo-1-azetidinesulfonic acid, potassium salt (first crop) in 0.5 ml of anisole is stirred at −12° C. under nitrogen and 2.5 ml of cold (−10° C.) trifluoroacetic acid is added. After 10 minutes, 10 ml of ether and 5 ml of hexane are added and the resulting slurry is stirred for 5 minutes at −12° C., and allowed to warm to room temperature. The solid is isolated by centrifugation and washed twice with ether. A solution of this solid in 5 ml of cold water is immediately adjusted to pH 5.5 with 0.4N potassium hydroxide and then applied to an 80 ml HP-20AG column. Elution with water gives 72 mg of the title compound in fractions (10 ml) 7–11 after evaporation (acetonitrile added and evaporated three times) and trituration with ether.

Analysis calc'd for $C_{13}H_{15}N_5O_8S_2K_2$: C, 30.51; H, 2.95; N, 13.69; S, 12.53; K, 15.28. Found: C, 29.63; H, 3.20; N, 12.96; S, 11.94; K, 12.78.

The remaining 1.22 g of [3S-[3α(Z),4β]]-3-[[(2-amino-4-thiazolyl)[(1-diphenylmethoxycarbonyl-1-methylethoxy)imino]acetyl]amino-4-methyl-2-oxo-1-azetidinesulfonic acid, potassium salt (crops 1 and 2) are treated as above (4.2 ml anisole, 16 ml of trifluoroacetic acid, 13 minutes at −15° C.). Chromatography on a 300 ml HP-20AG column gives 694 mg of the title compound in fractions (60 ml) 6–9 after treatment as above.

EXAMPLES 104–133

Following the procedure of Example 11, but substituting the acid listed in column I for (Z)-2-amino-α-[[[hydroxy(phenylmethoxy)phosphinyl]methoxy]imino]-4-thiazoleacetic acid, yields the compound listed in column II.

| | Column I | Column II |
|---|---|---|
| 104. | 2-amino-α-[[2-(1,1-dimethylethoxy)-1-methyl-2-oxoethoxy]imino]-4-thiazoleacetic acid | [3S(Z)]—3-[[[(2-amino-4-thiazolyl)[2-(1,1-dimethylethoxy)-1-methyl-2-oxoethoxy)-imino]acetyl]imino]-2-oxo-1-azetidinesulfonic acid, potassium salt, hydrate (1:1); melting point 280° C., dec. |
| 105. | (R)—α-[[(4-ethyl-2,3-dioxo-1-piperazinyl)-carbonyl]amino]-4-hydroxybenzeneacetic acid | [3S(R*)]—3-[[[[(4-Ethyl-2,3-dioxo-4-piperazinyl)carbonyl]amino](4-hydroxyphenyl)-acetyl]amino]-2-oxo-1-azetidinesulfonic acid, potassium salt; melting point 197° C., dec. |
| 106. | (±)-α-[[(4-ethyl-2,3-dioxo-1-piperazinyl)-carbonyl]amino]-2-furanacetic acid | [3S(±)-3-[[[[(4-ethyl-2,3-dioxo-4-piperazinyl) carbonyl]amino]-2-furanylacetyl]amino]-2-oxo-1-azetidinesulfonic acid, potassium salt; melting point 169–171° C. |
| 107. | (R)—α-[[(4-ethyl-2,3-dioxo-1-piperazinyl)-carbonyl]amino]-1,4-cyclohexadieneacetic acid | [3S(R*)]—3-[[1,4-cyclohexadien-1-yl[[(4-ethyl-2,3-dioxo-1-piperazinyl)carbonyl]-amino]acetyl]amino]-2-oxo-1-azetidinesulfonic acid, potassium salt; melting point 185° C., dec. |
| 108 | (R)—α-[[[2,3-dioxo-4-[(phenylmethylene)amino]-1-piperazinyl]carbonyl]amino]-4-hydroxybenzeneacetic acid | [3S(R*)]—3-[[[[[2,3-dioxo-4-[(phenylmethylene)-amino]-1-piperazinyl]carbonyl]amino](4-hydroxyphenyl)acetyl]amino]-2-oxo-1-azetidinesulfonic acid, potassium salt; melting point 194–197° C., dec. |
| 109. | (Z)—2-amino-α-[(1-methylethoxy)imino]-4-thiazoleacetic acid | [3S(Z)]—3-[[(2-amino-4-thiazolyl)[(1-methylethoxy)imino]acetyl]amino]-2-oxo-1-azetidinesulfonic acid, potassium salt; melting point 195° C., dec. |
| 110. | (Z)—2-amino-α-(phenoxyimino)-4-thiazoleacetic acid | [3S(Z)]—3-[[(2-amino-4-thiazolyl) (phenoxyimino)-acetyl]amino]-2-oxo-1-azetidinesulfonic acid, potassium salt; melting point 165° C., dec. |
| 111. | (R)—α-[[[3-[[(4-hydroxyphenyl) methylene]-amino]-2-oxo-1-imidazolidinyl]carbonyl]-amino]benzeneacetic acid | [3S(R*)]—3-[[[[[3-[[(4-hydroxyphenyl)methylene]-amino]-2-oxo-1-imidazolidinyl]carbonyl]amino]-phenylacetyl]amino]-2-oxo-1-azetidinesulfonic acid, potassium salt; melting point 236° C., dec. |
| 112. | (R)—α-[[[2-oxo-3-[(4-pyridinylmethylene)amino]-1-imidazolidinyl]carbonyl]amino]benzeneacetic acid | [3S(R*)]—2-oxo-3-[[[[2-oxo-3-[(4-pyridinyl-methylene) amino]-1-imidazolidinyl]carbonyl]-amino]-phenylacetyl]amino]-1-azetidinesulfonic acid, potassium salt; melting point 230° C., dec. |
| 113. | (Z)—2-amino-α-[[1-methyl-2-oxo-2-(phenylmethoxy)ethoxy]imino]-4-thiazoleacetic acid | [3S(Z)]—3-[[(2-amino-4-thiazolyl)[[1-methyl-2-oxo-2-(phenylmethoxy)ethoxy]imino]acetyl]amino]-2-oxo-1-azetidinesulfonic acid, potassium salt; melting point 110–115° C., dec. |
| 114. | (Z)—2-amino-α-[(cyclopentyloxy)imino]-4-thiazoleacetic acid | 3S(Z)]—3-[[(2-amino-4-thiazolyl)[(cyclo-pentyloxy)imino]acetyl]amino]-2-oxo-1-azetidinesulfonic acid, potassium salt; melting point 200° C., dec. |
| 115. | (R)—α-[[1-oxo-2-[[(phenylmethoxy)carbonyl]-amino]ethyl]amino]benzeneacetic acid | [3S(R*)]—2-oxo-3-[[phenyl[[[[(phenyl-methoxy)carbonyl]amino]acetyl]amino]-acetyl]amino]-1-azetidinesulfonic acid, potassium salt; melting point 260° C., dec. |
| 116. | 2-furanacetic acid | (S)—3-[(2-furanylacetyl)amino]-2-oxo-1-azetidinesulfonic acid, potassium salt; melting point 110° C., dec. |
| 117. | (R)—α-[[(2-oxo-3-pheynl-1-imidazolidinyl)-carbonyl[amino[benzeneacetic acid | (3S)—2-oxo-3-[[[[(2-oxo-3-phenyl-1-imidazolidinyl)carbonyl]amino]phenyl-acetyl]amino]-1-azetidinesulfonic acid, potassium salt; melting point 217–222° C., dec. |
| 118. | (R)—α-[[[2-oxo-3-(phenylmethyl)-1- | [3S(R*)]—2-oxo-3-[[[[[2-oxo-3-(phenylmethyl)- |

-continued

| | Column I | Column II |
|---|---|---|
| | imidazolidinyl]carbonyl]amino]benzeneacetic acid | 1-imidazolidinyl]carbonyl]amino]phenylacetyl]-amino]-1-azetidinesulfonic acid, potassium salt; melting point 195–200° C. |
| 119. | α-[[[3-[(2-furanylmethylene)amino]-2-oxo-1-imidazolidinyl]carbonyl]amino]-4-hydroxybenzeneacetic acid | (3S)—3-[[[[[3-[(2-furanylmethylene)amino]-2-oxo-1-imidazolidinyl]carbonyl]amino](4-hydroxyphenyl)acetyl]amino]-2-oxo-1-azetidinesulfonic acid, potassium salt; melting point 244° C., dec. |
| 120. | (R)—α-[[[3-[[3-(2-furanyl)-2-propenylidene]-amino]-2-oxo-1-imidazolidinyl]carbonyl]-amino]benzeneacetic acid | [3S(R*)]—3-[[[[[3-[[3-(2-furanyl)-2-propenylidene]amino]-2-oxo-1-imidazolidinyl]-carbonyl]amino]phenylacetyl]amino]-2-oxo-1-azetidinesulfonic acid, potassium salt; melting point 195° C., dec. |
| 121. | (Z)—2-amino-α-[[[(ethylamino)carbonyl]oxy]-imino]-4-thiazoleacetic acid | [3S(Z)]—3-[[(2-amino-4-thiazolyl)[[[(ethyl-amino)carbonyl]oxy]imino]acetyl]amino]-2-oxo-1-azetidinesulfonic acid, potassium salt; melting point 230° C., dec. |
| 122. | (R)—α-[[[2,3-dioxo-4-(phenylmethyl)-1-piperazinyl]carbonyl]amino]benzeneacetic acid | [3S(R*)]—3-[[[[[2,3-dioxo-4-(phenylmethyl)-1-piperazinyl]carbonyl]amino]phenylacetyl]-amino]-2-oxo-1-azetidinesulfonic acid, potassium salt; melting point 158–159° C., dec. |
| 123. | (R)—α-[[[4-(1-methylethyl)-2,3-dioxo-1-piperazinyl]carbonyl]amino]benzeneacetic acid | [3S(R*)]—3-[[[[[4-(1-methylethyl)-2,3-dioxo-1-piperazinyl]carbonyl]amino]phenyl-acetyl]amino]-2-oxo-1-azetidinesulfonic acid, potassium salt; melting point 185–187° C. |
| 124. | (Z)—α-(methoxyimino)-2-furanacetic acid | [3S(Z)]—3-[[(2-furanyl)(methoxyimino)-acetyl]amino-2-oxo-1-azetidinesulfonic acid, potassium salt; melting point 160° C., dec. |
| 125. | (R)—α-[[[3-[[(dimethylamino)methylene]-amino]-2-oxo-1-imidazolidinyl]carbonyl]-amino]benzeneacetic acid | [3S(R*)]—3-[[[[[3-[[(dimethylamino)-methylene]amino]-2-oxo-1-imidazolidinyl]-carbonyl]amino]phenylacetyl]amino]-2-oxo-1-azetidinesulfonic acid, potassium salt; melting point 195° C., dec. |
| 126. | (R)—α-[[(3-ethyl-2-oxo-1-imidazolidinyl)-carbonyl]amino]benzeneacetic acid | [3S(R*)]—3-[[[[(3-ethyl-2-oxo-1-imidazolidinyl]carbonyl]amino]phenyl-acetyl]amino]-2-oxo-1-azetidinesulfonic acid, potassium salt; melting point 185–190° C., dec. |
| 127. | (R)—α-[[[[[(4-methoxyphenyl) methoxy]carbonyl]-amino]acetyl]amino]benzeneacetic acid | [3S(R*)]—3-[[[[[[(4-methoxyphenyl)-methoxy]carbonyl]amino]acetyl]amino]-phenylacetyl]amino]-2-oxo-1-azetidine-sulfonic acid, potassium salt; melting point 268° C., dec. |
| 128. | (R)—α-[[[2-oxo-3-[[(phenymethoxy)carbonyl]-amino]-1-imidazolidinyl]carbonyl]amino]-benzeneacetic acid | [3S(R*)]—2-oxo-3-[[[[[2-oxo-3-[[(phenyl-methoxy)carbonyl]amino]-1-imidazolidinyl]-carbonyl]amino]phenylacetyl]amino]-1-azetidinesulfonic acid, potassium salt; melting point 175° C., dec. |
| 129. | (Z)—2-amino-α-[(2-amino-1,1-dimethyl-2-oxoethoxy)imino]-4-thiazoleacetic acid | [3S(Z)]—3-[[[(2-amino-1,1-dimethyl-2-oxo-ethoxy)-imino](2-amino-4-thiazolyl)acetyl]-amino]-2-oxo-1-azetidinesulfonic acid, potassium salt; melting point 210° C., dec. |
| 130. | (R)—α-[[[4-(1-methylethyl)-2,3-dioxo-1-piperazinyl]carbonyl]amino]-4-hydroxybenzene-acetic acid | [3S(R*)]—3-[[[[[4-(1-methylethyl)-2,3-dioxo-1-piperazinyl]carbonyl]amino](4-hydroxyphenyl)acetyl]amino]-2-oxo-1-azetidinesulfonic acid, potassium salt; melting point 201–203° C., dec. |
| 131. | (R)—α-[[[3-(1-methylethyl)-2-oxo-1-imidazolidinyl]carbonyl]amino]benzeneacetic acid | [3S(R*)]—3-[[[[[3-(1-methylethyl)-2-oxo-1-imidazolidinyl]carbonyl]amino]phenyl-acetyl]amino]-2-oxo-1-azetidinesulfonic acid, potassium salt; melting point 195–200° C., dec. |
| 132. | (Z)—2-amino-α-[[2-(diphenylmethoxy)-1-methyl-2-oxoethoxy]imino]-4-thiazoleacetic acid | [3S(Z)]—3-[[(2-amino-4-thiazolyl)[[2-(diphenylmethoxy)-1-methyl-2-oxoethoxy]-imino]acetyl]amino]-2-oxo-1-azetidine-sulfonic acid potassium salt; melting point 145–150° C. |
| 133. | 5-methyl-3-phenyl-4-isoxazolecarboxylic acid | (S)—3-[[(5-methyl-3-phenyl-4-isoxazolyl)-carbonyl]amino]-2-oxo-1-azetidinesulfonic acid, potassium salt; melting point 230–232° C., dec. |

EXAMPLE 134–135

Following the procedure of Example 70, but substituting the compound listed in column I for [3S(Z)]-3-[[(2-amino-4-thiazoly)[[2-diphenylmethoxy)-2-oxoethoxy[imino]acetyl]amino]-2-oxo-1-azetidinesulfonic acid, potassium salt, yields the compound listed in column II.

| | Column I | Column II |
|---|---|---|
| 134. | [3S(Z)]—3-[[(2-amino-4-thiazolyl)[[2-(1,1-dimethylethoxy)-1-(methylthio)-2-oxoethoxy]-imino]acetyl]amino]-2-oxo-1-azetidine-sulfonic acid, potassium salt (see Example 79) | [3S(Z)]—3-[[(2-amino-4-thiazolyl)[[carboxy-(methylthio)methoxy]imino]acetyl]amino]-2-oxo-1-azetidinesulfonic acid, potassium salt (1:2); melting point 165° C., dec. |
| 135. | [3S(R*)]—2-oxo-3-[[[[[2-oxo-3-[[(phenylmethoxy)-carbonyl]amino]-1-imidazolidinyl]carbonyl]-amino]phenylacetyl]amino]-1-azetidinesulfonic acid, potassium salt (see Example 128) | 3(S)—3-[[[[(3-amino-2-oxo-1-imidazolidinyl)-carbonyl]amino]phenylacetyl]amino]-2-oxo-1-azetidinesulfonic acid, potassium salt; melting point 250° C., dec. |

EXAMPLE 136

[3α(Z),4α]-3-[[(2-Amino-4-thiazolyl)(methoxyimino)acetyl]amino]-4-methyl-2-oxo-1-azetidinesulfonic acid, potassium salt A solution of 51.8 mg of (cis)-4-methyl-2-oxo-3-[[(phenylmethoxy)carbonyl]amino]-1-azetidinesulfonic acid, potassium salt and 51 mg of tetra-n-butylammonium bisulfate in 5 ml of water is extracted with methylene chloride (four 10 ml portions) to give 81 mg of oil. This is stirred in an atmosphere of hydrogen for 2 hours with 40 mg of 10% palladium on charcoal in 4 ml of dimethylformamide. The catalyst is filtered and washed with 1 ml of dimethylformamide. The filtrate and washings are combined and stirred for about 16 hours with 31 mg of (Z)-2-amino-α-(methoxyimino)-4-thiazoleacetic acid, 27 mg of N-hydroxybenzotriazole, and 31.5 mg of dicyclohexylcarbodiimide. The solution is evaporated in vacuo and the residue triturated with 3 ml of acetone. The resulting slurry is centrifuged and the liquid treated with 51 mg of potassium perfluorobutanesulfonate. Dilution with 5 ml of ether and filtration gives a solid. Chromatography on HP-20 AG (40 ml) gives Rydon positive material in fractions (20 ml) 3-5 (elution with water). Evaporation and ether trituration gives 23 mg of product.

Analysis calc'd for $C_{10}H_{12}N_5O_6S_2K$: C, 29.91; H, 3.01; N, 17.44. Found: C, 29.30; H, 3.31; N, 16.66.

EXAMPLE 137

(3S-cis)-3-Amino-4-methyl-2-oxo-1-azetidinesulfonic acid

(A)

t-Boc-1-allothreonine

A suspension of 6.72 g of 1-allothreonine in 70 ml of 50% aqueous dioxane is treated with 9.45 ml of triethylamine and 18.1 g of t-butylpyrocarbonate. The resulting mixture is stirred at room temperature for 4 hours, and then diluted with 70 ml of water and 140 ml of ethyl acetate. After thorough shaking, the layers are separated and the organic layer is washed with 30 ml of 2:1 water:brine. Combined aqueous layers are then back-extracted with 70 ml of ethyl acetate. The aqueous layer is cooled in an ice bath and 10% potassium bisulfite solution is added to pH 2.3. The acidified solution is extracted with ethyl acetate (four 150 ml portions). Combined organic layers are dried over anhydrous sodium sulfate and stripped of solvent to give 9.13 g of the title compound.

(B)

N-Methoxy-t-boc-1-allothreonine amide t-Boc-1-allothreonine (9.13 g) is dissolved in 85 ml of water and 41 ml of 1N potassium hydroxide solution. Methoxyamine hydrochloride (5.22 g) and 8.67 g of 1-ethyl-3,3-(dimethylaminopropyl)carbodiimide.HCl are added. The mixture is stirred at room temperature for 4 hours and then saturated with sodium potassium tartarate. The resulting mixture is extracted with ethyl acetate (four 150 ml portions) and the organic layer is dried over anhydrous sodium sulfate and stripped of solvent to give 7.38 g of the title compound as a solid.

(C)

O-Methanesulfonyl-N-methoxy-t-boc-1-allothreonine amide

N-Methoxy-t-boc-1-allothreonine amide (7.32 g) is dissolved in 40 ml of pyridine and cooled to −20° C. under nitrogen. Methanesulfonyl chloride (3 ml) is added dropwise by syringe over a 5-minute period. The resulting mixture is slowly warmed to 0° C. and stirred at that temperature for 3 hours. Ethyl acetate (500 ml) is added and the solution washed with 250 ml of ice-cold 3N HCl solution, then 100 ml of 5% NaHCO$_3$ solution. The ethyl acetate layer was dried over anhydrous sodium sulfate and stripped of solvent to give 8.64 g of the title compound as a white solid.

(D)

(3S-cis)-3-t-Butoxycarbonylamino-1-methoxy-4-methylazetidinone

O-Methanesulfonyl-N-methoxy-t-boc-1-allothreonine amide (8.64 g) is dissolved in 530 ml of acetone and 11 g of solid potassium carbonate is added. The mixture is slowly heated to 65° C. under nitrogen and stirred at this temperature for one hour. The reaction mixture is then filtered through Celite and the filter cake is washed with ethyl acetate. The filtrate is concentrated and the residue is taken up in 250 ml of ethyl acetate. The ethyl acetate solution is washed with 100 ml of 1N hydrochloric acid solution and 100 ml of 5% sodium bicarbonate solution. The ethyl acetate layer is dried over anhydrous sodium sulfate and stripped of solvent to give 6.63 g of crude product.

(E)

(3S-cis)-3-t-Butoxycarbonylamino-4-methylazetidinone

Sodium (1.35 g) is dissolved in about 300 ml of liquid ammonia at −50° C. and 5.87 g of (3S-cis)-3-t-Butoxycarbonylamino-1-methoxy-4-methylazetidinone in 35 ml tetrahydrofuran is added dropwise via syringe. An additional 10 ml of tetrahydrofuran is used for rinsing. Near the end of the addition about 100 mg of additional sodium is added. The mixture is stirred for five more minutes, then quenched by adding 3.35 g of solid ammonium chloride in one portion. Ammonia is blown off with a nitrogen stream and 250 ml of ethyl acetate is added to the residue. After filtration and washing the solid with ethyl acetate, the combined filtrate is stripped of solvent to give 4.82 g of the title compound.

(F)

(3S-cis)-3-t-Butoxycarbonylamino-4-methyl-2-oxo-1-azetidinesulfonic acid, tetrabutyl ammonium salt

[3S,4R]-3-t-Butoxycarbonylamino-4-methylazetidinone (4.98 g) is dissolved in 30 ml of dimethylformamide. Pyridine-sulfur trioxide complex 11.9 g is added and the mixture is stirred at room temperature under nitrogen. After 14 hours stirring, an additional 1.8 g of pyridine-sulfur trioxide complex is added and stirring is continued for 80 hours. The reaction mixture is poured into 700 ml of 0.5M monobasic potassium phosphate solution and washed with methylene chloride (three 300 ml portions). tetra-n-Butylammonium bisulfate (8.45 g) is added to the aqueous solution and the mixture is extracted with methylene chloride (four 300 ml portions). The combined methylene chloride layers are dried over anhydrous sodium sulfate and stripped of solvent to give 10.76 g of the title compound as a gum.

(G)

(3S-cis)-3-Amino-4-methyl-2-oxo-1-azetidinesulfonic acid (3S-cis)-3-t-Butoxycarbonylamino-4-methyl-2-oxo-1-azetidinesulfonic acid, tetrabutyl ammonium salt (10.76 g) is dissolved in 50 ml of 95–97% formic acid and stirred for 4 hours under nitrogen. A small amount of product from a previous reaction is added as seed and the mixture is stirred for one more hour. The mixture is stored in the freezer for about 16 hours and the frozen mixture is warmed to room temperature and stirred for an additional hour. The solid formed is filtered and washed with methylene chloride to yield 982 mg of the title compound. The filtrate is diluted with 1 liter of methylene chloride and kept at −20° C. for 4 hours. The precipitate that forms is recrystallized from water-methanol-acetone to give an additional 167 mg of title compound.

EXAMPLE 138

[3-S-[3α(Z),4α]]-3-[[2-Amino-4-thiazolyl)methoxyimino)acetyl]amino-4-methyl-2-oxo-1-azetidinesulfonic acid, potassium salt A solution of 201 mg of (Z)-2-amino-α-(methoxyimino)-4-thiazolacetic acid and 153 mg of N-hydroxybenzotriazole monohydrate in 3 ml of dimethylformamide is treated with 206 mg of dicyclohexylcarbodiimide. The mixture is stirred at room temperature for 20 minutes under nitrogen and a solution of 180 mg of (3S-cis)-3-amino-4-methyl-2-oxo-1-azetidinesulfonic acid and 0.14 ml of triethylamine in 2 ml of dimethylformamide is added (an additional 1 ml of dimethylformamide is used for rinsing) and the mixture is stirred for about 16 hours. The slurry is evaporated in vacuo, triturated with 12 ml of acetone, centrifuged and the liquid treated with 338 mg of potassium perfluorobutanesulfonate. Dilution with 10 ml of ether and filtration gives a solid product which is chromatographed on 200 ml of HP-20 resin eluting with water. Fractions (20 ml each) 18–30 are combined and lyophilized to give 274 mg of the title compound as a solid.

Anal. calc'd. for $C_{10}H_{12}N_5O_6S_2K$: C, 29.91; H, 3.01; N, 17.44. Found: C, 30.03; H, 3.21; N, 17.06.

EXAMPLE 139

(3S-trans)-3-Amino-4-methyl-2-oxo-1-azetidinesulfonic acid (A)

Threonine, methyl ester, hydrochloride

Under an atmosphere of nitrogen, a flask containing 500 ml of methanol is cooled to −5° C. (ice/brine) and 130 ml (excess) of thionyl chloride is added at such a rate as to maintain the reaction temperature between 0° and 10° C. After recooling to −5° C., 59.5 g of l-threonine is added and the mixture is allowed to reach room temperature and stirred for 16 hours. The mixture is concentrated and evacuated at $10^{-1}$ torr for 2 hours to yield a viscous oil. This material is used directly in the following step.

(B)

Threonine amide

The crude product from part A is dissolved in 2.5 l of methanol and cooled to −5° C. (ice/brine). The solution is saturated with ammonia gas, the cooling bath is removed and the sealed vessel is allowed to stand for 3 days. After removing the bulk of the unreacted ammonia via aspirator, 100 g of sodium bicarbonate and 50 ml of water is added and the mixture is stripped to a viscous oil.

(C)

Benzyloxycarbonylthreonine amide

The crude product from part B (already containing the requisite amount of sodium bicarbonate is diluted to a volume of 1 liter with water. To this rapidly stirring solution, 94 g (88 ml of 90% pure material) of benzyloxycarbonyl chloride is added as a solution in 80 ml of tetrahydrofuran over a 1 hour period. The reaction mixture is then stirred for an additional 16 hours and extracted with ethyl acetate (one 500 ml portion, two 250 ml portions). The combined extracts are dried over magnesium sulfate and concentrated. The crystalline residue is then dissolved in 250 ml of hot ethyl acetate and 300 ml of hexane is added followed by boiling until a clear solution is reached. Cooling and filtration of the crystalline mass give, after drying, 104 g of the title compound.

(D)

Benzyloxycarbonylthreonine amide, O-mesylate

Under an atmosphere of argon, 100 g of benzyloxycarbonylthreonine amide is dissolved in 400 ml of anhydrous pyridine and cooled in an ice/salt bath. To this stirring solution, 36.8 ml (54.5 g) of methanesulfonyl chloride is added over a 15 minute period. After 2 hours of stirring an additional 0.3 equivalents of methanesulfonyl chloride is added. The reaction is stirred for 1 hour and poured into a mixture of 1.5 l of ice and 2 l of water. The resulting slurry is stirred for about 30 minutes and filtered. Drying of the crude product at 60° C. for about 16 hours in a vacuum oven gives 109 g of the title compound.

(E)

N-Sulfonyl benzyloxycarbonylthreonine amide, O-mesylate, tetrabutylammonium salt A solution of 2-picoline (17.8 ml) in 90 ml of methylene chloride is cooled to −5° C. (ice-brine) and chlorosulfonic acid 5.97 ml is added at such a rate as to maintain the internal reaction temperature below 5° C. The resulting solution is added via canula, to a suspension of 7.56 g of benzyloxycarbonylthreonine amide, O-mesylate in 120 ml of methylene chloride. The resulting heterogeneous mixture is refluxed for about 16 hours yielding a clear solution. The solution is poured into 500 ml of pH 4.5 phosphate buffer (0.5M) and further diluted with 120 ml of methylene chloride. The separated organic layer is then washed once with 100 ml of buffer solution with the combined aqueous phases are treated with 10.2 g of tetra-n-butylammonium hydrogensulfate and extracted with methylene chloride (one 300 ml portion and two 150 ml portions). After drying the combined organic extracts over sodium sulfate, the solution is concentrated to yield 12.7 g of a foam.

(F)

(3S-trans)-3-Amino-4-methyl-2-oxo-1-azetidinesulfonic acid

A mixture consisting of 5.52 g of potassium carbonate in 20 ml of water and 160 ml of 1,2-dichloroethane is brought to reflux and 15.5 mmole of N-sulfonyl benzyloxycarbonylthreonine amide, O-mesylate, tetrabutylammonium salt is added in 20 ml of 1,2-dichloroethane (20 ml used as a rinse). After refluxing for 30 minutes, the mixture is poured into a separatory funnel, diluted with 50 ml of water and 100 ml of methylene chloride and the phases split. The resulting organic phase is dried over sodium sulfate and concentrated to yield crude (3S-trans)-3-benzyloxycarbonylamino-4-methyl-2-oxo-1-azetidinesulfonic acid, tetrabutylammonium salt. The crude azetidinone is treated in 250 ml of ethanol with 0.8 g of 5% palladium on charcoal catalyst and hydrogen is bubbled through the solution. After 90 minutes the mixture is filtered through Celite with 50 ml of ethanol used as a rinse. The addition of 1.2 ml of formic acid to this solution causes an immediate precipitation of the title zwitterion which is filtered after stirring for 1 hour to yield, after drying at 10$^{-1}$ torr for 1 hour, 1.1 g of product. A second crop of product is obtained upon concentration of the filtrate and addition of more formic acid to give 1.3 g of the title zwitterion.

EXAMPLES 140-143

Following the procedure of Example 138, but substituting (3S-trans)-3-amino-4-methyl-2-oxo-1-azetidinesulfonic acid for (3S-cis)-3-amino-4-methyl-2-oxo-1-azetidinesulfonic acid and the acid listed in column I for (Z)-2-amino-α-(methoxyimino)-4-thiazoleacetic acid, yields the compound listed in column II.

| | | |
|---|---|---|
| 140. | (R)—α-[[[3-[(2-furanylmethylene)amino]-2-oxo-1-imidazolidinyl]-carbonyl]amino]-benzeneacetic acid | [3S—[3α(R*),4β]]-3-[[[[3-[(2-furanyl-methylene)amino]-2-oxo-1-imidazolidinyl]-carbonyl]amino]phenylacetyl]amino]-4-methyl-2-oxo-1-azetidinesulfonic acid, potassium salt; melting point 213° C., dec. |
| 141. | (R)—α-[[(4-ethyl-2,3-dioxo-1-piperazinyl)-carbonyl]amino]benzeneacetic acid | [3S—[3α(R*),4β]]-3-[[[[(4-ethyl-2,3-dioxo-1-piperazinyl)carbonyl]amino]phenylacetyl]-amino]-4-methyl-2-oxo-1-azetidinesulfonic acid, potassium salt; melting point 177° C., dec. |
| 142. | (Z)—2-amino-α-(hydroxyimino)-4-thiazole-acetic acid | [3S—3α(Z),4β]]-3-[[(2-amino-4-thiazolyl)-(hydroxyimino)acetyl]amino]-4-methyl-2-oxo-1-azetidinesulfonic acid, potassium salt; melting point 230° C. |
| 143. | (±)-α-[(aminooxoacetyl)amino]-2-thio-pheneacetic acid | [3S—[3α(±),4β]]-3-[[[(aminooxoacetyl)amino]-2-thienylacetyl]amino]-4-methyl-2-oxo-1-azetidine-sulfonic acid, potassium salt; melting point 135° C., dec. |

EXAMPLE 144

[3S-[3α(Z),4β]]-3-[[(2-Amino-4-thiazolyl)[[1,1-dimethyl-2-[(4-nitrophenyl)methoxy]-2-oxoethoxy]imino]acetyl]amino]-4-methyl-2-oxo-1-azetidinesulfonic acid, potassium salt To a slurry of (3S-trans)-3-amino-4-methyl-2-oxo-1-azetidinesulfonic acid (0.36 g; see example 139) in dry dimethylformamide (30 ml) under nitrogen at 26° C. is added triethylamine (309 μl). After about 5 minutes a clear solution is obtained and (Z)-2-amino-α-[[1,1-dimethyl-2-[(4-nitrophenyl)methoxy]-2-oxoethoxy]imino]-4-thiazoleacetic acid (0.816 g) is added followed by N-hydroxybenzotriazole (0.334 g) and dicyclohexylcarbodiimide (0.453 g). The mixture is stirred for twelve hours at 26° C., whereupon the solvent is removed in vacuo, and the residue is triturated with acetone (30 ml). After stirring five minutes, the solids are removed and the filtrate is treated with potassium perfluorobutane sulfonate (3.680 g) in acetone, (5 ml). Addition of ether (approximately 40 ml) affords a precipitate which is collected and dried in vacuo (1.073 g; second crop 0.066 g; total of 1.14 g).

Anal. calc'd. for $C_{20}H_{21}N_6O_{10}S_2K \cdot 1H_2O$: C, 38.33; H, 3.70; N, 13.41; S, 10.23; K, 6.24. Found: C, 38.30; H, 3.63; N, 13.41; S, 9.88; K, 5.98.

EXAMPLE 145

[3α(Z),4α]-3-[[(2-Amino-4-thiazolyl)[(1-carboxy-1-methylethoxy)imino]acetyl]amino]-4-methyl-2-oxo-1-azetidinesulfonic acid, potassium salt (1:2)

(A)

[3α(Z),4α]-3-[[2-Amino-4-thiazolyl)[(1-diphenylmethoxycarbonyl-1-methylethoxy)imino]acetyl]amino]-4-methyl-2-oxo-1-azetidinesulfonic acid, potassium salt A solution of (cis)-4-methyl-2-oxo-3-[[(phenylmethoxy)carbonyl]amino]-1-azetidinesulfonic acid, tetrabutylammonium salt (201 mg.; prepared from the corresponding potassium salt of example 98 as described in example 136) in 5 ml of dimethylformamide is stirred with 90 mg of 10% palladium on calcium carbonate in an atmosphere of hydrogen for 2 hours. The slurry is filtered and the filtrate is stirred for about 16 hours with 146 mg of (Z)-2-amino-α-[1-diphenylmethoxycarbonyl-1-methylethoxy)imino]-4-thiazoleacetic acid, 73 mg of dicyclohexylcarbodiimide and 51 mg of N-hydroxybenzotriazole under nitrogen. The slurry is evaporated in vacuo and triturated with 4 ml of acetone. The slurry is filtered and the solid washed twice with 2 ml portions acetone. The filtrate and washings are combined and treated with 113 mg of potassium perfluorobutanesulfonate. Dilution with 24 ml of ether gives a solid that is isolated by centrifugation and washed three times with ether yielding 186 mg of the title compound.

(B)

[3α(Z),4α]-3-[[(2-Amino-4-thiazolyl)[1-carboxy-1-methylethoxy]imino]acetyl]amino]-2-methyl-4-oxo-1-azetidinesulfonic acid, potassium salt (1:2)

A slurry of 186 mg of [3α(Z),4α]-3-[[2-amino-4-thiazolyl)[(1-diphenylmethoxycarbonyl-1-methylethoxy)imino]acetyl]amino]-4-methyl-2-oxo-1-azetidinesulfonic acid, potassium salt in 0.6 ml of distilled anisole is cooled to −12° C. and 3.0 ml of distilled trifluoroacetic acid (at −10° C.) is added. The solution is stirred for 10 minutes and 12 ml of ether followed by 6 ml of hexane are added. After 5 minutes at −10° C. and stirring for 15 minutes at ambient temperature, the solid is isolated by centrifugation and washed four times with ether to give 141 mg of material. This is dried in vacuo, powdered, dissolved in 5 ml of cold water and immediately adjusted to pH 5.6 with 0.4N potassium hydroxide. The solution is applied to a 100 ml HP-20AG column and eluted with water. Fractions (10 ml) 8–12 are combined and evaporated in vacuo (acetonitrile is added three times and evaporated. The residue is triturated with ether to give 101.7 mg of product.
Anal. Calc'd for $C_{13}N_{15}N_5O_8S_2.2K$: C, 30.51; H, 2.95; N, 13.69; S, 12.53; K, 15.28. Found: C, 30.11; H, 3.26; N, 13.35; S, 12.12; K, 15.02.

EXAMPLE 146

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid

[3S-[3α(Z),4β]]-3-[[(2-Amino-4-thiazolyl)[(1-carboxy-1-methylethoxy)imino]acetyl]amino]-4-methyl-2-oxo-1-azetidinesulfonic acid, dipotassium salt (87.3 mg; see example 103) is dissolved in 1.38 ml of water, cooled to 0° C., treated with 0.34 ml of 1N hydrochloric acid and the resulting crystals separated by centrifugation. The wet solid is dissolved in methanol, filtered, concentrated to about 0.5 ml and mixed with 1 ml of water, giving 55.9 mg of the title compound.

EXAMPLE 147

[3S-[3α(Z),4β]]-3-[[(2-Amino-4-thiazolyl)[(1-carboxy-1-methylethoxy)imino]-4-methyl-2-oxo-1-azetidinesulfonic acid, sodium salt A 99.7 mg sample of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid (see example 146) is mixed with 0.207 ml of 1N sodium hydroxide and the resulting mixture is gently warmed to dissolve the remaining solid. Water is removed azeotropically with acetonitrile and the residue is crystallized from a mixture of 0.5 ml of methanol (to dissolve the residue) and 1 ml of acetonitrile, giving 81.8 mg of solid. A second recrystallization from 0.8 ml of methanol gives 47.9 mg, a third from 0.24 ml of methanol and 0.24 ml of absolute ethanol gives 44.8 mg, and a fourth from 0.225 ml of methanol and 0.225 ml of absolute ethanol gives 38.8 mg. The solid is dried at 20° C. and 0.01 mm of Hg for 18 hours and then equilibrated with atmospheric moisture for 24 hours, giving 40.9 mg of the title compound.

EXAMPLE 148

[3S-[3α(Z),4β]]-3-[[(2-Amino-4-thiazolyl)[(1-carboxy-1-methylethoxy)imino]-4-methyl-2-oxo-1-azetidinesulfonic acid, disodium salt A 3.00 g sample of [3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid, (see example 146), is suspended in 30 ml of water and titrated with 1N sodium hydroxide requiring 12.0 ml to give the title disodium salt. The pH is reduced to 6.5 by the addition of a little Dowex 50W-X2 (H+). The mixture is filtered and the filtrate diluted to 66.3 g with water. A 6.63-g portion is removed for other purposes. The remaining filtrate is lyophilized, giving 2.38 g of solid. Partial equilibration (24 hours) with atmosphereic moisture gives 2.54 g of the title compound.

EXAMPLES 149–151

Following the procedure of Example 138, but substituting the compound listed in column I for (Z)-2-amino-α-(methoxyimino)-4-thiazoleacetic acid, yields the compound listed in column II.

|  | Column I | Column II |
| --- | --- | --- |
| 149. | (R)—α-[[[2,3-dioxo-4-[[(phenylmethoxy)-carbonyl]amino]-1-piperazinyl]carbonyl]-amino]benzeneacetic acid | [3S—[3α(R*),4α]]-[4-[[[2-[(4-methyl-2-oxo-1-sulfo-3-azetidinyl)amino]-2-oxo-1-phenylethyl]amino]carbonyl]-2,3-dioxo-1-piperazinyl]carbamic acid, phenylmethyl ester, potassium salt, melting point 191° C., dec. |
| 150. | (R)—α-[[[[(2-furanylmethylene)amino]-2-oxo-imidazolidinyl]carbonyl]amino]benzeneacetic acid | [3S—[3α(R*),4α]]-3-[[[[3-[(2-furanylmethylene)-amino]-2-oxo-1-imidazolidinyl]carbonyl]-amino]phenylacetyl]amino]-4-methyl-2-oxo-1-azetidinesulfonic acid, potassium salt |
| 151. | (R)—α-[[(4-ethyl-2,3-dioxo-1-piperazinyl)-carbonyl]amino]benzeneacetic acid | [3S—[3α(R*),4α]]-3-[[[[(4-ethyl-2,3-dioxo-1-piperazinyl)carbonyl]amino]phenylacetyl]-amino]-4-methyl-2-oxo-1-azetidinesulfonic acid, potassium salt |

EXAMPLE 152

[3S-[3α(Z),4α]]-3-[[(2-Amino-4-thiazolyl)[(1-carboxy-1-methylethoxy)imino]acetyl]amino]-4-methyl-2-oxo-1-azetidinesulfonic acid, potassium salt (1:2)

(A)

[3S-[3α(Z),4α]]-3-[[(2-Amino-4-thiazolyl)[(1-diphenylmethoxycarbonyl-1-methylethoxy)imino]acetyl]amino]-4-methyl-2-oxo-1-azetidinesulfonic acid, potassium salt A solution of 440 mg of (Z)-2-amino-α-[(1-carboxy-1-methylethoxy)imino]-4-thiazoleacetic acid and 153 mg of N-hydroxybenzotriazole monohydrate in 3 ml of dimethylformamide is treated with 206 mg of dicyclohexylcarbodiimide. The mixture is stirred at room temperature for 30 minutes under nitrogen and a solution of 180 mg of (3S-cis)-3-amino-4-methyl-2-oxo-1-azetidinesulfonic acid, (see example 137) and 0.14 ml of triethylamine in 2 ml of dimethylformamide is added (an additional 1 ml of dimethylformamide is used for rinsing) and the mixture is stirred for about 16 hours. The slurry is evaporated in vacuo and triturated with 12 ml of acetone. The slurry is filtered and the solid washed with acetone (two 3 ml portions). The combined filtrate and washings are treated with 338 mg of potassium perfluorobutanesulfonate. Dilution with 30 ml of ether gives a gummy solid, which slowly solidifies. The solid is filtered and washed with ether to give 656 mg of the title compound.

(B)

[3S-[3α(Z),4α]]-3-[[(2-Amino-4-thiazolyl)[(1-carboxy-1-methylethoxy)imino]acetyl]amino]-4-methyl-2-oxo-1-azetidinesulfonic acid, potassium salt (1:2)

A slurry of 656 mg of [3S-[3α(Z),4α]]-3-[[(2-Amino-4-thiazolyl)[(1-diphenylmethoxycarbonyl-1-methylethoxy)imino]acetyl]amino]-4-methyl-2-oxo-1-azetidinesulfonic acid, potassium salt in 2.3 ml of distilled anisole is cooled to −12° C. and 11.5 ml of trifluoroacetic acid (precooled to −10° C.) is added. The solution is stirred for 15 minutes and 46 ml of ether followed by 23 ml of hexane are added. After 5 minutes at −10° C. and stirring for 15 minutes at room temperature, the solid is filtered and washed with ether to give 457 mg of a very hydroscopic gum. This is dissolved in 6 ml of cold water and immediately adjusted to pH 5.6 with 0.4N potassium hydroxide solution. The solution is applied to a 200 ml HP-20 resin and eluted with water. Fractions (50 ml each) 7-11 are combined and lyophilized to give 239 mg of the title compound as a solid.

Anal. Calc'd. for $C_{13}H_{15}O_8N_5S_2K_2 \cdot \frac{1}{2}H_2O$: C, 29.99; H, 3.10; N, 13.45; S, 12.32. Found: C, 29.94; H, 3.30; N, 13.30; S, 11.93.

EXAMPLE 153

(±)-3-Amino-4,4-dimethyl-2-oxo-1-azetidinesulfonic acid (A)

(±)-4,4-Dimethyl-2-oxo-1-azetidine-tertbutyldiphenylsilane

A solution of 40.5 ml of t-butylchlorodiphenylsilane in 112 ml of dimethylformamide is cooled to 0° C. To this is added 22 ml of triethylamine. A solution of 12.87 g of 4,4-dimethyl-2-azetidinone in 25 ml of dimethylformamide is added dropwise over 10 minutes to the cooled triethylamine solution. The resulting cloudy solution is stirred for 18 hours at 5° C. under argon. This mixture is poured into 400 ml of ice water and extracted with three 150 ml portions of 2:1 ether:ethyl acetate. The combined extracts are washed with four 100 ml portions of 0.5M monobasic potassium phosphate buffer, one 150 ml portion of sodium bicarbonate solution, two 150 ml portions of water and one 150 ml portion of saturated sodium chloride solution. The solution is dried over sodium sulfate and concentrated in vacuo to yield 33.03 g of the title compound as a solid.

(B)

(±)-3-azido-4,4-dimethyl-2-oxo-1-azetidine-tertbutyldiphenylsilane

A solution of 4.25 ml of 1.6M (in hexane) n-butyllithium and 11 ml of dry tetrahydrofuran is prepared at −50° C. under argon in a 100 ml three-necked flask. A solution of 0.083 g of triphenylmethane in 1 ml of tetrahydrofuran is added. The resulting solution is cooled to −60° C., and 1.0 ml of diisopropylamine is added dropwise by syringe. This is stirred for 15 minutes and then cooled to −78° C. A solution of 2.3 g of (±)-4,4-dimethyl-2-oxo-1-azetidine-tertbutyldiphenylsilane in 8 ml of tetrahydrofuran is added slowly by syringe. The resulting solution is stirred for 20 minutes at −78° C., during which time heavy precipitation occurs and uniform stirring becomes difficult. A solution of 1.33 g of p-toluenesulfonyl azide in 5 ml of tetrahydrofuran is added dropwise. The resulting mixture is allowed to stir at −78° C. for 20 minutes, and 2 ml of trimethylsilyl chloride is added dropwise. The reaction mixture is warmed to ambient temperature and stirred for 1 hour. Then the mixture is cooled to 0° C. and poured into 150 ml of 0° C. ethyl acetate. Enough 0.5M monobasic potassium phosphate buffer is added to make both the aqueous and organic layers clear. The two layers are separated and the organic layer is washed with three 150 ml portions of 0.5M monobasic potassium phosphate solution, one 150 ml portion of sodium chloride solution, one 150 ml portion of saturated sodium chloride solution and dried over sodium sulfate. The solution is concentrated in vacuo to 2.83 g of oil, which upon trituration with hexane yields 1.67 g of the title compound as a solid.

(C)

(±)-3-Azido-4,4-dimethyl-2-oxo-1-azetidine

In a 50 ml three-necked flask, 1.52 g of (±)-3-azido-4,4-dimethyl-2-oxo-1-azetidine-tertbutyldiphenylsilane is dissolved in 25 ml of acetonitrile. To this stirred solution is added 0.25 ml of 48% hydrofluoric acid. This is stirred at ambient temperature, and 0.5 ml portions of 48% hydrofluoric acid are added every 60 minutes until, after 6.5 hours, a total of 3.25 ml of 48% hydrofluoric acid has been added. The reaction mixture is then cooled to 0° C., neutralized with saturated sodium bicarbonate, and extracted with 120 ml of ethyl acetate. The organic layer is then washed with 100 ml of water, 100 ml of saturated sodium chloride solution, and dried over sodium sulfate. The dry solution is concentrated in vacuo to yield 1.34 g of oil. This impure oil is chromatographed on 27 g of silica gel with hexane, followed by 33% ethyl acetate in hexane, to yield 0.358 g of the title compound as a solid.

(D)

(±)-3-Azido-4,4-dimethyl-2-oxo-1-azetidinesulfonic acid, tetrabutylammonium salt To 0.100 g of (±)-3-azido-4,4-dimethyl-2-oxo-1-azetidine at 0° C. is added under argon 2.8 ml of 0.5M dimethylformamide-sulfur trioxide complex. This mixture is allowed to warm to ambient temperature and stir for 45 minutes. The solution is then poured into 20 ml of 0.5M pH 5.5 monobasic potassium phosphate buffer. This is washed with three 20 ml portions of methylene chloride (discarded) and 0.237 g of tetrabutylammonium hydrogen sulfate is added to the aqueous solution. This was extracted with four 20 ml portions of methylene chloride and the combined organic extracts are washed with 20 ml of 8% sodium chloride solution. The methylene chloride solution is dried (sodium sulfate) and concentrated in vacuo to yield 0.31 g of oil, which appeared by nmr to be 50% dimethylformamide and 50% of the title compound.

(E)

(±)-3-Amino-4,4-dimethyl-2-oxo-1-azetidinesulfonic acid

A solution of 0.155 g of (±)-3-azido-4,4-dimethyl-2-oxo-1-azetidinesulfonic acid, tetrabutylammonium in 0.6 ml of methanol is hydrogenated over 10% palladium on charcoal for 20 minutes at 1 atmosphere. The catalyst is filtered off and rinsed with methylene chloride which is combined with the methanol solution. This clear solution is treated with 0.123 ml 97% formic acid. Upon addition of the acid the solution immediately becomes cloudy. After standing for 1 hour at 5° C., the solid is filtered off to yield 0.0664 g of the title compound.

EXAMPLE 154

[3±(Z)]-3-[[(2-Amino-4-thiazolyl)(methoxyimino)acetyl]amino]-4,4-dimethyl-2-oxo-1-azetidinesulfonic acid, potassium salt A solution of N-hydroxybenzotriazole hydrate (50 mg) and (Z)-2-amino-E-(methoxyimino)-4-thiazoleacetic acid (0.323 mmole) in 0.5 ml of dimethylformamide is treated with 67 mg of dicyclohexylcarbodiimide under argon at ambient temperature. The resulting mixture is stirred for 1 hour at which time (±)-3-amino-4,4-dimethyl-2-oxo-1-azetidinesulfonic acid (57 mg; see example 153) is added as a solid followed by triethylamine dropwise (0.05 ml). The reaction is stirred at ambient temperature for 16 hours. The dimethylformamide is removed under high vacuum at 30° C., and the residue is slurried in 4 ml of acetone and filtered. The filter cake is washed with an additional 4 ml of acetone, and potassium perfluorobutanesulfonate (85 mg) is added to the filtrate, followed by ether. Trituration of the resulting gum with ether gives 40 mg of a tan solid which is chromatographed on a 70 ml HP-20AG column. Elution with water gives 20 mg of the title compound in fractions (5 ml) 16–40 after evaporation, trituration with 1:1 acetone-hexane and drying.

Anal. Calc'd. for $C_{11}H_{14}N_5O_6S_2.K$: C, 31.80; H, 3.40; N, 16.86; S, 15.43. Found: C, 29.47; H, 3.48; N, 14.98; S, 13.35.

EXAMPLE 155

(±)-4,4-Dimethyl-2-oxo-3-[(phenylacetyl)amino]-1-azetidinesulfonic acid, potassium salt A solution of N-hydroxybenzotriazole hydrate (45 mg) and phenylacetic acid (40 mg) in 0.5 ml of dimethylformamide is treated with dicyclohexylcarbodiimide (61 mg) under argon at ambient temperature. The resulting mixture is stirred for 1 hour and (±)-3-amino-4,4-dimethyl-2-oxo-1-azetinesulfonic acid, (52 mg; see example 153) is added as a solid, followed by triethylamine dropwise (0.04 ml). The reaction is stirred at ambient temperature for 24 hours. The dimethylformamide is removed under high vacuum at 30° C. and the residue is slurried in acetone and filtered. Potassium perfluorobutanesulfonate is added to the filtrate, ether is added and the mixture is cooled. The resulting solid is washed with acetone, hexane, and dried yielding the title compound as a powder.

Anal. calc'd. for $C_{13}H_{15}N_2O_5SK$: C, 44.55; H, 4.32; N, 8.00; S, 9.15; K, 11.16. Found: C, 43.83; H, 4.16; N, 7.96; S, 8.76; K, 11.43.

EXAMPLE 156

(3S-trans)-3-[[(2-Amino-4-thiazolyl)oxoacetyl]amino]-4-methyl-2-oxo-1-azetidinesulfonic acid, potassium salt To a solution of diphenylphosphinyl chloride (1.85 g) in dry dimethylformamide (15 ml) cooled in an ice-methanol bath (−15° to −20° C.) is added (2-amino-4-thiazolyl)glyoxylic acid, triethylamine salt (2.14 g). After stirring for 0.5 hour a solution of (3S-trans)-3-amino-4-methyl-2-oxo-1-azetidinesulfonic acid (1.08 g; see example 139) and triethylamine (1.92 ml) in dry dimethylformamide (5 ml) is added to the cold mixed anhydride solution and the reaction mixture is stirred at 5° C. for 24 hours. Solvent is removed in vacuo, the residual dark oil is dissolved in water, and chromatographed on Dowex 50X2-400 resin ($K^{\oplus}$ form, 200 ml). Upon elution with water (15 ml fractions) the crude product is collected in fractions 13–27 (3.37 g). Chromatography on HP-20 resin (200 ml), eluting with water (15 ml fractions), gives the desired product in fractions 18–26. Removal of water in vacuo gives the title compound as an amorphous powder.

Anal. Calc'd for $C_9H_9N_4O_6S_2K$ (372.42): C, 29.02; H, 2.44; N, 15.04; S, 17.22; K, 10.50. Found: C, 28.87; H, 2.62, N, 14.85; S, 15.09; K, 10.81.

EXAMPLE 157

[3S(R*)]-3-[[[(Aminoacetyl)amino]phenylacetyl]amino]-2-oxo-1-azetidinesulfonic acid, potassium salt, trifluoroacetate (1:1) salt The deprotection of [3S(R*)]-3-[[[[[[(4-methoxyphenyl)methoxy]carbonyl]amino]acetyl]amino]phenylacetyl]amino]-2-oxo-1-azetidinesulfonic acid potassium salt (see example 127) using trifluoroacetic acid and anisole yields the title compound, melting point 165° C., dec.

EXAMPLE 158

(3S-trans)-3-Methoxy-4-methyl-2-oxo-3-[[(phenylmethoxy)carbonyl]amino]-1-azetidinesulfonic acid, potassium salt (A)

(3S-trans)-4-Methyl-3-methoxy-2-oxo-4-[[(phenylmethoxy)carbonyl]amino]azetidine

A solution of 2.5 g (0.0106 mole) of (3R-trans)-4-methyl-2-oxo-3-[[(phenylmethoxy)carbonyl]amino]azetidine (prepared from d-threonine in 12.6% yield essentially as described for the racemic cis isomer in Example 98C) in 112 ml of 4% borax in methanol is cooled to 0° C. and 3.5 ml of t-butyl hypochlorite is added. After 20 minutes the solution is poured into 1 liter of cold water and extracted with two 750 ml portions of cold ethyl acetate. The organic layer is washed with cold water (two 750 ml portions), saturated salt, dried and evaporated to give 3.05 g of crude N,N'-dichloroamide.

A solution of 426 mg of lithium methoxide in 20 ml of dry methanol is cooled to −78° C. and diluted with 40 ml of dry tetrahydrofuran. Over 30 seconds a solution of the above chloroamide in 20 ml of tetrahydrofuran (−78° C.) are added via syringe. After 20 minutes at −78° C., 2 ml each of acetic acid and trimethyl phosphite are added. After 40 minutes at room temperature the solution is poured into 500 ml of water and extracted with ethyl acetate (two 300 ml portions). The organic layer is washed with water, dried, and evaporated to give an oil. Chromatography on a 200 ml silica gel column eluting with 3:1 chloroform-ethyl acetate gives a total of 1.25 g of the title compound.

(B)

(3S-trans)-3-Methoxy-4-methyl-2-oxo-3-[[(phenylmethoxy)carbonyl]amino-1-azetidinesulfonic acid, potassium salt A solution of 800 mg (0.00303 mole) of (3S-trans)-4-methyl-3-methoxy-2-oxo-4-[[(phenylmethoxy)carbonyl]amino]azetidine in 2 ml of dimethylformamide is cooled to 0° C. and 4 ml of dimethylformamide-sulfur trioxide complex is added. After 1 hour at 0° C. and 4 hours at room temperature the solution is poured into 80 ml of 0.5M monobasic potassium phosphate (adjusted to pH 5.5) and extracted with methylene chloride (two 50 ml portions, discard). The aqueous layer is treated with 1.04 g of tetrabutyl ammonium sulfate and extracted with dichloromethane to give 1.42 g of oil. This is dissolved in acetone and treated with 1.04 g of potassium perfluorobutanesulfonate in 10 ml of acetone. Dilution with 250 ml of ether and extensive trituration of the oily solid gives 584 mg of crude product. Chromatography on HP-20 AG (200 ml) gives 418 mg of purified product in fractions (100 ml) 13–16 (elution with 1 liter of water and then 9:1 water-acetone). Trituration of 114 mg of this material with ether gives 104 mg of an analytical sample.

Analysis calc'd for $C_{13}H_{14}N_2O_7SK \cdot H_2O$: C, 39.06; H, 4.04; N, 7.01; S, 8.03; K, 9.78. Found: C, 38.91; H, 3.62; N, 6.91; S, 8.06; K, 9.51.

EXAMPLE 159

(3S-trans)-3-Methoxy-4-methyl-2-oxo-3-[(phenylacetyl)amino]-1-azetidinesulfonic acid, potassium salt (3S-trans)-3-Amino-3-methoxy-4-methyl-2-oxo-1-azetidinesulfonic acid, tetrabutylammonium salt is prepared by the catalytic hydrogenation of (3S-trans)-3-methoxy-4-methyl-2-oxo-3-[[(phenylmethoxy)carbonyl]amino]-1-azetidinesulfonic acid, potassium salt (see example 158) after conversion to the tetrabutylammonium salt. Following the procedure of example 88, but utilizing (3S-trans)-3-amino-3-methoxy-4-methyl-2-oxo-1-azetidinesulfonic acid, tetrabutylammonium salt and phenylacetyl chloride yields the title compound.

Anal. calc'd for $C_{13}H_{15}N_2O_6SK$: C, 42.61; H, 4.31; N, 7.65. Found: C, 39.67; H, 4.09; N, 7.30.

EXAMPLE 160

[3S-[3α(Z),4β]]-3-[[(2-Amino-4-thiazolyl)[[2-(diphenylmethoxy)-2-oxoethoxy]imino]acetyl]amino]-2-methyl-4-oxo-1-azetidinesulfonic acid, potassium salt Following the procedure of example 138, but substituting (Z)-2-amino-α-[[2-(diphenylmethoxy)-2-oxoethoxy]imino]-4-thiazoleacetic acid for (Z)-2-amino-α-(methoxyimino)-4-thiazoleacetic acid and first treating the (3S-cis)-3-amino-4-methyl-2-oxo-1-azetidinesulfonic acid, with triethylamine, yields the title compound, melting point 155°–160° C., dec.

EXAMPLE 161

[3S-[3α(Z),4β]]-3-[[[(Carboxymethoxy)imino](2-amino-4-thiazolyl)acetyl]amino]-4-methyl-2-oxo-1-azetidinesulfonic acid, dipotassium salt The deprotection of [3S-[3α(Z),4β]]-3-[[(2-amino-4-thiazolyl)[[2-(diphenylmethoxy)-2-oxoethoxy]imino]acetyl]amino]-2-methyl-4-oxo-1-azetidinesulfonic acid, potassium salt (see example 160) using trifluoroacetic acid and anisole yields the title compound, which decomposes at >250° C.

EXAMPLE 162

(S)-3-[[[(2,6-Dichloro-4-pyridinyl)thio]acetyl]amino]-2-oxo-1-azetidinesulfonic acid, potassium salt Acylation of (S)-3-amino-2-oxo-1-azetidinesulfonic acid, tetrabutylammonium salt (see example 6A) with [(2,6-dichloro-4-pyridinyl)thio]acetic acid, 4-nitrophenyl ester, followed by treatment with potassium perfluorobutane sulfonate, yields the title compound, melting point 212°–214° C.

EXAMPLE 163

[3S(R*)]-3-[[[[(4-Amino-2,3-dioxo-1-piperazinyl)carbonyl]amino]phenylacetyl]amino]-4-methyl-2-oxo-1-azetidinesulfonic acid, potassium salt

[3S(R*)]-4-[[[2-[(4-methyl-2-oxo-1-sulfo-3-azetidinyl)amino]-2-oxo-1-phenylethyl]amino]carbonyl]-2,3-dioxo-1-piperazinyl]carbamic acid, phenylmethyl ester, potassium salt (see example 149) is hydrogenated using gaseous hydrogen and 10% palladium on charcoal as catalyst, yielding the title compound, melting point 165° C., dec.

EXAMPLE 164

[3S(Z)]-3-[[(2-Amino-4-thiazolyl)][(1-carboxy-1-methylethoxy)imino]acetyl]amino]-2-oxo-1-azetidinesulfonic acid, sodium salt (1:2)

[3S(Z)]-3-[[(2-Amino-4-thiazolyl)[[2-diphenylmethoxy)-1,1-dimethyl-2-oxoethoxy]imino]acetyl]amino]-2-oxo-1-azetidinesulfonic acid, tetrabutylammonium salt (see example 28) is deprotected using trifluoroacetic acid and anisole to yield the title compound, melting point 185° C., dec, after conversion to the disodium salt with aqueous sodium hydroxide and purification on HP-20.

EXAMPLES 165–168

Following the procedure of Example 11, but substituting the acid listed in column I for (Z)-2-amino-α-[[hydroxy(phenylmethoxy)phosphinyl]methoxy]imino]-4-thiazoleacetic acid, yields the compound listed in column II.

|     | Column I | Column II |
| --- | --- | --- |
| 165. | 2,6-dimethoxybenzoic acid | (S)—3-[(2,6-dimethoxybenzoyl)amino]-2-oxo-1-azetidinesulfonic acid, potassium salt; melting point 180° C., dec. |
| 166. | (Z)—2-amino-α-[[4-(diphenylmethoxy)-4-oxobutoxy]imino]-4-thiazoleacetic acid | [3S(Z)]—2-[[(2-amino-4-thiazolyl)[[4-(diphenylmethoxy)-4-oxobutoxy]imino]acetyl]amino]-2-oxo-1-azetidinesulfonic acid, potassium salt; melting point 125–130° C., dec. |
| 167. | 2-[[[(phenylmethoxy)carbonyl]amino]methyl]benzoic acid | (S)—2-oxo-3-[[2-[[[(phenylmethoxy)carbonyl]amino]methyl]benzoyl]amino]-1-azetidinesulfonic acid, potassium salt; melting point 234.5° C., dec. |
| 168. | α-[[[5-hydroxy-2-(4-formyl-1-piperazinyl)pyrido[2,3-d]pyrimidin-6-yl]carbonyl]amino]benzeneacetic acid | (3S)—3-[[[[[5-hydroxy-2-(4-formyl-1-piperazinyl)pyrido[2,3-d]pyrimidin-6-yl]carbonyl]amino]phenylacetyl]amino]-2-oxo-1-azetidinesulfonic acid, potassium salt; melting point 265–270° C., dec. |

EXAMPLE 169

(trans)-3-Amino-4-ethyl-2-oxo-1-azetidinesulfonic acid (A)

threo-t-Boc-N-methoxy-β-ethylserinamide threo-D,L-β-Ethylserine (1.33 g) is dissolved in 10 ml of 2N potassium hydroxide and 5 ml of t-butanol. After the addition of 2.46 g of di-t-butylpyrocarbonate the two-phase mixture is stirred for 4 hours at ambient temperature. O-Methylhydroxylammonium chloride (1.25 g) is added and the pH is adjusted to 4 with 1N hydrochloric acid. 1-Ethyl-3-(3-dimethylaminopropyl)carbodiimide, hydrochloride (1.92 g) is added and the pH is again adjusted to 4. After stirring for 1 hour the reaction mixture is saturated with sodium chloride and extracted with four 50 ml portions of ethyl acetate. The ethyl acetate extracts are combined and dried over MgSO₄. Removal of the solvent in vacuo yields 1 g of the title compound.

(B)

threo-t-Boc-O-methanesulfonyl-N-methoxy-β-ethylserinamide threo-t-Boc-N-methoxy-β-ethylserinamide (10.5 g) is dissolved in 65 ml of pyridine. Methanesulfonyl chloride (4.65 ml) is added dropwise at 0° C. After stirring for 3 hours at ambient temperature, the reaction mixture is poured into 200 g of ice and 300 ml of 1N hydrochloric acid. The pH is adjusted to 4 with concentrated hydrochloric acid. After extraction with three 85 ml portions of ethyl acetate the combined extracts are dried over MgSO₄ and concentrated in vacuo. The residue is treated with carbon tetrachloride and concentrated again. Stirring with ether followed by filtration yields 6.9 g of the title compound.

(C)

(trans)-3-t-Butoxycarbonylamino-4-ethyl-1-methoxy-2-azetidinone

Anhydrous potassium carbonate (4.15 g) and 125 ml of dry acetone are brought to reflux and 3.4 g of threo-t-Boc-O-methanesulfonyl-N-methoxy-β-ethylserinamide in 25 ml of acetone is added. After 1 hour the reaction mixture is cooled and filtered, and the filtrate is concentrated in vacuo. The oily residue is stirred with hexane to yield 2.2 g of the title compound.

(D)

(trans)-3-t-Butoxycarbonylamino-4-ethyl-2-azetidinone (trans)-3-t-Butoxycarbonylamino-4-ethyl-1-methoxy-2-azetidinone (3 g) is added to 170 ml of liquid ammonia at −78° C. under nitrogen and 1.68 g of sodium is added in 5 portions with stirring over a 5 minute period. Stirring is continued for 30 minutes. Ammonium chloride is then added slowly until the blue color of the reaction mixture disappears. After removal of the ammonia under nitrogen the solid is extracted with two 100 ml portions of ethyl acetate. Removal of the solvent followed by drying in vacuo yields 2.7 g of the title compound.

(E)

(trans)-3-t-Butoxycarbonylamino-4-ethyl-2-oxo-1-azetidinesulfonic acid, tetrabutylammonium salt To 2 ml of absolute pyridine in 20 ml of dry dichloromethane is added trimethylsilyloxysulfonyl chloride (3.7 ml) in 5 ml of dry dichloromethane. The addition is accomplished at −30° C., under nitrogen, over a 10 minute period. After stirring at ambient temperature for 30 minutes, the flask is evacuated to yield a pyridine-sulfur trioxide complex. (trans)-3-t-Butoxycarbonylamino-4-ethyl-2-azetidinone (2.67 g) and 20 ml of dry pyridine are added to the flask which is then placed in an oil bath preheated to 90° C. After 15 minutes a clear solution is obtained and poured into 200 ml of a 1M solution of dibasic potassium phosphate. After the addition of 27 g of dibasic potassium phosphate and 100 ml of water a clear solution is obtained. The solution is extracted with two 60 ml portions of ethyl acetate. Tetrabutylammonium hydrogensulfate is added to the aqueous layer, and the aqueous solution is extracted with three 100 ml portions of dichloromethane and the combined organic layers are dried over MgSO4. Concentration in vacuo yields 6.9 g of the title compound.

(F)

(trans)-3-Amino-4-ethyl-2-oxo-1-azetidinesulfonic acid (trans)-3-t-Butoxycarbonylamino-4-ethyl-2-oxo-1-azetidinesulfonic acid, tetrabutylammonium salt (6.75 g) in 40 ml of 98% formic acid is stirred for 3 hours at ambient temperature. Dichloromethane (60 ml) is added and the mixture is refrigerated for about 16 hours. The resulting precipitate is separated by filtration and then dried in vacuo to yield 0.85 g of the title compound, melting point 185° C., dec.

EXAMPLE 170

(trans,Z)-3-[[(2-Amino-4-thiazolyl)[(1-carboxy-1-methylethoxy)imino]acetyl]amino]-4-ethyl-2-oxo-1-azetidinesulfonic acid, dipotassium salt (A)

(trans,Z)-3-[[(2-Amino-4-thiazolyl)[(1-diphenylmethoxycarbonyl-1-methylethoxy)imino]acetyl]amino]-4-ethyl-2-oxo-1-azetidinesulfonic acid, dipotassium salt (trans)-3-Amino-4-ethyl-2-oxo-1-azetidinesulfonic acid (0.55 g) and 335 mg of triethylamine are dissolved in 50 ml of dry dimethylformamide. (Z)-2-Amino-α[(1-diphenylmethoxycarbonyl-1-methylethoxy)imino]-4-thiazoleacetic acid (1.14 g) is added with stirring at 0° C. followed by 450 mg of hydroxybenzotriazole and then 0.69 g of dicyclohexylcarbodiimide. After stirring for about 16 hours at 0° C. the flask is evacuated. Dry acetone (25 ml) is added to the solid with stirring. The mixture is filtered and 0.94 g of potassium perfluorobutanesulfonate is added to the filtrate followed by 100 ml of ether. After standing for 1 hour at 0° C. the solid is filtered, washed with ether and dried in vacuo yielding 1.58 g of the title compound.

(B)

(trans,Z)-3-[[(2-Amino-4-thiazolyl)[(1-carboxy-1-methylethoxy)imino]acetyl]amino]-4-ethyl-2-oxo-1-azetidinesulfonic acid, dipotassium salt To a suspension of 1.31 g of (trans,Z)-3-[[(2-Amino-4-thiazolyl)](1-diphenylmethoxycarbonyl-1-methylethoxy)imino]acetyl]amino]-4-ethyl-2-oxo-1-azetidinesulfonic acid, dipotassium salt in 10 ml of anisole is added 5 ml of trifluoroacetic acid over a 10 minute period at −15° C. After stirring for 2 hours at −10° C. a clear solution is obtained. At −30° C. 80 ml of dry ether is added and the resulting precipitate is filtered and then treated with 5 ml of water. The pH is adjusted to 5.5 with 1N potassium hydroxide at 0° C., and the mixture is filtered to remove unconverted starting material. The filtrate is chromatographed on HP-20 with water as eluent. Lyophilization yields 185 mg of the title compound, melting point 160° C., dec.

EXAMPLE 171

[3S(Z)]-3-[[(2-Amino-4-thiazolyl)[(4-hydroxy-4-oxobutoxy)imino]acetyl]amino]-2-oxo-1-azetidinesulfonic acid, potassium salt The deprotection of [3S(Z)]-3-[[(2-amino-4-thiazolyl)[[4-(diphenylmethoxy)-4-oxobutoxy]imino]acetyl]amino]-2-oxo-1-azetidinesulfonic acid, potassium salt (see example 166) using trifluoroacetic acid and anisole yields the title compound, melting point >200° C.

EXAMPLE 172

(S)-3-[[2-(Aminomethyl)benzoyl]amino]-2-oxo-1-azetidinesulfonic acid, inner salt The deprotection of (S)-2-oxo-3-[[2-[[[(phenylmethoxy)carbonyl]amino]methyl]benzoyl]amino]-1-azetidinesulfonic acid, potassium salt (see example 167) using hydrogen gas, palladium on charcoal, and hydrochloric acid, yields the title compound, melting point 162°–165° C.

EXAMPLE 173

(S)-3-[[[2-(4-Formyl-1-piperazinyl)-5-hydroxypyrido[2,3-d]pyrimidin-6-yl]carbonyl]amino]-2-oxo-1-azetidinesulfonic acid, potassium salt (S)-3-Amino-2-oxo-1-azetidinesulfonic acid, tetrabutylammonium salt (see example 6A) is coupled with 2-(4-formyl-1-piperazinyl)-5-hydroxy-6-[(4-nitrophenoxy)carbonyl]pyrido[2,3-d]pyrimidine and treated with potassium perfluorobutanesulfonate in acetone to yield the title compound, melting point 290° C., dec.

EXAMPLE 174

(3S-trans)-α-[[(4-Methyl-2-oxo-1-sulfo-3-azetidinyl)amino]carbonyl]benzeneacetic acid, dipotassium salt (3S-trans)-3-Amino-4-methyl-2-oxo-1-azetidinesulfonic acid (see example 139) is coupled with α-(carboxyl)benzeneacetyl chloride and treated with triethylamine and potassium perfluorobutanesulfonate to yield the title compound, melting point 147° C., dec.

EXAMPLE 175

(trans)-3-Amino-4-cyclohexyl-2-oxo-1-azetidinesulfonic acid (A)

threo-t-Boc-β-cyclohexylserine threo-β-Cyclohexylserine (15 g) is suspended in 150 ml of acetonitrile and 70 ml of water. Triethylamine (17.8 g) is added and the mixture is heated with stirring to 60° C. At this temperature a clear solution is obtained and 21.0 g of di-t-butylpyrocarbonate is added and stirring at 60° C. is continued for 1.5 hours. The solvent is removed in vacuo and 50 ml of water is added. The aqueous layer is extracted with ethyl acetate at a pH of 2, which is adjusted by addition of 3N HCl. The organic layer is separated, dried over Na2SO4 and evaporated to dryness. The remaining crystalline material is filtered with petrol ether, yielding 20.4 g of the title compound, melting point 113°–115° C.

(B)

threo-t-Boc-N-methoxy-β-cyclohexylserinamide threo-t-Boc-β-cyclohexylserine (20.2 g) and 7.6 g of O-methylhydroxyamine hydrochloride are suspended in 350 ml of water and 175 ml of t-butanol. The pH of the mixture is adjusted to 4 with potassium carbonate. 1-Ethyl-3-(3-dimethylaminopropyl)carbodiimide (16.4 g) is added and the pH is maintained at 4 with stirring for 1.5 hours. t-Butanol is removed in vacuo and the remaining aqueous solution is saturated with sodium chloride and extracted twice with 100 ml portions of ethyl acetate. The organic layers are combined, dried with $Na_2SO_4$ and evaporated to dryness. The remaining crystals are filtered off with petrol after yielding 18.6 g of the title compound, melting point 125°–127° C.

(C)

threo-t-Boc-O-methanesulfonyl-N-methoxy-β-cyclohexylserinamide threo-t-Boc-N-methoxy-β-cyclohexylserinamide (18.3 g) is dissolved with stirring in 100 ml of dry pyridine. The solution is cooled with stirring to 0° C. and 9.3 g of methanesulfonyl chloride is dropped in. After one hour at 0° C. an additional 3.3 g of methanesulfonyl chloride is added and stirring is continued for one more hour. The solution is poured into 300 ml of ice water, 200 ml of ethyl acetate is added and the pH is adjusted to 3 with dilute sulfuric acid. The organic layer is separated, dried with $Na_2SO_4$ and the solvent is removed in vacuo. The remaining solid is collected with petrol ether yielding 19.0 g of the title compound, melting point 150°–152° C.

(D)

(trans)-3-(t-Butoxycarbonylamino)-4-cyclohexyl-1-methoxy-2-azetidinone threo-t-Boc-O-methanesulfonyl-N-methoxy-β-cyclohexylserinamide (18.7 g) is dissolved in 500 ml of dry acetone. Potassium carbonate (9.8 g) is added and the suspension is heated to reflux temperature with stirring for 5 hours. The insoluble inorganic material is filtered off and the solvent removed in vacuo and the remaining oil is dissolved in 30 ml of ethyl acetate. Upon the addition of petrol ether, the title compound precipitates and is filtered off (12.9 g), melting point 110°–112° C.

(E)

(trans)-3-(t-Butoxycarbonylamino)-4-cyclohexyl-2-azetidinone (trans)-3-(t-Butoxycarbonylamino)-4-cyclohexyl-1-methoxy-2-azetidinone (1 g) is added to 50 ml of liquid ammonia with stirring. Sodium (0.154 g) is added in 5 to 6 portions within 5 minutes. After this time an additional amount of 0.025 g sodium is added and stirring is continued for 5 minutes. Ammonium chloride (0.89 g) is added and the ammonia is removed. The residue is extracted with warm ethyl acetate. The organic extract is evaporated to dryness and the remaining crystals of the title compound are filtered with petrol ether, yielding 0.5 g, melting point 130°–132° C.

(F)

(trans)-3-(t-Butoxycarbonylamino)-4-cyclohexyl-2-oxo-1-azetidinesulfonic acid, pyridine salt (trans)-3-(t-Butoxycarbonylamino)-4-cyclohexyl-2-azetidinone (5.3 g) is dissolved in 20 ml of methylene chloride and 80 ml of dimethylformamide. After the addition of 60 mmole of pyridine-sulfur trioxide complex the solution is stirred for 6 hours at room temperature. Removal of the solvent in vacuo yield 11.3 g of the title compound as an oil.

(G)

(trans)-3-(t-Butoxycarbonylamino)-4-cyclohexyl-2-oxo-1-azetidinesulfonic acid, tetrabutylammonium salt (trans)-3-(t-Butoxycarbonylamino)-4-cyclohexyl-2-oxo-1-azetidinesulfonic acid, pyridine salt (11.3 g) is dissolved in 250 ml of water. Tetrabutylammonium hydrogensulfate (9.0 g) is added with stirring and the pH is adjusted to 6.5 with 1N potassium hydroxide. The aqueous solution is extracted twice with 200 ml portions of methylene chloride. The organic portions are dried with $Na_2SO_4$, filtered and the solvent is distilled off, yielding 8 g of the title compound, melting point 135°–138° C.

(H)

(trans)-3-Amino-4-cyclohexyl-2-oxo-1-azetidinesulfonic acid (trans)-3-(t-Butoxycarbonylamino)-4-cyclohexyl-2-oxo-1-azetidinesulfonic acid, tetrabutylammonium salt (3.8 g) is stirred in 20 ml of formic acid for 3 hours, followed by the addition of 20 ml of methylene chloride. The precipitated title compound (1.0 g) is filtered off, melting point 217°–219° C.

EXAMPLE 176

[3α(Z),4β]-3-[[(2-Amino-4-thiazolyl)(methoxyimino)acetyl]amino]-4-cyclohexyl-2-oxo-1-azetidinesulfonic acid, potassium salt (trans)-3-Amino-4-cyclohexyl-2-oxo-1-azetidinesulfonic acid (0.25 g) is dissolved in 30 ml of dry dimethylformamide and 0.12 g of triethylamine with stirring. When a clear solution is obtained, (Z)-2-amino-α-(methoxyimino)-4-thiazoleacetic acid (0.2 g), 0.16 g of hydroxybenzotriazole and 0.42 g of dicyclohexylcarbodiimide are added. Stirring is continued for 48 hours at ambient temperature. The precipitated urea is filtered off and the solvent is removed in vacuo. The residue is dissolved in 10 ml of acetone and 0.41 g of potassium perfluorobutanesulfonate is added. After the addition of 50 ml of ether, the title compound precipitates and is filtered. Column chromatography using HP-20 and water/acetone (9:1) as eluent, yields 0.36 g of product, melting point 200°–205° C. (after lyophilization).

EXAMPLE 177

[3α(Z),4β]-3-[[(2-Amino-4-thiazolyl)[(1-carboxy-1-methylethoxy)imino]acetyl]amino]-4-cyclohexyl-2-oxo-1-azetidinesulfonic acid, dipotassium salt (A)

[3α(Z),4β]-3-[[(2-Amino-4-thiazolyl)[(1-diphenylmethoxycarbonyl-1-methylethoxy)imino]acetyl]amino]-4-cyclohexyl-2-oxo-1-azetidinesulfonic acid, potassium salt (trans)-3-Amino-4-cyclohexyl-2-oxo-1-azetidinesulfonic acid (0.2 g; see example 175) is dissolved in 30 ml of dimethylformamide and 0.09 g of triethylamine with stirring. Hydroxybenzotriazole (0.12 g), 0.30 g of (Z)-2-amino-α-[(1-diphenylmethoxycarbonyl-1-methylethoxy)imino]-4-thiazoleacetic acid and 0.33 g of dicyclohexylcarbodiimide are added and stirring at ambient temperature is continued for 12 hours. The precipitated urea is filtered off and the mother liquor is evaporated to dryness. The remaining oil is dissolved in 5 ml acetone, treated with 0.3 g of potassium perfluorobutanesulfonate and poured into 100 ml of ether with stirring. [3α(Z),4β]-3-[[(2-Amino-4-thiazolyl)[(1-diphenylmethoxycarbonyl-1-methylethoxy)imino]acetyl]amino]-4-cyclohexyl-2-oxo-1-azetidinesulfonic acid, potassium salt (0.61 g) precipitates and is filtered off.

(B)

[3α(Z),4β]-3-[[(2-Amino-4-thiazolyl)[(1-carboxy-1-methylethoxy)imino]acetyl]amino]-4-cyclohexyl-2-oxo-1-azetidinesulfonic acid, dipotassium salt

[3α(Z),4β]-3-[[(2-Amino-4-thiazolyl)[(1-diphenylmethoxycarbonyl-1-methylethoxy)imino]acetyl]amino]-4-cyclohexyl-2-oxo-1-azetidinesulfonic acid, potassium salt (0.61 g) is suspended in 6 ml of anisole, cooled to −15° C. and 5 ml of trifluoroacetic acid is dropped in with stirring. The temperature is maintained for one hour and then lowered to −30° C. About 100 ml of dry ether is added at such a rate, that the temperature does not exceed −10° C. The precipitated compound is filtered off and chromatographed using HP-20 resin and water/acetone (9:1) as eluent, yielding 0.3 g of the title compound, melting point 115°-120° C., dec. (after lyophilization).

EXAMPLE 178

[3α,4β]-4-Cyclohexyl-3-[[[[3-[(2-furanylmethylene)amino]-2-oxo-1-imidazolidinyl]carbonyl]amino]phenylacetyl]amino]-2-oxo-1-azetidinesulfonic acid, potassium salt (trans)-3-Amino-4-cyclohexyl-2-oxo-1-azetidinesulfonic acid (0.1 g; see example 175) is dissolved in a mixture of 30 ml of dry dimethylformamide and 0.05 g of triethylamine with stirring. [[[[(2-Furanylmethylene)amino]-2-oxo-1-imidazolidinyl]carbonyl]amino]phenylacetic acid (0.14 g), 0.06 g hydroxybenzotriazole and 0.17 g of dicyclohexylcarbodiimide are added and the solution is stirred for 5 days at room temperature. The solvent is removed in vacuo, the residue is dissolved in 10 ml of acetone and the precipitated urea is filtered off. The mother liquor is agitatd with 0.15 g of potassium perfluorobutanesulfonate and diluted with 50 ml of ether. The precipitate is filtered, and chromatographed with HP-20 resin using water/acetone (9:1) as eluent yielding 0.14 g of product, melting point 195°-200° C. dec. (after lyophiliaztion).

EXAMPLE 179

[3α(R*),4β]-4-Cyclohexyl-3-[[3-(4-ethyl-2,3-dioxo-1-piperazinyl)-1 3-dioxo-2-phenylpropyl]amino]-2-oxo-1-azetidinesulfonic acid, potassium salt (trans)-3-Amino-4-cyclohexyl-2-oxo-1-azetidinesulfonic acid (0.1 g; see example 175) is dissolved in 30 ml of dimethylformamide and 0.5 g of triethylamine with stirring. (R)-α-[[(4-ethyl-2,3-dioxo-1-piperazinyl)carbonyl)]amino]benzeneacetic acid, 0.06 g of hydroxybenzotriazole and 0.17 g of dicyclohexylcarbondiimide are added, and the mixture is stirred for about 16 hours at room temperature. The solvent is distilled off in vacuo and the remaining oil is dissolved in 10 ml of acetone. The precipitated urea is filtered off and the mother liquor is agitated with 0.15 g of potassium perfluorobutanesulfonate and diluted with 50 ml of ether. The precipitate is filtered off and chromatographed with HP-20 resin, using water/acetone (9:1) as eluent, yielding 0.15 g of the title compound, melting point 175°-180° C. (after lyophilization).

EXAMPLE 180

(trans,Z)-3-[[(2-Amino-4-thiazolyl)(methoxyimino)acetyl]amino]-4-ethyl-2-oxo-1-azetidinesulfonic acid, potassium salt Following the procedure of example 170, part A, but substituting (Z)-2-amino-α-(methoxyimino)-4-thiazoleacetic acid for (Z)-2-amino-α-[(1-diphenylmethoxycarbonyl-1-methylethoxy)imino]-4-thiazoleacetic acid, yields the title compound, meltng point 190° C., dec.

EXAMPLE 181

(±)-(trans)-3-Azido-2-oxo-4-phenyl-1-azetidinesulfonic acid (A)

(±)-(trans)-2-oxo-4-phenyl-1-azetidine-tert-butyldiphenylsilane

A solution of tert-butylchlorodiphenylsilane (20.56 g) in dimethylformamide (45 ml) is cooled to 0° C. under argon and treated with triethylamine (10.4 ml) and then (±)-2-oxo-4-phenyl-1-azetidine. After several hours at 0° C., the resulting mixture is treated with additional triethylamine (1 ml) and tert-butylchlorodiphenylsilane (2.11 g), and allowed to stir for 65 hours at 5° C. The reaction mixture is poured into ice water (300 ml) and extracted with 3:1 ether-ethyl acetate (three 125 ml portions). The organic extracts are washed with pH 4.5 phosphate buffer (three 50 ml portions), saturated sodium bicarbonate solution (50 ml), water (two 50 ml portions) saturated sodium chloride solution and dried ($Na_2SO_4$). Filtration, and concentration in vacuo yields a solid which is washed with hexane to give after drying (high vacuum) 15 g of the title compound as a solid.

(B)

(±)-(trans)-3-azido-2-oxo-4-phenyl-1-azetidine-tert-butyldiphenylsilane

A 50 ml flask equipped with stirring bar, gas inlet, and septum is flame dried under argon and charged with n-butyl lithium (0.65 ml of a 1.6M solution in hexane) which is cooled to −40° C. and dissolved in tetrahydrofuran (2 ml). Diisopropylamine (0.16 ml) is added dropwise, the resulting mixture is stirred for 30 minutes and cooled to −78° C. A solution of (±)-(trans)-2-oxo-4-phenyl-1-azetidine-tert-butyldiphenylsilane (400 mg) in tetrahydrofuran (1.5 ml) is added dropwise over about 5 minutes. After stirring an additional 20 minutes the solution is treated with p-toluenesulfonyl azide (204 mg) in tetrahydrofuran (0.5 ml). The resulting mixture is stirred 10 minutes at −78° C. and treated dropwise with chlorotrimethylsilane (0.4 ml). After an additional 10 minutes of stirring, the cooling bath is removed and the reaction mixture is stirred at ambient temperature for 2.5 hours. Then, while cooling at 0° C., ethyl acetate (20 ml) is added followed by pH 4.5 phosphate buffer (8 ml). The organic layer is washed with additional buffer (two 8 ml portions), 5% sodium bicarbonate solution (three 10 ml portions), 50% sodium chloride solution (10 ml), saturated sodium chloride solution (10 ml) and dried ($Na_2SO_4$). Filtration and concentration in vacuo yields 500 mg of oil which is flash chromatographed with 5% ethyl acetate-hexane, yielding the title compound (253 mg).

(C)

(±)-(trans)-3-azido-2-oxo-4-phenyl-1-azetidine

A solution of 17 g of crude (±)-(trans)-3-azido-2-oxo-4-phenyl-1-azetidine-tert butyl-diphenylsilane is dissolved in methanol (240 ml) and treated dropwise at 0° C. with concentrated HCl (35 ml). The cooling bath is removed, the reaction stirred at ambient temperature for 1 hour, and recooled to 0° C. whereupon saturated sodium bicarbonate solution is added to neutrality. The resulting mixture is extracted with ethyl acetate (one 300 ml portion and four 100 ml portions) and the organic extracts are washed with 1:1 5% sodium bicarbonate/50% sodium chloride solution, saturated sodium chloride solution, and dried ($Na_2SO_4$). Filtration and concentration in vacuo yields 15 g of a heavy oil which is chromatographed on 100 g of silica gel with 20% ethyl acetate-hexane, yielding 460 mg of the title compound.

(D)

(±)-(trans)-3-azido-2-oxo-4-phenyl-1-azetidinesulfonic acid, tetrabutylammonium salt A solution of (±)-(trans)-3-azido-2-oxo-4-phenyl-1-azetidine (300 mg) in dimethylformamide (3 ml) is cooled to 0° C. under argon and treated dropwise with a complex of dimethylformamide and sulfur trioxide (4.78 ml of a 0.5M solution in dimethylformamide). The cooling bath is removed, the reaction mixture is stirred at ambient temperature for 2 hours and poured into 80 ml of 0.5M monobasic potassium phosphate (pH 5.5). The solution is extracted with dichloromethane (discarded) and 541 mg of tetrabutylammonium bisulfate is added. The resulting mixture is extracted with dichloromethane and the organic extracts are washed with 10% sodium chloride solution and dried ($Na_2SO_4$). Filtration and concentration in vacuo affords 800 mg of oil; approximatly 40% the desired product, the remainder dimethylformamide. This mixture is used without purification in the next example.

EXAMPLE 182

(±)-(trans)-3-amino-2-oxo-4-phenyl-1-azetidinesulfonic acid

A solution of (±)-(trans)-3-azido-2-oxo-4-phenyl-1-azetidinesulfonic acid, tetrabutylammonium salt (see example 181) in 4 ml of methanol is hydrogenated over 30 mg of platinum oxide at 1 atmosphere and room temperature. After 15 minutes, the system is evacuated and fresh hydrogen is introduced. After an additional 45 minutes the reaction is complete, and the system is flushed with nitrogen. After several days at room temperature in dichloromethanemethanol (4:1, 200 ml) catalyst aggregation is complete and filtration is accomplished. The filtrate is concentrated in vacuo to 18 ml and 0.2 ml of 97% formic acid is added. After cooling at 5° C. for several hours the resulting solid is filtered and washed with dichloromethane to afford, after drying, 150 mg of the title compound as a solid.

Analysis calc'd for $C_9H_{19}N_2O_4S$: C, 44.62; H, 4.17; N, 11.57; S, 13.23. Found: C, 43.36; H, 4.31; N, 11.09; S, 13.02.

EXAMPLE 183

(±)-(trans,Z)-3-[[2-Amino-4-thiazolyl)(methoxyimino)acetyl]amino]-2-oxo-4-phenyl-1-azetidinesulfonic acid, potassium salt A solution of N-hydroxybenzotriazole hydrate (52 mg) and (Z)-2-amino-α-(methoxyimino)-4-thiazolacetic acid (69 mg) in dimethylformamide (0.3 ml) is treated with solid dicyclohexylcarbodiimide (70 mg) under argon, at ambient temperature. The resulting mixture is stirred for 1 hour, (±)-(trans)-3-amino-2-oxo-4-phenyl-1-azetidinesulfonic acid (75 mg; see example 181) is added as a solid, followed by triethylamine dropwise (0.05 ml). The reaction is stirred at ambient temperature for 23 hours. The dimethylformamide is removed under high vacuum at 30° C., and the residue triturated with 2 ml of acetone and filtered. The filter cake is washed with additional acetone (two 3 ml portions) and potassium perfluorobutanesulfonate (86 mg) is added to the filtrate. Dilution with 10 ml of ether produces a gummy solid which is triturated, washed with acetone and hexane to yield, after drying, 82 mg of the title compound as a solid.

Analysis for $C_{15}H_{14}N_5O_6S_2 \cdot K$: Calc'd: C, 40.26; H, 3.16; N, 15.65; S, 14.33; K, 8.74. Found: C, 38.60; H, 3.19; N, 15.07; S, 13.87; K, 7.5.

EXAMPLE 184

(±)-(cis)-4-Phenyl-2-oxo-3-azido-1-azetidinesulfonic acid, tetrabutylammonium salt (A)

N-Benzylidene-2,4-dimethoxybenzylamine 12.0 g of 2,4-dimethoxybenzylamine hydrochloride is added to 100 ml of 1N sodium hydroxide solution and the mixture is extracted with 125 ml of ethyl acetate. The organic layer is dried over anhydrous sodium sulfate and stripped of solvent to give 10.2 g of 2,4-dimethoxybenzylamine as an oil. This amine is dissolved in 150 ml of benzene; 6.47 g of benzaldehyde and 0.6 g of p-toluenesulfonic acid monohydrate are added. The mixture is heated under reflux removing water with a Dean-Stark separator and in two hours the calculated amount of water (1.1 ml) separates out. The mixture is cooled to room temperature. Upon further cooling the benzene solution deposits some precipitate. Benzene is removed under reduced pressure and 60 ml of petroleum ether is added to the residue. An oily layer separates out with more precipitate. Benzene (10 ml) is added to make the layers homogeneous and the remaining precipitate is filtered. The filtrate is stripped of solvent to give 14.2 g of the title compound as an oil.

(B)

(±)-(cis)-4-Phenyl-1-(2,4-dimethoxybenzyl)-2-oxo-3-azidoazetidine

α-Azidoacetic acid (1.62 g) is dissolved in 25 ml of methylene chloride under nitrogen. To this solution are added 3.24 g of triethylamine and 1.02 g (4.0 mmole) of the imine N-benzylidene-2,4-dimethoxybenzylamine dissolved in 10 ml of methylene chloride. The mixture is cooled in an ice-bath and 3.36 g of trifluoroacetic anhydride is added slowly; the solution becomes dark colored. After stirring for 1 hour in an ice-bath, the mixture is warmed to room temperature and stirred an additional 15 minutes. The solution is then washed with water (60 ml), 5% NaHCO₃ solution (two 50 ml portions), and 1N HCl solution (60 ml). The organic layer is dried over anhydrous sodium sulfate and stripped of solvent to give 1.72 g of crude product as dark gum. The gum is treated with charcoal several times and the resulting brown mixture is chromatographed on 40 g silica gel eluting with 1:1 petroleum ether:ethyl acetate. The combined fractions yield crystal upon quick-freezing in a dry ice-acetone bath. Using this is a seed the product is recrystallized from petroleum ether-ethyl acetate to give 817 mg of the title compound as needles which melt upon warming to room temperature.

(C)

(±)-(cis)-4-Phenyl-2-oxo-3-azidoazetidine (±)-(cis)-4-Phenyl-1-(2,4-dimethoxybenzyl)-2-oxo-3-azidoazetidine (737 mg) is dissolved in 25 ml of acetonitrile and heated to 80°–83° C. under nitrogen. To the resulting solution are added over a 1 hour period 943 mg of potassium persulfate and 570 mg of potassium monohydrogen phosphate, both dissolved in 25 ml of water. After the addition, the mixture is further heated at 80°–83° C. for 7 hours. The mixutre is cooled and the pH is adjusted to 6–7 by adding solid potassium monohydrogen phosphate. Most of the acetonitrile is removed under reduced pressure and the resulting mixture is extracted with 60 ml of chloroform. The chloroform layer is washed with water (60 ml), dried over anhydrous sodium sulfate and stripped of solvent to give a crude product as an oil. The crude product is chromatographed on 40 g of silica gel eluting with 1:1 petroleum ether-ethyl acetate. The combined fractions yield crystals and the product is recrystallized from petroleum ether-ethyl acetate to give 267 mg of the title compound.

(D)

(±)-(cis)-4-Phenyl-2-oxo-3-azido-1-azetidinesulfonic acid, tetrabutylammonium salt (±)-(cis)-4-Phenyl-2-oxo-3-azidoazetidine (162 mg) is cooled to 0° C. under nitrogen and 3.5 ml of ca. 0.5M dimethylformamide-sulfur trioxide complex solution in dimethylformamide is added dropwise via syringe. The resulting clear solution is stirred at 0° C. for 15 minutes. The mixture is then poured into 50 ml of 0.5M monobasic potassium phosphate solution and washed with methylene chloride (three 50 ml portions). tetra-n-Butylammonium bisulfate (292 mg) is added to the aqueous solution and the mixture is extracted with methylene chloride (six 50 ml portions). The combined methylene chloride layers are dried over anhydrous sodium sulfate and stripped of solvent to give 272 mg of the title compound as a gum.

EXAMPLE 185

(cis,Z)-3-[[(2-Amino-4-thiazolyl)(methoxyimino)acetyl]amino]-2-oxo-4-phenyl-1-azetidinesulfonic acid, potassium salt (cis)-2-Oxo-4-phenyl-3-azido-1-azetidinesulfonic acid, tetrabutylammonium salt (560 mg; see example 184) is dissolved in 5 ml of ethanol and hydrogenated with 110 mg of platinum oxide catalyst at one atmosphere. After one hour stirring the catalyst is filtered through a Millipore filter with Celite; catalyst particles pass through the filter to give a black filtrate. Ethanol is removed under reduced pressure and the residue is dissolved in 4 ml of diemthylformamide. N-Hydroxybenzotriazole monohydrate (168 mg), 221 mg of the (Z)-2-amino-α-(methoxyimino)-4-thiazoleacetic acid and 227 mg of dicyclohexylcarbodiimide are added and the mixture is stirred for about 16 hours under nitrogen. The slurry is evaporated in vacuo and triturated with 15 ml of acetone. The resulting slurry is filtered through a Millipore with Celite and the filtrate is treated with 372 mg of potassium perfluorobutane sulfonate. Upon adding 15 ml of ether a gum separates out. Liquid is removed and the gum is washed with ether. The gum is dissolved in 5 ml of water and applied on 150 ml of HP-20 resin eluting with water. Fractions (30 ml each) 16–34 are combined and lyophilized to give 201 mg of the title compound as a solid.

Analysis calc'd for $C_{15}H_{14}O_6N_5S_2K\cdot1\frac{1}{2}$ $H_2O$: C, 36.73; H, 3.49; N, 14.28; S, 13.07; K, 7.97. Found: C, 36.65; H, 3.00; N, 13.99; S, 13.48; K, 8.30.

EXAMPLE 186

(cis)-3-Amino-2-oxo-4-(2-phenylethenyl)-1-azetidinesulfonic acid

(A)

N-(3-phenyl-2-propenylidene)-4-methoxyaniline p-Anisidine (12.32 g) is dissolved in 160 ml of methylene chloride and 20 g of anhydrous magnesium sulfate is added. The mixture is cooled in an ice bath and 13.22 g of transcinnamaldehyde is added. The mixture is stirred under nitrogen for 2 hours and then filtered. The filtrate is evaporated to give a solid. The crude product is recrystallized from methylene chloride-petroleum ether to give 20.96 g of the title compound as a solid.

(B)

(±)-(cis)-3-Azido-1-(4-methoxyphenyl)-2-oxo-4-(2-phenylethenyl)azetidine

2-Azidoacetic acid (24.26 g) is dissolved in 100 ml of methylene chloride and cooled in an ice bath. To this solution is added 48.57 g of triethylamine and 14.24 g of N-(3-phenyl-2-propenylidene)-4-methoxyaniline dissolved in 250 ml of methylene chloride. To the resulting solution is added 50.41 g of trifluoroacetic anhydride dropwise over a one hour period. After stirring for one hour in an ice bath, the mixture is warmed to room temperature and stirred for about 16 hours. The mixture is then diluted with 250 ml of methylene chloride and washed with water (750 ml), 5% sodium bicarbonate solution (two 750 ml portions), and 1N HCl solution (750 ml). The organic layer is dried over anhydrous sodium sulfate and stripped of solvent to give a solid.

(C)

(±)-(cis)-3-Azido-2-oxo-4-(2-phenylethenyl)azetidine

To a solution of 10.22 g of ceric ammonium nitrate in 13 ml of water at 0° C. is added 1.99 g of (±)-(cis)-3-azido-1-(4-methoxyphenyl)-2-oxo-4-(2-phenylethenyl)azetidine dissolved in 65 ml of acetonitrile during a 15 minute period (additional 10 ml of acetonitrile is used for rinse). The mixture is stirred for an additional 15 minutes at 0° C., diluted with 750 ml of ethyl acetate, washed with water (six 600 ml portions), dried over anhydrous sodium sulfate, and stripped of solvent to give an oil. The crude product is chromatographed on 90 g of silica gel, eluting first with 250 ml of 30% ethyl acetate/petroleum ether, then 50% ethyl acetate/petroleum ether. Fractions (50 ml each) 11–16 are combined and evaporated to give 802 mg of the title compound as an oil.

(D)

(±)-(cis)-3-Azido-2-oxo-4-(2-phenylethenyl)-1-azetidinesulfonic acid, tetra-n-butylammonium salt (±)-(cis)-3-Azido-2-oxo-4-(2-phenylethenyl)azetidine (334 mg) is dissolved in 3 ml of dimethylformamide and 868 mg of pyridine-sulfur trioxide is added. The mixture is stirred at room temperature for 40 hours under nitrogen and then poured into 200 ml of 0.5M monobasic potassium phosphate solution and washed with 30 ml of methylene chloride. tetra-n-Butylammonium bisulfate (530 mg) is added to the aqueous solution and the mixture is extracted with methylene chloride (four 50 ml portions). The combined organic layers are back-washed with water (two 100 ml portions), dried over anhydrous magnesium sulfate and stripped of solvent to give 824 mg of the title compound as a gum.

(E)

(±)-(cis)-3-Amino-2-oxo-4-(2-phenylethenyl)-1-azetidinesulfonic acid (±)-(cis)-3-Azido-2-oxo-4-(2-phenylethenyl-1-azetidinesulfonic acid, tetra-n-butylammonium salt (300 mg) is dissolved in 4 ml of tetrahydrofuran and stirred rapidly. To the mixture is added 600 mg of zinc dust followed by 0.8 ml of 1N monobasic potassium phosphate solution. The mixture is heated to 45° C. and stirred at this temperature for 3 hours. The mixture is then filtered and the filtrate is taken in 40 ml of methylene chloride and 10 ml of water. The aqueous layer is further extracted with methylene chloride (thee 40 ml portions) and the combined methylene chloride layers are stripped of solvent to give 256 mg of a foam. This crude product is dissolved in a small amount of ca. 30% acetone/water and applied on 7.5 ml of Dowex (R+) resin (0.7 meq./ml) eluting with 40 ml of water. The eluent is evaporated to give 151 mg of foam, which is dissolved in 2 ml of water and acidified to pH 2 with 1N HCl solution. A small amount of acetonitrile is added to dissolve the precipitate and the resulting solution is applied on 15 ml of HP-20 resin, eluting with 150 ml of water, then 10% acetone/water. Fractions (15 ml each) 2–13 are combined and evaporated to give 101 mg of the title compound as a foam.

The crude product is recrystallized from ethyl acetate to give 11.39 g of the title compound as a solid.

EXAMPLE 187

(±)-(cis,Z)-3-[[(2-Amino-4-thiazolyl)(methoxyimino)acetyl]amino]-2-oxo-4-(2-phenylethenyl)-1-azetidinesulfonic acid, potassium salt A solution of 68 mg of (Z)-2-amino-α-(methoxyimino)-4-thiazoleacetic acid and 51 mg of N-hydroxybenzotriazole monohydrate in 2 ml of dimethylformamide is treated with 69 mg of dicyclohexylcarbodiimide. The mixture is stirred at room temperature for 30 minutes under nitrogen. (cis)-3-Amino-2-oxo-4-(2-phenylethenyl)-1-azetidinesulfonic acid (90 mg; see example 186) and 34 mg of triethylamine are added and the mixture is stirred for 20 hours under nitrogen. The slurry is evaporated in vacuo and triturated with 10 ml of acetone. The slurry is filtered and the filtrate is treated with 113 mg of potassium perfluorobutanesulfonate. Dilution with 30 ml of ether and filtration gives 169 mg of a solid product, which is dissolved in a small amount of ca. 10% acetonitrile/water and applied on 34 ml of HP-20 resin, eluting with 150 ml of water, then 10% acetone/water. Fractions (15 ml each) 18–19 are combined and stripped of solvent to give 100 mg of the title compound as a solid.

Analysis calc'd for $C_{17}H_{16}O_6N_5S_2K \cdot H_2O$: C, 40.23; H, 3.57; N, 13.80; S, 12.63; K, 7.70. Found: C, 40.03; H, 3.05; N, 13.61; S, 12.31; K, 7.56.

EXAMPLE 188

(cis)-3-Amino-4-(methoxycarbonyl)-2-oxo-1-azetidinesulfonic acid

(A)

[(4-Methoxyphenyl)imino]acetic acid, methyl ester

A dry 3-necked, 1 liter flask equipped with a nitrogen inlet and stirring bar is charged with 56.88 g of $MgSO_4$ followed by a solution of recrystallized anisidine (19.43 g) in dichloromethane (250 ml). After cooling to 0° C. a solution of methyl glyoxylate hemiacetal (19.92 g) in dichloromethane (250 ml) is added over 1.5 hours. After stirring an additional 20 minutes at 0° C., the reaction mixture is suction filtered, dried over sodium sulfate, filtered and concentrated in vacuo to one-quarter volume. Hexane (300 ml) is added, and the solution is concentrated to an oil which semi-solidifies on standing under high vacuum at 5° C.

(B)

(cis)-3-(1,3-Dihydro-1,3-dioxo-2H-isoindol-2-yl)-4-methoxycarbonyl-2-oxo-1-(4-methoxyphenyl)azetidine A dry 3-necked 500 ml flask equipped with stirring bar, addition funnel, septum and nitrogen inlet is charged with a solution of [(4-Methoxyphenyl)imino]acetic acid, methyl ester (21.09 g) in dichloromethane (150 ml) and cooled to 0° C. Triethylamine (19.2 ml) 0.14 mole is added dropwise followed by a solution of (N-phthalimido)acetyl acid chloride (28.4 g) in dichloromethane (150 ml) over 1 hour. The resulting mixture is stirred for 1.5 hours at 0° C., and diluted with 2.5 l of dichloromethane. The organic solution is washed with pH 4.5 monobasic potassium phosphate (two 500 ml portions), 5% sodium bicarbonate (two 500 ml portions), saturated sodium chloride solution (500 ml), and dried over sodium sulfate. Filtration and concentration in vacuo yields a solid which is washed with ethyl acetate, cold acetone and hexane to yield 18.65 g of product.

(C)

(cis)-4-(Methoxycarbonyl)-1-(4-methoxyphenyl)-2-oxo-3-[[(phenylmethoxy)carbonyl]amino]azetidine A dry 500 ml flask equipped with nitrogen inlet, stirring bar, and septum is charged with 18.65 g of (cis)-3-(1,3-dioxo-2H-isoindol-2-yl)-4-methoxycarbonyl-2-oxo-1-(4-methoxyphenyl)azetidine and 325 ml of dichloromethane. The resulting suspension is cooled to −30° C., and methyl hydrazine (3.52 ml) is added dropwise. The reaction is warmed to 0° C. and stirred for 1 hour. An additional 0.4 ml of methyl hydrazine is added and the mixture is stirred for 10 minutes. This sequence is repeated with a total of 2.9 equivalents of methyl hydrazine (7.7 ml). The solvent is removed in vacuo; 200 ml of fresh dichloromethane is added, and the mixture is again concentrated. This sequence is repeated two additional times, the resulting foam is dried under high volume for 20 minutes, redissolved in 225 ml dichloromethane, and allowed to stand at ambient temperature for about 16 hours during which time a considerable amout of solid precipitates. The mixture is filtered under nitrogen, the filtrate cooled to 0° C. (nitrogen atmosphere) and treated with diisopropylethyl amine (17 ml) followed by benzyl chloroformate (7 ml) dropwise. The reaction is stirred at 0° C. for 30 minutes, then at ambient temperature for 1.5 hours. The mixture is washed with two 300 ml portions of pH 4.5 monobasic potassium phosphate buffer, 5% sodium bicarbonate (two 300 ml portions), saturated sodium chloride (300 ml), dried (sodium sulfate), and filtered. Concentration in vacuo, yields a foam which on trituration with ether yields 9.9 g of the title compound as a solid.

(D)

(cis)-4-(Methoxycarbonyl)-2-oxo-3-[[(phenylmethoxy)carbonyl]amino]-1-azetidine

A solution of ceric ammonium nitrate (8.59 g) in 60 ml of 1:1 acetonitrile-water is treated with a slurry of 2 g (cis)-4-(methoxycarbonyl)-1-(4-methoxyphenyl)-2-oxo-3-[[(phenylmethoxy)carbonyl]amino]azetidine in 50 ml acetonitrile over 20 minutes. The reaction mixture is stirred an additional 10 minutes at ambient temperature and diluted with ethyl acetate (100 ml). The separated aqueous layer is washed with ethyl acetate (three 40 ml portions) and the combined organic extracts are washed with 5% sodium bicarbonate (three 70 ml portions). The basic washings are back-washed with ethyl acetate (50 ml) and the combined organic extracts are washed with aqueous sodium sulfite, 5% aqueous sodium carbonate (100 ml), 5% sodium chloride solution (two 100 ml portions), saturated sodium chloride (two 50 ml portions), and stirred over Darco G-60 charcoal for 30 minutes. Sodium sulfate is added, and the mixture is filtered and concentrated in vacuo to yield an oil which on trituration with ether yields 685 mg of the title compound as a solid.

(E)

(cis)-4-(Methoxycarbonyl)-2-oxo-3-[[(phenylmethoxy)carbonyl]amino]-1-azetidinesulfonic acid, tetrabutylammonium salt A mixture of (cis)-4-(methoxycarbonyl)-2-oxo-3-[[(phenylmethoxy)carbonyl]amino]-1-azetidine (100 mg) and 172 mg of a pyridine-sulfur trioxide complex in 1 ml of pyridine is stirred under argon for 3 hours at 80° C. The reaction mixture is poured into 70 ml of 0.5M monobasic potassium phosphate (pH 5.5) and extracted with four 30 ml portions of dichloromethane (discard). Tetrabutylammonium hydrogen sulfate (122 mg) is added to the aqueous layer which is then extracted with dichloromethane (four 30 ml portions). The organic extracts are washed with 8% sodium chloride solution, dried over sodium sulfate and filtered. Concentration in vacuo yields 186 mg of the title compound as a viscous oil.

(F)

(cis)-3-Amino-4-(methoxycarbonyl)-2-oxo-1-azetidinesulfonic acid

A solution of 186 mg of (cis)-4-(methoxycarbonyl)-2-oxo-3-[[(phenylmethoxy)carbonyl]amino]-1-azetidinesulfonic acid, tetrabutylammonium salt in 2 ml of methanol is hydrogenated over 10% palladium on charcoal (95 mg) for 1.5 hours at 1 atmosphere. The catalyst is filtered off and rinsed with dichloromethane and the filtrate is treated with 97% formic acid and cooled to −50° C. (the presence of a seed crystal at this stage is necessary to induce crystallization). After crystallization commences, the mixture is allowed to stand for about 16 hours at 10° C. The resulting solid is washed with dichloromethane, hexane, and dried in vacuo, yielding 50 mg of the title compound.

EXAMPLE 189

(cis)-3-[[2-Amino-4-thiazolyl)[[1-(diphenylmethoxycarbonyl)-1-methylethoxy]imino]acetyl]amino]-4-(methoxycarbonyl)-2-oxo-1-azetidinesulfonic acid, potassium salt A solution of N-hydroxybenzotriazole hydrate (34 mg) and 101 mg of 2-amino-α-[[1-(diphenylmethoxycarbonyl)-1-methylethoxy]imino]-4-thiazoleacetic acid in 0.5 ml of dimethylformamide is treated with solid dicyclohexylcarbodiimide (45 mg) and the mixture is stirred under argon for 45 minutes (ambient temperature). (cis)-3-Amino-4-(methoxycarbonyl)-2-oxo-1-azetidinesulfonic acid (45 mg; see example 188) is then added as a solid followed by triethylamine (0.03 ml) dropwise. The reaction is stirred at ambient temperature for about 16 hours. The dimethylformamide is removed under high vacuum at 30° C. and the residue is triturated with acetone. The supernatant is treated with potassium perfluorobutanesulfonate (67 mg). Dilution with ether produces a solid which is washed with ether and dried in vacuo to yield 93 mg of the title compound.

EXAMPLE 190

(cis)-3-[[(2-Amino-4-thiazolyl)[(1-carboxy-1-methylethoxy)imino]acetyl]amino]-4-(methoxycarbonyl)-2-oxo-1-azetidinesulfonic acid, dipotassium salt A slurry of (cis)-3-[[2-Amino-4-thiazolyl)[[1-(diphenylmethoxycarbonyl)-1-methylethoxy)imino]acetyl]amino]-4-(methoxycarbonyl)-2-oxo-1-azetidinesulfonic acid, potassium salt in 0.4 ml of anisole is stirred at −12° C. under argon, and 0.9 ml of cold (−10° C.) trifluoroacetic acid is added. After 1.5 hours, 4 ml of ether and 2 ml of hexane are added and the resulting slurry is stirred for 15 minutes at −10° C., then 15 minutes at ambient temperature. The solid is isolated by centrifugation and washed with ether. The pH of a suspension of this material in 0.5 ml of cold water is adjusted to 6 with 1N potassium hydroxide and then applied to a 30 ml HP-20AG column. Elution with water yields 30 mg of the title compound after evaporation (acetonitrile added and evaporated twice).

Analysis calc'd for $C_{14}H_{15}K_2N_5O_9S_2$: C, 31.15; H, 2.81; N, 12.98. Found: C, 29.08; H, 3.03; N, 12.19.

EXAMPLE 191

(S)-(trans)-3-Amino-4-ethynyl-2-oxo-1-azetidinesulfonic acid (A)

2-(Trimethylsilyl)ethynylmagnesium bromide

To a flame-dried 50 ml flask maintained under positive nitrogen pressure is added 20 ml of dry tetrahydrofuran, 2.20 ml of trimethylsilyl acetylene and ·5.05 ml of 3.06M solution of methylmagnesium bromide in ether. The mixture is stirred for 140 minutes yielding the title compound.

(B)

(S)-(trans)-4-[2-(trimethylsilyl)ethynyl]-2-oxo-3-[(triphenylmethyl)amino]azetidine To a flame dried 250 ml 3-necked flask is added 6.00 g of (S)-(cis)-4-(methylsulfonyl)-2-oxo-3-[(triphenylmethyl)amino]azetidine. The flask is flushed with nitrogen, and then maintained under positive nitrogen pressure. After the reaction mixture is cooled in a dry ice/isopropanol bath, 4.65 ml of a 3.06M solution of methylmagnesium bromide in ether is added dropwise via syringe with rapid stirring. The solution of 2-(trimethylsilyl)ethynylmagnesium bromide prepared in part A is added via a Teflon tube under positive nitrogen pressure (the flask containing the reactant is rinsed with 7 ml of tetrahydrofuran). When the addition is complete the cold bath is removed. After 45 minutes, a solution of 3.5 g of potassium bisulfate in 20 ml of water is added. Most of the tetrahydrofuran is removed on the rotary evaporator. The residue is transferred to a separatory funnel with ether and water. The water layer is separated and extracted twice with ether. The combined ether layers are washed once with saturated aqueous sodium chloride, dried over sodium sulfate, and filtered. Removal of the solvent gives a foam which is chromatographed on a silica column. Elution with 2 liters of dichloromethane, 1 liter of 1% ether/dichloromethane, 2 liters of 2% ether/dichloromethane and 1.5 liters of 10% ether/dichloromethane (fraction 1=1000 ml; fraction 2,3=500 ml; fraction 4-end=250 ml) gives 1.30 g of the title compound in fractions 2–8 and 1.80 g of the corresponding trans-isomer in fractions 12–19. Fractions 9–11 contain 1.19 g of a mixture of cis and trans isomers.

(C)

(S)-(trans)-4-ethynyl-2-oxo-3-[(triphenylmethyl)amino]azetidine (S)-(trans)-4-[2-(trimethylsilyl)ethynyl]-2-oxo-3-[(triphenylmethyl)amino]azetidine (2.97 g) is dissolved in 30 ml of dichloromethane and 330 mg of tetrabutylammonium fluoride (containing 20–25% water) is added. After 20 minutes, the solvent is removed in vacuo. The residue is taken up in ethyl acetate and water. The organic layer is separated, washed once with water and once with saturated aqueous sodium chloride, dried over sodium sulfate, and filtered. Removal of the solvent gives an oil which is stirred for 15 minutes with 60 ml of pentane to afford 2.35 g of the title compound as a powder (after drying in vacuo).

(D)

(S)-(trans)-3-Amino-4-ethynyl-2-oxo-1-azetidinesulfonic acid (S)-(trans)-4-ethynyl-2-oxo-3-[(triphenylmethyl)amino]azetidine (404 mg) and 560 mg of a complex of pyridine and sulfur trioxide are added to a 25 ml flask. After the flask is flushed with nitrogen, 4.0 ml of dry pyridine is added and the mixture is heated at 80°–85° C. for 3 hours. The mixture is added to a rapidly stirred mixture of 4.0 ml of concentrated hydrochloric acid, 50 ml of water, and 50 ml of ethyl acetate. The pH is adjusted to 3.15 with sodium carbonate. The water layer is separated and extracted once with ethyl acetate. The combined organic layer is washed once with saturated aqueous sodium chloride, dried over sodium sulfate and filtered. Solvent removal in vacuo gives a foam which is taken up in 10 ml of dichloromethane. Formic acid (98%, 8 ml) is added, and after 15 minutes the mixture is concentrated to 4 ml and 10 ml of dichloromethane is added to give a solid suspended in solution. Filtration gives 100 mg of the title compound as a solid (obvious discoloration with melting >180° C.).

EXAMPLE 192

[3S-[3α(Z),4β]]-3-[[(2-Amino-4-thiazolyl)(methoxyimino)acetyl]amino]-4-ethynyl-2-oxo-1-azetidinesulfonic acid, potassium salt (Z)-2-Amino-α-(methoxyimino)-4-thiazoleacetic acid (100 mg), 85 mg of N-hydroxybenzotriazole monohydrate, and 113 mg of dicyclohexylcarbodiimide are weighed into a 10 ml flask. The flask is flushed with nitrogen and cooled in an ice-water bath. Then 0.6 ml of dimethylformamide is added and the mixture is stirred for 10 minutes, at which point an additional 0.6 ml of dimethylformamide is added. (S)-(trans)-3-Amino-4-ethynyl-2-oxo-1-azetidinesulfonic acid (95 mg; see example 191) is added as a solid with 1.0 ml of dimethylformamide and 56 μl of triethylamine. The cold bath is removed and the mixture is stirred for 22 hours. Acetone (3 ml) is added and the solids present are removed by filtration and washed with an additional 4 ml of acetone. All solvents are removed in vacuo and the residue is taken up in 5 ml of methanol and 162 mg of potassium perfluorobutanesulfonate is added and dissolved. After standing, a solid is deposited and then isolated by centrifugation to afford 68 mg of the title compound, melting point >230° C.

EXAMPLE 193

(S)-3-[[[(2,5-Dichlorophenyl)thio]acetyl]amino]-2-oxo-1-azetidinesulfonic acid, potassium salt 3-Amino-2-oxo-1-azetidinesulfonic acid (100 mg) is dissolved in dry dimethylformamide (2 ml) with triethylamine (0.083 ml). 2,5-Dichlorophenylthioacetic acid (123 mg) 0.602 mmol, N-hydroxybenzotriazole hydrate (81 mg) and dicyclohexylcarbodiimide (124 mg) are added, the mixture is stirred for 2 hours at room temperature, and then 2 days at 5° C. Solvent is removed in vacuo, the residue is taken up in water, filtered through Celite, and the filtrate is washed with ethyl acetate. The aqueous layer is combined with dichloromethane, tetrabutylammonium bisulfate (612 mg) is added, the pH was raised to 3 with 1N potassium hydroxide solution, and after extracting a total of three times with dichloromethane, the combined extracts are dried ($Na_2SO_4$), and solvent is removed in vacuo yielding an oil. A solution of the oil in acetone is added to a solution of potassium perfluorobutanesulfonate (612 mg) in acetone causing precipitation of the product. After addition of a small amount of ether the solid is collected by filtration, washed several times with acetone, and dried to give a powder (206 mg).

Anal. Calc'd for $C_{11}H_9N_2O_5S_2Cl_2K$: C, 31.21; H, 2.14; N, 6.62; Cl. 16.75. Found: C, 27.90; H, 2.11; N, 5.84; Cl, 18.04.

EXAMPLE 194

(3S-trans)-3-[[[(2,5-Dichlorophenyl)thio]acetyl]amino]-4-methyl-2-oxo-1-azetidinesulfonic acid, potassium salt (3S-trans)-3-Amino-4-methyl-2-oxo-1-azetidinesulfonic acid (250 mg; see example 139) is dissolved in dimethylformamide (2 ml) with triethylamine (193 µl). 2,5-Dichlorophenylthioacetic acid (285 mg), N-hydroxybenzotriazole hydrate (213 mg) and dicyclohexylcarbodiimide (287 mg) are added. After stirring for about 16 hours at room temperature, the mixture is filtered and solvent is removed in vacuo. The residue is taken up in water and filtered. The filtrate is washed with ethyl acetate, layered with dichloromethane and tetrabutylammonium bisulfate (4.2 mmol) is added. After a total of three extractions with dichloromethane, the combined extracts are dried ($Na_2SO_4$) and solvent is removed in vacuo yielding an oil (920 mg). To a solution of the oil in acetone is added potassium perfluorobutanesulfonate (946 mg) dissolved in acetone. A solid slowly precipitates, is collected, washed twice with ether, and dried to give a powder (306 mg). Chromatography on HP-20 resin (100 ml column), eluting with 20% acetonitrile: 80% water, yields the desired product, which crystallizes upon evaporation of a water:methanol mixture. Trituration of the residue with acetone gives a powder (233 mg); melting point 212°–213° (dec.).

Anal. Calc'd for $C_{12}H_{11}N_2O_5Cl_2S_2K$: C, 32.95; H, 2.54; N, 6.41; Cl, 16.21; S, 14.66. Found: C, 32.91; H, 2.60; N, 6.42; Cl, 16.50; S, 13.77.

EXAMPLES 195–196

Following the procedure of example 138, but substituting (3S-trans)-3-amino-4-methyl-2-oxo-1-azetidinesulfonic acid for (3S-cis)-3-amino-4-methyl-2-oxo-1-azetidinesulfonic acid and the acid listed in column I for (Z)-2-amino-α-(methoxyimino)-4-thiazoleacetic acid, yields the compound listed in column II.

| | | |
|---|---|---|
| 195. | (R)—(aminooxoacetyl)amino] (4-hydroxyphenyl)acetic acid | [3S—[3α(R*),4β]]-3-[[[(aminooxoacetyl)amino]-(4-hydroxyphenyl)acetyl]-amino]-4-methyl-2-oxo-1-azetidinesulfonic acid, potassium salt |
| 196. | (R)—[(aminooxoacetyl)amino]-phenylacetic acid | [3S—[3α(R*),4β]]-3-[[[-(aminooxoacetyl)amino]-phenylacetyl]amino]-4-methyl-2-oxo-1-azetidinesulfonic acid, potassium salt; melting point 187° C., dec. |

EXAMPLE 197

[3S(R*)]-3-[[[(Aminooxoacetyl)amino](4-hydroxyphenyl)acetyl]amino]-2-oxo-1-azetidinesulfonic acid, potassium salt Following the procedure described in Example 28, but substituting (R)-[(aminooxoacetyl)amino](4-hydroxyphenyl)acetic acid for (Z)-2-amino-α-[[2-(diphenylmethoxy)-1,1-dimethyl-2-oxoethoxy]imino]-4-thiazoleacetic acid, yields the title compound melting point 128° C., dec.

EXAMPLE 198

[3S(R*)]-3-[[(2-Amino-4-thiazolyl)[[[3-[(2-furanylmethylene)amino]-2-oxo-1-imidazolidinyl]carbonyl]amino]acetyl]amino]-2-oxo-1-azetidinesulfonic acid, potassium salt Following the procedure of example 6, but substituting (R)-2-amino-α-[[[3-[(2-furanylmethylene)amino]-2-oxo-1-imidazolidinyl]carbonyl]amino]-4-thiazoleacetic acid for aminothiazoleacetic acid yields the title compound, melting point >250° C.

EXAMPLE 199

(S)-3-[[2-Amino-5-chloro-4-thiazolyl)acetyl]amino]-2-oxo-1-azetidinesulfonic acid, potassium salt Following the procedure of example 6B, but substituting 2-amino-5-chloro-4-thiazoleacetic acid for aminothiazoleacetic acid, yields the title compound, melting point >360° C.

EXAMPLE 200

Biological Production of EM5117

9 Liter Fermentation

Chromobacterium violaceum SC 11,378 A.T.C.C. No. 31532 is maintained on the following sterilized agar medium (A):

| | Grams |
|---|---|
| Yeast Extract | 1 |
| Beef Extract | 1 |
| NZ Amine A | 2 |
| Glucose | 10 |
| Agar | 15 |
| Distilled H₂O to 1 liter | |

The pH is adjusted to 7.3 before sterilization at 121° C. for 30 minutes.

A loopful of surface growth of the microorganism is used to inoculate each of three 500 ml Erlenmeyer flasks, each containing 100 ml of the following sterilized medium (B):

| | Grams |
|---|---|
| Oatmeal | 20 |
| Tomato Paste | 20 |
| Tap H₂O to 1 liter | |

Adjust pH to 7.0 before sterilization at 121° C. for 15 minutes.

The flasks are then incubated at 25° C. on a rotary shaker (300 rpm; 2 inch stroke) for approximately 24 hours.

After the appropriate incubation as described above, 1% (vol/vol) transfers are made from the growth culture flasks to one hundred 500 ml Erlenmeyer flasks each containing 100 ml of the following sterilized medium (C):

|  | Grams |
| --- | --- |
| Oatmeal | 20 |
| Tomato Paste | 20 |
| Glucose | 30 |
| Tap H$_2$O to 1 liter |  |

The pH is adjusted to 7.0 before sterilization of 121° C. for 15 minutes.

After inoculation, the flasks are incubated at 25° C. on a rotary shaker (300 rpm; 2 inch stroke) for approximately 18–24 hours. At this time the contents of the flasks are pooled and the broth is centrifuged yielding approximately 9 liters of supernatant broth.

250 Liter Fermentation

A loopful of surface growth from an agar slant (medium A) of *Chromobacterium violaceum* SC 11,378 A.T.C.C. No. 31532 is used to inoculate each of five 500 ml Erlenmeyer flasks each containing 100 ml of sterilized medium (B). The flasks are then incubated at 25° C. on a rotary shaker (300 rpm; 2 inch stroke) for approximately 24 hours. After the appropriate incubation, as described above, 1% (vol/vol) transfers are made from the growth culture flasks to five 4 liter Erlenmeyer flasks each containing 1.5 liters of sterilized medium B. After inoculation the flasks are then incubated at 25° C. on a rotary shaker (300 rpm; 2 inch stroke) for approximately 24 hours. After the appropriate incubation as described above, a 1% transfer (vol/vol) is made to an agitator equipped fermentation tank containing 250 liters of sterilized medium (C). After inoculation the fermentation is continued under the following conditions: temperature—25° C.; pressure—10 psig; aeration—10 cfm; agitation—155 rpm. Ucon is added as needed as antifoam agent. After approximately 18–24 hours the fermentation is completed. The fermentation broth is then adjusted to pH 5.0 using HCl and the broth contents of the tank is centrifuged yielding approximately 230 liters of supernatant broth.

Isolation and Purification

The broth supernatant from the 250 liter fermentation is adjusted to pH 5 using sulfuric acid and filtered using 3–5% diatomaceous earth (Celite). The broth filtrate is extracted with two 30 liter portions of 0.005M cetyldimethylbenzylammonium chloride in methylene chloride.

The combined lower phase is extracted with 6 liters of 0.05M sodium iodide which has been adjusted to pH 5 with acetic acid. The lower phase is discarded and the upper phase is concentrated in vacuo to 500 ml.

The concentrated material is extracted with 400 ml of n-butanol. The upper phase is discarded and the lower phase is concentrated to dryness in vacuo. The residue is dissolved (to the extent possible) in 150 ml of methanol. The insoluble material is discarded and the methanol solution is concentrated to dryness in vacuo, yielding 38.6 g of crude antibiotic.

The crude product is dissolved in 10 ml of methanol-water (1:1) and chromatographed on a 500 ml column of cross-linked dextran gel (Sephadex G-10) in the same solvent mixture, eluting at 2 ml/minute and collecting 20 ml fractions. Active fractions (19–26) are combined and concentrated in vacuo. The residue (5.23 g) is mixed with 50 ml of methanol. Insoluble material is filtered out and discarded. The filtrate is concentrated in vacuo.

The residue, 5.0 g of material, is dissolved in 10 ml of pH 5 sodium 0.01M phosphate buffer and applied to a column of DEAE cellulose (Whatman DE52 cellulose) packed and equilibrated in the same buffer. The column is eluted at 5 ml/minute with a linear gradient prepared from 4 liters of pH 5 sodium 0.01M phosphate buffer and 4 liters of pH 5 sodium 0.1M phosphate buffer, collecting 20 ml fractions. Active fractions (192–222) are combined and concentrated in vacuo, and methanol-insoluble material is removed, washing well with methanol. Removal of solvent leaves 576 mg of material.

The 576 mg of residue is dissolved in 4 ml of water and the pH adjusted to 5 with about 1 ml of 0.1N sodium hydroxide. The solution is chromatographed on a column of alkylated cross-linked dextran gel (Sephadex LH-20) in water, eluting at 1 ml/minute and collecting 10 ml fractions. Active fractions (38–44) are combined and concentrated, giving 459 mg of residue.

Three hundred and forty eight (348) mg of the above residue is dissolved in water and the solution placed on a column of macroreticular styrene-divinylbenzene copolymer resin (Diaion HP20AG); the column has been first prepared by washing with methanolic potassium hydroxide, methanol, methanolic hydrogen chloride, methanol and water, and then packed in water. The column is eluted with water at 1 ml/minute, collecting 10 ml fractions. Active fractions (36–43) are combined and concentrated giving 186.4 mg of material. Chromatography (in the same way) of another 100 mg of the 459 mg of residue from the previous step yields 51.5 mg of material. At this stage the 186.4 mg of material and 51.5 mg of material are nearly pure EM5117 as shown by thin-layer chromatography and nuclear magnetic resonance spectra.

The 186.4 mg portion of EM5117 from above is dissolved in water and passed through a column of ion-exchange resin (Dowex 50W-X2, 100–200 mesh, potassium form), washing with two bed volumes of water. Concentration of the effluent yields 189.0 mg of crystalline solid. Recrystallization of this material is accomplished by dissolving it in 0.38 ml of water and adding 3.42 ml of methanol. The resulting mixture is cooled on ice and filtered, yielding 145 mg of crystals. Two further recrystallization in this manner from water-methanol, 1:9, yield 95.9 mg of EM5117, potassium salt.

| Optical rotation in water at 21° C. (c = 1) | |
| --- | --- |
| λ (mn) | [α] |
| 589 | +94.3° |
| 579 | +98.6 |
| 546 | +113.1 |
| 436 | +203 |
| 365 | +348 |

The following fermentation media are effective for the production of EM5117, and may be substituted for medium (B) and (C) in the above example.

|  | Grams |
| --- | --- |
| MEDIUM D | |
| Nutrisoy Flour | 30 |
| Glucose | 50 |

-continued

|  | Grams |
|---|---|
| Yeastamine | 2.5 |
| CaCO$_3$ | 7 |
| Distilled H$_2$O to 1 liter | |
| MEDIUM E | |
| Yeast Extract | 4 |
| Malt Extract | 10 |
| Glucose | 30 |
| Glycerol | 2 |
| Distilled H$_2$O to 1 liter | |
| Adjust pH to 7.3 before sterilization | |
| MEDIUM F | |
| Glycerol | 10 |
| L-asparagine | 5 |
| KH$_2$PO$_4$ | 1 |
| Na$_2$HPO$_4$ | 2 |
| Glucose | 50 |
| MgSO$_4$.7H$_2$O | 0.2 |
| Yeast Extract | 2.5 |
| Tap H$_2$O to 1 liter | |
| MEDIUM G | |
| (NH$_4$)$_2$SO$_4$ | 2 |
| L-asparagine | 5 |
| Glucose | 50 |
| Glycerol | 10 |
| KH$_2$PO$_4$ | 3 |
| K$_2$HPO$_4$ | 7 |
| MgSO$_4$.7H$_2$O | 0.2 |
| Yeast Extract | 2.5 |
| Distilled H$_2$O to 1 liter | |
| Adjust pH to 7.0 | |
| MEDIUM H | |
| K$_2$HPO$_4$ | 7 |
| KH$_2$PO$_4$ | 3 |
| Na Citrate | 0.5 |
| MgSO$_4$ | 0.1 |
| (NH$_4$)$_2$SO$_4$ | 1 |
| Glucose | 30 |
| Yeast Extract | 2.5 |
| Distilled H$_2$O to 1 liter | |
| MEDIUM I | |
| Nutrisoy Flour | 10 |
| (NH$_4$)$_2$SO$_4$ | 5 |
| Glucose | 50 |
| Yeast Extract | 2.5 |
| CaCO$_3$ | 5 |
| Distilled H$_2$O to 1 liter | |
| MEDIUM J | |
| Gerber's Baby Oatmeal | 20 |
| Contadina Tomato Paste | 5 |
| Glucose | 20 |
| Tap H$_2$O to 1 liter | |
| Adjust pH 7.0 | |
| MEDIUM K | |
| Gerber's Baby Oatmeal | 5 |
| Contadina Tomato Paste | 20 |
| Glucose | 20 |
| Tap H$_2$O to 1 liter | |
| Adjust pH 7.0 | |
| MEDIUM L | |
| Yeast Extract | 4 |
| Malt Extract | 10 |
| Glucose | 34 |
| MEDIUM M | |
| Amberex (1003) | 5 |
| Glucose | 30 |
| Tap H$_2$O to 1 liter | |
| MEDIUM N | |
| Amberex | 5 |
| Cerelose | 33 |
| Tap H$_2$O to 1 liter | |

EXAMPLE 201

Biological Production of EM5210

Gluconobacter species SC11,435 A.T.C.C. No. 31581 is maintained on the following sterilized agar medium (A):

|  | Grams |
|---|---|
| Yeast Extract | 1 |
| Beef Extract | 1 |
| NZ amine A | 2 |
| Glucose | 10 |
| Agar | 15 |
| Distilled H$_2$O to 1 liter | |

The pH is adjusted to 7.3 before sterilization at 121° C. for 30 minutes.

A loopful of surface growth from the agar slant (medium A) of Gluconobacter species SC11,435 is used to inoculate each of three 500 ml Erlenmeyer flasks each containing 100 ml of the following sterilized medium (B):

|  | Grams |
|---|---|
| Yeast Extract | 4 |
| Malt Extract | 10 |
| Dextrose | 4 |
| Distilled H$_2$O 1 liter | |

The pH is adjusted to 7.3 before sterilization at 121° C. for 15 minutes.

After inoculation, the flasks are incubated at 25° C. on a rotary shaker (300 rpm; 2 inch stroke) for approximately 24 hours. After the appropriate incubation, as described above, 1% (vol/vol) transfers are made from the grown culture flasks to one hundred 500 ml Erlenmeyer flasks each containing 100 ml of the following sterilized medium (C):

|  | Grams |
|---|---|
| Yeast Extract | 5 |
| Glucose | 10 |
| Distilled H$_2$O 1 liter | |

The medium is sterilized at 121° C. for 15 minutes.

After inoculation, the flasks are incubated at 25° C. on a rotary shaker (300 rpm; 2 inch stroke) for 18 hours. At this time the contents of the flasks are pooled and the broth is centrifuged yielding approximately 9 liters of supernatant broth.

Isolation and Purification (small scale)

Activity from the broth supernatant (10 liters) is absorbed on a 500 g column of strongly basic anion exchange resin with quaternary ammonium groups attached to a styrene-divinylbenzene copolymer lattice (Dowex AG1-X2(Cl$^-$)), washed with water and eluted with 5% sodium chloride in aqueous 0.01M NaH$_2$PO$_4$. The eluate is concentrated in vacuo.

The residue is adsorbed on 250 g of charcoal which is washed with water. EM5210 is eluted with methanol-water (1:1). The active fractions are combined and concentrated in vacuo yielding crude EM5210.

The crude EM5210 is chromatographed on a 280 ml column of strong base anion exchange resin (Bio.Rad AG 1-X2 (Cl$^-$)) using a linear gradient prepared from 1 liter of water and 1 liter of 2M pyridinium acetate (pH 4.5). The active fractions are combined and concentrated in vacuo.

The partially purified EM5210 is further purified by gel filtration of the residue on a 500 ml column of cross-linked dextran gel (Sephadex G-10) eluting with water. The active fractions are combined and concentrated yielding 26 mg of EM5210. The potassium salt of EM5210 is prepared by passing EM5210 through a column of cation-exchange resin (Dowex 50-X2) in the potassium form.

Isolation and Purification (large scale)

The broth filtrate of a 250 liter fermentation (pH 3.7) of Gluconobacter species SC11,435 is absorbed on 10.8 kg of strong base anion exchange resin (Dowex 1-X8($Cl^-$)). The resin is washed with water and eluted with 5% sodium chloride in 0.01M sodium dihydrogen phosphate. The active fractions are combined and concentrated to a small volume. The precipitated salt is removed and the filtrate is desalted by passing it through a column of charcoal (1.1 kg of 20–40 mesh Darco) in water. The column is washed with water and the EM5210 is eluted with methanol-water, 1:1. Active fractions are combined and concentrated. The residue (16 g) is dissolved in water and chromatographed on a column (600 ml) of strong base ion exchange resin (Bio.-Rad Ag 1-X2($Cl^-$), 200–400 mesh), eluting with a linear gradient prepared from 1 liter of water and 1 liter of 10% sodium chloride in 0.01M sodium dihydrogen phosphate. Active fractions are combined, concentrated in vacuo to a small volume, and precipitated salts are removed by filtration. The filtrate is applied to a column of macroreticular styrene-divinylbenzene co-polymer resin (Diaion HP 20 AG). The column is eluted with water. The active fractions are combined, concentrated to a small volume and freeze-dried, yielding 120 mg of the sodium salt of EM5210.

To transform the sodium salt to the lithium salt an ion-exchange resin (Dowex 50 W-X2, lithium form) column is used. The sodium salt (100 mg) is dissolved in 0.5 ml of water, applied to the column and eluted with water. The active fractions are combined and directly freeze-dried, yielding 95 mg of the lithium salt of EM5210.

The free acid (inner salt) of EM5210 is prepared by passing a base salt of EM5210 through a column of weak acid ion-exchange resin in the $H^+$ form. For example, about 2.5 mg of the lithium salt can be applied to a column of Bio.Rad Bio.Rex 70 ($H^+$) and eluted with water to give 1.45 mg of the free acid (inner salt).

Chemical properties of EM5210

(1) Ninhydrin positive.

(2) Acid hydrolysis (6N HCl at 115° C. for 16 hours) gives two major ninhydrin positive spots by paper chromatography (Whatman No. 1, butanol-acetic acid-water (5:1:4)), and one weak ninhydrin positive spot that quenches UV-excited fluorescence. The two major ninhydrin positive spots are D-glutamic acid and D-alanine.

Physical characteristics of EM5210

(1) UV spectrum of the sodium salt in water: end absorption (2) IR—Major peaks of the lithium salt in KBr: 1770, 1640, 1530, 1384, 1242, and 1051 $cm^{-1}$.

(3) PMR—Chemical shifts of the lithium salt in deuterated water, ppm down field from TSP:
1.40 (d, J=7 Hz), ca. 2.14 (m), ca. 2.44 (m),
3.49 (s)
3.73 (t, J=6 Hz), 3.94 (s), 4.28 (m)

Optical rotation of the free acid (inner salt) in water at 24° C. (C=0.15%) (pH 2.7):

| λ (nm) | [α] |
|---|---|
| 589 | +73° |
| 578 | +79° |
| 546 | +91° |
| 436 | +159° |
| 365 | +263° |

The following fermentation media have been found effective for the production of EM5210 and may be substituted for medium (B) and (C) in the text.

| | Grams |
|---|---|
| MEDIUM D | |
| Oatmeal | 20 |
| Tomato Paste | 20 |
| Tap $H_2O$ to 1 liter | |
| Adjust pH to 7.0 Before sterilization of 121° C. for 15 minutes. | |
| MEDIUM E | |
| Yeastamine | 5 |
| Cerelose | 11 |
| Tap $H_2O$ to 1 liter | |
| Sterilization at 121° C. for 15 minutes. | |
| MEDIUM F | |
| Glucose | 5 |
| Tartaric Acid | 2 |
| Yeast Extract | 0.5 |
| $(NH_4)_2HPO_4$ | 1 |
| $(NH_4)_2SO_4$ | 2 |
| $K_2HPO_4$ | 0.5 |
| $NaH_2PO_4$ | 0.5 |
| $MgSO_4.7H_2O$ | 0.2 |
| $CaCO_3$ | 1 |
| Distilled $H_2O$ to 1 liter | |
| Adjust pH to 6.0 before sterilization of 121° C. for 15 minutes. | |
| MEDIUM G | |
| Nutrisoy flour | 30 |
| Glucose | 50 |
| Yeastamine | 2.5 |
| $CaCO_3$ | 7 |
| Distilled $H_2O$ to 1 liter | |
| Sterilization at 121° C. for 30 minutes. | |
| MEDIUM H | |
| NZ Amine A | 10 |
| Cerelose | 33 |
| Yeastamine | 2.5 |
| Tap $H_2O$ to 1 liter | |
| Sterilization at 121° C. for 15 minutes. | |
| MEDIUM I | |
| Nutrisoy flour | 15 |
| Soluble starch | 15 |
| Glucose | 50 |
| $CoCl_2.6H_2O$ | 0.005 |
| $CaCO_3$ | 10 |
| Distilled $H_2O$ to 1 liter | |
| Sterilization at 121° C. for 30 minutes. | |

BIOLOGICAL ACTIVITY

The following methodology is used to determine the minimum inhibitory concentration (hereinafter referred to as MIC) of the β-lactams of this invention.

The test organisms are grown in approximately 15–20 ml of Antibiotic Assay broth (Difco) by inoculating (in tubes) the broth with a loopful of the organism from a BHI (Difco) agar slant. The inoculated tubes are incubated at 37° C. for 18 to 20 hours. These cultures are assumed to contain $10^9$ colony forming units (hereinafter CFU) per milliliter. The cultures are diluted 1:100 to give a final inoculum level of $10^7$ CFU; dilutions are made with K-10 broth*.

The compounds are dissolved in the appropriate diluent at a concentration of 1000 μg/ml. Two-fold dilutions are made in K-10 broth resulting in a range from 1000 μg/ml to 0.5 μg/ml. 1.5 ml of each dilution is placed into individual square petri dishes to which 13.5 ml of K-10 agar** is added. The final drug concentration in the agar ranges from 100 μg/ml to 0.05 μg/ml. Organism growth control plates containing agar only are prepared and inoculated before and after the test plates. The organisms are applied to the agar surface of each plate with the Denley Multipoint Inoculator (which delivers approximately 0.001 ml of each organism) resulting in a final inoculum level of $10^4$ CFU on the agar surface.

The plates are incubated at 37° C. for 18 hours and the MIC's are determined. The MIC is the lowest concentration of compound inhibiting growth of the organism.

| *K-10 broth is a yeast beef broth containing: | |
|---|---|
| Beef extract | 1.5 g |
| Yeast extract | 3.0 g |
| Peptone | 6.0 g |
| Dextrose | 1.0 g |
| Distilled water q.s. 1 liter | |
| **K-10 agar | |
| Beef extract | 1.5 g |
| Yeast extract | 3.0 g |
| Peptone | 6.0 g |
| Dextrose | 1.0 g |
| Agar | 15.0 g |
| Distilled water q.s. 1 liter | |

The tables that follow are tabulated results obtained when the β-lactams of this invention are tested against various organisms. The number following each organism refers to the number of the organism in the collection of E. R. Squibb & Sons, Inc., Princeton, N.J. A dash (-) in the tables means that the compound tested did not show activity against the particular organism at 100 μg/ml. The symbol "N.T." means not tested.

| Organism | M.I.C. (μg/ml) Product of Example | | | | | | | | | | |
|---|---|---|---|---|---|---|---|---|---|---|---|
|  | 1 | 3 | 5 | 6 | 7 | 8 | 9 | 10 | 12 | 13 | 14 |
| *Staphylococcus aureus,* 1276 | 1.6 | 6.3 | 1.6 | 12.5 | 3.1 | 6.3 | 3.1 | 3.1 | 12.5 | 25 | 12.5 |
| *Staphylococcus aureus,* 2399 | 1.6 | 6.3 | 0.8 | 6.3 | 3.1 | 3.1 | 6.3 | 3.1 | 6.3 | 25 | 6.3 |
| *Staphylococcus aureus,* 2400 | 3.1 | 3.1 | 1.6 | 12.5 | 6.3 | 6.3 | 6.3 | 6.3 | 6.3 | 12.5 | 6.3 |
| *Staphylococcus aureus,* 10165 | 12.5 | 3.1 | 6.3 | 25 | 12.5 | 12.5 | 25 | 12.5 | — | — | — |
| *Streptococcus faecalis,* 9011 | — | — | — | — | — | — | 100 | 100 | 100 | — | 100 |
| *Streptococcus agalactiae,* 9287 | 3.1 | 25 | 0.8 | 6.3 | 1.6 | 6.3 | 3.1 | 3.1 | 1.6 | 12.5 | 1.6 |
| *Micrococcus luteus,* 2495 | 6.3 | 50 | 1.6 | 50 | 6.3 | 12.5 | 3.1 | 6.3 | 1.6 | 25 | 0.8 |
| *Escherichia coli,* 8294 | 50 | — | — | — | — | — | — | — | 0.4 | 25 | 0.4 |
| *Escherichia coli,* 10857 | 100 | — | 25 | — | 100 | 100 | 100 | — | 0.8 | 50 | 0.8 |
| *Escherichia coli,* 10896 | 25 | — | — | 100 | 100 | 100 | 100 | — | 1.6 | 50 | 3.1 |
| *Escherichia coli,* 10909 | 25 | — | — | 50 | 100 | 100 | 50 | — | 0.4 | 25 | 0.2 |
| *Klebsiella aerogenes,* 10440 | 100 | — | — | — | — | — | 100 | — | 0.4 | 25 | 0.4 |
| *Klebsiella pneumoniae,* 9527 | 100 | — | — | — | — | — | 100 | — | 0.1 | 12.5 | 0.2 |
| *Proteus mirabilis,* 3855 | — | — | — | 100 | 100 | — | 50 | — | 0.2 | 12.5 | 0.1 |
| *Proteus rettgeri,* 8479 | 25 | 100 | — | 12.5 | 100 | 50 | 50 | — | <0.05 | 1.6 | <0.05 |
| *Proteus vulgaris,* 9416 | — | — | 25 | — | 100 | — | 100 | 100 | 0.4 | 25 | 0.1 |
| *Salmonella typhosa,* 1195 | 50 | — | — | 100 | 100 | — | 50 | — | 0.1 | 12.5 | <0.05 |
| *Shigella sonnei,* 8449 | 50 | — | — | — | 100 | — | 100 | — | 0.4 | 25 | 0.8 |
| *Enterobacter cloacae,* 8236 | — | — | — | — | — | — | — | — | 0.4 | — | 0.4 |
| *Enterobacter aerogenes,* 10078 | — | — | — | — | — | — | — | — | 0.8 | 100 | 0.8 |
| *Citrobacter freundii,* 9518 | — | — | — | — | — | — | — | — | 3.1 | — | 3.1 |
| *Serratia marcescens,* 9783 | 100 | — | — | 50 | 100 | 50 | — | — | 12.5 | — | 3.1 |
| *Pseudomonas aeruginosa,* 9545 | 100 | — | — | — | 25 | 100 | 25 | 100 | 0.8 | 50 | 0.4 |
| *Pseudomonas aeruginosa,* 8329 | — | — | — | — | — | — | — | — | 12.5 | — | 12.5 |
| *Acinetobacter calcoaceticus,* 8333 | — | — | — | 100 | — | — | — | — | 25 | — | 100 |
|  | 15 | 16 | 17 | 18 | 19 | 20 | 21 | 22 | 23 | 24 | 25 |
| *Staphylococcus aureus,* 1276 | 100 | 3.1 | 12.5 | 50 | 25 | 3.1 | 12.5 | 50 | 50 | 6.3 | 1.6 |
| *Staphylococcus aureus,* 2399 | 50 | 6.3 | 12.5 | 50 | 12.5 | 3.1 | 12.5 | 100 | 50 | 6.3 | 1.6 |
| *Staphylococcus aureus,* 2400 | 50 | 12.5 | 12.5 | 25 | 12.5 | 3.1 | 12.5 | 100 | 50 | 3.1 | 1.6 |
| *Staphylococcus aureus,* 10165 | 50 | 12.5 | 12.5 | 50 | 12.5 | 6.3 | 100 | 100 | 100 | 6.3 | 25 |
| *Streptococcus faecalis,* 9011 | — | — | — | — | — | — | 100 | — | — | — | 50 |
| *Streptococcus agalactiae,* 9287 | 12.5 | 6.3 | 6.3 | 50 | 12.5 | 3.1 | 1.6 | 12.5 | 50 | 3.1 | 0.1 |
| *Micrococcus luteus,* 2495 | 50 | 25 | 25 | 100 | 50 | 6.3 | 6.3 | 50 | — | 12.5 | 0.8 |
| *Escherichia coli,* 8294 | — | — | — | — | — | 25 | 0.8 | — | — | — | 0.4 |
| *Escherichia coli,* 10857 | — | — | — | — | — | 25 | 0.8 | 100 | — | — | <0.05 |
| *Escherichia coli,* 10897 | — | 100 | 100 | — | — | 12.5 | 1.6 | 100 | — | 100 | 0.2 |
| *Escherichia coli,* 10909 | — | 100 | 100 | — | — | 6.3 | 0.8 | 100 | N.T. | 100 | <0.05 |
| *Klebsiella aerogenes,* 10440 | — | — | — | — | — | 50 | 0.8 | — | — | — | 0.4 |
| *Klebsiella pneumoniae,* 9527 | — | — | — | — | — | 25 | 0.8 | — | — | — | <0.05 |
| *Proteus mirabilis,* 3855 | — | 100 | — | — | — | 100 | 0.8 | — | — | — | 0.2 |
| *Proteus rettgeri,* 8479 | — | 25 | 25 | — | — | 12.5 | <0.05 | — | — | 100 | 0.4 |
| *Proteus vulgaris,* 9416· | — | 100 | — | — | — | 50 | 1.6 | — | — | — | <0.05 |
| *Salmonella typhosa,* 1195 | — | 100 | — | — | — | 50 | 0.8 | 100 | — | — | <0.05 |
| *Shigella sonnei,* 8449 | — | — | — | — | — | 12.5 | 0.8 | 100 | — | — | 0.2 |
| *Enterobacter cloacae,* 8236 | — | — | — | — | — | 100 | 1.6 | 100 | — | — | 0.4 |
| *Enterobacter aerogenes,* 10078 | — | — | — | — | — | — | 0.8 | — | — | — | 0.8 |
| *Citrobacter freundii,* 9518 | — | — | — | — | — | 50 | 6.3 | 100 | — | — | 0.4 |

-continued

| Organism | M.I.C. (μg/ml) Product of Example | | | | | | | | | | |
|---|---|---|---|---|---|---|---|---|---|---|---|
| Serratia marcescens, 9783 | 25 | 100 | 6.3 | 100 | 25 | 50 | 50 | 100 | 100 | 100 | 0.8 |
| Pseudomonas aeruginosa, 9545 | 50 | 25 | 50 | 50 | 25 | 25 | 3.1 | 6.3 | — | 50 | 0.4 |
| Pseudomonas aeroginosa, 8329 | — | — | — | 100 | 50 | — | 25 | 100 | — | — | 3.1 |
| Acinetobacter calcoaceticus, 8333 | 50 | — | 6.3 | — | 50 | 50 | 25 | — | — | — | 25 |

| | 26 | 27 | 28 | 29 | 30 | 31 | 32 | 33 | 35 | 36 | 37 |
|---|---|---|---|---|---|---|---|---|---|---|---|
| Staphylococcus aureus, 1276 | 1.6 | 6.3 | 12.5 | — | 12.5 | 1.6 | 1.6 | 1.6 | 3.1 | 6.3 | 6.3 |
| Staphylococcus aureus, 2399 | 1.6 | 12.5 | 25 | — | 12.5 | 3.1 | 0.8 | 1.6 | 3.1 | 6.3 | 6.3 |
| Staphylococcus aureus, 2400 | 3.1 | 25 | 25 | — | 25 | 6.3 | 1.6 | 1.6 | 3.1 | 3.1 | 1.6 |
| Staphylococcus aureus, 10165 | 25 | 100 | 100 | — | 100 | 6.3 | 12.5 | 3.1 | 12.5 | 50 | 100 |
| Streptococcus faecalis, 9011 | 50 | — | 25 | — | — | — | 100 | — | — | 0.4 | 0.4 |
| Streptococcus agalactiae, 9287 | 0.8 | 3.1 | 0.4 | 12.5 | 0.4 | 1.6 | 0.4 | 0.2 | 0.4 | 0.4 | 0.4 |
| Micrococcus luteus, 2495 | 3.1 | 12.5 | 3.1 | 25 | 12.5 | 6.3 | 1.6 | 0.8 | 1.6 | 6.3 | 1.6 |
| Escherichia coli, 8294 | 6.3 | 100 | 12.5 | 0.4 | 12.5 | — | — | — | — | — | — |
| Escherichia coli, 10857 | 3.1 | 25 | 1.6 | 0.2 | 6.3 | 50 | 3.1 | 3.1 | 12.5 | — | 50 |
| Escherichia coli, 10896 | 25 | 25 | 3.1 | 0.8 | 12.5 | 50 | 100 | 50 | — | — | — |
| Escherichia coli, 10909 | 1.6 | 50 | 1.6 | 0.1 | 3.1 | 50 | 50 | 50 | 100 | — | — |
| Klebsiella aerrogenes, 10440 | 6.3 | — | 25 | 0.4 | 12.5 | — | — | — | — | — | — |
| Klebsiella pneumoniae, 9527 | 0.4 | 50 | 1.6 | <0.05 | 6.3 | 100 | 100 | — | — | — | — |
| Proveus mirabilis, 3855 | 0.4 | 12.5 | 1.6 | <0.05 | 6.3 | 100 | 100 | 100 | — | — | — |
| Proteus rettgeri, 8479 | 0.4 | 6.3 | 0.2 | <0.05 | 0.8 | 25 | 100 | — | — | — | — |
| Proteus vulgaris, 9416 | 0.2 | 25 | 1.6 | 0.1 | 12.5 | 100 | 6.3 | 3.1 | 12.5 | — | 100 |
| Salmonella typshosa, 1195 | 0.4 | 25 | 0.8 | <0.05 | 3.1 | 50 | — | — | 100 | — | — |
| Shigella sonnei, 8449 | 6.3 | 100 | 3.1 | 0.2 | 6.3 | 100 | — | — | — | — | — |
| Enterobacter cloacae, 8236 | 6.3 | — | 6.3 | 0.8 | 6.3 | — | — | — | — | — | — |
| Enterobacter aerogenes, 10078 | 25 | — | 50 | 0.8 | 12.5 | — | — | — | — | — | — |
| Citrobacter freundii, 9518 | 25 | 100 | 25 | 1.6 | — | — | — | — | — | — | — |
| Serratia marcescens, 9783 | 50 | — | 12.5 | 0.8 | 50 | — | — | — | — | — | — |
| Pseudomonas aeruginosa, 9545 | 0.4 | 12.5 | 3.1 | 0.8 | 12.5 | 25 | 12.5 | 12.5 | 25 | — | 100 |
| Pseudomonas aeroginosa, 8329 | 12.5 | — | 50 | 3.1 | 50 | — | — | — | — | — | — |
| Acinetobacter calcoaceticus, 8333 | 50 | — | — | 100 | — | — | — | — | — | — | — |

| | 39 | 40 | 41 | 42 | 43 | 44 | 45 | 46 | 48 | 50 | 51 |
|---|---|---|---|---|---|---|---|---|---|---|---|
| Staphylococcus aureus, 1276 | 0.8 | 3.1 | 1.6 | 6.3 | 25 | 3.1 | 1.6 | 100 | 12.5 | 12.5 | 12.5 |
| Staphylococcus aureus, 2399 | 0.8 | 3.1 | 1.6 | 6.3 | 12.5 | 3.1 | 1.6 | 100 | 12.5 | 25 | 25 |
| Staphylococcus aureus, 2400 | 0.8 | 3.1 | 1.6 | 12.5 | 12.5 | 6.3 | 1.6 | 100 | 12.5 | 25 | 50 |
| Staphylococcus aureus, 10165 | 3.1 | 6.3 | 3.1 | 100 | 100 | 25 | 25 | 100 | 25 | 25 | 50 |
| Streptococcus faecalis, 9011 | 50 | 100 | — | — | — | 100 | — | — | — | — | — |
| Streptococcus agalactiae, 9287 | 0.4 | 0.8 | 1.6 | 1.6 | 3.1 | 1.6 | 1.6 | 50 | 6.3 | 12.5 | 6.3 |
| Micrococcus luteus, 2495 | 0.8 | 1.6 | 3.1 | 6.3 | 12.5 | 3.1 | 1.6 | 50 | 3.1 | 6.3 | 1.6 |
| Escherichia coli, 8294 | — | 1.6 | — | — | 50 | 3.1 | 0.8 | — | 50 | — | — |
| Escherichia coli, 10857 | 12.5 | 0.2 | 50 | 100 | 25 | 3.1 | 0.4 | — | 50 | 100 | 100 |
| Escherichia coli, 10896 | 100 | 1.6 | — | 50 | 25 | 6.3 | 0.8 | 100 | 25 | — | — |
| Escherichia coli, 10909 | — | 0.2 | 100 | 50 | 25 | 1.6 | 0.2 | N.T. | 12.5 | 100 | — |
| Klebsiella aerogenes, 10440 | — | 0.8 | — | — | 50 | 6.3 | 1.6 | — | 100 | — | — |
| Klebsiella pneumoniae, 9527 | — | 0.4 | — | — | 25 | 3.1 | <0.05 | — | 50 | — | — |
| Proteus mirabilis, 3855 | — | <0.05 | 50 | 100 | 25 | 3.1 | 0.1 | — | 100 | — | — |
| Proteus rettgeri, 8479 | 100 | <0.5 | 6.3 | 50 | 25 | 1.6 | 0.1 | — | 50 | 100 | — |
| Proteus vulgaris, 9416 | 25 | <0.5 | 50 | — | 50 | 3.1 | <0.05 | — | — | — | 100 |
| Salmonella typhosa, 1195 | — | <0.5 | 100 | 100 | 25 | 1.6 | 0.1 | — | 50 | — | — |
| Shigella sonnei, 8449 | — | 0.4 | 100 | 100 | 25 | 3.1 | 0.4 | — | 50 | — | — |
| Enterobacter cloacae, 8236 | — | 0.8 | — | 100 | 50 | 12.5 | 0.8 | 100 | — | — | — |
| Enterobacter aerogenes, 10078 | — | 1.6 | — | — | 50 | 6.3 | 1.6 | — | — | — | — |
| Citrobacter freundii, 9518 | — | 1.6 | — | — | 50 | 25 | 1.6 | 100 | 100 | — | — |
| Serratia marcescens, 9783 | — | 1.6 | 50 | 100 | 50 | 25 | 3.1 | 100 | 100 | — | — |
| Pseudomonas aeruginosa, 9545 | 12.5 | 0.2 | 100 | 50 | 12.5 | 3.1 | 0.4 | 12.5 | — | 50 | 100 |
| Pseudomonas aeruginosa, 8329 | — | 6.3 | — | — | — | 100 | 3.1 | — | — | — | — |
| Acinetobacter calcoaceticus, 8333 | — | 25 | — | — | 100 | — | 12.5 | 100 | — | — | — |

| | 52 | 53 | 54 | 55 | 56 | 57 | 58 | 59 | 60 | 61 | 62 |
|---|---|---|---|---|---|---|---|---|---|---|---|
| Staphylococcus aureus, 1276 | 50 | 12.5 | 3.1 | 6.3 | 12.5 | 25 | 0.8 | 12.5 | 1.6 | 3.1 | 3.1 |
| Staphylococcus aureus, 2399 | 50 | 12.5 | 3.1 | 6.3 | 12.5 | 25 | 0.8 | 6.3 | 1.6 | 1.6 | 1.6 |
| Staphylococcus aureus, 2400 | 100 | 12.5 | 6.3 | 12.5 | 12.5 | 50 | 1.6 | 6.3 | 3.1 | 3.1 | 3.1 |
| Staphylococcus aureus, 10165 | 100 | 100 | 100 | 50 | — | 100 | 12.5 | 25 | 50 | 50 | 50 |
| Streptococcus faecalis, 9011 | — | — | 100 | — | — | 100 | 50 | — | 100 | 100 | 50 |
| Streptococcus agalactiae, 9287 | 25 | 3.1 | 1.6 | 3.1 | 12.5 | 6.3 | 0.8 | 1.6 | 0.2 | 0.2 | 0.4 |
| Micrococcus luteus, 2495 | 12.5 | 6.3 | 1.6 | 12.5 | 6.3 | 25 | 1.6 | 3.1 | 0.4 | 0.8 | 1.6 |
| Escherichia coli, 8294 | 100 | 12.5 | 6.3 | 50 | — | — | 0.8 | 1.6 | 0.8 | 1.6 | 6.3 |
| Escherichia coli, 10857 | 100 | 12.5 | 6.3 | 25 | — | — | <0.05 | 1.6 | <0.05 | <0.05 | 0.4 |
| Escherichia coli, 10896 | 25 | 12.5 | 6.3 | 100 | 100 | — | 0.2 | 6.3 | 0.2 | 0.2 | 3.1 |
| Escherichia coli, 10909 | 25 | 12.5 | 3.1 | 25 | 100 | — | 0.1 | 0.8 | 0.1 | 0.1 | 1.6 |
| Klebsiella aerogenes, 10440 | 100 | 25 | 6.3 | 100 | — | — | 0.8 | 3.1 | 0.8 | 1.6 | 12.5 |
| Klebsiella pneumoniae, 9527 | 50 | 12.5 | 6.3 | 50 | — | — | 0.1 | 0.8 | 0.2 | 0.2 | 1.6 |
| Proteus mirabilis, 3855 | — | 12.5 | 3.1 | 25 | 100 | — | 0.1 | 1.6 | 1.6 | 0.8 | 0.8 |
| Proteus rettgeri, 8479 | 100 | 12.5 | 3.1 | 25 | 50 | 100 | 0.1 | 0.1 | 3. | 1.6 | 0.8 |
| Proteus vulgaris, 9416 | — | 25 | 6.3 | 25 | — | — | <0.05 | 3.1 | 0.2 | <0.05 | 0.1 |
| Salmonella typhosa, 1195 | 100 | 6.3 | 1.6 | 12.5 | 100 | — | 0.1 | 0.8 | 0.8 | 0.4 | 1.6 |
| Shigella sonnei, 8449 | 100 | 12.5 | 3.1 | 50 | 100 | — | 0.4 | 1.6 | 0.4 | 0.4 | 3.1 |
| Enterobacter cloacae, 8236 | 50 | 25 | 25 | 100 | — | — | 0.8 | 3.1 | 1.5 | 0.8 | 6.3 |
| Enterobacter aerogenes, 10078 | 100 | 50 | 12.5 | 100 | — | — | 1.6 | 3.1 | 3.1 | 3.1 | 12.5 |

-continued

| Organism | M.I.C. (μg/ml) Product of Example | | | | | | | | | |
|---|---|---|---|---|---|---|---|---|---|---|
| Citrobacter freundii, 9518 | 50 | 50 | 25 | — | — | — | 1.6 | 25 | 0.4 | 0.4 | 6.3 |
| Serratia marcescens, 9783 | 50 | 25 | 25 | — | 50 | — | 1.6 | 25 | 1.6 | 1.6 | 25 |
| Pseudomonas aeruginosa, 9545 | 50 | 12.5 | 6.3 | 12.5 | 50 | 50 | 0.8 | 6.3 | 0.4 | 0.2 | 3.1 |
| Pseudomonas aeruginosa, 8329 | — | — | 100 | — | — | — | 12.5 | — | 6.3 | 6.3 | 100 |
| Acinetobacter calcoaceticus, 8333 | 100 | — | — | — | — | 100 | 25 | 100 | 6.3 | 25 | — |

| | 63 | 64 | 65 | 66 | 67 | 68 | 69 | 70 | 71 | 72 | 73 |
|---|---|---|---|---|---|---|---|---|---|---|---|
| Staphylococcus aureus, 1276 | 6.3 | 3.1 | 100 | 25 | 25 | 50 | 3.1 | — | 3.1 | 12.5 | 6.3 |
| Staphylococcus aureus, 2399 | 6.3 | 6.3 | — | 25 | 12.5 | 50 | 3.1 | 100 | 3.1 | 12.5 | 6.3 |
| Staphylococcus aureus, 2400 | 12.5 | 12.5 | — | 25 | 12.5 | 50 | 3.1 | 100 | 3.1 | 12.5 | 12.5 |
| Staphylococcus aureus, 10165 | 12.5 | 12.5 | — | — | — | — | 50 | — | 50 | 50 | 12.5 |
| Streptococcus faecalis, 9011 | — | — | — | — | 25 | — | 25 | — | 50 | 100 | — |
| Streptococcus agalactiae, 9287 | 6.3 | 6.3 | 50 | 3.1 | 1.6 | 12.5 | 0.1 | 25 | 1.6 | 3.1 | 3.1 |
| Micrococcus luteus, 2495 | 50 | 12.5 | — | 0.8 | 0.4 | 25 | 0.1 | 100 | 3.1 | 6.3 | 6.3 |
| Escherichia coli, 8294 | — | — | — | 12.5 | 12.5 | 1.6 | 12.5 | 1.6 | 25 | 0.8 | 25 |
| Escherichia coli, 10857 | — | 100 | — | 1.6 | 1.6 | 1.6 | 0.8 | 1.6 | 3.1 | 1.6 | 25 |
| Escherichia coli, 10896 | — | 100 | — | 12.5 | 6.3 | 6.3 | 12.5 | 3.1 | 25 | 3.1 | 12.5 |
| Escherichia coli, 10909 | — | 100 | — | 3.1 | 1.6 | 0.8 | 1.6 | 0.4 | 12.5 | 0.8 | 12.5 |
| Klebsiella aerogenes, 10440 | — | — | — | 12.5 | 6.3 | 1.6 | 25 | 1.6 | 50 | 1.6 | 25 |
| Klebsiella pneumoniae, 9527 | — | — | — | 3.1 | 1.6 | 0.4 | 6.3 | 0.8 | 12.5 | 0.8 | 25 |
| Proteus mirabilis, 3855 | — | — | — | 0.8 | 0.4 | 0.4 | 1.6 | 1.6 | 12.5 | 1.6 | 12.5 |
| Proteus rettgeri, 8479 | — | 100 | 100 | 0.2 | 0.2 | <0.05 | 0.2 | <0.05 | 1.6 | 0.1 | 1.6 |
| Proteus vulgaris, 9416 | — | — | — | 0.1 | 0.2 | 0.8 | 0.4 | 0.8 | 3.1 | 1.6 | 25 |
| Salmonella typhosa, 1195 | — | 100 | — | 3.1 | 0.2 | 0.2 | 3.1 | 0.4 | 12.5 | 0.8 | 25 |
| Shigella sonnei, 8449 | — | 100 | — | 12.5 | 6.3 | 1.6 | 6.3 | 0.8 | 25 | 0.8 | 12.5 |
| Enterobacter cloacae, 8236 | — | — | — | 12.5 | 6.3 | 0.8 | 12.5 | 0.8 | 50 | 0.8 | 25 |
| Enterobacter aerogenes, 10078 | — | — | — | 25 | 12.5 | 1.6 | 25 | 1.6 | 100 | 1.6 | 25 |
| Citrobacter freundii, 9518 | — | — | — | 12.5 | 6.3 | 25 | 12.5 | 1.6 | 50 | 12.5 | 25 |
| Serratia marcescens, 9783 | 100 | 100 | 100 | 12.5 | 6.3 | 50 | 25 | 1.6 | 100 | 25 | 25 |
| Pseudomonas aeruginosa, 9545 | 100 | 12.5 | 6.3 | 25 | 6.3 | 3.1 | 1.6 | 1.6 | 12.6 | 6.3 | 25 |
| Pseudomonas aeruginosa, 8329 | — | — | — | — | 100 | 50 | 100 | 12.5 | — | 50 | 100 |
| Acinetobacter calcoaceticus, 88333 | — | — | — | — | — | — | — | — | — | 100 | 50 |

| | 74 | 76 | 77 | 78 | 79 | 80 | 81 | 82 | 86 | 88 | 89 |
|---|---|---|---|---|---|---|---|---|---|---|---|
| Staphylococcus aureus, 1276 | 12.5 | 6.3 | — | — | 25 | — | 6.3 | 12.5 | 25 | 12.5 | 25 |
| Staphylococcus aureus, 2399 | 25 | 6.3 | — | — | 25 | 100 | 12.5 | 25 | 12.5 | 12.5 | 25 |
| Staphylococcus aureus, 2400 | 25 | 6.3 | — | — | 12.5 | — | 25 | 25 | 25 | 12.5 | 50 |
| Staphylococcus aureus, 10165 | 50 | 12.5 | — | — | — | — | 25 | 100 | — | 50 | 50 |
| Streptococcus faecalis, 9011 | — | — | — | — | 100 | — | — | — | — | — | — |
| Streptococcus agalactiae, 9287 | 12.5 | 3.1 | — | — | 3.1 | — | 3.1 | 3.1 | 1.6 | 12.5 | 12.5 |
| Micrococcus luteus, 2495 | 3.1 | 0.8 | — | 50 | 1.6 | 25 | 0.4 | 0.8 | 12.5 | 0.8 | 0.4 |
| Escherichia coli, 8294 | 25 | 3.1 | 50 | 25 | 1.6 | — | — | — | — | — | — |
| Escherichia coli, 10857 | 25 | 3.1 | 100 | 12.5 | 0.4 | — | 100 | — | 25 | 12.5 | 12.5 |
| Escherichia coli, 10896 | 25 | 1.6 | 25 | 6.3 | 1.6 | — | — | — | — | 50 | 50 |
| Escherichia coli, 10909 | 12.5 | 0.8 | 25 | 6.3 | 0.4 | — | — | — | — | 100 | 50 |
| Klebsiella aerogenes, 10440 | 50 | 3.1 | 100 | 25 | 3.1 | — | — | — | — | — | — |
| Klebsiella pneumoniae, 9527 | 25 | 1.6 | 50 | 25 | 0.8 | — | — | — | — | 100 | 100 |
| Proteus mirabilis, 3855 | 50 | 3.1 | 25 | 25 | 0.2 | — | — | — | — | 100 | 100 |
| Proteus rettgeri, 8479 | 50 | 3.1 | 50 | 25 | <0.05 | — | — | — | — | 50 | 50 |
| Proteus vulgaris, 9416 | 100 | 3.1 | 50 | 50 | 0.2 | — | — | — | 100 | 100 | 50 |
| Salmonella typhosa, 1195 | 25 | 1.6 | 50 | 25 | 0.2 | — | — | — | — | 100 | 50 |
| Shigella sonnei, 8449 | 25 | 0.8 | 25 | 12.5 | 1.6 | — | — | — | — | — | — |
| Enterobacter cloacae, 8236 | 100 | 12.5 | 25 | 12.5 | 1.6 | — | — | — | — | — | — |
| Enterobacter aerogenes, 10078 | 100 | 6.3 | 100 | 25 | 6.3 | — | — | — | — | — | — |
| Citrobacter freundii, 9518 | 50 | 25 | 25 | 12.5 | 3.1 | — | — | — | — | — | — |
| Serratia marcescens, 9783 | 50 | 6.3 | 50 | 25 | 3.1 | — | — | — | — | — | — |
| Pseudomonas aeroginosa, 9545 | 50 | 12.5 | 6.3 | 6.3 | 3.1 | — | — | — | 25 | 25 | 25 |
| Pseudomonas aeruginosa, 8329 | — | 100 | 50 | 25 | 25 | — | — | — | — | — | — |
| Acinetobacter calcoaceticus, 8333 | — | 12.5 | — | — | — | — | — | — | — | — | — |

| | 90 | 91 | 92 | 93 | 94 | 95 | 96 | 97 | 98 | 99 | 100 |
|---|---|---|---|---|---|---|---|---|---|---|---|
| Staphylococcus aureus, 1276 | 12.5 | 3.1 | — | 50 | 100 | 50 | — | 6.3 | 100 | 100 | 50 |
| Staphylococcus aureus, 2399 | 25 | 3.1 | — | 50 | 100 | 50 | — | 6.3 | 50 | 100 | 50 |
| Staphylococcus aureus, 2400 | 25 | 6.3 | — | 50 | 100 | 50 | — | 12.5 | 50 | 100 | 50 |
| Staphylococcus aureus, 10165 | 100 | 25 | — | 50 | — | 100 | — | 25 | 100 | — | 100 |
| Streptococcus faecalis, 9011 | — | 100 | — | — | — | — | — | — | — | — | — |
| Streptococcus agalactiae, 9287 | 12.5 | 0.8 | — | 25 | 3.1 | 6.3 | 12.5 | 1.6 | 100 | 100 | 25 |
| Micrococcus luteus, 2495 | 12.5 | 1.6 | 100 | 25 | 3.1 | 6.3 | 6.3 | 1.6 | — | 100 | 25 |
| Escherichia coli, 8294 | 12.5 | — | — | — | 100 | 25 | — | 6.3 | — | — | 100 |
| Escherichia coli, 10857 | 0.8 | 50 | — | — | 25 | 25 | 100 | 0.2 | — | — | 50 |
| Escherichia coli, 10896 | 6.3 | — | — | — | 25 | 12.5 | 50 | 1.6 | — | — | 50 |
| Escherichia coli, 10909 | 1.6 | — | — | — | 25 | 6.3 | 50 | 0.8 | — | — | 25 |
| Klebsiella aerogenes, 10440 | 12.5 | — | — | — | 100 | 50 | — | 6.3 | — | — | 100 |
| Klebsiella pneumoniae, 9527 | 1.6 | — | — | — | 100 | 50 | — | 1.6 | — | — | 100 |
| Proteus mirabilis, 3855 | 6.25 | — | — | — | 25 | 50 | 100 | 3.1 | — | — | 100 |
| Proteus rettgeri, 8479 | 3.1 | — | — | 100 | 3.1 | 25 | 100 | 6.3 | — | — | 50 |
| Proteus vulgaris, 9416 | 0.1 | 100 | — | — | 50 | 50 | — | <0.05 | — | — | 100 |
| Salmonella typhosa, 1195 | 1.6 | — | — | — | 50 | 50 | — | 1.6 | — | — | 50 |
| Shigella sonnei, 8449 | 3.1 | — | — | — | 50 | 12.5 | 50 | 3.1 | — | — | 50 |
| Enterobacter cloacae, 8236 | 6.3 | — | — | — | — | 50 | 50 | 6.3 | — | — | — |

-continued

| Organism | | | | | | | | | | |
|---|---|---|---|---|---|---|---|---|---|---|
| Enterobacter aerogenes, 10078 | 12.5 | — | — | — | — | 50 | 100 | 12.5 | — | — | — |
| Citrobacter freundii, 9518 | 12.5 | — | — | — | — | 50 | 50 | 3.1 | — | — | 100 |
| Serratia marcescens, 9783 | 6.3 | — | — | — | 100 | 25 | 50 | 12.5 | — | — | 50 |
| Pseudomonas aeruginosa, 9545 | 3.1 | 100 | — | 25 | — | 50 | 50 | 6.3 | — | — | 50 |
| Pseudomonas aeruginosa, 8329 | 50 | — | — | — | — | — | — | 100 | — | — | — |
| Acinetobacter calcoaceticus, 8333 | — | — | — | — | — | 50 | 50 | — | — | — | — |

| Organism | 101 | 102 | 103 | 104 | 105 | 106 | 107 | 108 | 109 | 110 | 111 |
|---|---|---|---|---|---|---|---|---|---|---|---|
| Staphylococcus aureus, 1276 | 25 | 100 | — | 12.5 | 3.1 | 12.5 | 3.1 | 1.6 | 12.5 | 1.6 | 1.6 |
| Staphylococcus aureus, 2399 | 25 | 100 | — | 6.3 | 3.1 | 6.3 | 1.6 | 3.1 | 12.5 | 1.6 | 1.6 |
| Staphylococcus aureus, 2400 | 50 | 50 | — | 6.3 | 3.1 | 12.5 | 1.6 | 3.1 | 6.3 | 1.6 | 3.1 |
| Staphylococcus aureus, 10165 | 100 | — | — | 50 | 50 | 50 | 50 | 25 | 100 | 12.5 | 25 |
| Streptococcus faecalis, 9011 | — | — | — | 50 | 100 | — | — | 50 | 50 | 25 | 50 |
| Streptococcus agalactiae, 9287 | 12.5 | 3.1 | 50 | 1.6 | 1.6 | 0.8 | 0.8 | 0.8 | 1.6 | 0.4 | 0.2 |
| Micrococcus luteus, 2495 | 50 | 3.1 | 12.5 | 1.6 | 3.1 | 12.5 | 3.1 | 0.8 | 0.8 | 0.4 | 0.8 |
| Escherichia coli, 8294 | 100 | 0.1 | 0.4 | 6.3 | 0.4 | 0.8 | 3.1 | 0.8 | 0.8 | 12.5 | 6.3 |
| Escherichia coli, 10857 | 50 | <0.05 | <0.05 | 0.2 | 0.1 | 0.1 | 0.1 | <0.05 | 0.2 | 0.2 | <0.05 |
| Escherichia coli, 10896 | 100 | 0.1 | 0.2 | 6.3 | 0.8 | 1.6 | 1.6 | 0.2 | 0.8 | 6.3 | 1.6 |
| Escherichia coli, 10909 | 50 | <0.05 | <0.05 | 1.6 | 0.1 | 0.2 | 0.4 | 0.1 | 0.2 | 3.1 | 0.8 |
| Klebsiella aerogenes, 10440 | — | 0.2 | 0.4 | 25 | 0.4 | 0.8 | 3.1 | 0.8 | 1.6 | 25 | 6.3 |
| Klebsiella pneumoniae, 9527 | 100 | 0.1 | <0.05 | 3.1 | 0.1 | 0.2 | 0.4 | 0.05 | 0.2 | 6.3 | 1.6 |
| Proteus mirabilis, 3855 | — | 0.1 | <0.05 | 1.6 | 0.1 | 0.1 | 0.4 | 0.2 | 0.2 | 1.6 | 1.6 |
| Proteus rettgeri, 8479 | 100 | <0.05 | <0.05 | 0.2 | <0.05 | <0.05 | 0.1 | <0.05 | <0.05 | 0.4 | 3.1 |
| Proteus vulgaris, 9416 | — | <0.05 | <0.05 | 0.8 | <0.05 | <0.05 | 0.1 | <0.05 | 0.2 | 0.4 | 0.4 |
| Salmonella typhosa, 1195 | 100 | <0.05 | <0.05 | 0.8 | 0.1 | 0.1 | 0.4 | 0.1 | 0.1 | 6.3 | 3.1 |
| Shigella sonnei, 8449 | 100 | 0.1 | 0.2 | 3.1 | 0.4 | 0.4 | 0.8 | 0.4 | 0.8 | 12.5 | 3.1 |
| Enterobacter cloacae, 8236 | — | 0.2 | 0.4 | 6.3 | 0.8 | 0.8 | 1.6 | 1.5 | 1.6 | 25 | 6.3 |
| Enterobacter aerogenes, 10078 | — | 0.4 | 0.4 | 25 | 0.8 | 1.6 | 6.3 | 1.6 | 3.1 | 25 | 12.5 |
| Citrobacter freundii, 9518 | — | 0.1 | 0.4 | 12.5 | 1.6 | 6.3 | 3.1 | 0.8 | 1.6 | 12.5 | 3.1 |
| Serratia marcescens, 9783 | — | 0.8 | 0.2 | 12.5 | 3.1 | 12.5 | 6.3 | 1.6 | 12.5 | 25 | 6.3 |
| Pseudomonas aeruginosa, 9545 | — | 0.8 | 0.8 | 3.1 | 0.2 | 0.8 | 0.2 | 0.8 | 0.4 | 0.8 | 0.8 |
| Pseudomonas aeruginosa, 8329 | — | 100 | 3.1 | 50 | 3.1 | 12.5 | 12.5 | 12.5 | 12.5 | 25 | 12.5 |
| Acinetobacter calcoaceticus, 8333 | — | 12.5 | 100 | — | 25 | 50 | 25 | 50 | 100 | — | 25 |

| Organism | 112 | 113 | 114 | 115 | 116 | 117 | 118 | 119 | 120 | 121 | 122 |
|---|---|---|---|---|---|---|---|---|---|---|---|
| Staphylococcus aureus, 1276 | 1.6 | 3.1 | 12.5 | 1.6 | 6.3 | 3.1 | 1.6 | 6.3 | 3.1 | 25 | 0.8 |
| Staphylococcus aureus, 2399 | 1.6 | 3.1 | 12.5 | 0.8 | 6.3 | 3.1 | 1.6 | 6.3 | 3.1 | 25 | 1.6 |
| Staphylococcus aureus, 2400 | 1.6 | 3.1 | 6.3 | 0.8 | 6.3 | 6.3 | 3.1 | 3.1 | 3.1 | 12.5 | 3.1 |
| Staphylococcus aureus, 10165 | 50 | 6.3 | 25 | 3.1 | 12.5 | 25 | 12.5 | 100 | 100 | 100 | 6.3 |
| Streptococcus faecalis, 9011 | 100 | 50 | 50 | 100 | — | 50 | 100 | 100 | 100 | — | — |
| Streptococcus agalactiae, 9287 | 0.1 | 0.4 | 0.8 | 0.8 | 3.1 | 0.2 | 0.4 | <0.05 | <0.05 | 3.1 | 0.8 |
| Micrococcus luteus, 2495 | 0.8 | 0.8 | 0.2 | 3.1 | 12.5 | 1.6 | 3.1 | 0.8 | 0.8 | 6.3 | 0.4 |
| Escherichia coli, 8294 | 0.8 | 25 | 1.6 | — | 100 | 3.1 | 12.5 | 0.2 | 3.1 | 3.1 | 6.3 |
| Escherichia coli, 10857 | <0.05 | 0.4 | 0.2 | 6.3 | 50 | <0.05 | 0.1 | <0.05 | <0.05 | 1.6 | <0.05 |
| Escherichia coli, 10896 | 0.2 | 12.5 | 0.8 | — | 50 | 0.8 | 1.6 | 0.2 | 0.8 | 3.1 | 1.6 |
| Escherichia coli, 10909 | 0.1 | 6.3 | 0.4 | — | 50 | 0.2 | 0.8 | <0.05 | 0.2 | 1.6 | 0.4 |
| Klebsiella aerogenes, 10440 | 1.6 | 25 | 3.1 | — | 100 | 3.1 | 12.5 | 0.4 | 6.3 | 6.3 | 6.3 |
| Klebsiella pneumoniae, 9527 | 0.2 | 6.3 | 1.6 | 100 | 100 | 1.6 | 6.3 | 0.1 | 0.8 | 3.1 | 0.2 |
| Proteus mirabilis, 3855 | 0.4 | 6.3 | 0.4 | — | 100 | 0.8 | 3.1 | 0.4 | 3.1 | 3.1 | 1.6 |
| Proteus rettgeri, 8479 | 0.8 | 0.4 | <0.05 | 100 | 25 | 1.6 | 6.3 | 0.2 | 3.1 | 0.2 | 0.8 |
| Proteus vulgaris, 9416 | <0.05 | 1.6 | <0.05 | 6.3 | 100 | <0.05 | 0.2 | <0.05 | 0.1 | 3.1 | <0.05 |
| Salmonella typhosa, 1195 | 0.4 | 3.1 | 0.4 | — | 100 | 1.6 | 6.3 | 0.2 | 1.6 | 1.6 | 0.8 |
| Shigella sonnei, 8449 | 0.4 | 12.5 | 1.6 | — | 100 | 1.6 | 6.3 | 0.2 | 1.6 | 3.1 | 1.6 |
| Enterobacter cloacae, 8236 | 1.6 | 25 | 3.1 | — | 100 | 3.1 | 6.3 | 0.8 | 3.1 | 6.3 | 3.1 |
| Enterobacter aerogenes, 10078 | 3.1 | 25 | 6.3 | — | — | 6.3 | 25 | 0.8 | 6.3 | 12.5 | 12.5 |
| Citrobacter freundii, 9518 | 0.8 | 25 | 6.3 | — | — | 1.6 | 6.3 | 0.4 | 1.6 | 50 | 3.1 |
| Serratia marcescens, 9783 | 3.1 | 25 | 6.3 | — | 12.5 | 1.6 | 12.5 | 0.8 | 6.3 | 25 | 6.3 |
| Pseudomonas aeruginosa, 9545 | 0.8 | 3.1 | 0.8 | 12.5 | 12.5 | 6.3 | 1.6 | 0.4 | 0.2 | 6.3 | 3.1 |
| Pseudomonas aeruginosa, 8329 | 25 | 100 | 25 | — | — | 100 | 50 | 6.3 | 3.1 | 100 | 25 |
| Acinetobacter calcoaceticus, 8333 | 25 | — | — | — | 50 | 100 | 25 | 50 | 6.3 | 100 | 25 |

| Organism | 123 | 124 | 125 | 126 | 127 | 128 | 129 | 130 | 131 | 132 | 133 |
|---|---|---|---|---|---|---|---|---|---|---|---|
| Staphylococcus aureus, 1276 | 3.1 | 12.5 | 6.3 | 3.1 | 3.1 | 0.8 | 50 | 25 | 6.3 | 12.5 | 6.3 |
| Staphylococcus aureus, 2399 | 3.1 | 12.5 | 6.3 | 3.1 | 3.1 | 3.1 | 25 | 25 | 6.3 | 12.5 | 3.1 |
| Staphylococcus aureus, 2400 | 6.3 | 12.5 | 6.3 | 3.1 | 3.1 | 6.3 | 12.5 | 25 | 6.3 | 6.3 | 12.5 |
| Staphylococcus aureus, 10165 | 25 | 25 | 50 | 25 | 25 | 60 | 50 | 100 | 50 | 50 | 12.5 |
| Streptococcus faecalis, 9011 | — | — | 100 | 100 | 100 | 50 | 50 | — | 100 | 50 | — |
| Streptococcus agalactiae, 9287 | 1.6 | 0.8 | 0.4 | 0.8 | 1.6 | 0.8 | 1.6 | 12.5 | 0.4 | 0.4 | 12.5 |
| Micrococcus luteus, 2495 | 1.6 | 3.1 | 3.1 | 3.1 | 6.3 | 3.1 | 0.8 | 25 | 3.1 | 3.1 | 1.6 |
| Escherichia coli, 8294 | 1.6 | 25 | 6.3 | 12.5 | — | 25 | 0.4 | 1.6 | 25 | 3.1 | — |
| Escherichia coli, 10857 | <0.05 | 6.3 | 0.1 | 0.4 | 25 | 0.2 | 0.2 | 0.2 | 0.2 | 0.8 | 50 |
| Escherichia coli, 10896 | 0.4 | 12.5 | 3.1 | 6.3 | — | 6.3 | 0.8 | 1.6 | 6.3 | 3.1 | 100 |
| Escherichia coli, 10909 | 0.1 | 12.5 | 0.8 | 1.6 | — | 1.6 | 0.1 | 0.4 | 1.6 | 0.8 | — |
| Klebsiella aerogenes, 10440 | 1.6 | 25 | 12.5 | 25 | — | 50 | 0.8 | 1.6 | 50 | 6.3 | — |
| Klebsiella pneumoniae, 9527 | 0.2 | 25 | 0.8 | 6.3 | — | 3.1 | 0.2 | 0.2 | 3.1 | 1.6 | — |
| Proteus mirabilis, 3855 | 0.2 | 6.3 | 0.4 | 3.1 | — | 12.5 | <0.05 | 0.8 | 6.3 | 1.6 | — |
| Proteus rettgeri, 8479 | <0.05 | 1.6 | 1.6 | 3.1 | — | 12.5 | 0.05 | 0.2 | 6.3 | <0.05 | 100 |
| Proteus vulgaris, 9416 | <0.05 | 3.1 | <0.05 | 0.2 | 25 | 0.8 | 0.2 | 0.2 | 0.4 | 1.6 | 50 |
| Salmonella typhosa, 1195 | 0.2 | 6.3 | 3.1 | 6.3 | — | 12.5 | <0.05 | 0.4 | 12.5 | 0.4 | — |
| Shigella sonnei, 8449 | 0.4 | 12.5 | 3.1 | 6.3 | — | 12.5 | 0.4 | 0.8 | 12.5 | 1.6 | — |

-continued

| Organism | M.I.C. (μg/ml) Product of Example | | | | | | | | | | |
|---|---|---|---|---|---|---|---|---|---|---|---|
| *Enterobacter cloacae,* 8236 | 0.8 | 100 | 12.5 | 12.5 | — | 12.5 | 0.4 | 3.1 | 25 | 1.6 | — |
| *Enterobacter aerogenes,* 10078 | 3.1 | 100 | 50 | 50 | — | 50 | 0.8 | 3.1 | 50 | 6.3 | — |
| *Citrobacter freundii,* 9518 | 0.8 | 100 | 12.5 | 25 | — | 12.5 | 1.6 | 6.3 | 25 | 12.5 | — |
| *Serratia marcescens,* 9783 | 1.6 | 25 | 12.5 | 25 | — | 25 | 3.1 | 6.3 | 25 | 12.5 | — |
| *Pseudomonas aeruginosa,* 9545 | 0.8 | 25 | 12.5 | 1.6 | 25 | 3.1 | 0.4 | 0.8 | 25 | 3.1 | 100 |
| *Pseudomonas aeruginosa,* 8329 | 6.3 | — | 12.5 | 25 | — | 100 | 12.5 | 12.5 | 25 | 25 | — |
| *Acinetobacter calcoaceticus,* 8333 | 50 | — | — | 50 | — | — | — | — | 50 | 100 | — |

| | 134 | 135 | 136 | 138 | 140 | 141 | 142 | 143 | 144 | 145 | 149 |
|---|---|---|---|---|---|---|---|---|---|---|---|
| *Staphylococcus aureus,* 1276 | — | 3.1 | 100 | 100 | 25 | 25 | 25 | 50 | 6.3 | — | 6.3 |
| *Staphylococcus aureus,* 2399 | — | 3.1 | 100 | 50 | 25 | 50 | N.T. | 50 | 6.3 | — | 6.3 |
| *Staphylococcus aureus,* 2400 | — | 3.1 | 50 | 50 | 25 | 50 | 12.5 | 100 | 12.5 | — | 25 |
| *Staphylococcus aureus,* 10165 | — | 50 | — | — | — | — | 25 | — | 50 | — | — |
| *Streptococcus faecalis,* 9011 | — | 50 | — | — | — | — | — | — | — | — | — |
| *Streptococcus agalactiae,* 9287 | 50 | 0.8 | 3.1 | 1.6 | 0.4 | 6.3 | 25 | 3.1 | 0.8 | 50 | 3.1 |
| *Micrococcus luteus,* 2495 | 100 | 6.3 | 6.3 | 6.3 | 6.3 | 6.3 | 3.1 | 12.5 | 1.6 | 25 | 3.1 |
| *Escherichia coli,* 8294 | 3.1 | 6.3 | 0.2 | 0.1 | 1.6 | 1.6 | 1.6 | 1.6 | 50 | 0.4 | 3.1 |
| *Escherichia coli,* 10857 | 0.8 | 0.8 | <0.05 | <0.05 | <0.05 | <0.05 | 1.6 | 0.4 | 0.4 | 0.2 | <0.05 |
| *Escherichia coli,* 10896 | 3.1 | 12.5 | 0.2 | 0.1 | 0.4 | 1.6 | 1.6 | 1.6 | 6.3 | 0.2 | 0.8 |
| *Escherichia coli,* 10909 | 0.8 | 0.8 | 0.1 | <0.05 | 0.1 | 0.1 | 0.8 | 0.8 | 6.3 | <0.05 | 0.4 |
| *Klebsiella aerogenes,* 10440 | 3.1 | 3.1 | 0.4 | 0.2 | 0.8 | 1.6 | 1.6 | 3.1 | — | 0.8 | 12.5 |
| *Klebsiella pneumoniae,* 9527 | 0.8 | 0.8 | 0.1 | <0.05 | 0.1 | 0.1 | 1.6 | 1.6 | 12.5 | 0.1 | 0.4 |
| *Proteus mirabilis,* 3855 | 0.4 | 0.4 | <0.05 | <0.05 | 0.4 | 0.4 | 1.6 | 0.8 | 6.3 | <0.05 | 1.6 |
| *Proteus rettgeri,* 8479 | <0.05 | 0.4 | <0.05 | <0.05 | 0.4 | 0.4 | 0.1 | 0.8 | 1.6 | <0.05 | 1.6 |
| *Proteus vulgaris,* 9416 | 0.4 | 0.4 | <0.05 | <0.05 | <0.05 | <0.05 | 0.8 | 0.8 | 1.6 | <0.05 | <0.05 |
| *Salmonela typhosa,* 1195 | 0.4 | 0.8 | <0.05 | <0.05 | 0.2 | 0.2 | 0.8 | 0.8 | 6.3 | <0.05 | 1.6 |
| *Shigella sonnei,* 8449 | 1.6 | 3.1 | 0.2 | 0.1 | 0.4 | 0.8 | 1.6 | 0.8 | 25 | 0.4 | 1.6 |
| *Enterobacter cloacae,* 8236 | 0.8 | 3.1 | 0.2 | 0.1 | 0.8 | 1.6 | 1.6 | 3.1 | 25 | 0.8 | 1.6 |
| *Enterobacter aerogenes,* 10078 | 3.1 | 6.3 | 0.4 | 0.2 | 1.6 | 3.1 | 3.1 | 3.1 | 100 | 0.8 | 6.3 |
| *Citrobacter freundii,* 9518 | 3.1 | 12.5 | 0.2 | 0.1 | 0.8 | 1.6 | 0.8 | 1.6 | 25 | 0.8 | 3.1 |
| *Serratia marcescens,* 9783 | 6.3 | 25 | 0.4 | 0.2 | 0.8 | 1.6 | 0.8 | 3.1 | 50 | 0.4 | 3.1 |
| *Pseudomonas aeruginosa,* 9545 | 6.3 | 0.8 | 0.8 | 0.4 | 1.6 | 0.8 | 6.3 | 3.1 | 12.5 | 0.8 | 3.1 |
| *Pseudomonas aeruginosa,* 8329 | 50 | 12.5 | — | 100 | 12.5 | 12.5 | — | 100 | — | 3.1 | 100 |
| *Acinetobacter calcoaceticus,* 8333 | — | 25 | 50 | 25 | 12.5 | 12.5 | 12.5 | 100 | — | 50 | 50 |

| | 150 | 151 | 152 | 154 | 155 | 156 | 157 | 159 | 161 | 162 | 163 |
|---|---|---|---|---|---|---|---|---|---|---|---|
| *Staphylococcus aureus,* 1276 | 3.1 | 6.3 | — | — | — | — | 12.5 | — | — | 0.1 | 25 |
| *Staphylococcus aureus,* 2399 | 3.1 | 6.3 | — | — | — | — | 12.5 | — | — | 0.1 | 12.5 |
| *Staphylococcus aureus,* 2400 | 6.3 | 25 | — | — | — | — | 12.5 | — | — | 0.2 | 25 |
| *Staphylococcus aureus,* 10165 | 100 | 100 | — | — | — | — | 50 | — | — | 0.4 | — |
| *Streptococcus faecalis,* 9011 | — | — | — | — | — | — | 100 | — | — | 50 | — |
| *Streptococcus agalactiae,* 9287 | 0.4 | 6.3 | 12.5 | — | — | 12.5 | 6.3 | — | 100 | 0.4 | 6.3 |
| *Micrococcus luteus,* 2495 | 3.1 | 6.3 | 12.5 | — | — | 100 | 1.6 | — | — | 0.4 | 6.3 |
| *Escherichia coli,* 8294 | 1.6 | 3.1 | 0.2 | 50 | — | 6.3 | 50 | — | 0.4 | — | 3.1 |
| *Escherichia coli,* 10857 | <0.05 | 0.1 | 0.1 | 6.3 | 50 | 3.1 | 3.1 | — | 0.2 | 25 | 0.4 |
| *Escherichia coli,* 10896 | 0.4 | 1.6 | 0.2 | 25 | — | 3.1 | 25 | 100 | 0.1 | 100 | 12.5 |
| *Escherichia coli,* 10909 | 0.2 | 0.4 | N.T. | 25 | — | 1.6 | 25 | 100 | 0.1 | — | 0.8 |
| *Klebsiella aerogenes,* 10440 | 1.6 | 12.5 | 0.4 | 100 | — | 6.3 | 50 | — | 0.8 | — | 1.6 |
| *Klebsiella pneumoniae,* 9527 | 0.2 | 0.1 | 0.05 | 6.3 | — | 6.3 | 50 | 100 | 0.2 | — | 0.2 |
| *Proteus mirabilis,* 3855 | 0.3 | 0.4 | 0.05 | 12.5 | — | 3.1 | 50 | — | 0.2 | 50 | 0.4 |
| *Proteus rettgeri,* 8479 | 1.6 | 0.2 | 0.05 | 0.8 | 100 | 0.4 | 50 | — | 0.05 | — | 0.4 |
| *Proteus vulgaris,* 9416 | <0.05 | <0.05 | 0.05 | 12.5 | 100 | 6.3 | 50 | — | 0.2 | 25 | 0.2 |
| *Salmonella typhosa,* 1195 | 0.4 | 0.4 | 0.05 | 12.5 | — | 3.1 | 50 | — | 0.2 | 100 | 0.2 |
| *Shigella sonnei,* 8449 | 0.8 | 1.6 | 0.1 | 25 | — | 3.1 | 25 | — | 0.4 | — | 6.3 |
| *Enterobacter cloacae,* 8236 | 1.6 | 0.8 | 0.1 | 100 | — | 3.1 | 50 | — | 0.2 | — | 6.3 |
| *Enterobacter aerogenes,* 10078 | 3.1 | 6.3 | 0.8 | 100 | — | 6.3 | 100 | — | 0.4 | — | 6.3 |
| *Citrobacter freundii,* 9518 | 1.6 | 3.1 | 0.4 | 25 | — | 3.1 | 50 | — | 0.2 | — | 3.1 |
| *Serratia marcescens,* 9783 | 3.1 | 6.3 | 0.2 | 100 | — | 3.1 | 50 | — | 0.4 | — | 3.1 |
| *Pseudomonas aeruginosa,* 9545 | 12.5 | 6.3 | 0.4 | — | — | 50 | 12.5 | — | 0.8 | 25 | 6.3 |
| *Pseudomonas aeruginosa,* 8329 | 12.5 | 12.5 | 1.6 | — | — | — | 50 | — | 12.5 | — | 50 |
| *Acinetobacter calcoaceticus,* 8333 | 50 | 12.5 | 25 | — | — | — | 100 | — | 100 | — | 50 |

| | 164 | 165 | 166 | 167 | 168 | 170 | 171 | 172 | 173 | 174 | 176 |
|---|---|---|---|---|---|---|---|---|---|---|---|
| *Staphylococcus aureus,* 1276 | — | 6.3 | 3.1 | 1.6 | 3.1 | — | 100 | — | — | 50 | — |
| *Staphylococcus aureus,* 2399 | — | 12.5 | 3.1 | 1.6 | 3.1 | — | 100 | — | — | 50 | — |
| *Staphylococcus aureus,* 2400 | — | 12.5 | 1.6 | 3.1 | 6.3 | — | 50 | — | — | 100 | — |
| *Staphylococcus aureus,* 10165 | — | 25 | 6.3 | 3.1 | 100 | — | — | — | — | — | — |
| *Streptococcus faecalis,* 9011 | — | — | 25 | — | 50 | — | — | — | — | — | — |
| *Streptococcus agalactiae,* 9287 | 50 | 6.3 | 0.4 | 3.1 | 0.2 | — | 12.5 | 25 | 50 | 50 | — |
| *Micrococcus luteus,* 2495 | 25 | 3.1 | 0.8 | 3.1 | 3.1 | — | 12.5 | 100 | — | 100 | — |
| *Escherichia coli,* 8294 | 0.4 | 100 | 100 | — | 100 | 3.1 | 3.1 | — | — | 100 | — |
| *Escherichia coli,* 10857 | 0.1 | 25 | 6.3 | 50 | 0.8 | 0.2 | 1.6 | — | — | 50 | 0.8 |
| *Escherichia coli,* 10896 | 0.8 | 25 | 50 | — | 12.5 | 0.2 | 12.5 | — | — | 50 | 25 |
| *Escherichia coli,* 10909 | <0.05 | 50 | 12.5 | — | 6.3 | 0.1 | 1.6 | — | — | 50 | 25 |
| *Klebsiella aerogenes,* 10440 | 0.2 | 100 | 100 | — | — | 3.1 | 1.6 | — | — | — | — |
| *Klebsiella pneumoniae,* 9527 | <0.05 | 50 | — | — | 12.5 | 0.1 | 0.8 | — | — | 100 | — |
| *Proteus mirabilis,* 3855 | <0.05 | 25 | 25 | — | 25 | <0.05 | 0.4 | — | — | — | 50 |
| *Proteus rettgeri,* 8479 | <0.05 | 12.5 | 0.8 | 50 | 50 | <0.05 | 0.05 | — | — | N.T. | 12.5 |
| *Proteus vulgaris,* 9416 | <0.05 | 25 | 25 | 25 | 12.5 | <0.05 | 1.6 | — | — | — | 0.8 |
| *Salmonella typhosa,* 1195 | <0.05 | 50 | 12.5 | — | 50 | 0.1 | 0.4 | — | — | 100 | 50 |

| Organism | M.I.C. (μg/ml) Product of Example | | | | | | | | | |
|---|---|---|---|---|---|---|---|---|---|---|
| Shigella sonnei, 8449 | 0.1 | 100 | 100 | — | 50 | 1.6 | 6.3 | — | — | 100 | 100 |
| Enterobacter cloacae, 8236 | 0.1 | 100 | 100 | — | 50 | 0.8 | 12.5 | — | — | — | — |
| Enterobacter aerogenes, 10078 | 0.8 | — | 100 | — | 100 | 3.1 | 12.5 | — | — | — | — |
| Citrobacter freundii, 9518 | 0.4 | — | 100 | — | 50 | 1.6 | — | — | — | 100 | — |
| Serratia marcescens, 9783 | 0.8 | — | 100 | — | — | 1.6 | 100 | — | — | 100 | — |
| Pseudomonas aeruginosa, 9545 | 0.4 | 12.5 | 50 | — | 1.6 | 3.1 | 12.5 | — | — | — | — |
| Pseudomonas aeruginosa, 8329 | 1.6 | — | — | — | 50 | 12.5 | 25 | — | — | — | — |
| Acinetobacter calcoaceticus, 8333 | 100 | — | 100 | — | — | — | 100 | — | — | — | — |

| | 177 | 178 | 179 | 180 | 183 | 185 | 187 | 190 | 192 | 193 | 194 |
|---|---|---|---|---|---|---|---|---|---|---|---|
| Staphylococcus aureus, 1276 | — | — | — | — | — | — | — | — | — | 0.1 | 1.6 |
| Staphylococcus aureus, 2399 | — | — | — | — | — | — | — | — | — | 0.1 | 0.8 |
| Staphylococcus aureus, 2400 | — | — | — | — | — | — | — | — | — | 0.1 | 3.1 |
| Staphylococcus aureus, 10165 | — | — | — | — | — | — | — | — | — | 0.2 | 25 |
| Streptococcus faecalis, 9011 | — | — | — | — | — | — | 50 | — | — | 50 | — |
| Streptococcus agalactiae, 9287 | — | — | — | 25 | — | — | 6.3 | — | 100 | 0.4 | 3.1 |
| Micrococcus luteus, 2495 | — | — | — | 25 | — | — | 6.3 | 50 | 100 | 0.8 | 0.8 |
| Escherichia coli, 8294 | — | — | — | 0.8 | 25 | 50 | 12.5 | 6.3 | 0.8 | — | — |
| Escherichia coli, 10857 | 12.5 | 0.8 | 6.3 | 0.2 | 0.2 | 0.4 | 0.1 | 0.4 | 0.4 | 50 | 12.5 |
| Escherichia coli, 10896 | 25 | 12.5 | 100 | 0.2 | 1.6 | 3.1 | 0.8 | 0.2 | 0.4 | 100 | — |
| Escherichia coli, 10909 | 25 | 6.3 | 100 | 0.4 | 1.5 | 3.1 | 0.8 | 0.1 | 0.4 | — | — |
| Klebsiella aerogenes, 10440 | — | — | — | 1.6 | 100 | 100 | 25 | 6.3 | 1.6 | — | — |
| Klebsiella pneumoniae, 9527 | — | 100 | — | 0.2 | 3.1 | 6.3 | 6.3 | 0.4 | 0.4 | — | — |
| Proteus mirabilis, 3855 | 100 | — | — | 0.2 | 0.8 | 3.1 | 1.6 | 0.2 | 0.8 | — | — |
| Proteus rettgeri, 8479 | 100 | — | — | <0.05 | 0.1 | 0.8 | 0.4 | <0.05 | <0.5 | 50 | 100 |
| Proteus vulgaris, 9416 | 0.8 | 6.3 | 12.5 | 0.1 | 0.1 | 0.2 | <0.05 | <0.05 | 0.8 | 25 | 12.5 |
| Salmonella typhosa, 1195 | — | 100 | — | 0.1 | 1.5 | 3.1 | 3.1 | 0.4 | 0.4 | — | — |
| Shigella sonnei, 8449 | — | 100 | — | 0.8 | 12.5 | 25 | 6.3 | 3.1 | 0.4 | — | — |
| Enterobacter cloacae, 8236 | — | 100 | — | 3.1 | 12.5 | 25 | 12.5 | 0.8 | 0.8 | — | — |
| Enterobacter aerogenes, 10078 | — | — | — | 3.1 | 50 | 50 | 25 | 3.1 | 1.6 | — | — |
| Citrobacter freundii, 9518 | — | 50 | — | 0.8 | 12.5 | 25 | 6.3 | 1.6 | 0.8 | — | — |
| Serratia marcescens, 9783 | — | — | — | 3.1 | 12.5 | 50 | 12.5 | 1.6 | 3.1 | — | — |
| Pseudomonas aeruginosa, 9545 | — | — | — | 12.5 | — | 100 | 25 | 1.6 | 6.3 | 50 | 100 |
| Pseudomonas aeruginosa, 8329 | — | — | — | — | — | — | — | 25 | — | — | — |
| Acinetobacter calcoaceticus, 8333 | — | — | — | — | — | — | — | — | 100 | — | — |

| | 195 | 196 | 197 | 198 | 199 |
|---|---|---|---|---|---|
| Staphylococcus aureus, 1276 | 25 | 25 | 3.1 | 1.6 | 0.4 |
| Staphylococcus aureus, 2399 | 25 | 25 | 1.6 | 1.6 | 0.2 |
| Staphylococcus aureus, 2400 | 50 | 100 | 3.1 | 3.1 | 0.2 |
| Staphylococcus aureus, 10165 | — | — | 100 | 50 | 0.8 |
| Streptococcus faecalis, 9011 | — | — | 50 | 100 | — |
| Streptococcus agalactiae, 9287 | 3.1 | 12.5 | 0.4 | 0.4 | 0.8 |
| Micrococcus luteus, 2495 | 25 | 25 | 6.3 | 6.3 | 3.1 |
| Escherichia coli, 8294 | 3.1 | 1.6 | 12.5 | 0.4 | — |
| Escherichia coli, 10857 | 0.8 | 0.4 | 6.3 | <0.05 | — |
| Escherichia coli, 10896 | 3.1 | 3.1 | 50 | 0.1 | — |
| Escherichia coli, 10909 | 0.8 | 0.8 | 6.3 | 0.1 | — |
| Klebsiella aerogenes, 10440 | 12.5 | 3.1 | 12.5 | 0.4 | — |
| Klebsiella pneumoniae, 9527 | 6.3 | 0.8 | 12.5 | <0.05 | — |
| Proteus mirabilis, 3855 | 3.1 | 1.6 | 6.3 | 0.4 | — |
| Proteus rettgeri, 8479 | 1.6 | 0.8 | 3.1 | 0.4 | 50 |
| Proteus vulgaris, 9416 | 3.1 | 1.6 | 100 | <0.05 | 100 |
| Salmonella typhosa, 1195 | 0.8 | 0.4 | 3.1 | 0.2 | — |
| Shigella sonnei, 8449 | 1.6 | 1.6 | 12.5 | 0.1 | — |
| Enterobacter cloacae, 8236 | 6.3 | 3.1 | 100 | 0.4 | — |
| Enterobacter aerogenes, 10078 | 3.1 | 3.1 | 50 | 0.4 | — |
| Citrobacter freundii, 9518 | 6.3 | 6.3 | — | 0.4 | — |
| Serratia marcescens, 9783 | 6.3 | 3.1 | — | 3.1 | — |
| Pseudomonas aeruginosa, 9545 | 6.3 | 100 | 6.3 | 1.6 | 100 |
| Pseudomonas aeruginosa, 8329 | 50 | — | 100 | 12.5 | — |
| Acinetobacter calcoaceticus, 8333 | — | — | — | — | — |

What is claimed is:

1. A β-lactam having a sulfonic acid salt substituent —SO$_3^\ominus$M$^\oplus$, wherein M$^\oplus$ is hydrogen or a cation, in the 1-position and an amino substituent —NH$_2$ in the 3-position.

2. A β-lactam in accordance with claim 1 having a sulfonic acid salt substituent —SO$_3^\ominus$M$^\oplus$, wherein M$^\oplus$ is hydrogen or a cation, in the 1-position, an amino substituent —NH$_2$ in the 3-position and an alkoxy substituent having 1 to 4 carbon atoms in the 3-position.

3. A β-lactam in accordance with claim 2 having a sulfonic acid salt substituent —SO$_3^\ominus$M$^\oplus$, wherein M$^\oplus$ is hydrogen or a cation, in the 1-position, an amino substituent —NH$_2$ in the 3-position and a methoxy substituent in the 3-position.

4. A β-lactam in accordance with claim 1 having the formula

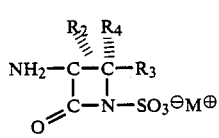

wherein R$_2$ is hydrogen or alkoxy of 1 to 4 carbon atoms; R$_3$ and R$_4$ are the same or different and each is hydrogen, alkyl, cycloalkyl, phenyl, or substituted phenyl, or one of $R_3$ and $R_4$ is hydrogen and the other is alkoxycarbonyl, alken-1-yl, alkyn-1-yl, 2-phenylethenyl, or 2-phenylethynyl; and $M^{\oplus}$ is hydrogen or a cation.

5. A β-lactam in accordance with claim 4 wherein $R_2$ is hydrogen.

6. A β-lactam in accordance with claim 4 wherein $R_2$ is methoxy.

7. A β-lactam in accordance with claim 5 wherein $R_3$ and $R_4$ are hydrogen.

8. A β-lactam in accordance with claim 5 wherein $R_3$ is hydrogen and $R_4$ is methyl.

9. A β-lactam in accordance with claim 5 wherein $R_3$ is methyl and $R_4$ is hydrogen.

10. A pharmaceutically acceptable salt, including inner salt, of a β-lactam having a sulfonic acid substituent —$SO_3H$ in the 1-position and an acylamino substituent other than N-(γ-glutamylalanyl)amino in the 3-position, wherein the acyl portion of the group is derived from a carboxylic acid.

11. A pharmaceutically acceptable salt, including inner salt, or a β-lactam in accordance with claim 10 having a sulfonic acid substituent —$SO_3H$ in the 1-position, an acylamino substituent other than N-(γ-glutamylalanyl)amino in the 3-position, wherein the acyl portion of the group is derived from a carboxylic acid, and an alkoxy substituent having 1 to 4 carbon atoms in the 3-position.

12. A pharmaceutically acceptable salt, including inner salt, or a β-lactam in accordance with claim 10 having a sulfonic acid substituent —$SO_3H$ in the 1-position, an acylamino substituent other than N-(γ-glutamylalanyl)amino in the 3-position, wherein the acyl portion of the group is derived from a carboxylic acid, and a methoxy substituent in the 3-position.

13. A pharmaceutically acceptable salt, including inner salt of a β-lactam in accordance with claim 10 having the formula $$R_1-NH-\underset{O=C-N-SO_3^{\ominus}M^{\oplus}}{\overset{R_2\ R_4}{C-C-R_3}}$$

$$R_1-NH-\underset{O=C-N-SO_3H}{\overset{R_2\ R_4}{C-C-R_3}}$$

wherein $R_1$—NH— is acylamino, other than N-(γ-glutamylalanyl)amino, wherein the acyl portion of the group is derived from a carboxylic acid; $R_2$ is hydrogen or alkoxy of 1 to 4 carbon atoms; and $R_3$ and $R_4$ are the same or different and each is hydrogen, alkyl, cycloalkyl, phenyl, or substituted phenyl or one of $R_3$ and $R_4$ is hydrogen and the other is alkoxycarbonyl, alken-1-yl, alkyn-1-yl, 2-phenylethenyl, or 2-phenylethynyl.

14. A β-lactam in accordance with claim 13 wherein $R_2$ is hydrogen.

15. A β-lactam in accordance with claim 13 wherein $R_2$ is methoxy.

16. A β-lactam in accordance with claim 14 wherein $R_3$ and $R_4$ are hydrogen.

17. A β-lactam in accordance with claim 14 wherein $R_3$ is hydrogen and $R_4$ is methyl.

18. A β-lactam in accordance with claim 14 wherein $R_3$ is methyl and $R_4$ is hydrogen.

19. A β-lactam in accordance with claim 13 wherein $R_1$ is an aliphatic group having the formula $$R_5-\overset{O}{\underset{\|}{C}}-$$

wherein $R_5$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

20. A β-lactam in accordance with claim 13 wherein $R_1$ is a carbocyclic aromatic group having the formula

[phenyl ring with $R_6$, $R_7$, $R_8$ substituents]—$(CH_2)_n$—$\overset{O}{\underset{\|}{C}}$—,

[phenyl ring with $R_6$, $R_7$, $R_8$ substituents]—$\underset{R_9}{\overset{}{CH}}$—$\overset{O}{\underset{\|}{C}}$—,

[phenyl ring with $R_6$, $R_7$, $R_8$ substituents]—$CH_2$—O—$\overset{O}{\underset{\|}{C}}$—,

[phenyl ring with $R_6$, $R_7$, $R_8$ substituents]—O—$CH_2$—$\overset{O}{\underset{\|}{C}}$—,

[phenyl ring with $R_6$, $R_7$, $R_8$ substituents]—S—$CH_2$—$\overset{O}{\underset{\|}{C}}$—, or

[phenyl ring with $R_6$, $R_7$, $R_8$ substituents]—$CH_2$—S—$\overset{O}{\underset{\|}{C}}$— wherein n is 0, 1, 2 or 3; $R_6$, $R_7$, and $R_8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_9$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

21. A β-lactam in accordance with claim 13 wherein $R_1$ is a heteroaromatic group having the formula $$R_{10}-(CH_2)_n-\overset{O}{\underset{\|}{C}}-,\ R_{10}-\underset{R_9}{\overset{}{CH}}-\overset{O}{\underset{\|}{C}}-,\ R_{10}-O-CH_2-\overset{O}{\underset{\|}{C}}-,$$

-continued

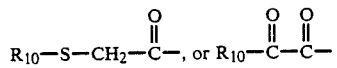

wherein n is 0, 1, 2 or 3; $R_9$ is amino, hydroxyl, a carboxyl salt, protected carboxyl, formyloxy, a sulfo salt, a sulfoamino salt, azido, halogen, hydrazino, alkylhydrazino, phenylhydrazino or [(alkylthio)thioxomethyl]thio; and $R_{10}$ is a substituted or unsubstituted 5-, 6-, or 7-membered heterocyclic aromatic ring containing 1, 2, 3 or 4 nitrogen, oxygen and sulfur atoms.

22. A β-lactam in accordance with claim 13 wherein $R_1$ is a group having the formula

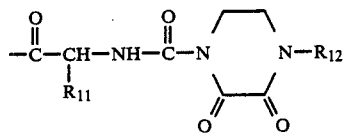

wherein $R_{11}$ is (i) a group having the formula

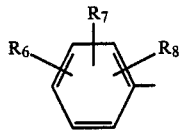

wherein $R_6$, $R_7$ and $R_8$ each is independently hydrogen, halogen, hydroxyl, nitro, amino, cyano, trifluoromethyl, alkyl of 1 to 4 carbon atoms, alkoxy of 1 to 4 carbon atoms, or aminomethyl, or (ii) a substituted or unsubstituted 5-, 6-, or 7-membered heterocyclic ring containing 1, 2, 3 or 4 nitrogen, oxygen and sulfur atoms; and $R_{12}$ is —N=CH—$R_{11}$,

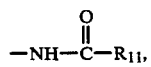

alkylcarbonylamino, alkyl or alkyl substituted with one or more halogen, cyano, nitro, amino or mercapto groups.

23. A β-lactam in accordance with claim 13 wherein $R_1$ is a group having the formula

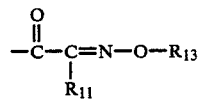

wherein $R_{11}$ is (i) a group having the formula

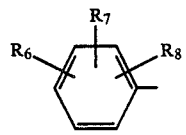

wherein $R_6$, $R_7$ and $R_8$ each is independently hydrogen, halogen, hydroxyl, nitro, amino, cyano, trifluoromethyl, alkyl of 1 to 4 carbon atoms, alkoxy or 1 to 4 carbon atoms or aminomethyl, or (ii) a substituted or unsubstituted 5-, 6- or 7-membered heterocyclic ring containing 1, 2, 3 or 4 nitrogen, oxygen and sulfur atoms; and $R_{13}$ is hydrogen, alkyl, cycloalkyl, alkylaminocarbonyl,

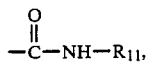

or alkyl substituted with one or more halogen, cyano, nitro, amino, mercapto, alkylthio, $R_{11}$, carboxyl, carboxyl salt, amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents.

24. A β-lactam in accordance with claim 13 wherein $R_1$ is a group having the formula

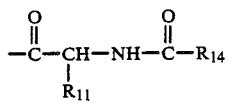

wherein $R_{11}$ is (i) a group having the formula

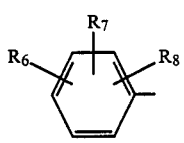

wherein $R_6$, $R_7$ and $R_8$ each is independently hydrogen, halogen, hydroxyl, nitro, amino, cyano, trifluoromethyl, alkyl or 1 to 4 carbon atoms, alkoxy of 1 to 4 carbon atoms, or aminomethyl, or (ii) a substituted or unsubstituted 5-, 6- or 7-membered heterocyclic ring containing 1, 2, 3 or 4 nitrogen, oxygen and sulfur atoms; and $R_{14}$ is

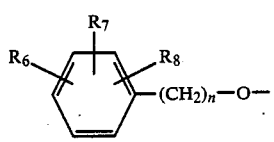

wherein n is 0, 1, 2, or 3, amino, alkylamino, (cyanoalkyl)amino, amido, alkylamido, (cyanoalkyl)amido,

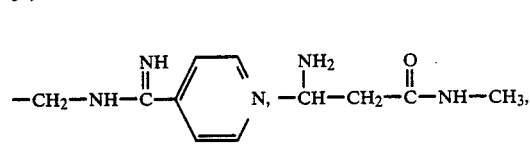

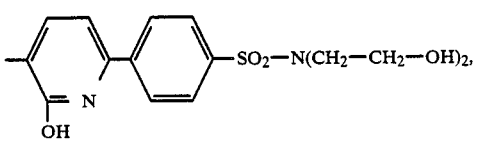

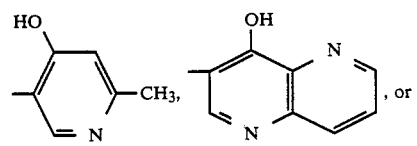

25. A β-lactam in accordance with claim 13 wherein R₁ is a group having the formula wherein R₁₁ is (i) a group having the formula wherein R₆, R₇ and R₈ each is independently hydrogen, halogen, hydroxyl, nitro, amino, cyano, trifluoromethyl, alkyl of 1 to 4 carbon atoms, alkoxy of 1 to 4 carbon atoms, or aminomethyl, or (ii) a substituted or unsubstituted 5-, 6-, or 7-membered heterocyclic ring containing 1, 2, 3 or 4 nitrogen, oxygen and sulfur atoms; and R₁₅ is hydrogen, alkylsulfonyl, —N═CH—R₁₁, $$-\overset{O}{\underset{\|}{C}}-R_{16}$$

wherein R₁₆ is hydrogen, alkyl, or halogen substituted alkyl, R₁₁, alkyl, or alkyl substituted with one more more halogen, cyano, nitro, amino or mercapto groups.

26. A β-lactam in accordance with claim 23 wherein R₁₁ is 2-amino-4-thiazolyl.

27. A β-lactam in accordance with claim 26: a salt of [3S(Z)]-3-[[(2-amino-4-thiazolyl)(methoxyimino)acetyl]amino]-2-oxo-1-azetidinesulfonic acid.

28. A β-lactam in accordance with claim 26: a salt of [3S(Z)]-3-[[(2-amino-4-thiazolyl)[(carboxymethoxy)imino]acetyl]amino]-2-oxo-1-azetidinesulfonic acid.

29. A β-lactam in accordance with claim 26: a salt of [3S(Z)]-3-[[(2-amino-4-thiazolyl)[(1-carboxy-1-methylethoxy)imino]acetyl]amino]-2-oxo-1-azetidinesulfonic acid.

30. A β-lactam in accordance with claim 26: a salt of [3S-[3α(Z),4β]]-3-[[(2-amino-4-thiazolyl)(methoxyimino)acetyl]amino]-4-methyl-2-oxo-1-azetidinesulfonic acid.

31. A β-lactam in accordance with claim 26: a salt of [3S-[3α(Z),4β]]-3-[[[(carboxymethoxy)imino](2-amino-4-thiazolyl)acetyl]amino]-4-methyl-2-oxo-1-azetidinesulfonic acid.

32. A β-lactam in accordance with claim 26: a salt of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid.

33. A β-lactam in accordance with claim 32: [3S-[3α(Z),4β]]-3-[[(2-amino-4-thiazolyl[(1-carboxy-1-methylethoxy)imino]acetyl]amino]-4-methyl-2-oxo-1-azetidinesulfonic acid, dipotassium salt.

34. A β-lactam in accordance with claim 26: a salt of [3S-[3α(Z),4α]]-3-[[2-amino-4-thiazolyl)methoxyimino)acetyl]amino]-4-methyl-2-oxo-1-azetidinesulfonic acid.

35. A β-lactam in accordance with claim 26: a salt of [3S-[3α(Z),4α]]-3-[[(2-amino-4-thiazolyl)[(1-carboxy-1-methylethoxy)imino]acetyl]amino]-4-methyl-2-oxo-1-azetidinesulfonic acid.

36. A β-lactam in accordance with claim 25 wherein R₁ is a group having the formula 37. A β-lactam in accordance with claim 36 wherein R₁ is a group having the formula 38. A β-lactam in accordance with claim 37: a salt of [3S(R*)]-3-[[[[3-[(2-furanylmethylene)amino]-2-oxo-1-imidazolidinyl]carbonyl]amino]phenylacetyl]amino]-2-oxo-1-azetidinesulfonic acid.

39. A β-lactam in accordance with claim 37: a salt of [3S-[3α(R*),4β]]-3-[[[[3-[(2-furanylmethylene)amino]-2-oxo-1-imidazolidinyl]carbonyl]amino]phenylacetyl]amino]-4-methyl-2-oxo-1-azetidinesulfonic acid.

40. A β-lactam in accordance with claim 37: a salt of [3S-[3α(R*),4α]]-3-[[[[3-[(2-furanylmethylene)amino]-2-oxo-1-imidazolidinyl]carbonyl]amino]phenylacetyl]amino]-4-methyl-2-oxo-1-azetidinesulfonic acid.

41. A β-lactam in accordance with claim 22 wherein R₁ is a group having the formula 42. A β-lactam in accordance with claim 41: a salt of [3S(R*)]-3-[[[[(4-ethyl-2,3-dioxo-1-piperazinyl)carbonyl]amino]phenylacetyl]amino]-2-oxo-1-azetidinesulfonic acid.

43. A β-lactam in accordance with claim 41: a salt of [3S-[3α(R*),4β]]-3-[[[[(4-ethyl-2,3-dioxo-1-piperazinyl)-carbonyl]amino]phenylacetyl]amino]-4-methyl-2-oxo-1-azetidinesulfonic acid.

44. A β-lactam in accordance with claim 41: a salt of [3S-[3α(R*),4α]]-3-[[[[(4-ethyl-2,3-dioxo-1-piperazinyl)- carbonyl]amino]phenylacetyl]amino]-4-methyl-2-oxo-1-azetidinesulfonic acid.

45. A method of treating bacterial infections in mammals which comprises administering to a mammal in need thereof an effective amount of a pharmaceutically acceptable salt, including inner salt, of a β-lactam having the formula

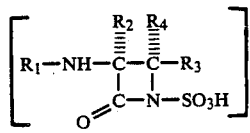

wherein $R_1$ is acyl, other than N-(γ-glutamylalanyl), derived from a carboxylic acid; $R_2$ is hydrogen or alkoxy of 1 to 4 carbon atoms; and $R_3$ and $R_4$ are the same or different and each is hydrogen, alkyl, cycloalkyl, phenyl or substituted phenyl, or one of $R_3$ and $R_4$ is hydrogen and the other is alkoxycarbonyl, alken-1-yl, alkyn-1-yl, 2-phenylethenyl or 2-phenylethynyl.

46. An antibacterial composition comprising an effective amount of a pharmaceutically acceptable salt, including inner salt, of a β-lactam having the formula

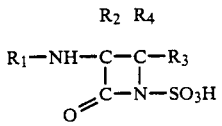

wherein $R_1$ is acyl, other than N-(γ-glutamylalanyl), derived from a carboxylic acid; $R_2$ is hydrogen or alkoxy of 1 to 4 carbon atoms; and $R_3$ and $R_4$ are the same or different and each is hydrogen, alkyl, cycloalkyl, phenyl or substituted phenyl, or one of $R_3$ and $R_4$ is hydrogen and the other is alkoxycarbonyl, alken-1-yl, alkyn-1-yl, 2-phenylethenyl or 2-phenylethynyl, and a pharmaceutically acceptable carrier therefor.

47. A β-lactam having the formula

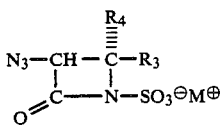

wherein $R_3$ and $R_4$ are the same or different and each is hydrogen, alkyl, cycloalkyl, phenyl or substituted phenyl, or one of $R_3$ and $R_4$ is hydrogen and the other is alkoxycarbonyl, alken-1-yl, alkyn-1-yl, 2-phenylethenyl or 2-phenylethynyl; and $M^{\oplus}$ is a cation.

48. A β-lactam in accordance with claim 13: [3S-[3α(Z),4β]]-3-[[(2-amino-4-thiazolyl)-[(1-carboxy-1-methylethoxy)imino]acetyl]amino]-4-methyl-2-oxo-1-azetidinesulfonic acid.

* * * * *